(12) United States Patent
Yamashita et al.

(10) Patent No.: US 8,703,758 B2
(45) Date of Patent: Apr. 22, 2014

(54) BICYCLIC COMPOUND

(75) Inventors: Tohru Yamashita, Osaka (JP); Makoto Kamata, Osaka (JP); Hideki Hirose, Osaka (JP); Masataka Murakami, Osaka (JP); Takuya Fujimoto, Osaka (JP); Zenichi Ikeda, Osaka (JP); Tsuneo Yasuma, Osaka (JP); Ikuo Fujimori, Osaka (JP); Ryo Mizojiri, Osaka (JP); Tomoya Yukawa, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 114 days.

(21) Appl. No.: 13/094,015

(22) Filed: Apr. 26, 2011

(65) Prior Publication Data

US 2011/0263562 A1    Oct. 27, 2011

(30) Foreign Application Priority Data

Apr. 27, 2010  (JP) ................. 2010-102718

(51) Int. Cl.

| | | |
|---|---|---|
| *A01N 43/00* | (2006.01) | |
| *A61K 31/00* | (2006.01) | |
| *A01N 43/42* | (2006.01) | |
| *A61K 31/44* | (2006.01) | |
| *A01N 43/76* | (2006.01) | |
| *A61K 31/42* | (2006.01) | |
| *A01N 43/56* | (2006.01) | |
| *A61K 31/415* | (2006.01) | |
| *A01N 43/08* | (2006.01) | |
| *A61K 31/34* | (2006.01) | |
| *C07D 413/14* | (2006.01) | |
| *C07D 405/02* | (2006.01) | |
| *C07D 401/02* | (2006.01) | |
| *C07D 401/14* | (2006.01) | |
| *C07D 403/02* | (2006.01) | |
| *C07D 491/048* | (2006.01) | |
| *A61K 31/41* | (2006.01) | |
| *A61K 31/439* | (2006.01) | |
| *A61K 31/444* | (2006.01) | |
| *A61K 31/4439* | (2006.01) | |

(52) U.S. Cl.
CPC ............ *C07D 413/14* (2013.01); *C07D 405/02* (2013.01); *C07D 401/02* (2013.01); *C07D 401/14* (2013.01); *C07D 403/02* (2013.01); *C07D 491/048* (2013.01); *A61K 31/41* (2013.01); *A61K 31/415* (2013.01); *A61K 31/439* (2013.01); *A61K 31/444* (2013.01); *A61K 31/4439* (2013.01)
USPC ...... 514/210.21; 514/304; 514/375; 514/406; 514/469; 514/302; 546/115; 546/126; 546/198; 548/361.1

(58) Field of Classification Search
CPC .. C07D 413/14; C07D 405/02; C07D 417/14; C07D 401/02; C07D 403/02; C07D 255/04; C07D 491/08; A61K 31/41; A61K 31/439; A61K 31/444; A61K 31/4439
USPC ............ 514/210.21, 302, 304, 375, 406, 409; 546/115, 126, 198; 548/361.1
See application file for complete search history.

(56) References Cited

U.S. PATENT DOCUMENTS

| | | |
|---|---|---|
| 2002/0156111 A1 | 10/2002 | Clark et al. |
| 2007/0037834 A1 | 2/2007 | Arai et al. |
| 2009/0281088 A1 | 11/2009 | Ding et al. |
| 2010/0093777 A1 | 4/2010 | Fukatsu et al. |
| 2011/0166167 A1 | 7/2011 | Neelamkavil et al. |
| 2012/0010247 A1 | 1/2012 | Kamata et al. |
| 2012/0142714 A1 | 6/2012 | Yasuma et al. |

FOREIGN PATENT DOCUMENTS

| | | |
|---|---|---|
| EP | 2 128 163 | 12/2009 |
| WO | 00/68213 | 11/2000 |
| WO | 03/104230 | 12/2003 |
| WO | 2009/120789 | 10/2009 |
| WO | 2010/009208 | 1/2010 |
| WO | 2010/050445 | 5/2010 |
| WO | 2012/074126 | 6/2012 |
| WO | 2012/108478 | 8/2012 |

OTHER PUBLICATIONS

J. Kondo et al., "6-Methoxy-2-(4-substituted phenyl)benzoxazoles as Fluorescent Chiral Derivatization Reagents for Carboxylic Acid Enantiomers", Analytical Sciences, vol. 10, No. 1, pp. 17-23, Feb. 1994.
International Search Report and Written Opinion corresponding to PCT/JP2011/060616.

(Continued)

*Primary Examiner* — Samira Jean-Louis
(74) *Attorney, Agent, or Firm* — Wenderoth, Lind & Ponack, L.L.P.

(57) ABSTRACT

The present invention provides to a compound having an ACC inhibitory action, which is useful as an agent for the prophylaxis or treatment of obesity, diabetes, hypertension, hyperlipidemia, cardiac failure, diabetic complications, metabolic syndrome, sarcopenia, cancer and the like, and has superior efficacy.
The present invention relates to a compound represented by the formula (I):

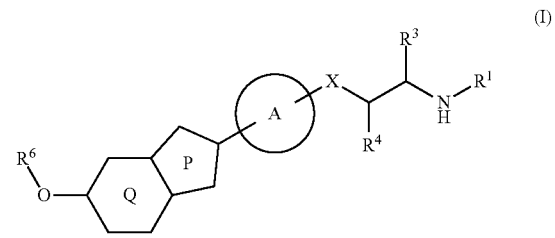

wherein each symbol is as defined in the specification.

9 Claims, No Drawings

(56) References Cited

OTHER PUBLICATIONS

J. W. Corbett et al., "Discovery of Small Molecule Isozyme Non-Specific Inhibitors of Mammalian Acetyl-CoA Carboxylase 1 and 2", Bioorganic & Medicinal Chemistry Letters, vol. 20, No. 7, pp. 2383-2388, 2010.

J. W Corbett et al , "Inhibitors of Mammalian Acetyl-CoA Carboxylase", Recent Patents on Cardiovascular Drug Discovery, vol. 2, No. 3, pp. 162-180, 2007.

Opposition published Feb. 21, 2013 in corresponding Costa Rican Patent Application No. 2012-0598, with English translation.

```
SEQUENCE LISTING

<160> NUMBER OF SEQ ID NOS: 4

<210> SEQ ID NO 1
<211> LENGTH: 41
<212> TYPE: DNA
<213> ORGANISM: Artificial sequence
<220> FEATURE:
<223> OTHER INFORMATION: Synthetic construct; PCR primer for hACC2 gene
      cloning

<400> SEQUENCE: 1
aaaagtcgac ccaccatggt cttgcttctt tgtctatctt g                           41

<210> SEQ ID NO 2
<211> LENGTH: 35
<212> TYPE: DNA
<213> ORGANISM: Artificial sequence
<220> FEATURE:
<223> OTHER INFORMATION: Synthetic construct; PCR primer for hACC2 gene
      cloning

<400> SEQUENCE: 2
tttttctaga tcaggtagag gccgggctgt ccatg                                  35

<210> SEQ ID NO 3
<211> LENGTH: 35
<212> TYPE: DNA
<213> ORGANISM: Artificial sequence
<220> FEATURE:
<223> OTHER INFORMATION: Synthetic construct; PCR primer for constuction
      of ACC2-expressing plasmid

<400> SEQUENCE: 3
ccaggtcgac ccgccaacgg gactgggaca caagg                                  35

<210> SEQ ID NO 4
<211> LENGTH: 25
<212> TYPE: DNA
<213> ORGANISM: Artificial sequence
<220> FEATURE:
<223> OTHER INFORMATION: Synthetic construct; PCR primer for constuction
      of ACC2-expressing plasmid

<400> SEQUENCE: 4
cgcactctca gtttcccgga ttccc                                             25
```

BICYCLIC COMPOUND

TECHNICAL FIELD

The present invention relates to a bicyclic compound having an acetyl-CoA carboxylase (in the present specification, sometimes to be abbreviated as ACC) inhibitory action, which is useful for the prophylaxis or treatment of obesity, diabetes, hypertension, hyperlipidemia, cardiac failure, diabetic complications, metabolic syndrome, sarcopenia, cancer and the like.

BACKGROUND OF THE INVENTION

ACC is an enzyme that converts acetyl-CoA to malonyl-CoA, and catalyzes a rate determining reaction in fatty acid metabolism. Malonyl-CoA, which is produced by an ACC catalyst reaction, inhibits fatty acid oxidation in mitochondria based on the feedback inhibition of carnitine palmitoyl transferase-1 (CPT-1). Accordingly, ACC plays a key role in controlling the balance between use of carbohydrate and fatty acid in the liver and skeletal muscle, and further, controlling insulin sensitivity in the liver, skeletal muscle and adipose tissue.

A reduced level of malonyl-CoA by ACC inhibition can promote an increase in fatty acid oxidation, decreased secretion of triglyceride (TG)-rich lipoprotein (VLDL) in the liver, regulation of insulin secretion in the pancreas, and further, improvement in the insulin sensitivity in the liver, skeletal muscle and adipose tissue.

In addition, long-term administration of a compound having an ACC inhibitory action can strikingly decrease the TG content of the liver and adipose tissues and selectively decrease body fat in obese test subjects taking low fat diet, by promoting fatty acid oxidation and suppressing de novo synthesis of fatty acid.

Accordingly, a compound having an ACC inhibitory action is extremely useful for the prophylaxis or treatment of metabolic syndrome, obesity, hypertension, diabetes, cardiovascular diseases associated with atherosclerosis and the like.

On the other hand the following compounds

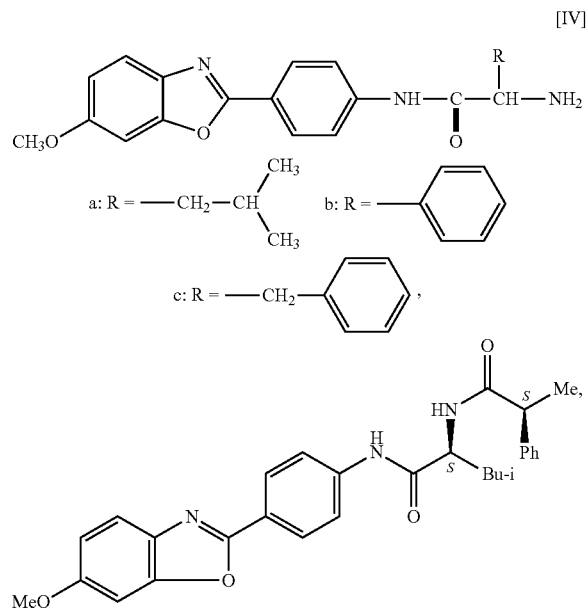

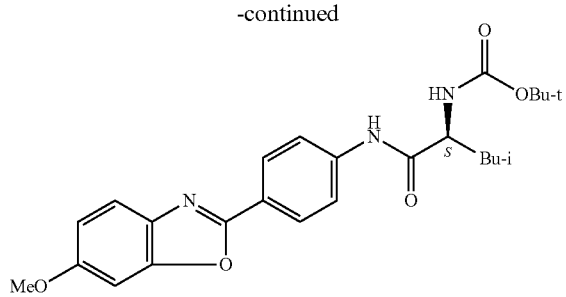

and the like, have been reported (Analytical Sciences (1994), 10(1), pages 17-23).

SUMMARY OF THE INVENTION

Problems to be Solved by the Invention

There is a demand for the development of a compound having an ACC inhibitory action, which is useful as an agent for the prophylaxis or treatment of obesity, diabetes, hypertension, hyperlipidemia, cardiac failure, diabetic complications, metabolic syndrome, sarcopenia, cancer and the like, and has superior efficacy.

Means of Solving the Problems

The present inventors have found for the first time that a compound represented by the formula (I):

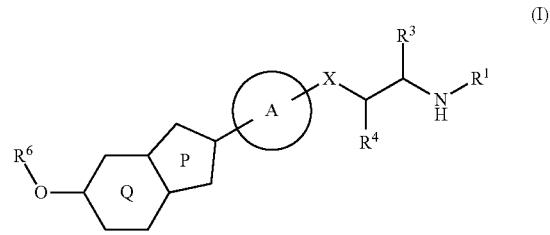

wherein
$R^1$ is a group represented by the formula: $—COR^2$ wherein $R^2$ is a hydrogen atom or a substituent, an optionally substituted 5- or 6-membered aromatic heterocyclic group or an optionally substituted phenyl group;
$R^3$ is a $C_{1-6}$ alkyl group optionally substituted by halogen atom(s), or an optionally substituted $C_{3-6}$ cycloalkyl group;
$R^4$ is a hydrogen atom or a substituent;
X is O, CO, $CR^{5a}R^{5b}$ wherein $R^{5a}$ and $R^{5b}$ are each independently a hydrogen atom, a halogen atom or an optionally substituted $C_{1-6}$ alkyl group, $NR^{5c}$ wherein $R^{5c}$ is a hydrogen atom or an optionally substituted $C_{1-6}$ alkyl group, S, SO or $S(O)_2$;
ring A is an optionally further substituted 4- to 7-membered non-aromatic ring (the ring is optionally crosslinked);
ring P is a 5-membered aromatic heterocycle, and
ring Q is an optionally further substituted 6-membered ring, and
ring P and ring Q are condensed to form an optionally further substituted bicyclic aromatic heterocycle; and
$R^6$ is an optionally substituted $C_{1-6}$ alkyl group or an optionally substituted $C_{3-6}$ cycloalkyl group,
or a salt thereof [hereinafter sometimes to be referred to as compound (I)] has a superior ACC inhibitory action, which is useful for the prophylaxis or treatment of obesity, diabetes, hypertension, hyperlipidemia, cardiac failure, diabetic complications, metabolic syndrome, sarcopenia, cancer and the like, and has superior efficacy. Based on this finding, the present inventors have conducted intensive studies and completed the present invention.

Accordingly, the present invention relates to

[1] compound (I);

[2] a compound represented by the formula (I)

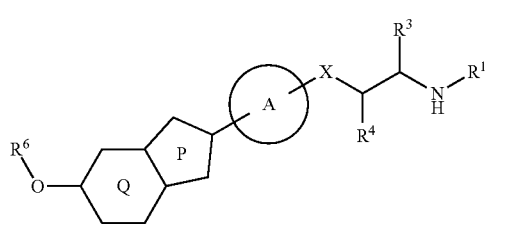

wherein
$R^1$ is a group represented by the formula: —$COR^2$ wherein $R^2$ is a hydrogen atom or a substituent, an optionally substituted 5- or 6-membered aromatic heterocyclic group or an optionally substituted phenyl group;
$R^3$ is a $C_{1-6}$ alkyl group optionally substituted by halogen atom(s), or an optionally substituted $C_{3-6}$ cycloalkyl group;
$R^4$ is a hydrogen atom or a substituent;
X is O, CO, $CR^{5a}R^{5b}$ wherein $R^{5a}$ and $R^{5b}$ are each independently a hydrogen atom, a halogen atom or an optionally substituted $C_{1-6}$ alkyl group, $NR^{5c}$ wherein $R^{5a}$ is a hydrogen atom or an optionally substituted $C_{1-6}$ alkyl group, S, SO or $S(O)_2$;
ring A is an optionally further substituted 4- to 7-membered non-aromatic ring (the ring is optionally crosslinked);
ring P is a 5-membered aromatic heterocycle, and
ring Q is an optionally further substituted 6-membered aromatic ring, and
ring P and ring Q are condensed to form an optionally further substituted bicyclic aromatic heterocycle; and
$R^6$ is an optionally substituted $C_{1-6}$ alkyl group or an optionally substituted $C_{3-6}$ cycloalkyl group,
or a salt thereof;

[3] the compound or salt of the above-mentioned [1] or [2], wherein $R^1$ is (1) a group represented by the formula: —$COR^2$ wherein $R^2$ is
  (a) a $C_{1-6}$ alkyl group;
  (b) a $C_{1-6}$ alkoxy group;
  (c) an amino group optionally mono- or di-substituted by $C_{1-6}$ alkyl group(s); or
(2) a 5-membered aromatic heterocyclic group optionally substituted by 1 to 3 substituents selected from a halogen atom and a $C_{1-6}$ alkyl group;

[3A] the compound or salt of the above-mentioned [1] or [2], wherein $R^1$ is (1) a group represented by the formula: —$COR^2$ wherein $R^2$ is
  (a) a $C_{1-6}$ alkyl group;
  (b) a $C_{1-6}$ alkoxy group;
  (c) an amino group optionally mono- or di-substituted by $C_{1-6}$ alkyl group(s); or
(2) isoxazolyl optionally substituted by 1 to 3 substituents selected from a halogen atom and a $C_{1-6}$ alkyl group;

[4] the compound or salt of the above-mentioned [1], [2], [3] or [3A], wherein $R^3$ is a $C_{1-6}$ alkyl group optionally substituted by 1 to 3 halogen atoms, or a $C_{3-6}$ cycloalkyl group optionally substituted by 1 to 5 halogen atoms or 1 to 5 $C_{1-3}$ alkyl groups;

[4A] the compound or salt of the above-mentioned [1], [2], [3] or [3A], wherein $R^3$ is a $C_{1-6}$ alkyl group optionally substituted by 1 to 3 halogen atoms;

[5] the compound or salt of the above-mentioned [1], [2], [3], [3A], [4] or [4A], wherein
$R^4$ is a hydrogen atom;
$R^6$ is a $C_{1-6}$ alkyl group optionally substituted by 1 to 3 substituents selected from a halogen atom and a $C_{3-6}$ cycloalkyl group; and
X is O or $CH_2$;

[5A] the compound or salt of the above-mentioned [1], [2], [3], [3A], [4], [4A] or [5], wherein ring A is a 4- to 6-membered nitrogen-containing non-aromatic heterocycle (the heterocycle is optionally crosslinked) or cyclohexane;

[6] the compound or salt of the above-mentioned [1], [2], [3], [3A], [4], [4A] or [5], wherein ring A is azetidine, pyrrolidine, piperidine, piperazine, 8-azabicyclo[3.2.1]octane or cyclohexane;

[6A] the compound or salt of the above-mentioned [1], [2], [3], [3A], [4], [4A] or [5], wherein ring A is piperidine;

[6B] the compound or salt of the above-mentioned [1], [2], [3], [3A], [4], [4A], [5], [5A], [6] or [6A], wherein ring P is pyrrole, imidazole, tetrazole, oxazole, isoxazole, thiazole, isothiazole, oxadiazole, thiadiazole, furan, pyrazole, thiophene, 1,2,3-triazole, 1,2,4-triazole or 1,3,4-triazole;

[7] the compound or salt of the above-mentioned [1], [2], [3], [3A], [4], [4A], [5], [5A], [6] or [6A], wherein ring P is oxazole, thiazole, furan, pyrazole or 1,2,3-triazole;

[7A] the compound or salt of the above-mentioned [1], [2], [3], [3A], [4], [4A], [5], [5A], [6] or [6A], wherein ring P is oxazole or thiazole;

[8] the compound or salt of the above-mentioned [1], [2], [3], [3A], [4], [4A], [5], [5A], [6], [6A], [6B], [7] or [7A], wherein ring Q is benzene, pyridine or cyclohexa-1,3-diene, each of which is optionally further substituted by 1 to 3 halogen atoms;

[9] the compound or salt of the above-mentioned [1], [2], [3], [3A], [4], [4A], [5], [5A], [6] or [6A], wherein ring P and ring Q are condensed to form a fused ring represented by the formula:

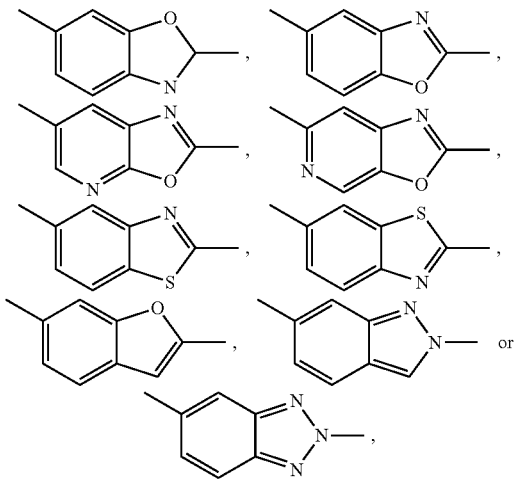

each of which optionally has additional 1 to 3 halogen atoms on the ring Q;

[10] N-[(1S)-2-({1-[6-(cyclopropylmethoxy)-1,3-benzoxazol-2-yl]piperidin-4-yl}oxy)-1-methylethyl]acetamide or a salt thereof;

[11] N-[(1S)-2-({1-[5-(cyclopropylmethoxy)-1,3-benzoxazol-2-yl]piperidin-4-yl}oxy)-1-methylethyl]acetamide or a salt thereof;

[12] N-[(1S)-3-{1-[6-(cyclopropylmethoxy)-1,3-benzoxazol-2-yl]piperidin-4-yl}-1-methylpropyl]acetamide or a salt thereof;

[13] N-[(1S)-2-({1-[6-(2-cyclopropylethoxy)-1,3-benzoxazol-2-yl]piperidin-4-yl}oxy)-1-methylethyl]acetamide or a salt thereof;

[13A] a prodrug of the compound or salt of the above-mentioned [1], [2], [3], [3A], [4], [4A], [5], [5A], [6], [6A], [6B], [7], [7A], [8], [9], [10], [11], [12] or [13];

[14] a medicament comprising the compound or salt of the above-mentioned [1], [2], [3], [3A], [4], [4A], [5], [5A], [6], [6A], [6B], [7], [7A], [8], [9], [10], [11], [12] or [13] or a prodrug thereof;

[15] the medicament of the above-mentioned [14], which is an acetyl-CoA carboxylase inhibitor;

[16] the medicament of the above-mentioned [14], which is an agent for the prophylaxis or treatment of obesity, diabetes, hypertension, hyperlipidemia, cardiac failure, diabetic complications, metabolic syndrome, sarcopenia or cancer;

[17] a method for the prophylaxis or treatment of obesity, diabetes, hypertension, hyperlipidemia, cardiac failure, diabetic complications, metabolic syndrome, sarcopenia or cancer in a mammal, which comprises administering an effective amount of the compound or salt of the above-mentioned [1], [2], [3], [3A], [4], [4A], [5], [5A], [6], [6A], [6B], [7], [7A], [8], [9], [10], [11], [12] or [13] or a prodrug thereof to the mammal;

[18] use of the compound or salt of the above-mentioned [1], [2], [3], [3A], [4], [4A], [5], [5A], [6], [6A], [6B], [7], [7A], [8], [9], [10], [11], [12] or [13] or a prodrug thereof, for the production of an agent for the prophylaxis or treatment of obesity, diabetes, hypertension, hyperlipidemia, cardiac failure, diabetic complications, metabolic syndrome, sarcopenia or cancer;

[18A] the compound or salt of the above-mentioned [1], [2], [3], [3A], [4], [4A], [5], [5A], [6], [6A], [6B], [7], [7A], [8], [9], [10], [11], [12] or [13] or a prodrug thereof for use in the prophylaxis or treatment of obesity, diabetes, hypertension, hyperlipidemia, cardiac failure, diabetic complications, metabolic syndrome, sarcopenia or cancer;

[19] a method of producing a compound represented by the formula (I'):

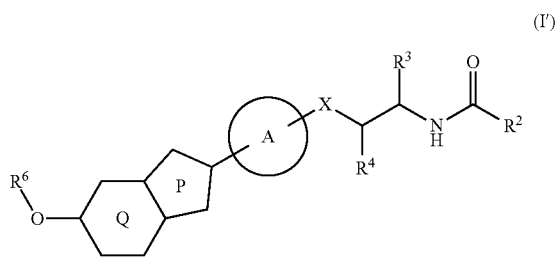

(I')

wherein each symbol is as defined in the above-mentioned [1], or a salt thereof, which comprising subjecting a compound represented by the formula (II):

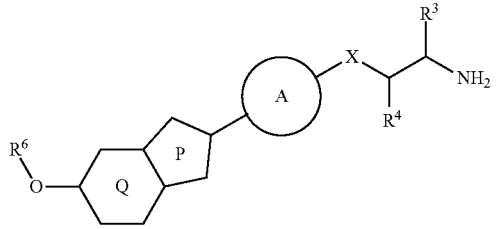

(II)

wherein each symbol is as defined in the above-mentioned [1], or a salt thereof to an acylation reaction; and the like.

Effect of the Invention

Compound (I) has an ACC inhibitory action, which is useful for the prophylaxis or treatment of obesity, diabetes, hypertension, hyperlipidemia, cardiac failure, diabetic complications, metabolic syndrome, sarcopenia, cancer and the like, and has superior efficacy.

DETAILED DESCRIPTION OF THE INVENTION

The definition of each symbol in the formula (I), (II) and (I') is described in detail in the following.

The "halogen atom" in the present specification means, unless otherwise specified, a fluorine atom, a chlorine atom, a bromine atom or an iodine atom.

The "$C_{1-3}$ alkylenedioxy group" in the present specification means, unless otherwise specified, methylenedioxy, ethylenedioxy or the like.

The "$C_{1-6}$ alkyl group" in the present specification means, unless otherwise specified, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like.

The "$C_{1-6}$ alkoxy group" in the present specification means, unless otherwise specified, methoxy, ethoxy, propoxy, isopropoxy, butoxy, isobutoxy, sec-butoxy, tert-butoxy or the like.

The "$C_{1-6}$ alkoxy-carbonyl group" in the present specification means, unless otherwise specified, methoxycarbonyl, ethoxycarbonyl, propoxycarbonyl, tert-butoxycarbonyl or the like.

The "$C_{1-6}$ alkyl-carbonyl group" in the present specification means, unless otherwise specified, acetyl, propanoyl, butanoyl, isobutanoyl, pentanoyl, isopentanoyl, hexanoyl or the like.

$R^1$ is a group represented by the formula: —$COR^2$ wherein $R^2$ is a hydrogen atom or a substituent, an optionally substituted 5- or 6-membered aromatic heterocyclic group or an optionally substituted phenyl group;

Examples of the "substituent" for $R^2$ include an "optionally substituted hydrocarbon group", an "optionally substituted heterocyclic group", an "optionally substituted hydroxy group", an "optionally substituted amino group", an "optionally substituted mercapto group", an "acyl group" and the like.

Examples of the "hydrocarbon group" of the above-mentioned "optionally substituted hydrocarbon group" include a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-13}$ aralkyl group, a $C_{8-13}$ arylalkenyl group and the like.

Examples of the $C_{1-10}$ alkyl group include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like. Of these, a $C_{1-6}$ alkyl group is preferable.

Examples of the $C_{2-10}$ alkenyl group include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like. Of these, a $C_{2-6}$ alkenyl group is preferable.

Examples of the $C_{2-10}$ alkynyl group include ethynyl, 1-propynyl, 2-propynyl, 1-butyryl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like. Of these, a $C_{2-6}$ alkynyl group is preferable.

Examples of the $C_{3-10}$ cycloalkyl group include cyclopropyl, cyclobutyl, cyclopentyl, cyclohexyl, cycloheptyl, cyclooctyl and the like. Of these, a $C_{3-6}$ cycloalkyl group is preferable.

Examples of the $C_{3-10}$ cycloalkenyl group include 2-cyclopenten-1-yl, 3-cyclopenten-1-yl, 2-cyclohexen-1-yl, 3-cyclohexen-1-yl and the like. Of these, a $C_{3-6}$ cycloalkenyl group is preferable.

Examples of the $C_{4-10}$ cycloalkadienyl group include 2,4-cyclopentadien-1-yl, 2,4-cyclohexadien-1-yl, 2,5-cyclohexadien-1-yl and the like. Of these, a $C_{4-6}$ cycloalkadienyl group is preferable.

The above-mentioned $C_{3-10}$ cycloalkyl group, $C_{3-10}$ cycloalkenyl group and $C_{4-10}$ cycloalkadienyl group are each optionally condensed with a benzene ring to form a fused ring group. Examples of the fused ring group include indanyl, dihydronaphthyl, tetrahydronaphthyl, fluorenyl and the like.

In addition, the above-mentioned $C_{3-10}$ cycloalkyl group, $C_{3-10}$ cycloalkenyl group and $C_{4-10}$ cycloalkadienyl group may be each a $C_{7-10}$ crosslinked hydrocarbon group. Examples of the $C_{7-10}$ crosslinked hydrocarbon group include bicyclo[2.2.1]heptyl (norbornyl), bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

Moreover, the above-mentioned $C_{3-10}$ cycloalkyl group, $C_{3-10}$ cycloalkenyl group and $C_{4-10}$ cycloalkadienyl group each optionally forms a spiro ring group together with a $C_{3-10}$ cycloalkane, a $C_{3-10}$ cycloalkene or a $C_{4-10}$ cycloalkadiene. Examples of the $C_{3-10}$ cycloalkane, $C_{3-10}$ cycloalkene and $C_{4-10}$ cycloalkadiene include rings corresponding to the above-mentioned $C_{3-10}$ cycloalkyl group, $C_{3-10}$ cycloalkenyl group and $C_{4-10}$ cycloalkadienyl group. Examples of the spiro ring group include spiro[4.5]decan-8-yl and the like.

Examples of the $C_{6-14}$ aryl group include phenyl, naphthyl, anthryl, phenanthryl, acenaphthyl, biphenylyl and the like. Of these, a $C_{6-12}$ aryl group is preferable.

Examples of the $C_{7-13}$ aralkyl group include benzyl, phenethyl, naphthylmethyl, biphenylylmethyl and the like.

Examples of the $C_{8-13}$ arylalkenyl group include styryl and the like.

The $C_{1-10}$ alkyl group, $C_{2-10}$ alkenyl group and $C_{2-10}$ alkynyl group, which are exemplified as the above-mentioned "hydrocarbon group", optionally have 1 to 7 (preferably 1 to 3) substituents at substitutable positions.

Examples of the substituent include
(1) a $C_{3-10}$ cycloalkyl group (e.g., cyclopropyl, cyclohexyl);
(2) a $C_{6-14}$ aryl group (e.g., phenyl, naphthyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(3) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(4) a non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms,
  (d) a halogen atom, and
  (e) an oxo group;
(5) an amino group optionally mono- or di-substituted by substituent(s) selected from
  (a) a $C_{1-6}$ alkyl group optionally substituted by 1 to 3 halogen atoms,
  (b) a $C_{1-6}$ alkyl-carbonyl group optionally substituted by 1 to 3 halogen atoms,
  (c) a $C_{1-6}$ alkoxy-carbonyl group optionally substituted by 1 to 3 halogen atoms,
  (d) a $C_{1-6}$ alkylsulfonyl group (e.g., methylsulfonyl) optionally substituted by 1 to 3 halogen atoms,
  (e) a carbamoyl group optionally mono- or di-substituted by $C_{1-6}$ alkyl group(s) optionally substituted by 1 to 3 halogen atoms, and
  (f) an aromatic heterocyclic group (e.g., thienyl, furyl, pyridyl, pyrazolyl, imidazolyl, tetrazolyl, oxazolyl, thiazolyl, oxadiazolyl, thiadiazolyl);
(6) a $C_{1-6}$ alkyl-carbonyl group optionally substituted by 1 to 3 halogen atoms;
(7) a $C_{1-6}$ alkoxy-carbonyl group optionally substituted by 1 to 3 substituents selected from
  (a) a halogen atom,
  (b) a $C_{1-6}$ alkoxy group,
  (c) a $C_{6-14}$ aryl group (e.g., phenyl), and
  (d) a heterocyclic group (e.g., tetrahydrofuryl);
(8) a $C_{1-6}$ alkylsulfonyl group (e.g., methylsulfonyl, ethylsulfonyl, isopropylsulfonyl) optionally substituted by 1 to 3 halogen atoms;
(9) a carbamoyl group optionally mono- or di-substituted by $C_{1-6}$ alkyl group(s) optionally substituted by 1 to 3 halogen atoms;
(10) a thiocarbamoyl group optionally mono- or di-substituted by $C_{1-6}$ alkyl group(s) optionally substituted by 1 to 3 halogen atoms;
(11) a sulfamoyl group optionally mono- or di-substituted by $C_{1-6}$ alkyl group(s) optionally substituted by 1 to 3 halogen atoms;
(12) a carboxy group;
(13) a hydroxy group;
(14) a $C_{1-6}$ alkoxy group optionally substituted by 1 to 3 substituents selected from (a) a halogen atom,
(b) a carboxy group,
(c) a $C_{1-6}$ alkoxy group,
(d) a $C_{1-6}$ alkoxy-carbonyl group optionally substituted by 1 to 3 $C_{6-14}$ aryl groups (e.g., phenyl),
(e) an amino group optionally mono- or di-substituted by substituent(s) selected from a $C_{1-6}$ alkyl group and a $C_{1-6}$ alkoxy-carbonyl group,
(f) a heterocyclic group (e.g., tetrahydrofuryl), and
(g) a $C_{3-10}$ cycloalkyl group;
(15) a $C_{2-6}$ alkenyloxy group (e.g., ethenyloxy) optionally substituted by 1 to 3 halogen atoms;
(16) a $C_{7-13}$ aralkyloxy group (e.g., benzyloxy);
(17) a $C_{6-14}$ aryloxy group (e.g., phenyloxy, naphthyloxy);
(18) a $C_{1-6}$ alkyl-carbonyloxy group (e.g., acetyloxy, tert-butylcarbonyloxy);
(19) a $C_{6-14}$ aryl-carbonyl group (e.g., benzoyl) optionally substituted by 1 to 3 substituents selected from
(a) a halogen atom, and
(b) a $C_{1-6}$ alkyl group optionally substituted by 1 to 3 halogen atoms;
(20) a non-aromatic heterocyclylcarbonyl group (e.g., pyrrolidinylcarbonyl, morpholinylcarbonyl) optionally substituted by 1 to 3 $C_{1-6}$ alkyl groups optionally substituted by 1 to 3 halogen atoms;
(21) a mercapto group;
(22) a $C_{1-6}$ alkylthio group (e.g., methylthio, ethylthio) optionally substituted by 1 to 3 substituents selected from
(a) a halogen atom, and
(b) a $C_{1-6}$ alkoxy-carbonyl group;
(23) a $C_{7-13}$ aralkylthio group (e.g., benzylthio);
(24) a $C_{6-14}$ arylthio group (e.g., phenylthio, naphthylthio);
(25) a cyano group;
(26) a nitro group;
(27) a halogen atom;
(28) a $C_{1-3}$ alkylenedioxy group;
(29) a $C_{1-3}$ alkyleneoxy group (e.g., methyleneoxy, ethyleneoxy);
(30) an aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 substituents selected from a $C_{1-6}$ alkyl group optionally substituted by 1 to 3 halogen atoms;
(31) a $C_{3-10}$ cycloalkoxy group (e.g., cyclopropoxy, cyclopentyloxy) optionally substituted by 1 to 3 substituents selected from
(a) a halogen atom (e.g., a fluorine atom), and
(b) a $C_{1-6}$ alkoxy group (e.g., methoxy)
and the like. When the number of the substituents is not less than 2, the respective substituents may be the same or different.

The $C_{3-10}$ cycloalkyl group, $C_{3-10}$ cycloalkenyl group, $C_{4-10}$ cycloalkadienyl group, $C_{6-14}$ aryl group, $C_{7-13}$ aralkyl group and $C_{8-13}$ arylalkenyl group, which are exemplified as the above-mentioned "hydrocarbon group", optionally have 1 to 3 substituents at substitutable positions.

Examples of the substituent include
(1) the groups exemplified as the substituents for the above-mentioned $C_{1-10}$ alkyl group and the like;
(2) a $C_{1-6}$ alkyl group optionally substituted by 1 to 3 substituents selected from
(a) a halogen atom,
(b) a carboxy group,
(c) a hydroxy group,
(d) a $C_{1-6}$ alkoxy-carbonyl group,
(e) a $C_{1-6}$ alkoxy group, and
(f) an amino group optionally mono- or di-substituted by $C_{1-6}$ alkyl group(s);
(3) a $C_{2-6}$ alkenyl group (e.g., ethenyl, 1-propenyl) optionally substituted by 1 to 3 substituents selected from
(a) a halogen atom,
(b) a carboxy group,
(c) a hydroxy group,
(d) a $C_{1-6}$ alkoxy-carbonyl group,
(e) a $C_{1-6}$ alkoxy group, and
(f) an amino group optionally mono- or di-substituted by $C_{1-6}$ alkyl group(s);
(4) a $C_{7-13}$ aralkyl group (e.g., benzyl) optionally substituted by 1 to 3 substituents selected from
(a) a $C_{1-6}$ alkyl group optionally substituted by 1 to 3 halogen atoms,
(b) a hydroxy group,
(c) a $C_{1-6}$ alkoxy group, and
(d) a halogen atom;
and the like. When the number of the substituents is not less than 2, the respective substituents may be the same or different.

Examples of the "heterocyclic group" of the above-mentioned "optionally substituted heterocyclic group" include an "aromatic heterocyclic group" and a "non-aromatic heterocyclic group".

Examples of the aromatic heterocyclic group include a 4- to 7-membered (preferably 5- or 6-membered) monocyclic aromatic heterocyclic group containing, as a ring-constituting atom besides carbon atoms, 1 to 4 hetero atoms selected from an oxygen atom, a sulfur atom and a nitrogen atom, and a fused aromatic heterocyclic group. Examples of the fused aromatic heterocyclic group include a group derived from a fused ring wherein a ring corresponding to the 4- to 7-membered monocyclic aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are condensed, and the like.

Preferable examples of the aromatic heterocyclic group include
monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like;
fused aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), thienopyridinyl (e.g., thieno[2,3-b]pyridin-3-yl), imidazopyrazinyl (e.g., 1H-imidazo[4,5-b]pyrazin-2-3-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl), pyridopyridinyl (e.g., pyrido[2,3-b]pyridin-3-yl), thienopyridyl (e.g., thieno[2,3-b]pyridin-3-yl) and the like; and the like.

Examples of the non-aromatic heterocyclic group include a 4- to 7-membered (preferably 5- or 6-membered) monocyclic non-aromatic heterocyclic group containing, as a ring-constituting atom besides carbon atoms, 1 to 4 hetero atoms selected from an oxygen atom, a sulfur atom and a nitrogen atom, and a fused aromatic heterocyclic group. Examples of the fused aromatic heterocyclic group include a group derived from a fused ring wherein a ring corresponding to the 4- to 7-membered monocyclic non-aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are condensed, a group wherein the above-mentioned group is partially saturated, and the like.

Preferable examples of the non-aromatic heterocyclic group include
monocyclic non-aromatic heterocyclic groups such as azetidinyl (e.g., 1-azetidinyl, 2-azetidinyl, 3-azetidinyl), pyrrolidinyl (e.g., 1-pyrrolidinyl, 2-pyrrolidinyl), piperidyl (e.g., piperidino, 2-piperidyl, 3-piperidyl, 4-piperidyl), morpholinyl (e.g., morpholino), thiomorpholinyl (e.g., thiomorpholino), piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl) and the like;
fused non-aromatic heterocyclic groups such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl), dihydrochromenyl (e.g., 3,4-dihydro-2H-chromen-2-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl) and the like;
and the like.

The "heterocyclic group" of the "optionally substituted heterocyclic group" optionally has 1 to 3 substituents at substitutable positions. Examples of the substituent include those similar to the substituents that the $C_{3-10}$ cycloalkyl group and the like exemplified as the "hydrocarbon group" of the above-mentioned "optionally substituted hydrocarbon group" optionally has. When the heterocyclic group is a "non-aromatic heterocyclic group", the substituent further includes an oxo group. When the number of the substituents is not less than 2, the respective substituents may be the same or different.

Examples of the above-mentioned "optionally substituted hydroxy group" include a hydroxy group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a heterocyclic group and the like, each of which is optionally substituted.

Examples of the $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those exemplified as the "hydrocarbon group" of the above-mentioned "optionally substituted hydrocarbon group".

Examples of the heterocyclic group include those similar to the "aromatic heterocyclic group" and "non-aromatic heterocyclic group" exemplified as the "heterocyclic group" of the above-mentioned "optionally substituted heterocyclic group".

The above-mentioned $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group, $C_{1-6}$ alkyl-carbonyl group and heterocyclic group optionally have 1 to 3 substituents at substitutable positions. When the number of the substituents is not less than 2, the respective substituents may be the same or different.

Examples of the substituent for the $C_{1-10}$ alkyl group, $C_{2-10}$ alkenyl group and $C_{1-6}$ alkyl-carbonyl group include those similar to the substituent that the $C_{1-10}$ alkyl group and the like exemplified as the "hydrocarbon group" of the above-mentioned "optionally substituted hydrocarbon group" optionally has.

Examples of the substituent for the $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those similar to the substituent that the $C_{3-10}$ cycloalkyl group and the like exemplified as the "hydrocarbon group" of the above-mentioned "optionally substituted hydrocarbon group" optionally has. Examples of the substituent for the heterocyclic group include those similar to the substituent that the "heterocyclic group" of the above-mentioned "optionally substituted heterocyclic group" optionally has.

Examples of the above-mentioned "optionally substituted mercapto group" include a mercapto group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a heterocyclic group and the like, each of which is optionally substituted.

Examples of the substituent include those exemplified as the substituents of the above-mentioned "optionally substituted hydroxy group".

Examples of the above-mentioned "optionally substituted amino group" include an amino group optionally mono- or di-substituted by substituent(s) selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group and a heterocyclic group, each of which is optionally substituted; an acyl group and the like.

Examples of the $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those exemplified as the "hydrocarbon group" of the above-mentioned "optionally substituted hydrocarbon group".

Examples of the heterocyclic group include those similar to the "aromatic heterocyclic group" and "non-aromatic heterocyclic group" exemplified as the "heterocyclic group" of the above-mentioned "optionally substituted heterocyclic group". Of these, a 5- to 7-membered monocyclic aromatic heterocyclic group is preferable.

The $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group and heterocyclic group optionally have 1 to 3 substituents at substitutable positions. When the number of the substituents is not less than 2, the respective substituents may be the same or different.

Examples of the substituent for the $C_{1-10}$ alkyl group and $C_{2-10}$ alkenyl group include those similar to the substituent that the $C_{1-10}$ alkyl group and the like exemplified as the "hydrocarbon group" of the above-mentioned "optionally substituted hydrocarbon group" optionally has.

Examples of the substituent for the $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those similar to the substituent that the $C_{3-10}$ cycloalkyl group and the like exemplified as the "hydrocarbon group" of the above-mentioned "optionally substituted hydrocarbon group" optionally has. Examples of the substituent for the heterocyclic group include those similar to the substituent that the "heterocyclic group" of the above-mentioned "optionally substituted heterocyclic group" optionally has.

Examples of the "acyl group" exemplified as the substituent for the "optionally substituted amino group" include those similar to the "acyl group" below, which is exemplified as the "substituent" for $R^2$.

Examples of the "acyl group" exemplified as the "substituent" for $R^2$ include a group represented by the formula: $-COR^A$, $-CO-OR^A$, $-SO_3R^A$, $-S(O)_2R^A$, $-SOR^A$, $-CO-NR^{A'}R^{B'}$, $-CS-NR^{A'}R^{B'}$ or $-S(O)_2NR^{A'}R^{B'}$ wherein $R^A$ is a hydrogen atom, an optionally substituted hydrocarbon group or an optionally substituted heterocyclic group, $R^{A'}$ and $R^{B'}$ are the same or different and each is a hydrogen atom, an optionally substituted hydrocarbon group or an optionally substituted heterocyclic group, or $R^{A'}$ and $R^{B'}$ form, together with the adjacent nitrogen atom, an optionally substituted nitrogen-containing heterocycle, and the like.

Examples of the "optionally substituted hydrocarbon group" and "optionally substituted heterocyclic group" for $R^A$, $R^{A'}$ or $R^{B'}$ include those similar to the "optionally substituted hydrocarbon group" and "optionally substituted heterocyclic group", which are exemplified as the "substituent" for $R^2$.

Examples of the "nitrogen-containing heterocycle" of the "optionally substituted nitrogen-containing heterocycle" formed by $R^{A'}$ and $R^{B'}$ together with the adjacent nitrogen atom include a 5- to 7-membered nitrogen-containing heterocycle containing, as a ring-constituting atom besides carbon atoms, at least one nitrogen atom and optionally further containing one or two hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine and the like.

The nitrogen-containing heterocycle optionally has 1 to 5 (preferably 1 or 2) substituents at substitutable positions. Examples of the substituent include those similar to the substituent that the "heterocyclic group" of the "optionally substituted heterocyclic group", which is exemplified as the "substituent" for $R^2$, optionally has. When the number of the substituents is not less than 2, the respective substituents may be the same or different.

Preferable examples of the "acyl group" include
(1) a formyl group;
(2) a carboxy group;
(3) a $C_{1-6}$ alkyl-carbonyl group (e.g., acetyl) optionally substituted by 1 to 3 halogen atoms;
(4) a $C_{1-6}$ alkoxy-carbonyl group (e.g., methoxycarbonyl, ethoxycarbonyl, propoxycarbonyl, tert-butoxycarbonyl) optionally substituted by 1 to 3 halogen atoms;
(5) a $C_{3-10}$ cycloalkyl-carbonyl group (e.g., cyclopropylcarbonyl, cyclopentylcarbonyl, cyclohexylcarbonyl);
(6) a $C_{6-14}$ aryl-carbonyl group (e.g., benzoyl, 1-naphthoyl, 2-naphthoyl) optionally substituted by 1 to 3 halogen atoms;
(7) a carbamoyl group optionally mono- or di-substituted by substituent(s) selected from
  (a) a $C_{1-6}$ alkyl group optionally substituted by 1 to 3 substituents selected from a halogen atom, a $C_{1-6}$ alkoxy group, a $C_{1-6}$ alkoxy-carbonyl group and a carboxy group, and
  (b) an amino group optionally mono- or di-substituted by $C_{1-6}$ alkoxy-carbonyl group(s);
(8) a $C_{1-6}$ alkylsulfonyl group (e.g., methylsulfonyl, ethylsulfonyl, isopropylsulfonyl) optionally substituted by 1 to 3 halogen atoms;
(9) a $C_{6-14}$ arylsulfonyl group (e.g., benzenesulfonyl);
(10) a sulfamoyl group;
(11) a thiocarbamoyl group;
(12) an aromatic heterocyclylcarbonyl group (e.g., furylcarbonyl, thienylcarbonyl) optionally substituted by 1 to 3 substituents selected from a $C_{1-6}$ alkyl group optionally substituted by 1 to 3 halogen atoms;
(13) a non-aromatic heterocyclylcarbonyl group (e.g., tetrahydrofurylcarbonyl, pyrrolidinylcarbonyl) optionally substituted by 1 to 3 substituents selected from a $C_{1-6}$ alkyl group optionally substituted by 1 to 3 halogen atoms; and the like.

$R^2$ is preferably an optionally substituted $C_{1-6}$ alkyl group, an optionally substituted $C_{1-6}$ alkoxy group, an optionally substituted $C_{3-10}$ cycloalkyl group, an optionally substituted $C_{6-14}$ aryl group, an optionally substituted amino group, an optionally substituted aromatic heterocyclic group, an optionally substituted non-aromatic heterocyclic group or the like.

$R^2$ is more preferably
(a) a $C_{1-6}$ alkyl group (e.g., methyl, ethyl, propyl, butyl, isobutyl, isopentyl) optionally substituted by 1 to 3 substituents selected from
  (i) an amino group,
  (ii) a carboxy group,
  (iii) a $C_{1-6}$ alkoxy-carbonyl group (e.g., methoxycarbonyl, ethoxycarbonyl),
  (iv) a $C_{6-14}$ aryl group (e.g., phenyl), and
  (v) a $C_{1-6}$ alkoxy group (e.g., methoxy);

(b) a $C_{1-6}$ alkoxy group (e.g., methoxy, tert-butoxy);
(c) a $C_{3-10}$ cycloalkyl group (e.g., cyclopropyl, cyclopentyl);
(d) a $C_{6-14}$ aryl group (e.g., phenyl);
(e) an amino group optionally mono- or di-substituted by substituent(s) selected from
   (i) a $C_{1-6}$ alkyl group (e.g., methyl, ethyl, propyl, isopropyl) optionally substituted by 1 to 3 $C_{6-14}$ aryl groups (e.g., phenyl),
   (ii) a $C_{6-14}$ aryl group (e.g., phenyl),
   (iii) a $C_{3-10}$ cycloalkyl group (e.g., cyclopentyl, cyclohexyl),
   (iv) a $C_{1-6}$ alkylsulfonyl group (e.g., methylsulfonyl), and
   (v) an aromatic heterocyclic group (e.g., pyridyl) optionally substituted by 1 to 3 $C_{1-6}$ alkyl groups (e.g., methyl);
(f) an aromatic heterocyclic group (e.g., furyl, pyrazolyl, pyridyl, isoxazolyl, thiazolyl) optionally substituted by 1 to 3 substituents selected from a $C_{1-6}$ alkyl group optionally substituted by 1 to 3 halogen atoms (e.g., a fluorine atom);
(g) a non-aromatic heterocyclic group (e.g., tetrahydropyranyl);
or the like.

$R^2$ is further more preferably
(a) a $C_{1-6}$ alkyl group (e.g., methyl, ethyl, propyl, butyl, isobutyl, isopentyl) optionally substituted by 1 to 3 substituents selected from
   (i) an amino group,
   (ii) a carboxy group,
   (iii) a $C_{1-6}$ alkoxy-carbonyl group (e.g., methoxycarbonyl, ethoxycarbonyl),
   (iv) a $C_{6-14}$ aryl group (e.g., phenyl), and
   (v) a $C_{1-6}$ alkoxy group (e.g., methoxy);
(b) a $C_{1-6}$ alkoxy group (e.g., methoxy, tert-butoxy);
(c) an amino group optionally mono- or di-substituted by substituent(s) selected from
   (i) a $C_{1-6}$ alkyl group (e.g., methyl, ethyl, propyl, isopropyl) optionally substituted by 1 to 3 $C_{6-14}$ aryl groups (e.g., phenyl),
   (ii) a $C_{6-14}$ aryl group (e.g., phenyl),
   (iii) a $C_{3-10}$ cycloalkyl group (e.g., cyclopentyl, cyclohexyl),
   (iv) a $C_{1-6}$ alkylsulfonyl group (e.g., methylsulfonyl), and
   (v) an aromatic heterocyclic group (e.g., pyridyl) optionally substituted by 1 to 3 $C_{1-6}$ alkyl groups (e.g., methyl);
or the like.

$R^2$ is particularly preferably
(a) a $C_{1-6}$ alkyl group (e.g., methyl, ethyl, propyl, butyl, isobutyl, isopentyl);
(b) a $C_{1-6}$ alkoxy group (e.g., methoxy, tert-butoxy);
(c) an amino group optionally mono- or di-substituted by $C_{1-6}$ alkyl group(s) (e.g., methyl, ethyl, propyl, isopropyl);
or the like.

The "group represented by the formula: —COR$^2$" for $R^1$ is preferably a group represented by the formula: —COR$^2$ wherein $R^2$ is an optionally substituted $C_{1-6}$ alkyl group, an optionally substituted $C_{1-6}$ alkoxy group, an optionally substituted $C_{3-10}$ cycloalkyl group, an optionally substituted $C_{6-14}$ aryl group, an optionally substituted amino group, an optionally substituted aromatic heterocyclic group, an optionally substituted non-aromatic heterocyclic group or the like.

The "group represented by the formula: —COR$^2$" for $R^1$ is more preferably a group represented by the formula: —COR$^2$ wherein $R^2$ is
(a) a $C_{1-6}$ alkyl group (e.g., methyl, ethyl, propyl, butyl, isobutyl, isopentyl) optionally substituted by 1 to 3 substituents selected from
   (i) an amino group,
   (ii) a carboxy group,
   (iii) a $C_{1-6}$ alkoxy-carbonyl group (e.g., methoxycarbonyl, ethoxycarbonyl),
   (iv) a $C_{6-14}$ aryl group (e.g., phenyl), and
   (v) a $C_{1-6}$ alkoxy group (e.g., methoxy);
(b) a $C_{1-6}$ alkoxy group (e.g., methoxy, tert-butoxy);
(c) a $C_{3-10}$ cycloalkyl group (e.g., cyclopropyl, cyclopentyl);
(d) a $C_{6-14}$ aryl group (e.g., phenyl);
(e) an amino group optionally mono- or di-substituted by substituent(s) selected from
   (i) a $C_{1-6}$ alkyl group (e.g., methyl, ethyl, propyl, isopropyl) optionally substituted by 1 to 3 $C_{6-14}$ aryl groups (e.g., phenyl),
   (ii) a $C_{6-14}$ aryl group (e.g., phenyl),
   (iii) a $C_{3-10}$ cycloalkyl group (e.g., cyclopentyl, cyclohexyl),
   (iv) a $C_{1-6}$ alkylsulfonyl group (e.g., methylsulfonyl), and
   (v) an aromatic heterocyclic group (e.g., pyridyl) optionally substituted by 1 to 3 $C_{1-6}$ alkyl groups (e.g., methyl);
(f) an aromatic heterocyclic group (e.g., furyl, pyrazolyl, pyridyl, isoxazolyl, thiazolyl) optionally substituted by 1 to 3 substituents selected from a $C_{1-6}$ alkyl group optionally substituted by 1 to 3 halogen atoms (e.g., a fluorine atom);
(g) a non-aromatic heterocyclic group (e.g., tetrahydropyranyl);
or the like.

The "group represented by the formula: —COR$^2$" for $R^1$ is further more preferably a group represented by the formula: —COR$^2$ wherein $R^2$ is
(a) a $C_{1-6}$ alkyl group (e.g., methyl, ethyl, propyl, butyl, isobutyl, isopentyl) optionally substituted by 1 to 3 substituents selected from
   (i) an amino group,
   (ii) a carboxy group,
   (iii) a $C_{1-6}$ alkoxy-carbonyl group (e.g., methoxycarbonyl, ethoxycarbonyl),
   (iv) a $C_{6-14}$ aryl group (e.g., phenyl), and
   (v) a $C_{1-6}$ alkoxy group (e.g., methoxy);
(b) a $C_{1-6}$ alkoxy group (e.g., methoxy, tert-butoxy);
(c) an amino group optionally mono- or di-substituted by substituent(s) selected from
   (i) a $C_{1-6}$ alkyl group (e.g., methyl, ethyl, propyl, isopropyl) optionally substituted by 1 to 3 $C_{6-14}$ aryl groups (e.g., phenyl),
   (ii) a $C_{6-14}$ aryl group (e.g., phenyl),
   (iii) a $C_{3-10}$ cycloalkyl group (e.g., cyclopentyl, cyclohexyl),
   (iv) a $C_{1-6}$ alkylsulfonyl group (e.g., methylsulfonyl), and
   (v) an aromatic heterocyclic group (e.g., pyridyl) optionally substituted by 1 to 3 $C_{1-6}$ alkyl groups (e.g., methyl);
or the like.

The "group represented by the formula: —COR$^2$" for $R^1$ is particularly preferably a group represented by the formula: —COR$^2$ wherein $R^2$ is
(a) a $C_{1-6}$ alkyl group (e.g., methyl, ethyl, propyl, butyl, isobutyl, isopentyl);
(b) a $C_{1-6}$ alkoxy group (e.g., methoxy, tert-butoxy);
(c) an amino group optionally mono- or di-substituted by $C_{1-6}$ alkyl group(s) (e.g., methyl, ethyl, propyl, isopropyl); or the like.

Examples of the "5- or 6-membered aromatic heterocyclic group" of the "optionally substituted 5- or 6-membered aromatic heterocyclic group" for $R^1$ include pyrrolyl, pyrazolyl, imidazolyl, triazolyl (1,2,3-triazolyl, 1,2,4-triazolyl, 1,3,4- triazolyl), tetrazolyl, oxazolyl, isoxazolyl, thiazolyl, isothiazolyl, oxadiazolyl, thiadiazolyl, furyl, thienyl, pyridyl, pyridazinyl, pyrimidinyl, pyrazinyl, triazinyl and the like.

The "5- or 6-membered aromatic heterocyclic group" is preferably a 5-membered aromatic heterocyclic group, more preferably pyrazolyl, oxazolyl, isoxazolyl, thiazolyl, isothiazolyl, thiadiazolyl or the like, particularly preferably isoxazolyl.

The "5- or 6-membered aromatic heterocyclic group" of the "optionally substituted 5- or 6-membered aromatic heterocyclic group" for $R^1$ optionally has 1 to 3 substituents at substitutable positions. Examples of the substituent include those similar to the substituents that the $C_{3-10}$ cycloalkyl group and the like exemplified as the "hydrocarbon group" of the "optionally substituted hydrocarbon group", which is exemplified as the "substituent" for $R^2$, optionally has.

The "optionally substituted 5- or 6-membered aromatic heterocyclic group" for $R^1$ is preferably a 5-membered aromatic heterocyclic group (e.g., pyrazolyl, oxazolyl, isoxazolyl, thiazolyl, isothiazolyl, thiadiazolyl, preferably isoxazolyl) optionally substituted by 1 to 3 substituents selected from
(1) a $C_{1-6}$ alkyl-carbonyl group optionally substituted by 1 to 3 halogen atoms;
(2) a $C_{1-6}$ alkoxy-carbonyl group optionally substituted by 1 to 3 substituents selected from
  (a) a halogen atom,
  (b) a $C_{1-6}$ alkoxy group, and
  (c) a $C_{6-14}$ aryl group (e.g., phenyl);
(3) a carbamoyl group optionally mono- or di-substituted by $C_{1-6}$ alkyl group(s) optionally substituted by 1 to 3 halogen atoms;
(4) a carboxy group;
(5) a hydroxy group;
(6) a halogen atom; and
(7) a $C_{1-6}$ alkyl group optionally substituted by 1 to 3 substituents selected from
  (a) a halogen atom,
  (b) a carboxy group,
  (c) a hydroxy group,
  (d) a $C_{1-6}$ alkoxy-carbonyl group, and
  (e) a $C_{1-6}$ alkoxy group.

The "optionally substituted 5- or 6-membered aromatic heterocyclic group" for $R^1$ is more preferably a 5-membered aromatic heterocyclic group (e.g., pyrazolyl, oxazolyl, isoxazolyl, thiazolyl, isothiazolyl, thiadiazolyl, preferably isoxazolyl) optionally substituted by 1 to 3 substituents selected from (i) a halogen atom and (ii) a $C_{1-6}$ alkyl group.

The "optionally substituted 5- or 6-membered aromatic heterocyclic group" for $R^1$ is further more preferably a 5-membered aromatic heterocyclic group (e.g., pyrazolyl, oxazolyl, isoxazolyl, thiazolyl, isothiazolyl, thiadiazolyl, preferably isoxazolyl) optionally substituted by 1 to 3 substituents selected from a $C_{1-6}$ alkyl group.

The "phenyl group" of the "optionally substituted phenyl group" for $R^1$ optionally has 1 to 3 substituents at substitutable positions. Examples of the substituent include those similar to the substituents that the $C_{3-10}$ cycloalkyl group and the like exemplified as the "hydrocarbon group" of the "optionally substituted hydrocarbon group", which is exemplified as the "substituent" for $R^2$, optionally has.

The "optionally substituted phenyl group" for $R^1$ is preferably a phenyl group optionally substituted by 1 to 3 substituents selected from
(1) a $C_{1-6}$ alkyl-carbonyl group optionally substituted by 1 to 3 halogen atoms;
(2) a $C_{1-6}$ alkoxy-carbonyl group optionally substituted by 1 to 3 substituents selected from
  (a) a halogen atom,
  (b) a $C_{1-6}$ alkoxy group, and
  (c) a $C_{6-14}$ aryl group (e.g., phenyl);
(3) a carbamoyl group optionally mono- or di-substituted by $C_{1-6}$ alkyl group(s) optionally substituted by 1 to 3 halogen atoms;
(4) a carboxy group;
(5) a hydroxy group;
(6) a halogen atom; and
(7) a $C_{1-6}$ alkyl group optionally substituted by 1 to 3 substituents selected from
  (a) a halogen atom,
  (b) a carboxy group,
  (c) a hydroxy group,
  (d) a $C_{1-6}$ alkoxy-carbonyl group, and
  (e) a $C_{1-6}$ alkoxy group.

The "optionally substituted phenyl group" for $R^1$ is more preferably a phenyl group optionally substituted by 1 to 3 substituents selected from (i) a halogen atom and (ii) a $C_{1-6}$ alkyl group.

$R^1$ is preferably
(1) a group represented by the formula: —$COR^2$ wherein $R^2$ is an optionally substituted $C_{1-6}$ alkyl group, an optionally substituted $C_{1-6}$ alkoxy group, an optionally substituted $C_{3-10}$ cycloalkyl group, an optionally substituted $C_{6-14}$ aryl group, an optionally substituted amino group, an optionally substituted aromatic heterocyclic group, an optionally substituted non-aromatic heterocyclic group or the like;
(2) an optionally substituted 5- or 6-membered aromatic heterocyclic group; or
(3) an optionally substituted phenyl group.

$R^1$ is more preferably
(1) a group represented by the formula: —$COR^2$
wherein $R^2$ is
  (a) a $C_{1-6}$ alkyl group (e.g., methyl, ethyl, propyl, butyl, isobutyl, isopentyl) optionally substituted by 1 to 3 substituents selected from
    (i) an amino group,
    (ii) a carboxy group,
    (iii) a $C_{1-6}$ alkoxy-carbonyl group (e.g., methoxycarbonyl, ethoxycarbonyl),
    (iv) a $C_{6-14}$ aryl group (e.g., phenyl), and
    (v) a $C_{1-6}$ alkoxy group (e.g., methoxy);
  (b) a $C_{1-6}$ alkoxy group (e.g., methoxy, tert-butoxy);
  (c) a $C_{3-10}$ cycloalkyl group (e.g., cyclopropyl, cyclopentyl);
  (d) a $C_{6-14}$ aryl group (e.g., phenyl);
  (e) an amino group optionally mono- or di-substituted by substituent(s) selected from
    (i) a $C_{1-6}$ alkyl group (e.g., methyl, ethyl, propyl, isopropyl) optionally substituted by 1 to 3 $C_{6-14}$ aryl groups (e.g., phenyl),
    (ii) a $C_{6-14}$ aryl group (e.g., phenyl),
    (iii) a $C_{3-10}$ cycloalkyl group (e.g., cyclopentyl, cyclohexyl),
    (iv) a $C_{1-6}$ alkylsulfonyl group (e.g., methylsulfonyl), and
    (v) an aromatic heterocyclic group (e.g., pyridyl) optionally substituted by 1 to 3 $C_{1-6}$ alkyl groups (e.g., methyl);
  (f) an aromatic heterocyclic group (e.g., furyl, pyrazolyl, pyridyl, isoxazolyl, thiazolyl) optionally substituted by 1 to 3 substituents selected from a $C_{1-6}$ alkyl group optionally substituted by 1 to 3 halogen atoms (e.g., a fluorine atom);

(g) a non-aromatic heterocyclic group (e.g., tetrahydropyranyl);
or the like.
(2) a 5-membered aromatic heterocyclic group (e.g., pyrazolyl, oxazolyl, isoxazolyl, thiazolyl, isothiazolyl, thiadiazolyl, preferably isoxazolyl) optionally substituted by 1 to 3 substituents selected from
(i) a $C_{1-6}$ alkyl-carbonyl group optionally substituted by 1 to 3 halogen atoms;
(ii) a $C_{1-6}$ alkoxy-carbonyl group optionally substituted by 1 to 3 substituents selected from
(a) a halogen atom,
(b) a $C_{1-6}$ alkoxy group, and
(c) a $C_{6-14}$ aryl group (e.g., phenyl);
(iii) a carbamoyl group optionally mono- or di-substituted by $C_{1-6}$ alkyl group(s) optionally substituted by 1 to 3 halogen atoms;
(iv) a carboxy group;
(v) a hydroxy group;
(vi) a halogen atom; and
(vii) a $C_{1-6}$ alkyl group optionally substituted by 1 to 3 substituents selected from
(a) a halogen atom,
(b) a carboxy group,
(c) a hydroxy group,
(d) a $C_{1-6}$ alkoxy-carbonyl group, and
(e) a $C_{1-6}$ alkoxy group; or
(3) a phenyl group optionally substituted by 1 to 3 substituents selected from
(i) a $C_{1-6}$ alkyl-carbonyl group optionally substituted by 1 to 3 halogen atoms;
(ii) a $C_{1-6}$ alkoxy-carbonyl group optionally substituted by 1 to 3 substituents selected from
(a) a halogen atom,
(b) a $C_{1-6}$ alkoxy group, and
(c) a $C_{6-14}$ aryl group (e.g., phenyl);
(iii) a carbamoyl group optionally mono- or di-substituted by $C_{1-6}$ alkyl group(s) optionally substituted by 1 to 3 halogen atoms;
(iv) a carboxy group;
(v) a hydroxy group;
(vi) a halogen atom; and
(vii) a $C_{1-6}$ alkyl group optionally substituted by 1 to 3 substituents selected from
(a) a halogen atom,
(b) a carboxy group,
(c) a hydroxy group,
(d) a $C_{1-6}$ alkoxy-carbonyl group, and
(e) a $C_{1-6}$ alkoxy group.
$R^1$ is further more preferably
(1) a group represented by the formula: —$COR^2$
wherein $R^2$ is
(a) a $C_{1-6}$ alkyl group (e.g., methyl, ethyl, propyl, butyl, isobutyl, isopentyl) optionally substituted by 1 to 3 substituents selected from
(i) an amino group,
(ii) a carboxy group,
(iii) a $C_{1-6}$ alkoxy-carbonyl group (e.g., methoxycarbonyl, ethoxycarbonyl),
(iv) a $C_{6-14}$ aryl group (e.g., phenyl), and
(v) a $C_{1-6}$ alkoxy group (e.g., methoxy);
(b) a $C_{1-6}$ alkoxy group (e.g., methoxy, tert-butoxy);
(c) an amino group optionally mono- or di-substituted by substituent(s) selected from
(i) a $C_{1-6}$ alkyl group (e.g., methyl, ethyl, propyl, isopropyl) optionally substituted by 1 to 3 $C_{6-14}$ aryl groups (e.g., phenyl),
(ii) a $C_{6-14}$ aryl group (e.g., phenyl),
(iii) a $C_{3-10}$ cycloalkyl group (e.g., cyclopentyl, cyclohexyl),
(iv) a $C_{1-6}$ alkylsulfonyl group (e.g., methylsulfonyl), and
(v) an aromatic heterocyclic group (e.g., pyridyl) optionally substituted by 1 to 3 $C_{1-6}$ alkyl groups (e.g., methyl);
or the like;
(2) a 5-membered aromatic heterocyclic group (e.g., pyrazolyl, oxazolyl, isoxazolyl, thiazolyl, isothiazolyl, thiadiazolyl, preferably isoxazolyl) optionally substituted by 1 to 3 substituents selected from (i) a halogen atom and (ii) a alkyl group; or
(3) a phenyl group optionally substituted by 1 to 3 substituents selected from (i) a halogen atom and (ii) a $C_{1-6}$ alkyl group.
$R^1$ is still more preferably
(1) a group represented by the formula: —$COR^2$
wherein $R^2$ is
(a) a $C_{1-6}$ alkyl group (e.g., methyl, ethyl, propyl, butyl, isobutyl, isopentyl);
(b) a $C_{1-6}$ alkoxy group (e.g., methoxy, tert-butoxy);
(c) an amino group optionally mono- or di-substituted by $C_{1-6}$ alkyl group(s) (e.g., methyl, ethyl, propyl, isopropyl);
or the like; or
(2) a 5-membered aromatic heterocyclic group (e.g., pyrazolyl, oxazolyl, isoxazolyl, thiazolyl, isothiazolyl, thiadiazolyl, preferably isoxazolyl) optionally substituted by 1 to 3 substituents selected from a halogen atom and a $C_{1-6}$ alkyl group.
$R^1$ is particularly preferably
(1) a group represented by the formula: —$COR^2$
wherein $R^2$ is
(a) a $C_{1-6}$ alkyl group (e.g., methyl, ethyl, propyl, butyl, isobutyl, isopentyl);
(b) a $C_{1-6}$ alkoxy group (e.g., methoxy, tert-butoxy);
(c) an amino group optionally mono- or di-substituted by $C_{1-6}$ alkyl group(s) (e.g., methyl, ethyl, propyl, isopropyl); or the like; or
(2) a 5-membered aromatic heterocyclic group (e.g., pyrazolyl, oxazolyl, isoxazolyl, thiazolyl, isothiazolyl, thiadiazolyl, preferably isoxazolyl) optionally substituted by 1 to 3 substituents selected from a $C_{1-6}$ alkyl group.
Ring P is a 5-membered aromatic heterocycle, and ring Q is an optionally further substituted 6-membered ring, and ring P and ring Q are condensed to form an optionally further substituted bicyclic aromatic heterocycle.
Examples of the "5-membered aromatic heterocycle" for ring P include pyrrole, pyrazole, imidazole, triazole (1,2,3-triazole, 1,2,4-triazole, 1,3,4-triazole), tetrazole, oxazole, isoxazole, thiazole, isothiazole, oxadiazole, thiadiazole, furan, thiophene and the like. Of these, oxazole, thiazole, furan, pyrazole and 1,2,3-triazole are preferable, and oxazole and thiazole are particularly preferable.
Examples of the "6-membered ring" of the "optionally further substituted 6-membered ring" for ring Q include benzene, pyridine, pyridazine, pyrimidine, pyrazine, triazine, cyclohexa-1,3-diene, dihydropyridine and the like. Of these, benzene, pyridine and cyclohexa-1,3-diene are preferable.
The "6-membered ring" of the "optionally further substituted 6-membered ring" for ring Q optionally has, besides the group —O—$R^6$, 1 to 3 substituents at substitutable positions. Examples of the substituent include those similar to the substituents that the $C_{3-10}$ cycloalkyl group and the like exemplified as the "hydrocarbon group" of the "optionally substituted hydrocarbon group", which is exemplified as the "substituent" for R², optionally has.

Preferable examples of the additional substituent for the "6-membered ring" of the "optionally further substituted 6-membered ring" for ring Q include (1) a halogen atom (e.g., a fluorine atom, a chlorine atom), (2) a $C_{1-6}$ alkyl group (e.g., methyl)

and the like. Of these, a halogen atom (e.g., a fluorine atom, a chlorine atom) is more preferable.

Ring Q is preferably benzene, pyridine or cyclohexa-1,3-diene, each of which is optionally substituted by 1 to 3 substituents selected from (1) a halogen atom (e.g., a fluorine atom, a chlorine atom), (2) a $C_{1-6}$ alkyl group (e.g., methyl)

and the like.

Ring Q is more preferably benzene, pyridine or cyclohexa-1,3-diene, each of which is optionally substituted by 1 to 3 halogen atoms (e.g., a fluorine atom, a chlorine atom).

Specific examples of the "bicyclic aromatic heterocycle" of the "optionally further substituted bicyclic aromatic heterocycle" formed by the condensation of ring P and ring Q include

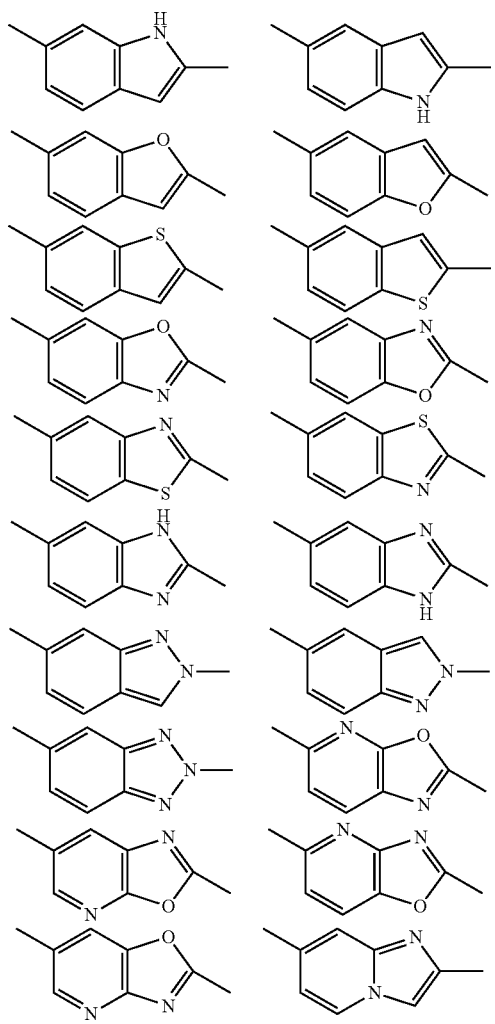

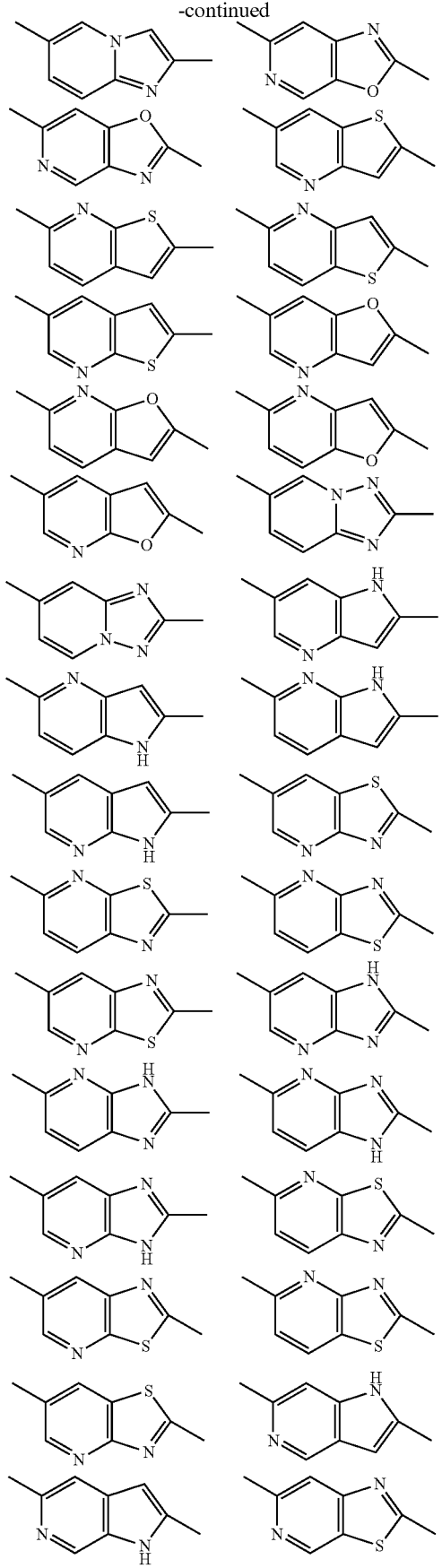

-continued

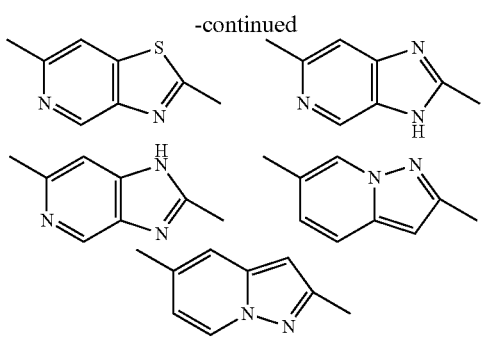

and the like.

The "bicyclic aromatic heterocycle" of the "optionally further substituted bicyclic aromatic heterocycle" formed by the condensation of ring P and ring Q optionally has, besides the group —O—$R^6$, 1 to 3 substituents at substitutable positions on the ring Q. Examples of the substituent include those similar to the substituents that the $C_{3-10}$ cycloalkyl group and the like exemplified as the "hydrocarbon group" of the "optionally substituted hydrocarbon group", which is exemplified as the "substituent" for $R^2$, optionally has.

Preferable examples of the additional substituent for the "bicyclic aromatic heterocycle" of the "optionally further substituted bicyclic aromatic heterocycle" formed by the condensation of ring P and ring Q include (1) a halogen atom (e.g., a fluorine atom, a chlorine atom), (2) a $C_{1-6}$ alkyl group (e.g., methyl)

and the like. Of these, a halogen atom (e.g., a fluorine atom, a chlorine atom) is more preferable.

The "optionally further substituted bicyclic aromatic heterocycle" formed by the condensation of ring P and ring Q is preferably

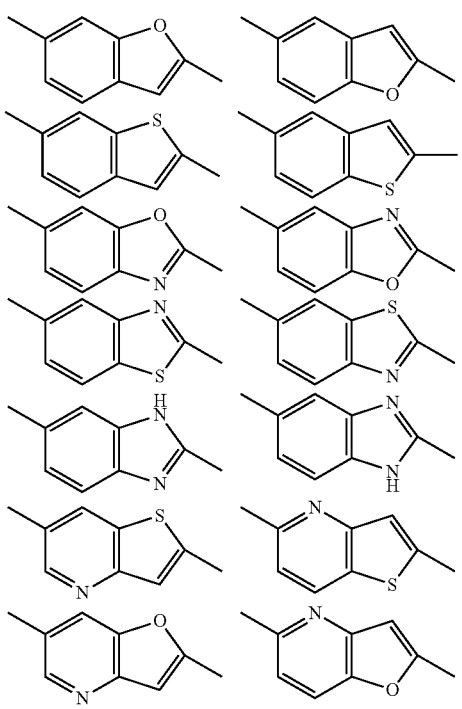

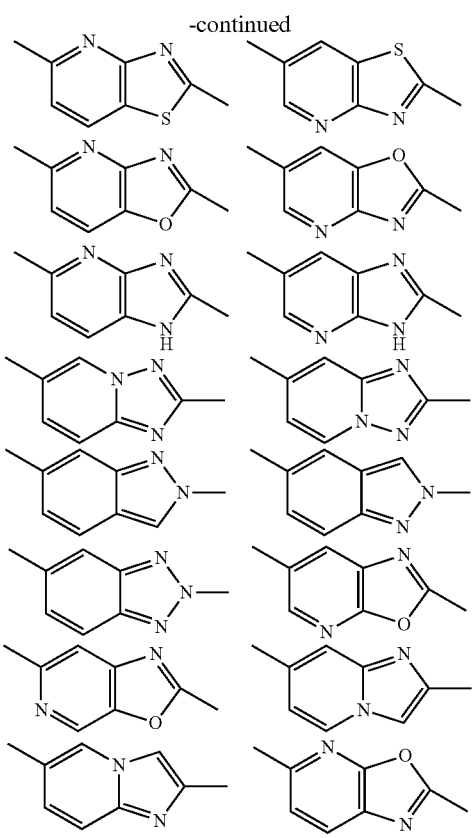

or the like, in each of which ring Q is optionally substituted by 1 to 3 substituents selected from (1) a halogen atom (e.g., a fluorine atom, a chlorine atom), (2) a $C_{1-6}$ alkyl group (e.g., methyl)

and the like.

The "optionally further substituted bicyclic aromatic heterocycle" formed by the condensation of ring P and ring Q is more preferably

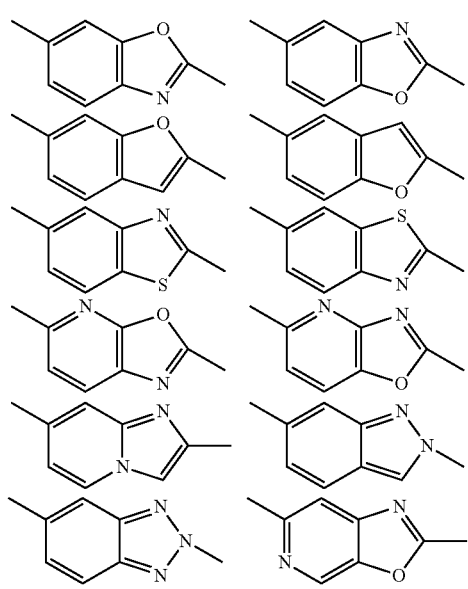

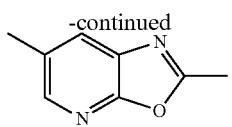

or the like, in each of which ring Q is optionally substituted by 1 to 3 halogen atoms.

Alternatively, the "optionally further substituted bicyclic aromatic heterocycle" formed by the condensation of ring P and ring Q is more preferably

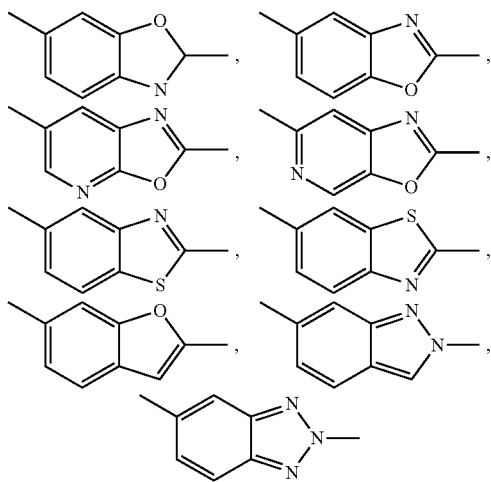

or the like, in each of which the ring Q is optionally substituted by 1 to 3 halogen atoms.

$R^3$ is a $C_{1-6}$ alkyl group optionally substituted by halogen atom(s), or an optionally substituted $C_{3-6}$ cycloalkyl group.

The "$C_{1-6}$ alkyl group" of the "$C_{1-6}$ alkyl group optionally substituted by halogen atom(s)" for $R^3$ optionally has preferably 1 to 7, more preferably 1 to 3 halogen atoms, at substitutable positions.

Examples of the "$C_{3-6}$ cycloalkyl group" of the "optionally substituted $C_{3-6}$ cycloalkyl group" for $R^3$ include cyclopropyl, cyclobutyl, cyclopentyl and cyclohexyl.

The "$C_{3-6}$ cycloalkyl group" of the "optionally substituted $C_{3-6}$ cycloalkyl group" for $R^3$ optionally has 1 to 5 substituents at substitutable positions. Examples of the substituent include those similar to the substituents that the $C_{3-10}$ cycloalkyl group and the like exemplified as the "hydrocarbon group" of the "optionally substituted hydrocarbon group", which is exemplified as the "substituent" for $R^2$, optionally has.

$R^3$ is preferably a $C_{1-6}$ alkyl group optionally substituted by 1 to 7 (preferably 1 to 3) halogen atoms (e.g., a fluorine atom), or a $C_{3-6}$ cycloalkyl group optionally substituted by 1 to 5 halogen atoms or 1 to 5 $C_{1-3}$ alkyl groups.

$R^3$ is more preferably a $C_{1-6}$ alkyl group optionally substituted by 1 to 7 (preferably 1 to 3) halogen atoms (e.g., a fluorine atom), or a $C_{3-6}$ cycloalkyl group, particularly preferably a $C_{1-6}$ alkyl group optionally substituted by 1 to 3 halogen atoms (e.g., a fluorine atom).

$R^4$ is a hydrogen atom or a substituent.

Examples of the "substituent" for $R^4$ include those similar to the "substituent" for $R^2$.

$R^4$ is preferably a hydrogen atom.

X is O, CO, $CR^{5a}R^{5b}$ wherein $R^{5a}$ and $R^{5b}$ are each independently a hydrogen atom, a halogen atom or an optionally substituted $C_{1-6}$ alkyl group, $NR^{5c}$ wherein $R^{5c}$ is a hydrogen atom or an optionally substituted $C_{1-6}$ alkyl group, S, SO or $S(O)_2$.

The "$C_{1-6}$ alkyl group" of the "optionally substituted $C_{1-6}$ alkyl group" for $R^{5a}$, $R^{5b}$ or $R^{5c}$ optionally has 1 to 3 substituents at substitutable positions. Examples of the substituent include those similar to the substituents that the $C_{1-10}$ alkyl group and the like exemplified as the "hydrocarbon group" of the "optionally substituted hydrocarbon group", which is exemplified as the "substituent" for $R^2$, optionally has.

X is preferably O or $CR^{5a}R^{5b}$ wherein $R^{5a}$ and $R^{5b}$ are as defined above, more preferably O or $CH_2$.

$R^6$ is an optionally substituted $C_{1-6}$ alkyl group or an optionally substituted $C_{3-6}$ cycloalkyl group.

The "$C_{1-6}$ alkyl group" of the "optionally substituted $C_{1-6}$ alkyl group" for $R^6$ optionally has 1 to 3 substituents at substitutable positions. Examples of the substituent include those similar to the substituents that the $C_{1-10}$ alkyl group and the like exemplified as the "hydrocarbon group" of the "optionally substituted hydrocarbon group", which is exemplified as the "substituent" for $R^2$, optionally has.

Examples of the "optionally substituted $C_{3-6}$ cycloalkyl group" for $R^6$ include those similar to the "optionally substituted $C_{3-6}$ cycloalkyl group" for $R^3$.

$R^6$ is preferably
(1) a $C_{1-6}$ alkyl group (e.g., methyl, ethyl, propyl, isopropyl, isobutyl) optionally substituted by 1 to 3 substituents selected from a halogen atom (e.g., a fluorine atom) and a $C_{3-6}$ cycloalkyl group (e.g., cyclopropyl, cyclobutyl);
(2) a $C_{3-6}$ cycloalkyl group (e.g., cyclopropyl, cyclobutyl); or the like.

$R^6$ is more preferably a $C_{1-6}$ alkyl group (e.g., methyl, ethyl, propyl, isopropyl, isobutyl) optionally substituted by 1 to 3 substituents selected from a halogen atom (e.g., a fluorine atom) and a $C_{3-6}$ cycloalkyl group (e.g., cyclopropyl, cyclobutyl).

Ring A is an optionally further substituted 4- to 7-membered non-aromatic ring (the ring is optionally crosslinked).

Examples of the "4- to 7-membered non-aromatic ring (the ring is optionally crosslinked)" of the "optionally further substituted 4- to 7-membered non-aromatic ring (the ring is optionally crosslinked)" for ring A include a $C_{4-7}$ cycloalkane, a $C_{4-7}$ cycloalkene, a $C_{4-7}$ cycloalkadiene and a 4- to 7-membered non-aromatic heterocycle.

Examples of the $C_{4-7}$ cycloalkane include cyclobutane, cyclopentane, cyclohexane and cycloheptane. Of these, a $C_{4-6}$ cycloalkane is preferable.

Examples of the $C_{4-7}$ cycloalkene include cyclobutene, cyclopentene, cyclohexene and cycloheptene. Of these, a $C_{4-6}$ cycloalkene is preferable.

Examples of the $C_{4-7}$ cycloalkadiene include 2,4-cyclopentadiene, 2,4-cyclohexadiene, 2,5-cyclohexadiene and the like. Of these, a $C_{4-6}$ cycloalkadiene is preferable.

Examples of the 4- to 7-membered non-aromatic heterocycle include azetidine, pyrrolidine, piperidine, morpholine, thiomorpholine, piperazine, hexamethylenimine, oxazolidine, thiazolidine, imidazolidine, oxazoline, thiazoline, imidazoline, dioxole, dioxolane, dihydrooxadiazole, pyran, tetrahydropyran, thiopyran, tetrahydrothiopyran, tetrahydrofuran, pyrazolidine, pyrazoline, tetrahydropyrimidine, dihydrotriazole, tetrahydrotriazole and the like. Of these, a 4- to 7-membered (preferably a 4- to 6-membered) nitrogen-containing non-aromatic heterocycle (preferably, azetidine, pyrrolidine, piperidine, piperazine) is preferable.

The "4- to 7-membered non-aromatic ring" may be crosslinked. Examples of the crosslinked ring include 8-azabicyclo[3.2.1]octane and the like.

The "4- to 7-membered non-aromatic ring (the ring is optionally crosslinked)" of the "optionally further substituted 4- to 7-membered non-aromatic ring (the ring is optionally crosslinked)" optionally has, besides the group —XCH($R^4$)CH($R^3$)—NH—$R^1$ and ring P, 1 to 3 substituents at substitutable positions. Examples of the substituent include those similar to the substituents that the "heterocyclic group" of the "optionally substituted heterocyclic group", which is exemplified as the "substituent" for $R^2$, optionally has.

Ring A is preferably an optionally further substituted 4- to 7-membered non-aromatic heterocycle (the heterocycle is optionally crosslinked), more preferably a 4- to 7-membered (preferably 4- to 6-membered) nitrogen-containing non-aromatic heterocycle (the heterocycle is optionally crosslinked), cyclohexane or the like, further more preferably azetidine, pyrrolidine, piperidine, piperazine, 8-azabicyclo[3.2.1]octane, cyclohexane or the like, particularly preferably piperidine.

Preferable examples of compound (I) include the following compounds.

[Compound A]
Compound (I) wherein
$R^1$ is
(1) a group represented by the formula: —$COR^2$ wherein $R^2$ is an optionally substituted $C_{1-6}$ alkyl group, an optionally substituted $C_{1-6}$ alkoxy group, an optionally substituted $C_{3-10}$ cycloalkyl group, an optionally substituted $C_{6-14}$ aryl group, an optionally substituted amino group, an optionally substituted aromatic heterocyclic group or an optionally substituted non-aromatic heterocyclic group;
(2) an optionally substituted 5- or 6-membered aromatic heterocyclic group; or
(3) an optionally substituted phenyl group;
$R^3$ is a $C_{1-6}$ alkyl group optionally substituted by halogen atom(s), or an optionally substituted $C_{3-6}$ cycloalkyl group;
$R^4$ is a hydrogen atom;
X is O, CO, $CR^{5a}R^{5b}$ wherein $R^{5a}$ and $R^{5b}$ is as defined above, $NR^{5C}$ wherein $R^{5c}$ is as defined above, S, SO or S(O)$_2$;
ring A is an optionally further substituted 4- to 7-membered non-aromatic ring (the ring is optionally crosslinked);
ring P is a 5-membered aromatic heterocycle, ring Q is an optionally further substituted 6-membered ring, and ring P and ring Q are condensed to form an optionally further substituted bicyclic aromatic heterocycle; and
$R^6$ is an optionally substituted $C_{1-6}$ alkyl group or an optionally substituted $C_{3-6}$ cycloalkyl group. [Compound B]
Compound (I) wherein
$R^1$ is
(1) a group represented by the formula: —$COR^2$
wherein $R^2$ is
(a) a $C_{1-6}$ alkyl group (e.g., methyl, ethyl, propyl, butyl, isobutyl, isopentyl) optionally substituted by 1 to 3 substituents selected from
(i) an amino group,
(ii) a carboxy group,
(iii) a $C_{1-6}$ alkoxy-carbonyl group (e.g., methoxycarbonyl, ethoxycarbonyl),
(iv) a $C_{6-14}$ aryl group (e.g., phenyl), and
(v) a $C_{1-6}$ alkoxy group (e.g., methoxy);
(b) a $C_{1-6}$ alkoxy group (e.g., methoxy, tert-butoxy);
(c) a $C_{3-10}$ cycloalkyl group (e.g., cyclopropyl, cyclopentyl);
(d) a $C_{6-14}$ aryl group (e.g., phenyl);
(e) an amino group optionally mono- or di-substituted by substituent(s) selected from (i) a alkyl group (e.g., methyl, ethyl, propyl, isopropyl) optionally substituted by 1 to 3 $C_{6-14}$ aryl groups (e.g., phenyl),
(ii) a $C_{6-14}$ aryl group (e.g., phenyl),
(iii) a $C_{3-10}$ cycloalkyl group (e.g., cyclopentyl, cyclohexyl),
(iv) a $C_{1-6}$ alkylsulfonyl group (e.g., methylsulfonyl), and
(v) an aromatic heterocyclic group (e.g., pyridyl) optionally substituted by 1 to 3 $C_{1-6}$ alkyl groups (e.g., methyl);
(f) an aromatic heterocyclic group (e.g., furyl, pyrazolyl, pyridyl, isoxazolyl, thiazolyl) optionally substituted by 1 to 3 substituents selected from a $C_{1-6}$ alkyl group optionally substituted by 1 to 3 halogen atoms (e.g., a fluorine atom);
(g) a non-aromatic heterocyclic group (e.g., tetrahydropyranyl);
or the like.
(2) a 5-membered aromatic heterocyclic group (e.g., pyrazolyl, oxazolyl, isoxazolyl, thiazolyl, isothiazolyl, thiadiazolyl, preferably isoxazolyl) optionally substituted by 1 to 3 substituents selected from
(i) a $C_{1-6}$ alkyl-carbonyl group optionally substituted by 1 to 3 halogen atoms;
(ii) a $C_{1-6}$ alkoxy-carbonyl group optionally substituted by 1 to 3 substituents selected from
(a) a halogen atom,
(b) a $C_{1-6}$ alkoxy group, and
(c) a $C_{6-14}$ aryl group (e.g., phenyl);
(iii) a carbamoyl group optionally mono- or di-substituted by $C_{1-6}$ alkyl group(s) optionally substituted by 1 to 3 halogen atoms;
(iv) a carboxy group;
(v) a hydroxy group;
(vi) a halogen atom; and
(vii) a $C_{1-6}$ alkyl group optionally substituted by 1 to 3 substituents selected from
(a) a halogen atom,
(b) a carboxy group,
(c) a hydroxy group,
(d) a $C_{1-6}$ alkoxy-carbonyl group, and
(e) a $C_{1-6}$ alkoxy group; or
(3) a phenyl group optionally substituted by 1 to 3 substituents selected from
(i) a $C_{1-6}$ alkyl-carbonyl group optionally substituted by 1 to 3 halogen atoms;
(ii) a $C_{1-6}$ alkoxy-carbonyl group optionally substituted by 1 to 3 substituents selected from
(a) a halogen atom,
(b) a $C_{1-6}$ alkoxy group, and
(c) a $C_{6-14}$ aryl group (e.g., phenyl);
(iii) a carbamoyl group optionally mono- or di-substituted by $C_{1-6}$ alkyl group(s) optionally substituted by 1 to 3 halogen atoms;
(iv) a carboxy group;
(v) a hydroxy group;
(vi) a halogen atom; and
(vii) a $C_{1-6}$ alkyl group optionally substituted by 1 to 3 substituents selected from
(a) a halogen atom,
(b) a carboxy group,
(c) a hydroxy group,
(d) a $C_{1-6}$ alkoxy-carbonyl group, and
(e) a $C_{1-6}$ alkoxy group;

$R^3$ is a $C_{1-6}$ alkyl group optionally substituted by 1 to 7 (preferably 1 to 3) halogen atoms (e.g., a fluorine atom), or a $C_{3-6}$ cycloalkyl group;

$R^4$ is a hydrogen atom;

X is O or $CR^{5a}R^{5b}$ wherein $R^{5a}$ and $R^{5b}$ is as defined above;

ring A is an optionally further substituted 4- to 7-membered non-aromatic heterocycle (the heterocycle is optionally crosslinked) or cyclohexane;

ring P and ring Q are condensed to form

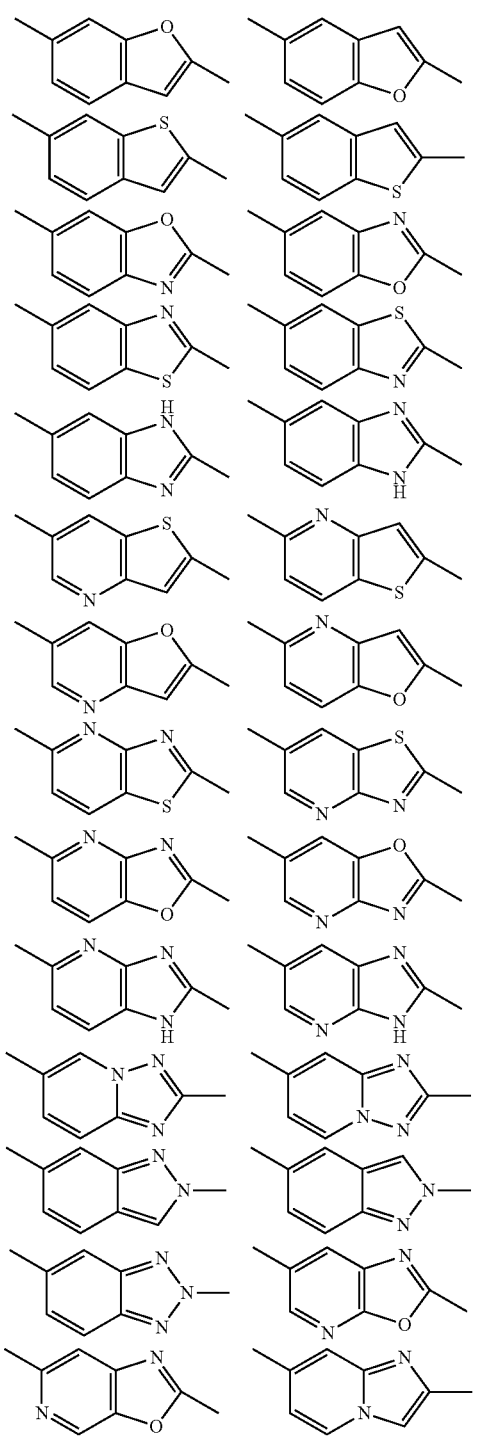

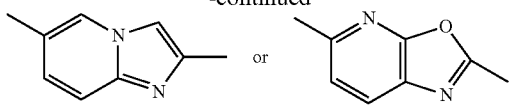

in each of which ring Q is optionally substituted by 1 to 3 substituents selected from (1) a halogen atom (e.g., a fluorine atom, a chlorine atom), (2) a $C_{1-6}$ alkyl group (e.g., methyl)

and the like; and $R^6$ is (1) a $C_{1-6}$ alkyl group (e.g., methyl, ethyl, propyl, isopropyl, isobutyl) optionally substituted by 1 to 3 substituents selected from a halogen atom (e.g., a fluorine atom) and a $C_{3-6}$ cycloalkyl group (e.g., cyclopropyl, cyclobutyl); or (2) a $C_{3-6}$ cycloalkyl group (e.g., cyclopropyl, cyclobutyl).

[Compound C]

Compound (I) wherein $R^1$ is (1) a group represented by the formula: —$COR^2$ wherein $R^2$ is (a) a $C_{1-6}$ alkyl group (e.g., methyl, ethyl, propyl, butyl, isobutyl, isopentyl) optionally substituted by 1 to 3 substituents selected from (i) an amino group, (ii) a carboxy group, (iii) a $C_{1-6}$ alkoxy-carbonyl group (e.g., methoxycarbonyl, ethoxycarbonyl), (iv) a $C_{6-14}$ aryl group (e.g., phenyl), and (v) a $C_{1-6}$ alkoxy group (e.g., methoxy);

(b) a $C_{1-6}$ alkoxy group (e.g., methoxy, tert-butoxy);

(c) an amino group optionally mono- or di-substituted by substituent(s) selected from (i) a $C_{1-6}$ alkyl group (e.g., methyl, ethyl, propyl, isopropyl) optionally substituted by 1 to 3 $C_{6-14}$ aryl groups (e.g., phenyl), (ii) a $C_{6-14}$ aryl group (e.g., phenyl), (iii) a $C_{3-10}$ cycloalkyl group (e.g., cyclopentyl, cyclohexyl), (iv) a $C_{1-6}$ alkylsulfonyl group (e.g., methylsulfonyl), and (v) an aromatic heterocyclic group (e.g., pyridyl) optionally substituted by 1 to 3 $C_{1-6}$ alkyl groups (e.g., methyl);

or the like;

(2) a 5-membered aromatic heterocyclic group (e.g., pyrazolyl, oxazolyl, isoxazolyl, thiazolyl, isothiazolyl, thiadiazolyl, preferably isoxazolyl) optionally substituted by 1 to 3 substituents selected from (i) a halogen atom and (ii) a $C_{1-6}$ alkyl group; or (3) a phenyl group optionally substituted by 1 to 3 substituents selected from (i) a halogen atom and (ii) a $C_{1-6}$ alkyl group;

$R^3$ is a $C_{1-6}$ alkyl group optionally substituted by 1 to 3 halogen atoms (e.g., a fluorine atom);

$R^4$ is a hydrogen atom;

X is O or $CR^{5a}R^{5b}$ wherein $R^{5a}$ and $R^{5b}$ is as defined above;

ring A is a 4- to 7-membered (preferably 4- to 6-membered) nitrogen-containing non-aromatic heterocycle (the heterocycle is optionally crosslinked) or cyclehexane;

ring P and ring Q are condensed to form

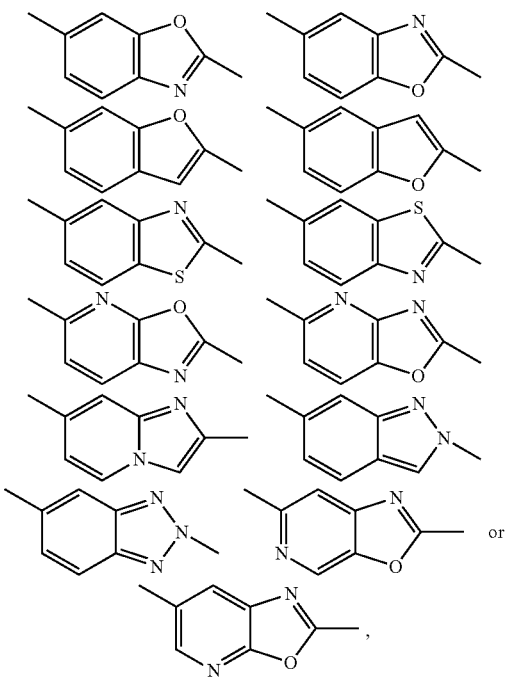

in each of which ring Q is optionally substituted by 1 to 3 halogen atoms; and $R^6$ is a $C_{1-6}$ alkyl group (e.g., methyl, ethyl, propyl, isopropyl, isobutyl) optionally substituted by 1 to 3 substituents selected from a halogen atom (e.g., a fluorine atom) and a $C_{3-6}$ cycloalkyl group (e.g., cyclopropyl, cyclobutyl).

[Compound C-1]

Compound (I) wherein $R^1$ is (1) a group represented by the formula: —$COR^2$
wherein $R^2$ is
 (a) a $C_{1-6}$ alkyl group (e.g., methyl, ethyl, propyl, butyl, isobutyl, isopentyl) optionally substituted by 1 to 3 substituents selected from
  (i) an amino group,
  (ii) a carboxy group,
  (iii) a $C_{1-6}$ alkoxy-carbonyl group (e.g., methoxycarbonyl, ethoxycarbonyl),
  (iv) a $C_{6-14}$ aryl group (e.g., phenyl), and
  (v) a $C_{1-6}$ alkoxy group (e.g., methoxy);
 (b) a $C_{1-6}$ alkoxy group (e.g., methoxy, tert-butoxy);
 (c) an amino group optionally mono- or di-substituted by substituent(s) selected from
  (i) a $C_{1-6}$ alkyl group (e.g., methyl, ethyl, propyl, isopropyl) optionally substituted by 1 to 3 $C_{6-14}$ aryl groups (e.g., phenyl),
  (ii) a $C_{6-14}$ aryl group (e.g., phenyl),
  (iii) a $C_{3-10}$ cycloalkyl group (e.g., cyclopentyl, cyclohexyl),
  (iv) a $C_{1-6}$ alkylsulfonyl group (e.g., methylsulfonyl), and
  (v) an aromatic heterocyclic group (e.g., pyridyl) optionally substituted by 1 to 3 $C_{1-6}$ alkyl groups (e.g., methyl);
 or the like;

(2) a 5-membered aromatic heterocyclic group (e.g., pyrazolyl, oxazolyl, isoxazolyl, thiazolyl, isothiazolyl, thiadiazolyl, preferably isoxazolyl) optionally substituted by 1 to 3 substituents selected from (i) a halogen atom and (ii) a $C_{1-6}$ alkyl group; or (3) a phenyl group optionally substituted by 1 to 3 substituents selected from (i) a halogen atom and (ii) a $C_{1-6}$ alkyl group;

$R^3$ is a $C_{1-6}$ alkyl group optionally substituted by 1 to 3 halogen atoms (e.g., a fluorine atom);

$R^4$ is a hydrogen atom;

X is O or $CR^{5a}R^{5b}$ wherein $R^{5a}$ and $R^{5b}$ is as defined above;

ring A is a 4- to 7-membered (preferably 4- to 6-membered) nitrogen-containing non-aromatic heterocycle (the heterocycle is optionally crosslinked) or cyclohexane;

ring P and ring Q are condensed to form

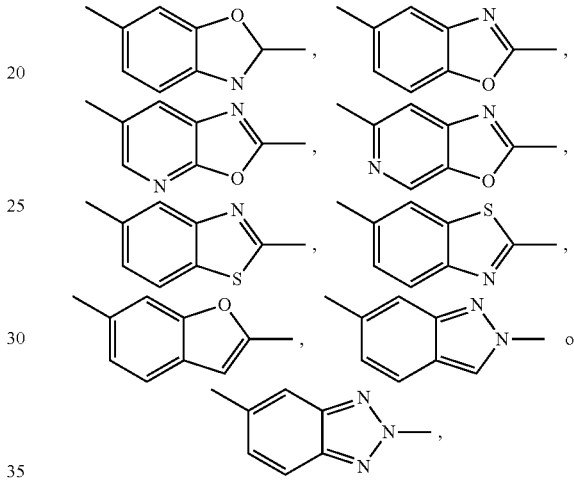

in each of which ring Q is optionally substituted by 1 to 3 halogen atoms; and $R^6$ is a $C_{1-6}$ alkyl group (e.g., methyl, ethyl, propyl, isopropyl, isobutyl) optionally substituted by 1 to 3 substituents selected from a halogen atom (e.g., a fluorine atom) and a $C_{3-6}$ cycloalkyl group (e.g., cyclopropyl, cyclobutyl).

[Compound D]

Compound (I) wherein $R^1$ is (1) a group represented by the formula: —$COR^2$
wherein $R^2$ is
 (a) a $C_{1-6}$ alkyl group (e.g., methyl, ethyl, propyl, butyl, isobutyl, isopentyl);
 (b) a $C_{1-6}$ alkoxy group (e.g., methoxy, tert-butoxy);
 (c) an amino group optionally mono- or di-substituted by $C_{1-6}$ alkyl group(s) (e.g., methyl, ethyl, propyl, isopropyl); or the like; or (2) a 5-membered aromatic heterocyclic group (e.g., pyrazolyl, oxazolyl, isoxazolyl, thiazolyl, isothiazolyl, thiadiazolyl, preferably isoxazolyl) optionally substituted by 1 to 3 substituents selected from a $C_{1-6}$ alkyl group;

$R^3$ is a $C_{1-6}$ alkyl group optionally substituted by 1 to 3 halogen atoms (e.g., a fluorine atom);

$R^4$ is a hydrogen atom;

X is O or $CH_2$;

ring A is a 4- to 6-membered nitrogen-containing non-aromatic heterocycle (the heterocycle is optionally crosslinked) or cyclhexane;

ring P and ring Q are condensed to form

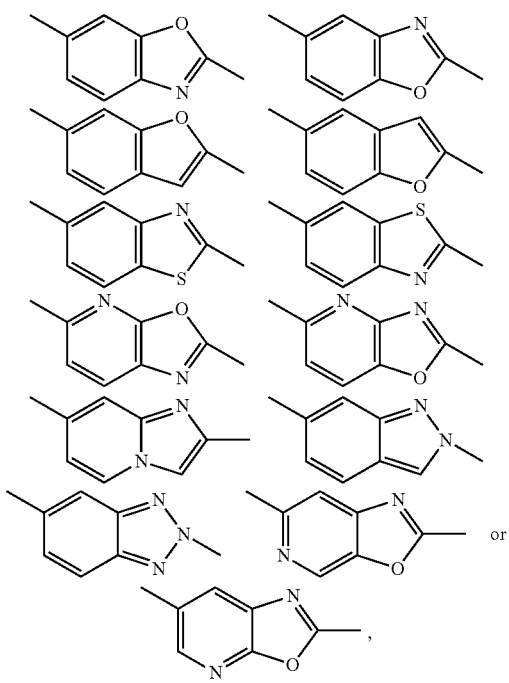

in each of which ring Q is optionally substituted by 1 to 3 halogen atoms; and $R^6$ is a $C_{1-6}$ alkyl group (e.g., methyl, ethyl, propyl, isopropyl, isobutyl) optionally substituted by 1 to 3 substituents selected from a halogen atom (e.g., a fluorine atom) and a $C_{3-6}$ cycloalkyl group (e.g., cyclopropyl, cyclobutyl).

[Compound D-1]

Compound (I) wherein $R^1$ is (1) a group represented by the formula: —$COR^2$ wherein $R^2$ is (a) a $C_{1-6}$ alkyl group (e.g., methyl, ethyl, propyl, butyl, isobutyl, isopentyl);

(b) a $C_{1-6}$ alkoxy group (e.g., methoxy, tert-butoxy);

(c) an amino group optionally mono- or di-substituted by $C_{1-6}$ alkyl group(s) (e.g., methyl, ethyl, propyl, isopropyl); or the like; or (2) a 5-membered aromatic heterocyclic group (e.g., pyrazolyl, oxazolyl, isoxazolyl, thiazolyl, isothiazolyl, thiadiazolyl, preferably isoxazolyl) optionally substituted by 1 to 3 substituents selected from a $C_{1-6}$ alkyl group;

$R^3$ is a $C_{1-6}$ alkyl group optionally substituted by 1 to 3 halogen atoms (e.g., a fluorine atom);

$R^4$ is a hydrogen atom;

X is O or $CH_2$;

ring A is a 4- to 6-membered nitrogen-containing non-aromatic heterocycle (the heterocycle is optionally crosslinked) or cyclohexane;

ring P and ring Q are condensed to form

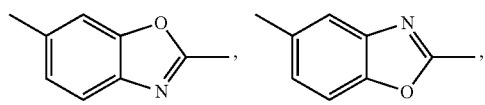

in each of which ring Q is optionally substituted by 1 to 3 halogen atoms; and $R^6$ is a $C_{1-6}$ alkyl group (e.g., methyl, ethyl, propyl, isopropyl, isobutyl) optionally substituted by 1 to 3 substituents selected from a halogen atom (e.g., a fluorine atom) and a $C_{3-6}$ cycloalkyl group (e.g., cyclopropyl, cyclobutyl).

As a salt of the compound represented by the formula (I), (II) and (I'), a pharmacologically acceptable salt is preferable. Examples of such salt include salts with inorganic base, salts with organic base, salts with inorganic acid, salts with organic acid, salts with basic or acidic amino acid, and the like.

Preferable examples of the salt with inorganic base include alkali metal salts such as sodium salt, potassium salt and the like; alkaline earth metal salts such as calcium salt, magnesium salt and the like; aluminum salt; ammonium salt and the like.

Preferable examples of the salt with organic base include salts with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

A prodrug of compound (I) means a compound which is converted to compound (I) with a reaction due to an enzyme, an gastric acid, etc. under the physiological condition in the living body, that is, a compound which is converted to compound (I) by oxidation, reduction, hydrolysis, etc. according to an enzyme; a compound which is converted to compound (I) by hydrolysis etc. due to gastric acid, etc.

Examples of the prodrug of compound (I) include a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation or dimethylaminomethylcarbonylation); a compound obtained by subjecting a carboxy group in compound (I) to an esterification or amidation (e.g., a compound obtained by subjecting a carboxy group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methyl amidation etc.) and the like. These compounds can be produced from compound (I) according to a method known per se.

A prodrug for compound (I) may also be one which is converted to compound (I) under a physiological condition, such as those described in IYAKUHIN no KAIHATSU, Development of Pharmaceuticals, Vol. 7, Design of Molecules, p. 163-198, Published by HIROKAWA SHOTEN, 1990.

In the present specification, a prodrug may be in the form of a salt. Examples of the salt include those exemplified as the salt of the compound represented by the aforementioned formula (I).

In addition, compound (I) may be labeled with an isotope (e.g., $^3$H, $^{13}$C, $^{14}$C, $^{18}$F, $^{35}$S, $^{125}$I) and the like.

Compound (I) may be a hydrate or a non-hydrate, and a solvate or a non-solvate.

Compound (I) also encompasses a deuterium conversion form wherein $^1$H is converted to $^2$H(D).

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization known per se.

Compound (I) or a prodrug thereof (hereinafter sometimes to be abbreviated simply as the compound of the present invention) has low toxicity, and can be used as an agent for the prophylaxis or treatment of various diseases mentioned below in a mammal (e.g., human, mouse, rat, rabbit, dog, cat, bovine, horse, swine, monkey) directly or in the form of a pharmaceutical composition by admixing with a pharmacologically acceptable carrier and the like.

Here, examples of the pharmacologically acceptable carrier include various organic or inorganic carrier substances conventionally used as preparation materials, which are added as excipient, lubricant, binder or disintegrant for solid dosage forms; as solvent, solubilizing agent, suspending agent, isotonicity agent, buffer or soothing agent for liquid preparation, and the like. Where necessary, preparation additives such as preservative, antioxidant, colorant, sweetener and the like can also be used.

Preferable examples of the excipient include lactose, sucrose, D-mannitol, D-sorbitol, starch, pregelatinized starch, dextrin, crystalline cellulose, low-substituted hydroxypropylcellulose, sodium carboxymethylcellulose, gum arabic, pullulan, light anhydrous silicic acid, synthetic aluminum silicate and magnesium aluminometasilicate.

Preferable examples of the lubricant include magnesium stearate, calcium stearate, talc and colloidal silica.

Preferable examples of the binder include pregelatinized starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, sodium croscarmellose, sodium carboxymethylstarch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionic acid, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates and polyoxyethylene hydrogenated castor oil.

Preferable examples of the isotonicity agent include sodium chloride, glycerol, D-mannitol, D-sorbitol and glucose.

Preferable examples of the buffer include buffers such as phosphate, acetate, carbonate, citrate and the like.

Preferable examples of the soothing agent include benzyl alcohol.

Preferable examples of the preservative include paraoxybenzoates, chlorobutanol, benzyl alcohol, phenethyl alcohol, dehydroacetic acid and sorbic acid.

Preferable examples of the antioxidant include sulfite, ascorbate and the like.

Preferable examples of the colorant include aqueous food tar colors (e.g., food colors such as Food Red No. 2 and No. 3, Food Yellow No. 4 and No. 5, Food Blue No. 1 and No. 2, etc.), water insoluble lake dye (e.g., aluminum salt of the above-mentioned aqueous food tar color) and natural dye (e.g., β-carotene, chlorophyll, ferric oxide red).

Preferable examples of the sweetening agent include sodium saccharin, dipotassium glycyrrhizinate, aspartame and stevia.

The medicament containing the compound of the present invention can be safely administered solely or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

These preparations may be release control preparations (e.g., sustained-release microcapsule) such as immediate-release preparation, sustained-release preparation and the like.

A pharmaceutical composition can be produced by a method conventionally used in the technical field of pharmaceutical preparation, for example, the method described in the Japanese Pharmacopoeia and the like.

While the content of the compound of the present invention in the pharmaceutical composition varies depending on the dosage form, dose of the compound of the present invention, and the like, it is, for example, about 0.1 to 100 wt %.

During production of an oral preparation, coating may be applied as necessary for the purpose of masking of taste, enteric property or durability.

Examples of the coating base to be used for coating include sugar coating base, aqueous film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the aqueous film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, red ferric oxide and the like can be used.

The compound of the present invention shows low toxicity (e.g., acute toxicity, chronic toxicity, genetic toxicity, reproductive toxicity, cardiotoxicity, carcinogenicity and the like) and a few side effects. Therefore, it can be used as an agent for the prophylaxis or treatment or a diagnostic of various diseases in a mammal (e.g., human, bovine, horse, dog, cat, monkey, mouse, rat).

The compound of the present invention has a superior ACC (acetyl-CoA carboxylase) inhibitory action. Examples of ACC include liver, adipose tissue or pancreas-specific isozyme (ACC1); and muscle specific isozyme (ACC2). The compound of the present invention has ACC2 selectivity. Particularly, the compounds of Examples of the present invention have high ACC2 selectivity.

The compound of the present invention is superior in the metabolism stability and has advantages such as long half-life of compound, difficult in vivo metabolism and the like.

Moreover, the compound of the present invention is superior in the in vivo kinetics (e.g., oral absorbability, bioavailability).

The compound of the present invention can be used as an agent for the prophylaxis or treatment of obesity, diabetes (e.g., type 1 diabetes, type 2 diabetes, gestational diabetes, obese diabetes), hyperlipidemia (e.g., hypertriglyceridemia, hypercholesterolemia, high LDL-cholesterolemia, hypo-HDL-emia, postprandial hyperlipemia), hypertension, cardiac failure, diabetic complications [e.g., neuropathy, nephropathy, retinopathy, diabetic cardiomyopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], metabolic syndrome (pathology having three or more selected from hypertriglyceridemia (TG), low HDL cholesterol (HDL-C), hypertension, abdomen obesity and impaired glucose tolerance), sarcopenia, cancer and the like.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 hr level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 hr level (glucose concentration of intravenous plasma) of less than 140 mg/dl" (normal type) is called a "borderline type".

In addition, ADA (American Diabetes Association) in 1997 and WHO in 1998 reported new diagnostic criteria of diabetes.

According to these reports, diabetes is a condition showing a fasting blood glucose level (glucose concentration of intravenous plasma) of not less than 126 mg/dl and a 75 g oral glucose tolerance test 2 hr level (glucose concentration of intravenous plasma) of not less than 200 mg/dl.

According to the above-mentioned reports, impaired glucose tolerance is a condition showing fasting blood sugar level (glucose concentration of intravenous plasma) of less than 126 mg/dl and a 75 g oral glucose tolerance test 2 hr level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 hr level (glucose concentration of intravenous plasma) of less than 140 mg/dl is called IFG (Impaired Fasting Glycemia).

The compound of the present invention can be also used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycemia) into diabetes.

Since the compound of the present invention has an activity of inhibiting body weight gain, it can be used as a body weight gain inhibitor to mammals. Target mammals may be any mammals of which body weight gain is to be avoided. The mammals may have a risk of body weight gain genetically or may be suffering from lifestyle-related diseases such as diabetes, hypertension and/or hyperlipidemia and the like. The body weight gain may be caused by excessive feeding or diet without nutrient balance, or may be derived from concomitant drug (e.g., agents for enhancing insulin sensitivity having PPARγ-agonistic activity such as troglitazone, rosiglitazone, englitazone, ciglitazone, pioglitazone and the like). In addition, body weight gain may be preliminary to obesity, or may be body weight gain of obesity patients. Here, obesity is defined that BMI (body mass index; body weight (kg)/[height (m)]$^2$) is not less than 25 for Japanese (criterion by Japan Society for the Study of Obesity), or not less than 30 for westerner (criterion by WHO).

The compound of the present invention is also useful as an agent for the prophylaxis or treatment of obesity without body weight increase.

The compound (I) is useful as an agent for the prophylaxis or treatment of metabolic syndrome. Because patients with metabolic syndrome have an extreme high incidence of cardiovascular diseases as compared to patients with single lifestyle-related disease, the prophylaxis or treatment of metabolic syndrome is quite important to prevent cardiovascular diseases.

Criteria for diagnosis of metabolic syndrome are announced by WHO in 1999, and by NCEP in 2001. According to the criterion of WHO, patients with at least two of abdominal obesity, dyslipidemia (high TG or low HDL) and hypertension in addition to hyperinsulinemia or impaired glucose tolerance are diagnosed as metabolic syndrome (World Health Organization: Definition, Diagnosis and Classification of Diabetes Mellitus and Its Complications. Part I: Diagnosis and Classification of Diabetes Mellitus, World Health Organization, Geneva, 1999). According to the criterion of Adult Treatment Panel III of National Cholesterol Education Program, that is an indicator for managing ischemic heart diseases in America, patients with at least three of abdominal obesity, high triglycerides, low HDL cholesterol, hypertension and impaired glucose tolerance are diagnosed as metabolic syndrome (National Cholesterol Education Program: Executive Summary of the Third Report of National Cholesterol Education Program (NCEP) Expert Panel on Detection, Evaluation, and Treatment of High Blood Cholesterol in Adults (Adults Treatment Panel III). The Journal of the American Medical Association, Vol. 285, 2486-2497, 2001).

The compound of the present invention can also be used, for example, as an agent for the prophylaxis or treatment of osteoporosis, cachexia (e.g., carcinomatous cachexia, tuberculous cachexia, diabetic cachexia, hemopathic cachexia, endocrinopathic cachexia, infectious cachexia or cachexia induced by acquired immunodeficiency syndrome), fatty liver, polycystic ovary syndrome, renal disease (e.g., diabetic nephropathy, glomerulonephritis, glomerulosclerosis, nephrosis syndrome, hypertensive nephrosclerosis, terminal renal disorder), muscular dystrophy, myocardial infarction, angina pectoris, cerebrovascular disorder (e.g., cerebral infarction, cerebral apoplexy), Alzheimer's disease, Parkinson's disease, anxiety, dementia, insulin resistance syndrome, syndrome X, hyperinsulinemia, sensory abnormality in hyperinsulinemia, irritable bowel syndrome, acute or chronic diarrhea, inflammatory disease (e.g., rheumatoid arthritis, spondylitis deformans, osteoarthritis, lumbago, gout, postoperative or posttraumatic inflammation, swelling, neuralgia, pharyngolaryngitis, cystitis, hepatitis (including nonalcoholic steatohepatitis), pneumonia, pancreatitis, enteritis, inflammatory bowel disease (including inflammatory colitis), ulcerative colitis, stomach mucosainjury (including stomach mucosainjury caused by aspirin)), small intestine mucosainjury, malabsorption, testis dysfunction, visceral obesity syndrome or sarcopenia.

In addition, the compound of the present invention can also be used as an agent for the prophylaxis or treatment of various carcinomas (particularly breast cancer (e.g., invasive ductal carcinoma, ductal carcinoma in situ, inflammatory breast cancer and the like), prostate cancer (e.g., hormone-dependent prostate cancer, non-hormone dependent prostate cancer and the like), pancreatic cancer (e.g., pancreatic duct cancer and the like), gastric cancer (e.g., papillary adenocarcinoma, mucinous adenocarcinoma, adenosquamous carcinoma and the like), lung cancer (e.g., non-small cell lung cancer, small cell lung cancer, malignant mesothelioma and the like), colorectal cancer (e.g., gastrointestinal stromal tumor and the like), rectal cancer (e.g., gastrointestinal stromal tumor and the like), colorectal cancer (e.g., familial colorectal cancer, hereditary nonpolyposis colorectal cancer, gastrointestinal stromal tumor and the like), small intestinal cancer (e.g., non-Hodgkin lymphoma, gastrointestinal stromal tumor and the like), esophagus cancer, duodenal cancer, cancer of the tongue, pharyngeal cancer (e.g., nasopharyngeal cancer, mesopharyngeal cancer, hypopharyngeal cancer and the like), salivary gland cancer, brain tumor (e.g., pineal astrocytoma, pilocytic astrocytoma, diffuse astrocytoma, anaplastic astrocytoma and the like), schwannoma, liver cancer (e.g., primary liver cancer, Extrahepatic Bile Duct Cancer and the like), kidney cancer (e.g., renal cell carcinoma, transitional carcinoma of kidney pelvis and urinary duct, and the like), biliary tract cancer, endometrial carcinoma, cervical cancer, ovarian cancer (e.g., ovarian epithelial carcinoma, extragonadal germ cell tumor ovarian germ cell tumor ovarian low malignant potential tumor and the like), urinary bladder cancer, urinary tract cancer, skin cancer (e.g., intraocular (ocular) melanoma, Merkel cell carcinoma and the like), Hemangioma, malignant lymphoma, malignant melanoma, thyroid cancer (e.g., medullary thyroid carcinoma and the like), parathyroid cancer, nasal cavity cancer, paranasal sinus cancer, bone tumor (e.g., osteosarcoma, Ewing's tumor uterus sarcoma, soft tissue sarcoma and the like), vascular fibroma, retinoblastoma, penile cancer, testis tumor solid cancer in childhood (e.g., Wilms' tumor childhood kidney tumor and the like), Kaposi's sarcoma, Kaposi's sarcoma derived from AIDS, maxillary tumor fibrous histiocytoma, leiomyosarcoma, rhabdomyosarcoma, leukemia (e.g., acute myeloid leukemia, acute lymphoblastic leukemia and the like) etc.).

The compound of the present invention can also be used for secondary prevention or suppression of progression of the above-mentioned various diseases (e.g., cardiovascular events such as myocardial infarction and the like).

While the dose of the compound of the present invention varies depending on the subject of administration, administration route, target disease, symptom and the like, for example, for oral administration to an adult obese patient, it is generally about 0.01 to 100 mg/kg body weight, preferably 0.05 to 30 mg/kg body weight, more preferably 0.1 to 10 mg/kg body weight for one dose, further preferably 0.1 to 2 mg/kg body weight for one dose, which is desirably administered once to 3 times a day.

With the aim of enhancing the action of the compound of the present invention or decreasing the dose of the compound and the like, the compound can be used in combination with medicaments such as therapeutic agents for diabetes, therapeutic agents for diabetic complications, therapeutic agents for hyperlipidemia, antihypertensive agents, antiobesity agents, diuretics, antithrombotic agents and the like (hereinafter to be abbreviated as concomitant drug). The time of administration of the compound of the present invention and that of the concomitant drug are not limited, and these concomitant drugs may be low-molecular-weight compounds or high-molecular-weight protein, polypeptide, antibody, vaccine and the like. They may be administered simultaneously or in a staggered manner to the administration subject. In addition, the compound of the present invention and the concomitant drug may be administered as two kinds of preparations containing respective active ingredients or a single preparation containing both active ingredients.

The dose of the concomitant drug can be appropriately determined based on the dose employed clinically. In addition, the mixing ratio of the compound of the present invention and the concomitant drug can be appropriately determined according to the administration subject, administration route, target disease, condition, combination, and the like. For example, when the administration subject is a human, the concomitant drug may be used in an amount of 0.01 to 100 parts by weight per 1 part by weight of the compound of the present invention.

Examples of the therapeutic agents for diabetes include insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compound described in WO 2007/013694, WO 2007/018314, WO 2008/093639 or WO 2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues [sulfonylureas (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof], dipeptidyl peptidase IV inhibitors (e.g., Alogliptin, Vildagliptin, Sitagliptin, Saxagliptin, BI1356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof), β3 agonists (e.g., N-5984), GPR40 agonists (e.g., compound described in WO 2004/041266, WO 2004/106276, WO 2005/063729, WO 2005/063725, WO 2005/087710, WO 2005/095338, WO 2007/013689 or WO 2008/001931), GLP-1 receptor agonists [e.g., GLP-1, GLP-1MR, Liraglutide, Exenatide, AVE-0010, BIM-51077, Aib(8,35)hGLP-1(7,37)NH$_2$, CJC-1131, Albiglutide], amylin agonists (e.g., pramlintide), phosphotyrosine phosphatase inhibitors (e.g., sodium vanadate), gluconeogenesis inhibitors (e.g., glycogen phosphorylase inhibitors glucose-6-phosphatase inhibitors, glucagon antagonists, FBPase inhibitors), SGLT2(sodium-glucose cotransporter 2) inhibitors (e.g., Depagliflozin, AVE2268, TS-033, YM543, TA-7284, Remogliflozin, ASP1941), SGLT1 inhibitors, 11β-hydroxysteroid dehydrogenase inhibitors (e.g., BVT-3498), adiponectin or an agonist thereof, IKK inhibitors (e.g., AS-2868), leptin resistance improving drugs, somatostatin receptor agonists, glucokinase activators (e.g., Piragliatin, AZD1656, AZD6370, TTP-355, compound described in WO 2006/112549, WO 2007/028135, WO 2008/047821, WO 2008/050821, WO 2008/136428 or WO 2008/156757), GIP (Glucose-dependent insulinotropic peptide) and the like.

Examples of the therapeutic agents for diabetic complications include aldose reductase inhibitors (e.g., tolrestat, epalrestat, zopolrestat, fidarestat, CT-112, ranirestat (AS-3201), lidorestat), neurotrophic factor and increasing drugs thereof (e.g., NGF, NT-3, BDNF, neurotrophic factors and increasing drugs thereof (e.g., 4-(4-chlorophenyl)-2-(2-methyl-1-imidazolyl)-5-[3-(2-methylphenoxy)propyl]oxazole) described in WO01/14372, a compound described in WO 2004/039365), nerve regeneration promoter (e.g., Y-128), PKC inhibitors (e.g., ruboxistaurin mesylate), AGE inhibitors (e.g., ALT946, pyratoxanthine, N-phenacylthiazolium bromide (ALT766), ALT-711, EXO-226, Pyridorin, pyridoxamine), GABA receptor agonists (e.g., gabapentin, Pregabalin), serotonin noradrenaline re-uptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), apoptosis signal regulating kinase-1 (ASK-1) inhibitors and the like.

Examples of the therapeutic agent for hyperlipidemia include statin compounds (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., a compound described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), anion exchange resins (e.g., colestyramine), probucol, nicotinic acid drugs (e.g., nicomol, niceritrol, niaspan), ethyl icosapentate, phytosterols (e.g., soysterol), γ-oryzanol), cholesterol absorption inhibitors (e.g., Zetia), CETP inhibitors (e.g., dalcetrapib, anacetrapib), ω-3 fatty acid preparations (e.g., ω-3-acid ethyl esters 90) and the like.

Examples of the antihypertensive agent include angiotensin converting enzyme inhibitors (e.g., captopril, enalapril, delapril etc.), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, amlodipine, efonidipine, nicardipine, amlodipine, cilnidipine and the like), β blockers (e.g., metoprolol, atenolol, propranolol, carvedilol, pindolol), clonidine and the like.

Examples of the antiobesity agent include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptor GABA modulator (e.g., topiramate), MCH receptor antagonists (e.g., SB-568849; SNAP-7941; compound described in WO 01/82925 or WO 01/87834), neuropeptide Y antagonists (e.g., velneperit), cannabinoid receptor antagonists (e.g., rimonabant, taranabant), ghrelin antagonists, ghrelin receptor antagonists, ghrelinacylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1(DGAT1) inhibitors, acetylCoAcarboxylase(ACC) inhibitors, stearoyl-CoA desaturated enzyme inhibitors, microsomal triglyceride transfer protein inhibitors (e.g., R-256918), Na-glucose cotransporter inhibitors (e.g., JNJ-28431754, remogliflozin), NFκ inhibitory (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821), glucokinase activators (e.g., AZD-1656), leptin, leptin derivatives (e.g., metreleptin), CNTF(ciliary neurotrophic factor), BDNF (brain-derived neurotrophic factor), cholecystokinin agonists, glucagon-like peptide-1 (GLP-1) preparations (e.g., animal GLP-1 preparations extracted from the pancreas of bovine and pig; human GLP-1 preparations genetically synthesized using *Escherichia coli* or yeast; fragments or derivatives of GLP-1 (e.g., exenatide, liraglutide)), amylin preparations (e.g., pramlintide, AC-2307), neuropeptide Y agonists (e.g., PYY3-36, derivatives of PYY3-36, obineptide, TM-30339, TM-30335), oxyntomodulin preparations: FGF21 preparations (e.g., animal FGF21 preparations extracted from the pancreas of bovine and pig; human FGF21 preparations genetically synthesized using *Escherichia coli* or yeast; fragments or derivatives of FGF21)), combination agents of a naltrexone hydrochloride sustained release preparation and a bupropion hydrochloride sustained release preparation, thyroxine (thyroid gland hormone)-related derivatives, anorexigenic agents (e.g., P-57) and the like.

Examples of the diuretics include xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonic anhydrase inhibitors (e.g., acetazolamide), chlorobenzenesulfonamide agents (e.g., chlortalidone, mefruside, indapamide), azosemide, isosorbide, ethacrynic acid, piretanide, bumetanide, furosemide and the like.

Examples of the antithrombotic agent include heparins (e.g., heparin sodium, heparin calcium, enoxaparin sodium, dalteparin sodium), warfarins (e.g., warfarin potassium), anti-thrombin drugs (e.g., argatroban, dabigatran), thrombolytic agents (e.g., urokinase, tisokinase, alteplase, nateplase, monteplase, pamiteplase), platelet aggregation inhibitors (e.g., ticlopidine hydrochloride, clopidogrel, E5555, SHC530348, cilostazol, ethyl icosapentate, beraprost sodium, sarpogrelate hydrochloride, prasugrel, E5555, SHC530348), FXa inhibitors (e.g., rivaroxaban, apixaban, edoxaban, YM150, compound described in WO 02/06234, WO 2004/048363, WO 2005/030740, WO 2005/058823 or WO 2005/113504) and the like.

In addition, the compound of the present invention can be used in combination with traditional Chinese medicines such as bohu-tusyosan, daisaikoto, boi-ogito and the like.

The administration time of the aforementioned concomitant drug is not limited, and the compound of the present invention and the concomitant drug may be administered to an administration subject simultaneously, or may be administered at different times. The dosage of the concomitant drug may be determined according to the dosage clinically used, and can be appropriately selected depending on the administration subject, administration route, diseases, combination thereof and the like.

The administration mode of the concomitant drug is not particularly limited, and the compound of the present invention and the concomitant drug only need to be combined on administration. Examples of such administration mode include the following:
(1) administration of a single preparation obtained by simultaneously processing the compound of the present invention and the concomitant drug,
(2) simultaneous administration of two kinds of preparations of the compound of the present invention and the concomitant drug, which have been separately produced, by the same administration route,
(3) administration of two kinds of preparations of the compound of the present invention and the concomitant drug, which have been separately produced, by the same administration route in a staggered manner,
(4) simultaneous administration of two kinds of preparations of the compound of the present invention and the concomitant drug, which have been separately produced, by different administration routes,
(5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The compounding ratio of the compound of the present invention to the concomitant drug can be appropriately selected depending on the administration subject, administration route, diseases and the like.

The production method of the compound of the present invention is explained in the following.

In the following Reaction Schemes, starting material compounds may be each in the foLm of a salt as long as it inhibits the reaction. Examples of the salt include those exemplified as the above-mentioned salt of the compound represented by formula (I).

When a specific production method is not described, the starting material compound may be easily commercially available, or can also be produced according to a method known per se, or a method analogous thereto.

In each reaction of the following Reaction Schemes, the product can be used for the next reaction as the reaction mixture or as a crude product, or can also be isolated according to a conventional method from the reaction mixture, and can also be easily purified according to a conventional separation means (e.g., recrystallization, distillation, chromatography).

When alkylation reaction, hydrolysis, amination reaction, esterification reaction, amidation reaction, esterification reaction, etherification reaction, oxidation reaction, reduction reaction and the like are to be performed in the following Reaction Schemes, these reactions are performed according to a method known per se. Examples of such method include the methods described in ORGANIC FUNCTIONAL GROUP PREPARATIONS, 2nd ed., ACADEMIC PRESS, INC., 1989; Comprehensive Organic Transformations, VCH Publishers Inc., 1989 and the like, and the like.

The following are explanations of the solvents in generic terms, which are used for the following reactions.

Examples of the "nitrile solvents" include acetonitrile, propionitrile and the like.

Examples of the "amide solvents" include N,N-dimethylfoimamide (DMF), N,N-dimethylacetamide, N-methylpyrrolidone and the like.

Examples of the "halogenated hydrocarbon solvents" include dichloromethane, chloroform, 1,2-dichloroethane, carbon tetrachloride and the like.

Examples of the "ether solvents" include diethyl ether, diisopropyl ether, tert-butyl methyl ether, tetrahydrofuran (THF), 1,4-dioxane, 1,2-dimethoxyethane and the like.

Examples of the "aromatic solvents" include benzene, toluene, xylene, chlorobenzene, (trifluoromethyl)benzene, pyridine and the like.

Examples of the "aliphatic hydrocarbon solvents" include hexane, pentane, cyclohexane and the like.

Examples of the "sulfoxide solvents" include dimethyl sulfoxide (DMSO) and the like.

Examples of the "alcohol solvents" include methanol, ethanol, propanol, 2-propanol, butanol, isobutanol, tert-butanol and the like.

Examples of the "ester solvents" include methyl acetate, ethyl acetate, n-butyl acetate, tert-butyl acetate and the like.

Examples of the "ketone solvents" include acetone, methyl ethyl ketone and the like.

Examples of the "organic acid solvents" include formic acid, acetic acid, propionic acid, trifluoroacetic acid, methanesulfonic acid and the like.

The following are explanations of the bases in generic terms, which are used for the following reactions.

Examples of the "inorganic bases" include sodium hydroxide, potassium hydroxide, lithium hydroxide, barium hydroxide and the like.

Examples of the "basic salt" include sodium carbonate, potassium carbonate, cesium carbonate, sodium hydrogen carbonate, potassium hydrogen carbonate and the like.

Examples of the "aromatic amines" include pyridine, imidazole, 2,6-lutidine and the like.

Examples of the "tertiary amines" include triethylamine, diisopropylethylamine, N-methylmorpholine, DBU (1,8-diazabicyclo[5.4.0]undec-7-ene), DBN (1,5-diazabicyclo[4.3.0]non-5-ene) and the like.

Examples of the "hydrides of alkali metal or alkaline earth metal" include lithium hydride, sodium hydride, potassium hydride, calcium hydride and the like.

Examples of the "metal amides" include lithium amide, sodium amide, lithium diisopropylamide, lithium dicyclohexylamide, lithium hexamethyldisilazide, sodium hexamethyldisilazide, potassium hexamethyldisilazide and the like.

Examples of the "alkyl metals" include n-butyllithium, sec-butyllithium, tert-butyllithium, methylmagnesium bromide and the like.

Examples of the "aryl metals" include phenyllithium, phenylmagnesium bromide and the like.

Examples of the "metal alkoxides" include sodium methoxide, sodium ethoxide, potassium tert-butoxide and the like.

In the following production methods, when the starting compound has an amino group, a carboxyl group, a hydroxy group, a carbonyl group or a sulfanyl group as a substituent, a protecting group generally used in peptide chemistry and the like may be introduced into these groups. By removing the protecting group as necessary after the reaction, the object compound can be obtained.

Examples of the amino-protecting group include a formyl group, a $C_{1-6}$ alkyl-carbonyl group, a $C_{1-6}$ alkoxy-carbonyl group, a benzoyl group, a $C_{7-10}$ aralkyl-carbonyl group (e.g., benzylcarbonyl), a $C_{7-14}$ aralkyloxy-carbonyl group (e.g., benzyloxycarbonyl, 9-fluorenylmethoxycarbonyl), a trityl group, a phthaloyl group, a N,N-dimethylaminomethylene group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl), a substituted $C_{7-10}$ aralkyl group (e.g., 2,4-dimethoxybenzyl) and the like. These groups are optionally substituted by 1 to 3 substituents selected from a halogen atom, a $C_{1-6}$ alkoxy group and a nitro group.

Examples of the carboxyl-protecting group include a $C_{1-6}$ alkyl group, a $C_{7-10}$ aralkyl group (e.g., benzyl), a phenyl group, a trityl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a alkoxy group and a nitro group.

Examples of the hydroxy-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl, tri-isopropylsilyl, tert-butyldiphenylsilyl), a $C_{2-6}$ alkenyl group (e.g., 1-allyl) and the like. These groups are optionally substituted by 1 to 3 substituents selected from a halogen atom, a $C_{1-6}$ alkyl group, a $C_{1-6}$ alkoxy group and a nitro group.

Examples of the protected carbonyl group include a cyclic acetal (e.g., 1,3-dioxane, 1,3-dioxolane), a non-cyclic acetal (e.g., a di-$C_{1-6}$ alkylacetal) and the like.

Examples of the sulfanyl-protecting group include a $C_{1-6}$ alkyl group, a phenyl group, a trityl group, a $C_{7-10}$ aralkyl group (e.g., benzyl), a $C_{1-6}$ alkyl-carbonyl group, a benzoyl group, a $C_{7-10}$ aralkyl-carbonyl group (e.g., benzylcarbonyl), a $C_{1-6}$ alkoxy-carbonyl group, a $C_{6-14}$ aryloxy-carbonyl group (e.g., phenyloxycarbonyl), a $C_{7-14}$ aralkyloxy-carbonyl group (e.g., benzyloxycarbonyl, 9-fluorenylmethoxycarbonyl), a 2-tetrahydropyranyl group, a $C_{1-6}$ alkylamino-carbonyl group (e.g., methylaminocarbonyl, ethylaminocarbonyl) and the like. These groups are optionally substituted by 1 to 3 substituents selected from a halogen atom, a $C_{1-6}$ alkyl group, a $C_{1-6}$ alkoxy group and a nitro group.

The removal method of the protecting group can be carried out according to a method known per se, for example, the method described in Protective Groups in Organic Synthesis, John Wiley and Sons (1980) or the like. Specifically, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like can be employed.

Compounds Nos. (X-1), (X-2), (X-3), (X-4), (X-A) and the like are encompassed in the Markush structure of compound (X). Here, X of compound No. X indicates letters of alphabet such as A, I and the like or number such as 2, 3 and the like.

<Reaction Scheme 1>

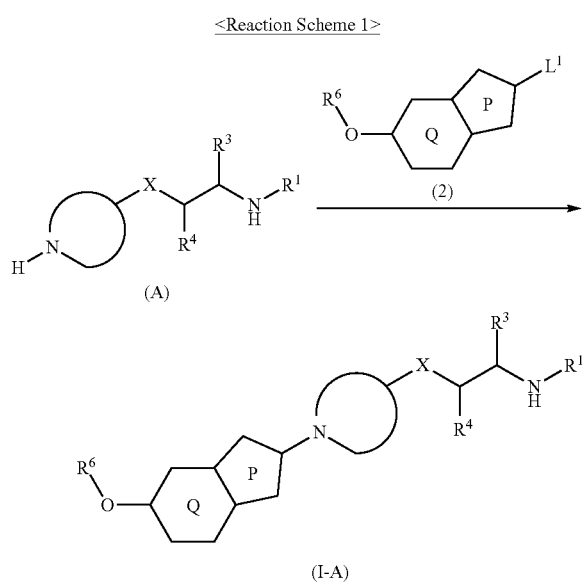

wherein $L^1$ is a halogen atom, a $C_{1-6}$ alkylsulfonyl group, a $C_{1-6}$ alkylsulfinyl group or a $C_{1-6}$ alkylsulfanyl group, and the other symbol are as defined above.

Compound (I-A) can be produced, for example, by reacting compound (A) with compound (2).

This reaction is carried out by reacting compound (A) with compound (2) in the presence of a base, in an inert solvent. The reaction may be carried out under microwave irradiation, as necessary.

The amount of compound (2) to be used is generally 1 to 20 equivalents, preferably 1 to 5 equivalents, relative to compound (A).

Examples of the above-mentioned "base" include "inorganic bases", "basic salts", "aromatic amines", "tertiary amines", "hydrides of alkali metal or alkaline earth metal", "alkyl metals", "aryl metals", "metal alkoxides" and the like. The amount of the "base" to be used is generally 1 to 10 equivalents, preferably 1 to 5 equivalents, relative to compound (A).

Examples of the above-mentioned "inert solvent" include "nitrile solvents", "amide solvents", "halogenated hydrocarbon solvents", "ether solvents" and the like. These solvents may be used in a mixture of two or more kinds thereof mixed at an appropriate ratio. Of these, THF, DMF and the like are preferable.

The reaction temperature is generally −100° C. to 200° C., preferably 0° C. to 150° C.

The reaction time is generally 5 min to 48 hr, preferably 30 min to 24 hr.

Compound (A) and compound (2) can be produced according to a method known per se.

<Reaction Scheme 2>

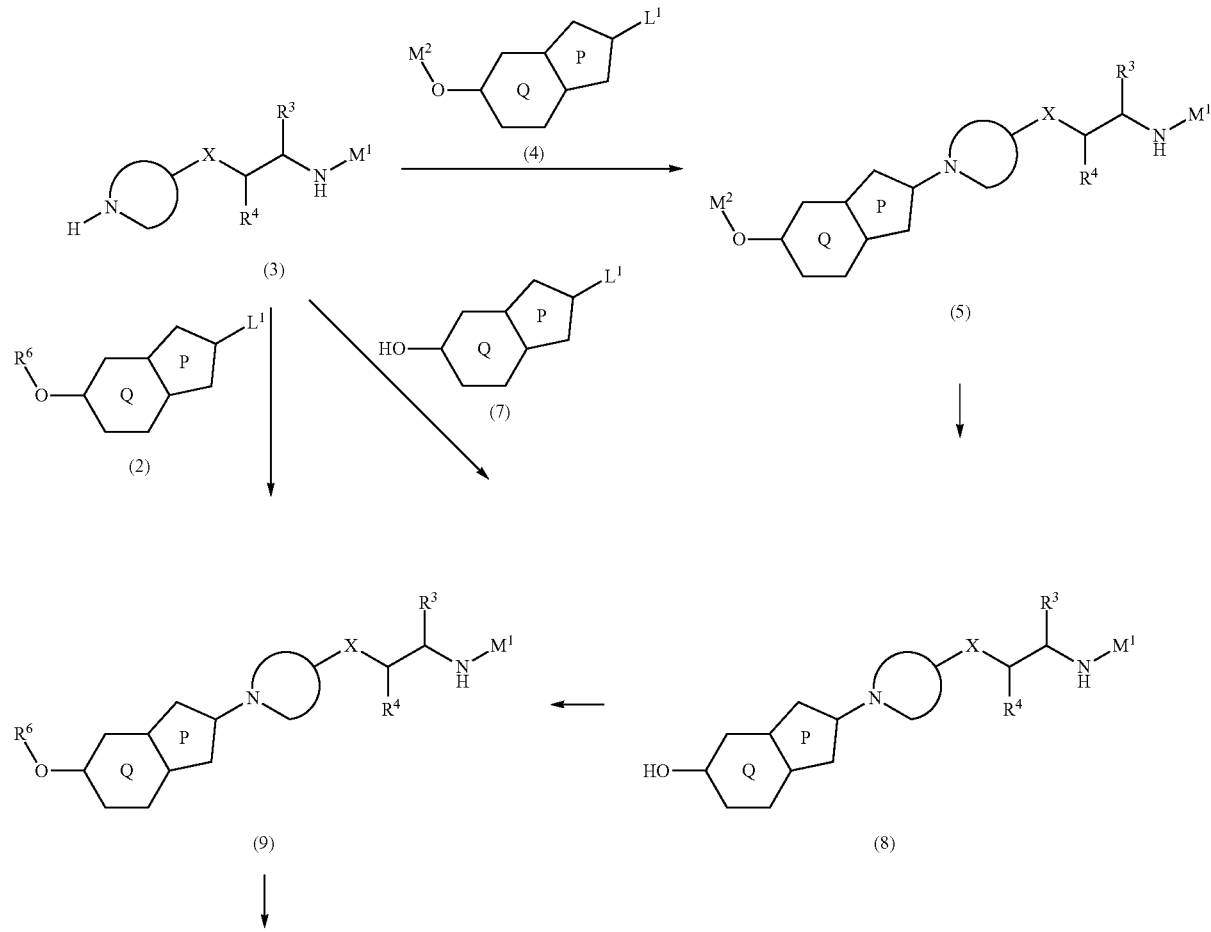

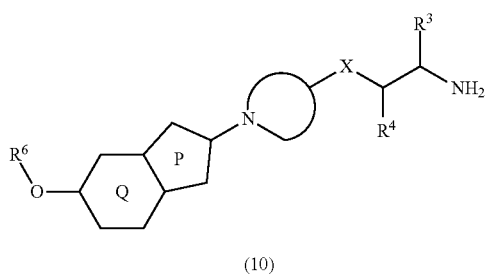

(10)

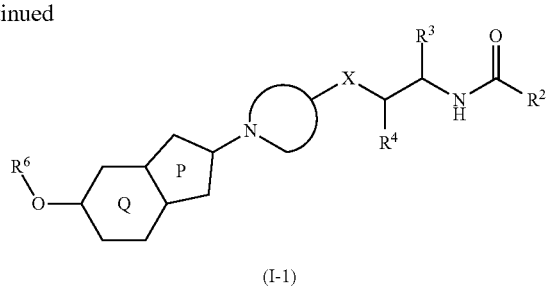

(I-1)

wherein $M^1$ is an amino-protecting group, $M^2$ is a hydroxy-protecting group, and the other symbols are as defined above.

Compound (5) can be produced, for example, by reacting compound (3) with compound (4).

This reaction is carried out in the same manner as in the production method of compound (I-A) in Reaction Scheme 1.

Compound (8) can be produced, for example, by subjecting compound (5) to a deprotection reaction. The deprotection reaction can be carried out according to a method known per se, for example, the method described in Protective Groups in Organic Synthesis, John Wiley and Sons (1980) or the like.

Compound (8) can also be produced, for example, by reacting compound (3) with compound (7).

This reaction is carried out in the same manner as in the production method of compound (I-A) in Reaction Scheme 1.

Compound (9) can be produced, for example, by reacting compound (3) with compound (2).

This reaction is carried out in the same manner as in the production method of compound (I-A) in Reaction Scheme 1.

Compound (9) can also be produced, for example, by subjecting compound (8) to an alkylation reaction.

Examples of the alkylation reaction include the following "method using a base and the corresponding halide or sulfonate", "method employing the Mitsunobu reaction" and the like.

The "method using a base and the corresponding halide or sulfonate" can be carried out according to a method known per se, for example, the method described in Journal of Chemical Society, pages 1530-1534, 1937 or the like, or a method analogous thereto.

This reaction is carried out by reacting compound (8) with the corresponding halide or sulfonate in the presence of a base, in an inert solvent.

Examples of the above-mentioned "halide" include optionally substituted $C_{1-6}$ alkyl halides and optionally substituted $C_{3-6}$ cycloalkyl halides. The amount of the "halide" to be used is generally 1 to 10 equivalents, preferably 1 to 5 equivalents, relative to compound (8).

Examples of the above-mentioned "sulfonate" include optionally substituted $C_{1-6}$ alkyl sulfonates and optionally substituted $C_{3-6}$ cycloalkyl sulfonates. Examples of the "sulfonic acid" include methanesulfonic acid, p-toluenesulfonic acid, trifluoromethanesulfonic acid and the like. The amount of the "sulfonate" to be used is generally 1 to 10 equivalents, preferably 1 to 5 equivalents, relative to compound (8).

Examples of the above-mentioned "base" include "inorganic bases", "basic salts", "aromatic amines", "hydrides of alkali metal or alkaline earth metal", "alkyl metals", "aryl metals", "metal alkoxides" and the like. The amount of the "base" to be used is generally 1 to 10 equivalents, preferably 1 to 5 equivalents, relative to compound (8).

Examples of the above-mentioned "inert solvent" include "nitrile solvents", "amide solvents", "halogenated hydrocarbon solvents", "ether solvents" and the like. These solvents may be used in a mixture of two or more kinds thereof mixed at an appropriate ratio. Of these, THF, DMF and the like are preferable.

The reaction temperature is generally −100° C. to 150° C., preferably 0° C. to 100° C.

The reaction time is generally 5 min to 48 hr, preferably 30 min to 24 hr.

The "method employing the Mitsunobu reaction" can be carried out according to a method known per se, for example, the method described in Tetrahedron Letters, pages 769-770, 1980 or the like, or a method analogous thereto.

This reaction is carried out by reacting compound (8) with the compound $R^6OH$ in the presence of a hydroxy group-activator, in an inert solvent.

The amount of the above-mentioned "compound $R^6OH$" to be used is generally 1 to 10 equivalents, preferably 1 to 5 equivalents, relative to compound (8).

Examples of the above-mentioned "hydroxy group-activator" include cyanomethylenetri-n-butylphosphorane, a combination of diisopropyl azodicarboxylate and triphenylphosphine, and the like. The amount of the "hydroxy group-activator" to be used is generally 1 to 10 equivalents, preferably 1 to 5 equivalents, relative to compound (8).

Examples of the above-mentioned "inert solvent" include "aromatic solvents", "aliphatic hydrocarbon solvents", "ether solvents", "ester solvents", "amide solvents" and the like. These solvents may be used in a mixture of two or more kinds thereof mixed at an appropriate ratio.

The reaction temperature is generally −70 to 150° C., preferably −20 to 100° C.

The reaction time is generally 0.1 to 100 hr, preferably 0.1 to 48 hr.

Compound (10) can be produced, for example, by subjecting compound (9) to a deprotection reaction. The deprotection reaction can be carried out according to a method known per se, for example, the method described in Protective Groups in Organic Synthesis, John Wiley and Sons (1980) or the like.

Compound (I-1) can be produced, for example, by subjecting compound (10) to an acylation reaction.

The above-mentioned "acylation reaction" encompasses, for example, synthetic reactions of an amide derivative, a carbamate derivative and a urea derivative, and the like.

The production of the "amide derivative" is carried out by the following "method using a dehydration-condensation agent" or "method using a reactive derivative of carboxylic acid".

i) The Method Using a Dehydration-Condensation Agent

The reaction is carried out by reacting compound (10) with the corresponding carboxylic acid in the presence of a dehydration-condensation agent, in an inert solvent. This reaction may be carried out in the presence of a catalytic amount to 5 equivalents of a base, a catalytic amount to 5 equivalents of 1-hydroxybenzotriazole (HOBt), and the like, as necessary.

The amount of the above-mentioned "carboxylic acid" to be used is generally 0.5 to 5 equivalents, preferably 0.8 to 1.5 equivalents, relative to compound (10).

Examples of the above-mentioned "dehydration-condensation agent" include dicyclohexylcarbodiimide (DCC), 1-ethyl-3-(3-dimethylaminopropyl)carbodiimide hydrochloride (WSC) and the like. Of these, WSC is preferable. The amount of the "dehydration-condensation agent" to be used is generally 1 to 10 equivalents, preferably 1 to 5 equivalents, relative to compound (10).

Examples of the above-mentioned "inert solvent" include "nitrile solvents", "amide solvents", "halogenated hydrocarbon solvents", "ether solvents" and the like. These solvents may be used in a mixture of two or more kinds thereof mixed at an appropriate ratio. Of these, amide solvents are preferable.

Examples of the above-mentioned "base" include "aromatic amines", "tertiary amines" and the like.

The reaction temperature is generally −70 to 150° C., preferably −20 to 100° C.

The reaction time is generally 0.1 to 100 hr, preferably 1 to 48 hr.

ii) The Method Using a Reactive Derivative of Carboxylic Acid

The reaction is carried out by reacting compound (10) with 0.5 to 5 equivalents (preferably 0.8 to 3 equivalents) of the corresponding reactive derivative of carboxylic acid in an inert solvent. This reaction may be carried out in the presence of 1 to 10 equivalents, preferably 1 to 3 equivalents, of a base, as necessary.

Examples of the above-mentioned "reactive derivative of carboxylic acid" include acid halides (e.g., acid chlorides, acid bromides), mixed anhydrides (e.g., acid anhydrides with a $C_{1-6}$ alkyl-carboxylic acid, a $C_{6-10}$ aryl-carboxylic acid, a $C_{1-6}$ alkyl-carbonic acid or the like), activated esters (e.g., esters with a phenol optionally having substituent(s), HOBt, N-hydroxysuccinimide or the like), activated amides (e.g., amides with imidazole, triazole or the like) and the like.

Examples of the above-mentioned "phenol optionally having substituent(s)" include phenols such as phenol, pentachlorophenol, pentafluorophenol, p-nitrophenol and the like.

The above-mentioned "reactive derivative of carboxylic acid" is preferably an acid anhydride.

Examples of the above-mentioned "inert solvent" include "ether solvents", "halogenated hydrocarbon solvents", "aromatic solvents", "aliphatic hydrocarbon solvents", "nitrile solvents", "amide solvents", "sulfoxide solvents" and the like. These solvents may be used in a mixture of two or more kinds thereof mixed at an appropriate ratio. Of these, pyridine, acetonitrile, THF, dichloromethane, chloroform and the like are preferable.

Examples of the above-mentioned "base" include "aromatic amines", "tertiary amines" and the like.

The reaction temperature is generally −20 to 100° C., preferably −20° C. to 50° C.

The reaction time is generally 5 min to 40 hr, preferably 30 min to 18 hr.

The production of the above-mentioned "carbamate derivative" is carried out by reacting compound (10) with 0.5 to 5 equivalents (preferably 0.8 to 3 equivalents) of the corresponding dicarbonate or chloroformate in an inert solvent. This reaction may be carried out in the presence of 1 to 10 equivalents, preferably 1 to 3 equivalents, of a base, as necessary.

Examples of the above-mentioned "inert solvent" include "ether solvents", "halogenated hydrocarbon solvents", "aromatic solvents", "aliphatic hydrocarbon solvents", "nitrile solvents", "amide solvents" and the like. These solvents may be used in a mixture of two or more kinds thereof mixed at an appropriate ratio. Of these, pyridine, acetonitrile, THF, DMF, dichloromethane, chloroform and the like are preferable.

Examples of the above-mentioned "base" include "aromatic amines", "tertiary amines" and the like.

The reaction temperature is generally −20 to 100° C., preferably −20° C. to 50° C.

The reaction time is generally 5 min to 40 hr, preferably 30 min to 18 hr.

The production of the above-mentioned "urea derivative" is carried out by reacting compound (10) with 0.5 to 5 equivalents (preferably 0.8 to 3 equivalents) of the corresponding isocyanate or carbamoyl chloride derivative in an inert solvent. This reaction may be carried out in the presence of a catalytic amount to 5 equivalents a base, as necessary.

Examples of the above-mentioned "inert solvent" include "ether solvents", "halogenated hydrocarbon solvents", "aromatic solvents", "aliphatic hydrocarbon solvents", "nitrile solvents", "amide solvents" and the like. These solvents may be used in a mixture of two or more kinds thereof mixed at an appropriate ratio. Of these, pyridine, acetonitrile, THF, DMF, dichloromethane, chloroform and the like are preferable.

Examples of the above-mentioned "base" include "aromatic amines", "tertiary amines" and the like.

The reaction temperature is generally −20 to 100° C., preferably −20° C. to 50° C.

The reaction time is generally 5 min to 40 hr, preferably 30 min to 18 hr.

Compound (3), compound (4) and compound (7) can be produced according to a method known per se.

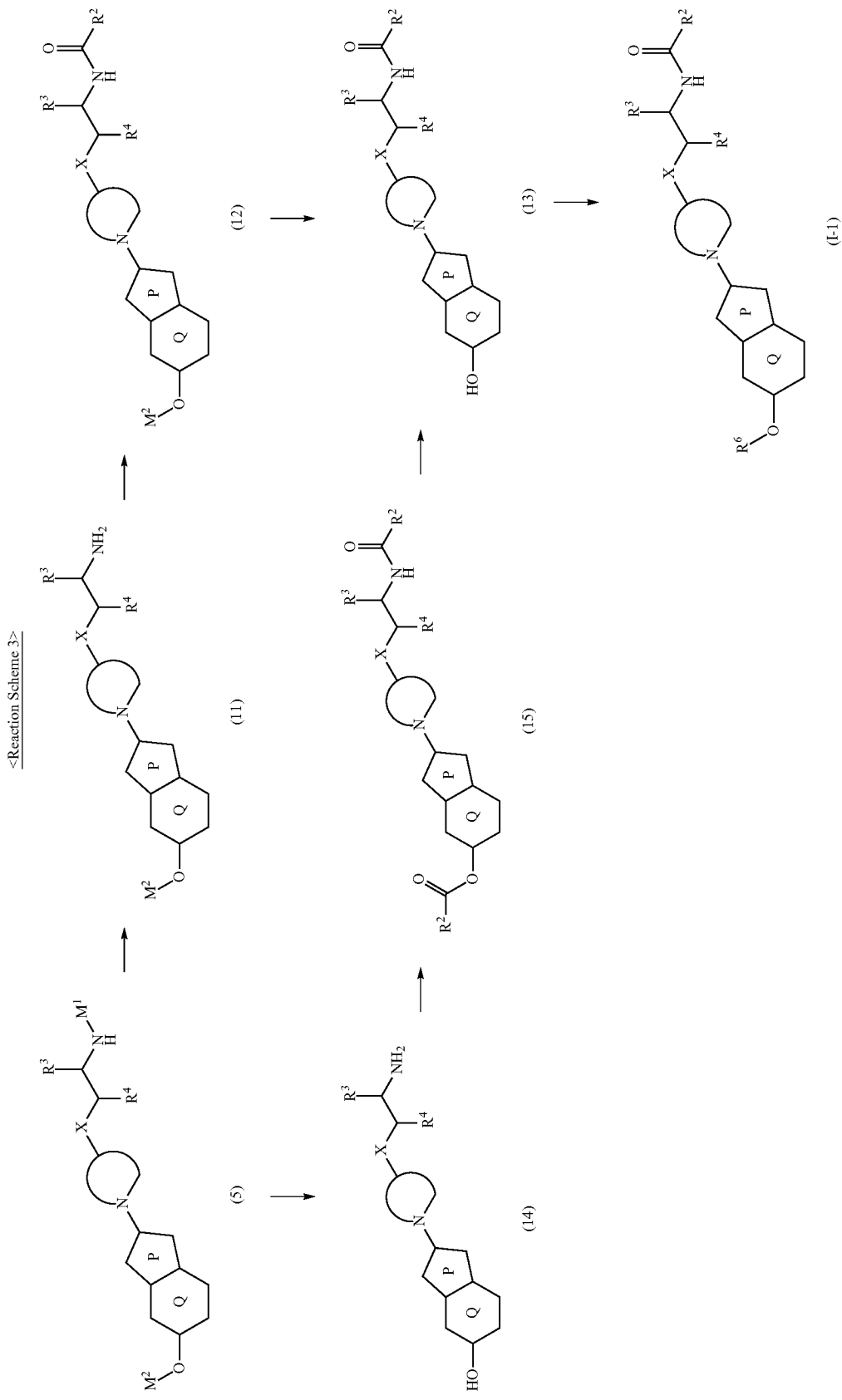

wherein each symbol is as defined above.

Compound (11) can be produced, for example, by subjecting compound (5) to a deprotection reaction. The deprotection reaction can be carried out according to a method known per se, for example, the method described in Protective Groups in Organic Synthesis, John Wiley and Sons (1980) or the like.

Compound (12) can be produced, for example, by subjecting compound (11) to an acylation reaction.

This reaction is carried out in the same manner as in the production method of compound (I-1) in Reaction Scheme 2.

Compound (14) can be produced, for example, by subjecting compound (5) to a deprotection reaction. The deprotection reaction can be carried out according to a method known per se, for example, the method described in Protective Groups in Organic Synthesis, John Wiley and Sons (1980) or the like.

Compound (15) can be produced, for example, by subjecting compound (14) to an amidation reaction.

The above-mentioned "amidation reaction" is carried out in the same manner as in the production method of the "amide derivative" described as one of the production methods of compound (I-1) in Reaction Scheme 2.

Compound (13) can be produced, for example, by subjecting compound (12) to a deprotection reaction. The deprotection reaction can be carried out according to a method known per se, for example, the method described in Protective Groups in Organic Synthesis, John Wiley and Sons (1980) or the like.

Compound (13) can also be produced, for example, by subjecting compound (15) to a deacylation reaction.

This reaction is carried out by reacting compound (15) with a base in an inert solvent.

Examples of the above-mentioned "base" include "inorganic bases" and the like. The amount of the "base" to be used is generally 1 to 10 equivalents, preferably 1 to 1.5 equivalents, relative to compound (15).

Examples of the above-mentioned "inert solvent" include "alcohol solvents", "nitrile solvents", "aromatic solvents", "aliphatic hydrocarbon solvents", "ether solvents", "amide solvents", "halogenated hydrocarbon solvents" and the like. These solvents are preferably used in a mixture with water at an appropriate ratio. Of these, "alcohol solvents" containing water are preferable.

The reaction temperature is generally −78° C. to 150° C., preferably −20° C. to 100° C.

The reaction time is generally 5 min to 100 hr, preferably 30 min to 48 hr.

The production method of compound (13) by a deacylation reaction of compound (15) can also be carried out according to a method known per se, for example, the method described in Protective Groups in Organic Synthesis, John Wiley and Sons (1980) or the like.

Compound (I-1) can be produced by, for example, by subjecting compound (13) to an alkylation reaction.

This reaction is carried out in the same manner as in the method of producing compound (9) by an alkylation reaction of compound (8), as shown in Reaction Scheme 2.

Compound (5) can be produced according to the method described in Reaction Scheme (2).

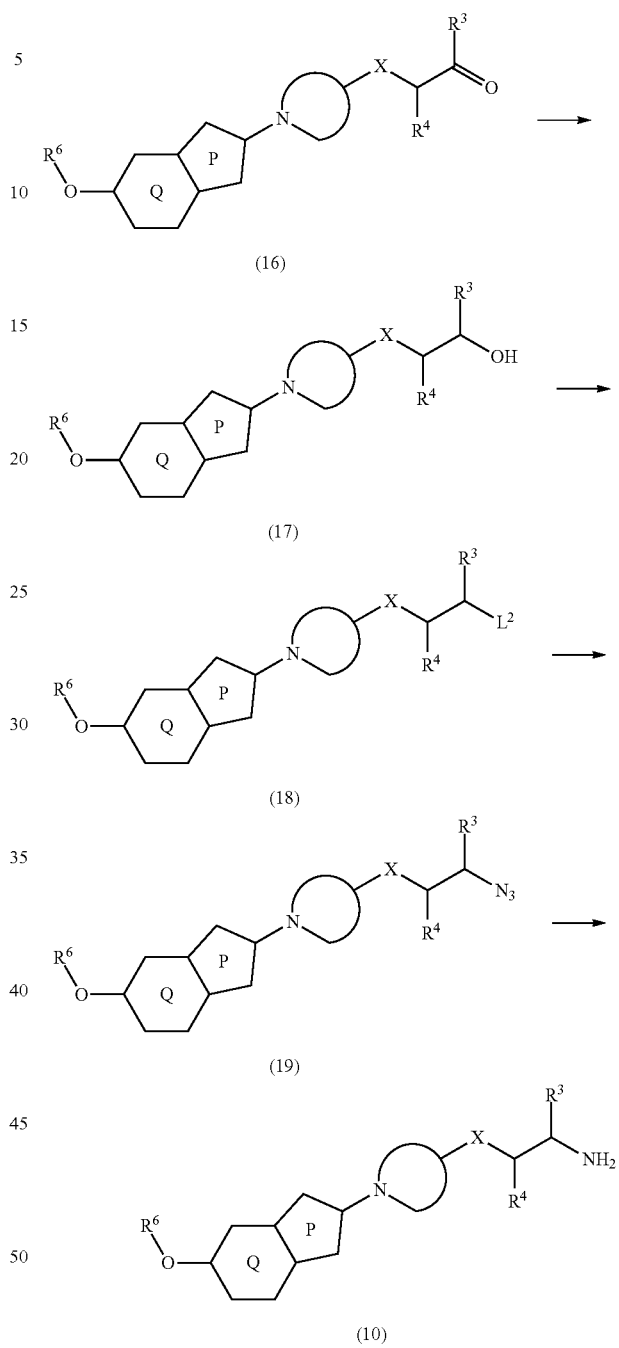

wherein $L^2$ is a sulfonyloxy group, and the other symbols are as defined above.

Compound (16) is the same compound as compound (29).

Compound (17) can be produced, for example, by subjecting compound (16) to a reduction reaction.

This reaction is carried out by reacting compound (16) with a reducing agent in an inert solvent.

Examples of the above-mentioned "reducing agent" include metal hydrides (e.g., diisobutylaluminum hydride), metal hydride complex compounds (e.g., sodium borohydride, sodium cyanoborohydride, lithium aluminum hydride, sodium aluminum hydride, sodium bis(2-methoxyethoxy)

aluminum hydride) and the like. The amount of the "reducing agent" to be used is generally 0.1 to 20 equivalents, preferably 1 to 5 equivalents, relative to compound (16).

Examples of the above-mentioned "inert solvent" include "alcohol solvents", "aromatic solvents", "aliphatic hydrocarbon solvents", "ether solvents", "amide solvents", "halogenated hydrocarbon solvents" and the like. These solvents may be used in a mixture of two or more kinds thereof mixed at an appropriate ratio. Of these, THF, ethanol, methanol and the like are preferable.

The reaction temperature is generally −78° C. to 150° C., preferably −20° C. to 100° C.

The reaction time is generally 5 min to 48 hr, preferably 30 min to 24 hr.

Compound (18) can be produced, for example, by subjecting compound (17) to a sulfonylation reaction.

This reaction is carried out by reacting compound (17) with a sulfonylating agent in the presence of a base, in an inert solvent.

Examples of the above-mentioned "sulfonylating agent" include methanesulfonyl chloride, p-toluenesulfonyl chloride and the like. The amount of the "sulfonylating agent" to be used is generally 1 to 10 equivalents, preferably 1 to 1.5 equivalents, relative to compound (17).

Examples of the above-mentioned "base" include "aromatic amines", "tertiary amines" and the like. The amount of the "base" to be used is generally 1 to 20 equivalents, preferably 1 to 10 equivalents, relative to compound (17).

Examples of the above-mentioned "inert solvent" include "aromatic solvents", "aliphatic hydrocarbon solvents", "ether solvents", "ester solvents", "amide solvents" and the like. These solvents may be used in a mixture of two or more kinds thereof mixed at an appropriate ratio.

The reaction temperature is generally −70 to 150° C., preferably −20 to 100° C.

The reaction time is generally 0.1 to 100 hr, preferably 0.1 to 48 hr.

Compound (19) can be produced, for example, by subjecting compound (18) to an azidation reaction.

This reaction is carried out by reacting compound (18) with an azidating agent in an inert solvent.

Examples of the above-mentioned "azidating agent" include sodium azide, lithium azide, trimethylsilyl azide and the like. The amount of the "azidating agent" to be used is generally 1 to 20 equivalents, preferably 1 to 10 equivalents, relative to compound (18).

Examples of the above-mentioned "inert solvent" include "ether solvents", "amide solvents", "sulfoxide solvents" and the like. These solvents may be used in a mixture of two or more kinds thereof mixed at an appropriate ratio.

The reaction temperature is generally −70 to 200° C., preferably 0 to 150° C.

The reaction time is generally 0.1 to 100 hr, preferably 0.1 to 48 hr.

Compound (10) can be produced, for example, by subjecting compound (19) to a reduction reaction.

This reaction can be carried out by reacting compound (19) in the presence of a metal catalyst and a hydrogen source, in an inert solvent.

Examples of the above-mentioned "metal catalyst" include reduced iron, palladium-carbon, palladium black, palladium chloride, platinum oxide, platinum black, Raney-nickel, Raney-cobalt and the like. The amount of the "metal catalyst" to be used is generally 0.001 to 100 equivalents, preferably 0.01 to 10 equivalents, relative to compound (19).

Examples of the above-mentioned "hydrogen source" include hydrogen gas, formic acid, formic acid amine salt, phosphinate, hydrazine and the like.

Examples of the above-mentioned "inert solvent" include "alcohol solvents", "ester solvents", "ether solvents", "amide solvents", "halogenated hydrocarbon solvents", "organic acid solvents" and the like. These solvents are preferably used in a mixture with water at an appropriate ratio. Of these, "alcohol solvents" are preferable.

The reaction temperature is generally −70 to 150° C., preferably −20 to 100° C.

The reaction time is generally 0.1 to 100 hr, preferably 0.1 to 48 hr.

This reaction can also be carried out by reacting compound (19) with triphenylphosphine and water in an inert solvent.

The amount of the above-mentioned "triphenylphosphine" to be used is generally 1 to 10 equivalents, preferably 1 to 5 equivalents, relative to compound (19).

Examples of the above-mentioned "inert solvent" include "aromatic solvents", "aliphatic hydrocarbon solvents", "ether solvents", "amide solvents", "sulfoxide solvents", "halogenated hydrocarbon solvents" and the like. These solvents are preferably used in a mixture with water at an appropriate ratio. Of these, "ether solvents" is preferable.

The reaction temperature is generally −70 to 150° C., preferably −20 to 100° C.

The reaction time is generally 0.1 to 100 hr, preferably 0.1 to 40 hr.

Compound (16) can be produced according to a method known per se.

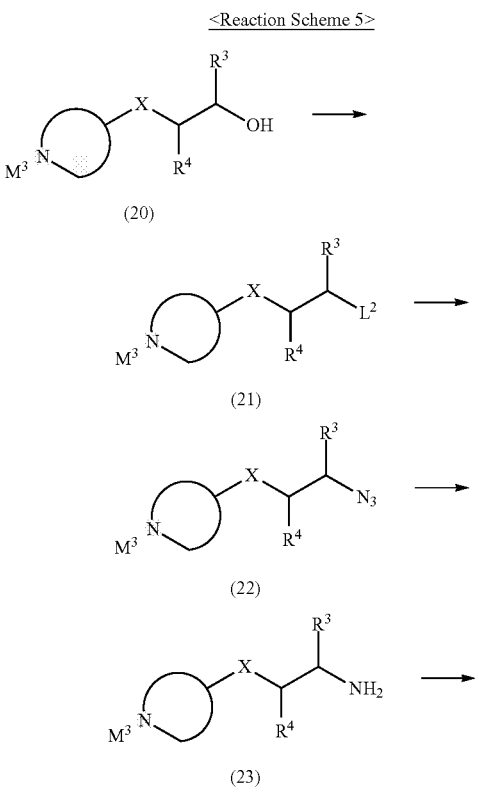

<Reaction Scheme 5>

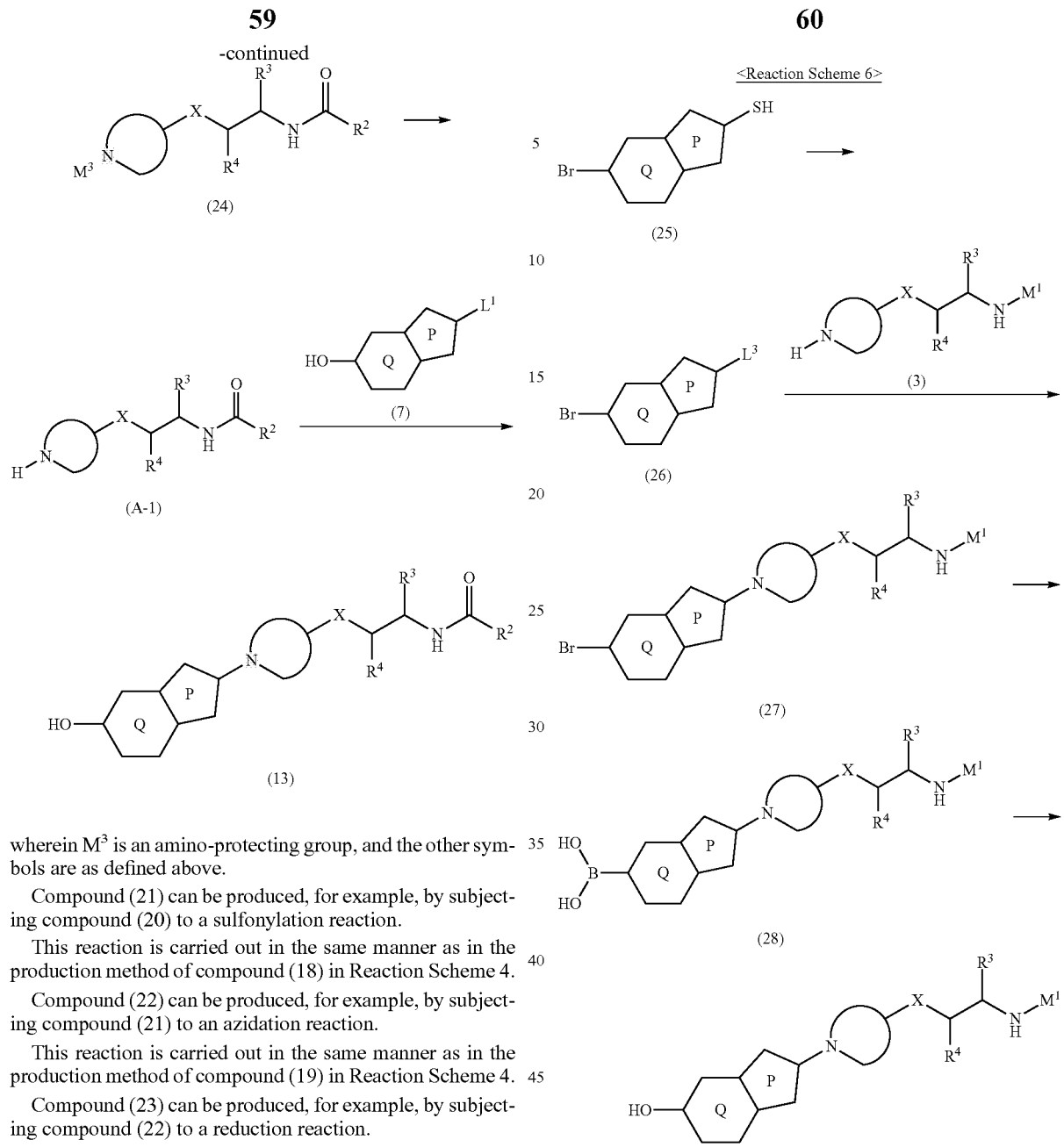

wherein $M^3$ is an amino-protecting group, and the other symbols are as defined above.

Compound (21) can be produced, for example, by subjecting compound (20) to a sulfonylation reaction.

This reaction is carried out in the same manner as in the production method of compound (18) in Reaction Scheme 4.

Compound (22) can be produced, for example, by subjecting compound (21) to an azidation reaction.

This reaction is carried out in the same manner as in the production method of compound (19) in Reaction Scheme 4.

Compound (23) can be produced, for example, by subjecting compound (22) to a reduction reaction.

This reaction is carried out in the same manner as in the production method of compound (10) in Reaction Scheme 4.

Compound (24) can be produced, for example, by subjecting compound (23) to an acylation reaction.

This reaction is carried out in the same manner as in the production method of compound (I-1) in Reaction Scheme 2.

Compound (A-1) can be produced, for example, by subjecting compound (24) to a deprotection reaction. The deprotection reaction can be carried out according to a method known per se, for example, the method described in Protective Groups in Organic Synthesis, John Wiley and Sons (1980) or the like.

Compound (13) can be produced, for example, by reacting compound (A-1) with compound (7).

This reaction is carried out in the same manner as in the production method of compound (I-A) in Reaction Scheme 1.

Compound (20) can be produced according to a method known per se.

wherein $L^3$ is a halogen atom or a $C_{1-6}$ alkylsulfanyl group, and the other symbols are as defined above.

Compound (26) can be produced, for example, by subjecting compound (25) to a halogenation or alkylation reaction.

The above-mentioned "halogenation reaction" is carried out by reacting compound (25) with a halogenating agent in an inert solvent or without solvent.

Examples of the above-mentioned "halogenating agent" include thionyl chloride and the like. The amount of the "halogenating agent" to be used is generally 1 equivalent to an excess amount, relative to compound (25).

Examples of the above-mentioned "inert solvent" include "aliphatic hydrocarbon solvents", "aromatic solvents", "halogenated hydrocarbon solvents", "ether solvents" and the like. These solvents may be used in a mixture of two or more kinds thereof mixed at an appropriate ratio.

The reaction temperature is generally −100° C. to 200° C., preferably −20° C. to 150° C.

The reaction time is generally 1 min to 100 hr, preferably 5 min to 72 hr.

The above-mentioned "alkylation reaction" is carried out by reacting compound (25) with the corresponding alkylating agent in an inert solvent. A base may be used as necessary.

Examples of the above-mentioned "alkylating agent" include methyl iodide, dimethylsulfuric acid, diazomethane, trimethylsilyldiazomethane, ethyl iodide and the like. The amount of the "alkylating agent" to be used is generally 1 to 10 equivalents, preferably 1 to 5 equivalents, relative to compound (25).

Examples of the above-mentioned "base" include "inorganic bases", "basic salts", "aromatic amines", "tertiary amines", "hydrides of alkali metal or alkaline earth metal", "alkyl metals", "metal alkoxides" and the like. The amount of the "base" to be used is generally 1 to 10 equivalents, preferably 1 to 5 equivalents, relative to compound (25).

Examples of the above-mentioned "inert solvent" include "amide solvents", "nitrile solvents", "aliphatic hydrocarbon solvents", "aromatic solvents", "halogenated hydrocarbon solvents", "alcohol solvents", "ether solvents" and the like. These solvents may be used in a mixture of two or more kinds thereof mixed at an appropriate ratio.

The reaction temperature is generally −100° C. to 200° C., preferably −20° C. to 100° C.

The reaction time is generally 5 min to 48 hr, preferably 5 min to 24 hr.

Compound (27) can be produced, for example, by reacting compound (26) with compound (3).

This reaction is carried out in the same manner as in the production method of compound (I-A) in Reaction Scheme 1.

Compound (28) can be produced, for example, by subjecting compound (27) to a boronation reaction.

The above-mentioned "boronation reaction" is carried out by converting the bromine atom of compound (27) to a metal atom using an alkyl metal in an inert solvent, and then reacting the resulting compound with an organic boron compound.

Examples of the above-mentioned "alkyl metal" include alkyllithium, alkylmagnesium halide and the like. The amount of the "alkyl metal" to be used is generally 1 to 10 equivalents, relative to compound (27).

Examples of the above-mentioned "organic boron compound" include trialkylborane, trialkoxyborane and the like. The amount of the "organic boron compound" to be used is generally 2 to 10 equivalents, relative to compound (27).

Examples of the above-mentioned "inert solvent" include "aliphatic hydrocarbon solvents", "aromatic solvents", "ether solvents" and the like. These solvents may be used in a mixture of two or more kinds thereof mixed at an appropriate ratio.

The reaction temperature is generally −100° C. to 200° C., preferably −100° C. to 100° C.

The reaction time is generally 1 min to 48 hr, preferably 5 min to 24 hr.

Compound (8) can be produced, for example, by subjecting compound (28) to an oxidation reaction.

The above-mentioned "oxidation reaction" is carried out by reacting compound (28) with an oxidant in an inert solvent. A base may be used as necessary.

Examples of the above-mentioned "oxidant" include oxygen, hydrogen peroxide, organic peroxides (e.g., m-chloroperbenzoic acid), inorganic peroxides (e.g., sodium perborate) and the like. The amount of the "oxidant" to be used is generally 1 to 10 equivalents, relative to compound (28).

Examples of the above-mentioned "base" include "inorganic bases" and the like. The amount of the "base" to be used is generally 1 to 100 equivalents, preferably 1 to 50 equivalents, relative to compound (28).

Examples of the above-mentioned "inert solvent" include water, "aliphatic hydrocarbon solvents", "aromatic solvents", "ether solvents" and the like. These solvents may be used in a mixture of two or more kinds thereof mixed at an appropriate ratio.

The reaction temperature is generally −100° C. to 200° C., preferably −100° C. to 100° C.

The reaction time is generally 1 min to 48 hr, preferably 5 min to 24 hr.

Compound (25) can be produced according to a method known per se.

<Reaction Scheme 7>

(29)

(I-2)

wherein $R^{1a}$ is an optionally substituted 5- or 6-membered aromatic heterocyclic group or an optionally substituted phenyl group, and the other symbols are as defined above.

Compound (29) is the same compound as compound (16).

Compound (I-2) can be produced, for example, by subjecting compound (29) to a reductive amination reaction.

The reductive amination reaction can be carried out according to a method known per se, for example, the method described in Tetrahedron Letters, pages 8345-8349, 2001 or the like, or a method analogous thereto.

This reaction is carried out by reacting compound (29) with the compound $R^{1a}NH_2$ in the presence of a reducing agent, in an inert solvent. This reaction may be carried out in the presence of 1 equivalent to an excess amount of an organic acid, as necessary.

The amount of the above-mentioned "compound $R^{1a}NH_2$" to be used is generally 1 to 5 equivalents, preferably 1 to 4 equivalents, relative to compound (29).

Examples of the above-mentioned "reducing agent" include metal hydrides (e.g., diisobutylaluminum hydride), metal hydride complex compounds (e.g., sodium bis(2-methoxyethoxy)aluminum hydride, sodium borohydride, sodium cyanoborohydride, sodium triacetoxyborohydride, lithium aluminum hydride, sodium aluminum hydride), decaborane and the like. The amount of the "reducing agent" to be used is generally 0.1 to 20 equivalents, preferably 1 to 5 equivalents, relative to compound (29).

Examples of the above-mentioned "inert solvent" include "alcohol solvents", "amide solvents", "halogenated hydrocarbon solvents", "ester solvents", "ether solvents" and the like. These solvents may be used in a mixture of two or more kinds thereof mixed at an appropriate ratio. Of these, methanol, THF, dichloroethane, dichloromethane and the like are preferable.

Examples of the above-mentioned "organic acid" include acetic acid and the like.

The reaction temperature is generally −78° C. to 100° C., preferably −20° C. to 50° C.

The reaction time is generally 5 min to 48 hr, preferably 30 min to 24 hr.

Compound (29) can be produced according to a method known per se.

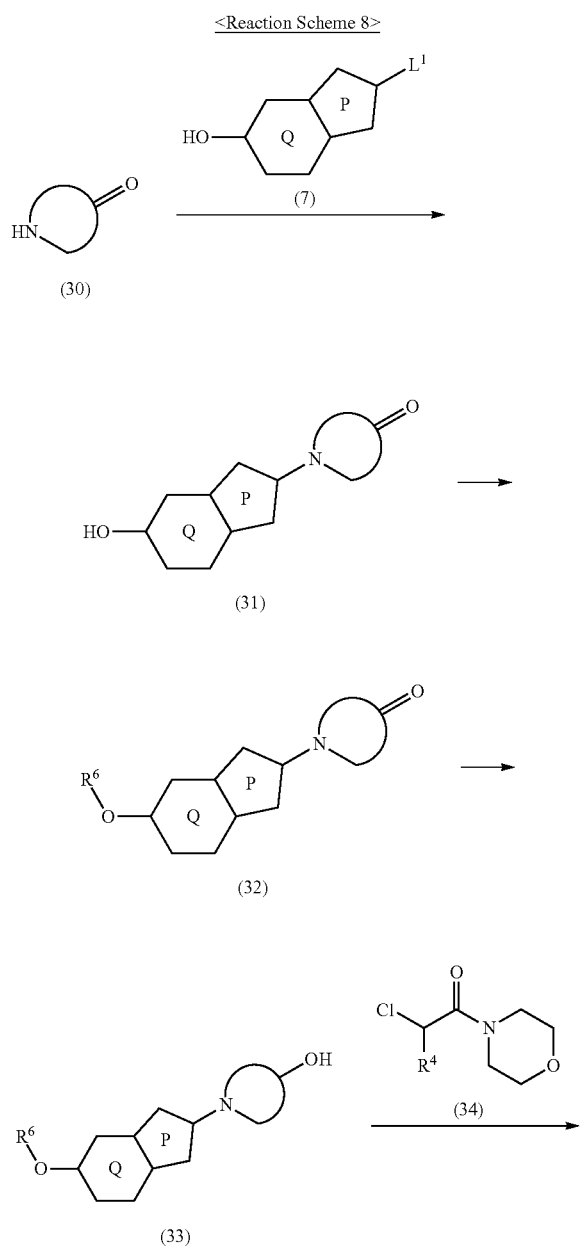

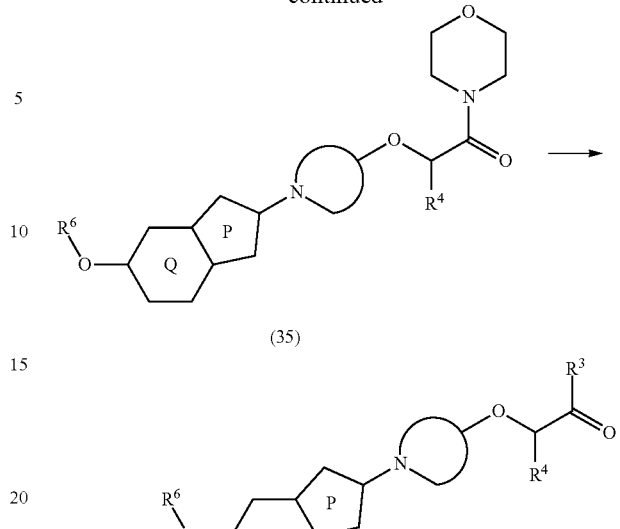

wherein each symbol is as defined above.

Compound (31) can be produced, for example, by reacting compound (7) with compound (30).

This reaction is carried out in the same manner as in the production method of compound (I-A) in Reaction Scheme 1.

Compound (32) can be produced, for example, by subjecting compound (31) to an alkylation reaction.

This reaction is carried out in the same manner as in the method of producing compound (9) by an alkylation reaction of compound (8), as shown in Reaction Scheme 2.

Compound (33) can be produced, for example, by subjecting compound (32) to a reduction reaction.

This reaction is carried out by reacting compound (32) with a reducing agent in an inert solvent.

Examples of the above-mentioned "reducing agent" include metal hydrides (e.g., diisobutylaluminum hydride), metal hydride complex compounds (e.g., sodium borohydride, sodium cyanoborohydride, lithium aluminum hydride, sodium aluminum hydride, sodium bis(2-methoxyethoxy) aluminum hydride) and the like. The amount of the "reducing agent" to be used is generally 0.1 to 20 equivalents, preferably 1 to 5 equivalents, relative to compound (32).

Examples of the above-mentioned "inert solvent" include "alcohol solvents", "aromatic solvents", "aliphatic hydrocarbon solvents", "ether solvents", "amide solvents", "halogenated hydrocarbon solvents" and the like. These solvents may be used in a mixture of two or more kinds thereof mixed at an appropriate ratio. Of these, THF, ethanol, methanol and the like are preferable.

The reaction temperature is generally −78° C. to 150° C., preferably −20° C. to 100° C.

The reaction time is generally 5 min to 48 hr, preferably 30 min to 24 hr.

Compound (35) can be produced, for example, by reacting compound (33) with compound (34) in the presence of a base, in an inert solvent. This reaction may be carried out in the presence of a phase-transfer catalyst, as necessary.

The amount of compound (34) to be used is generally 1 to 5 equivalents, preferably 1 to 3 equivalents, relative to compound (33).

Examples of the above-mentioned "base" include "inorganic bases", "basic salts", "aromatic amines", "tertiary amines", "hydrides of alkali metal or alkaline earth metal", "metal alkoxides" and the like. The amount of the "base" to be used is generally 1 to 10 equivalents, preferably 1 to 5 equivalents, relative to compound (33).

Examples of the above-mentioned "phase-transfer catalyst" include quaternary ammonium salts (e.g., tetrabutylammonium bromide, benzyltrioctylammonium chloride, tetrabutylammonium hydrogensulfate) and the like. The amount of the "phase-transfer catalyst" to be used is generally 0.001 to 10 equivalents, preferably 0.01 to 1 equivalent, relative to compound (33).

Examples of the above-mentioned "inert solvent" include "aromatic solvents", "nitrile solvents", "amide solvents", "halogenated hydrocarbon solvents", "ether solvents", "alcohol solvents" and the like. These solvents are preferably used in a mixture with water or a mixture of two or more kinds thereof mixed at an appropriate ratio. Of these, THF, DMF and the like are preferable.

The reaction temperature is generally −100° C. to 200° C., preferably 0° C. to 150° C.

The reaction time is generally 5 min to 48 hr, preferably 30 min to 24 hr.

Compound (29-1) can be produced, for example, by reacting compound (35) with the corresponding organic metal reagent in an inert solvent.

Examples of the above-mentioned "organic metal reagent" include Grignard reagents (e.g., methylmagnesium bromide, methylmagnesium chloride), organic lithium reagents (e.g., methyllithium) and the like. The amount of the "organic metal reagent" to be used is generally 0.1 to 20 equivalents, preferably 1 to 5 equivalents, relative to compound (35).

Examples of the above-mentioned "inert solvent" include "aromatic solvents", "aliphatic hydrocarbon solvents", "ether solvents" and the like. These solvents may be used in a mixture of two or more kinds thereof mixed at an appropriate ratio. Of these, THF and the like are preferable.

The reaction temperature is generally −78° C. to 150° C., preferably −20° C. to 100° C.

The reaction time is generally 5 min to 48 hr, preferably 30 min to 24 hr.

Compound (30) and compound (34) can be produced according to a method known per se.

<Reaction Scheme 9>

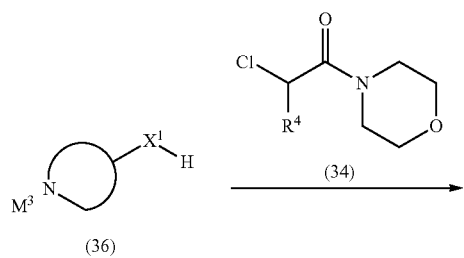

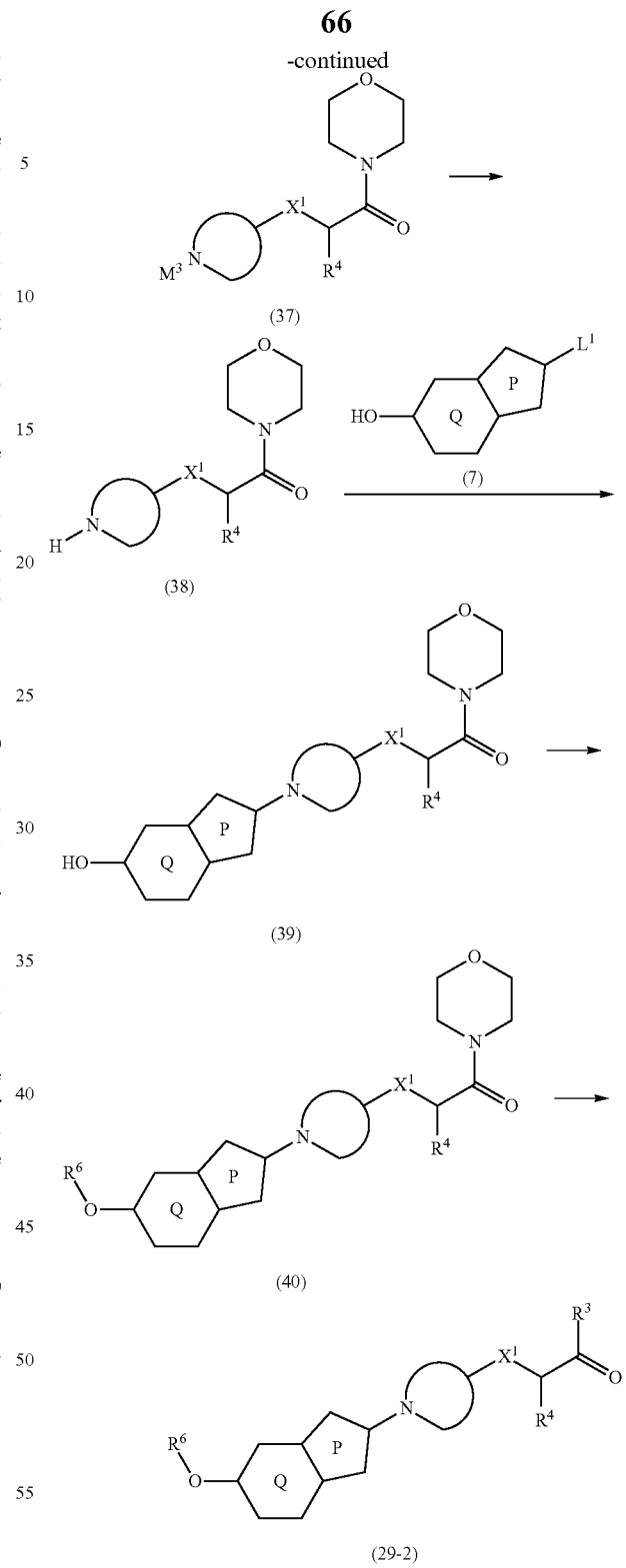

wherein $X^1$ is an oxygen atom, an optionally oxidized sulfur atom or an optionally substituted nitrogen atom, and the other symbols are as defined above.

Compound (37) can be produced, for example, by reacting compound (34) with compound (36) in the presence of a base, in an inert solvent.

This reaction is carried out in the same manner as in the production method of compound (35) in Reaction Scheme 8.

Compound (38) can be produced, for example, by subjecting compound (37) to a deprotection reaction. The deprotection reaction can be carried out according to a method known per se, for example, the method described in Protective Groups in Organic Synthesis, John Wiley and Sons (1980) or the like.

Compound (39) can be produced, for example, by reacting compound (38) with compound (7).

This reaction is carried out in the same manner as in the production method of compound (I-A) in Reaction Scheme 1.

Compound (40) can be produced, for example, compound (39) by subjecting to an alkylation reaction.

This reaction is carried out in the same manner as in the method of producing compound (9) by an alkylation reaction of compound (B), as shown in Reaction Scheme 2.

Compound (29-2) can be produced, for example, by reacting compound (40) with the corresponding organic metal reagent in an inert solvent.

This reaction is carried out in the same manner as in the production method of compound (29-1) in Reaction Scheme 8.

Compound (36) can be produced according to a method known per se.

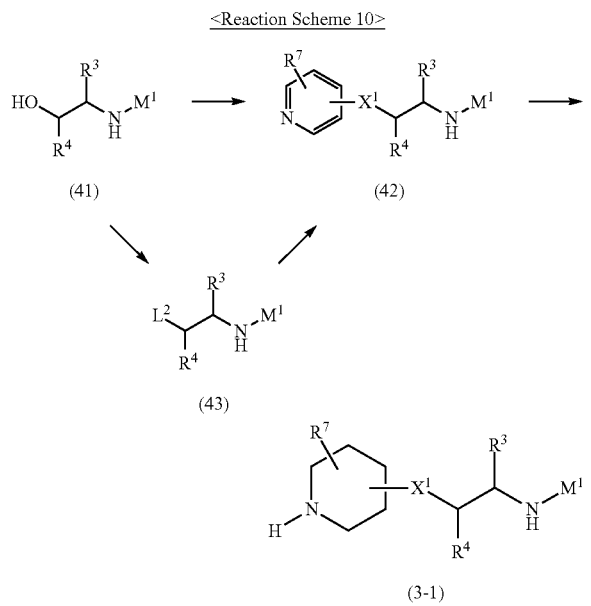

wherein 0 to 4 of $R^7$ are the same or different and each is a substituent, and the other symbols are as defined above.

Compound (42) can be produced, for example, by subjecting compound (41) to the Mitsunobu reaction.

The above-mentioned "Mitsunobu reaction" can be carried out according to a method known per se, for example, the method described in Tetrahedron Letters, pages 769-770, 1980% or the like, or a method analogous thereto.

This reaction is carried out by reacting compound (41) with an aminopyridine, mercaptopyridine or hydroxypyridine, each of which is optionally substituted, in the presence of an activator, in an inert solvent.

The amount of the above-mentioned "aminopyridine, mercaptopyridine or hydroxypyridine, each of which is optionally substituted" to be used is generally 1 to 10 equivalents, preferably 1 to 5 equivalents, relative to compound (41).

Examples of the above-mentioned "activator" include cyanomethylenetri-n-butylphosphorane, a combination of diisopropyl azodicarboxylate and triphenylphosphine, and the like. The amount of the "activator" to be used is generally 1 to 10 equivalents, preferably 1 to 5 equivalents, relative to compound (41).

Examples of the above-mentioned "inert solvent" include "aromatic solvents", "aliphatic hydrocarbon solvents", "ether solvents", "ester solvents", "amide solvents" and the like. These solvents may be used in a mixture of two or more kinds thereof mixed at an appropriate ratio.

The reaction temperature is generally −70 to 150° C., preferably −20 to 100° C.

The reaction time is generally 0.1 to 100 hr, preferably 0.1 to 40 hr.

Compound (43) can be produced, for example, by subjecting compound (41) to a sulfonylation reaction.

This reaction is carried out in the same manner as in the production method of compound (18) in Reaction Scheme 4.

Compound (42) can also be produced, for example, by reacting compound (43) with an aminopyridine, mercaptopyridine or hydroxypyridine, each of which is optionally substituted.

This reaction is carried out by reacting compound (43) with an aminopyridine, mercaptopyridine or hydroxypyridine, each of which is optionally substituted, in the presence of a base, in an inert solvent.

The amount of the above-mentioned "aminopyridine, mercaptopyridine or hydroxypyridine, each of which is optionally substituted" to be used is generally 1 to 10 equivalents, preferably 1 to 5 equivalents, relative to compound (43).

Examples of the above-mentioned "base" include "inorganic bases", "basic salts", "aromatic amines", "tertiary amines", "hydrides of alkali metal or alkaline earth metal", "metal alkoxides" and the like. The amount of the "base" to be used is generally 1 to 10 equivalents, preferably 1 to 5 equivalents, relative to compound (43).

Examples of the above-mentioned "inert solvent" include "nitrile solvents", "amide solvents", "halogenated hydrocarbon solvents", "ether solvents", "alcohol solvents" and the like. These solvents are preferably used in a mixture with water or a mixture of two or more kinds thereof mixed at an appropriate ratio. Of these, THF, DMF and the like are preferable.

The reaction temperature is generally −100° C. to 150° C., preferably 0° C. to 100° C.

The reaction time is generally 5 min to 48 hr, preferably 30 min to 24 hr.

Compound (3-1) can be produced, for example, by subjecting compound (42) to a reduction reaction.

This reaction is carried out by reacting compound (42) in the presence of a metal catalyst and a hydrogen source, in an inert solvent. This reaction may be carried out in the presence of a catalytic amount to an excess amount of an organic acid or 1 to 50 equivalents of hydrogen chloride, as necessary.

Examples of the above-mentioned "metal catalyst" include palladium-carbon, palladium black, palladium chloride, rhodium-carbon, platinum oxide, platinum black, platinum-palladium, Raney-nickel, Raney-cobalt and the like. The amount of the "metal catalyst" to be used is generally 0.001 to 1000 equivalents, preferably 0.01 to 100 equivalents, relative to compound (42).

Examples of the above-mentioned "hydrogen source" include hydrogen gas and the like.

Examples of the above-mentioned "organic acid" include acetic acid and the like.

Examples of the above-mentioned "inert solvent" include "alcohol solvents", "nitrile solvents", "aromatic solvents", "aliphatic hydrocarbon solvents", "ether solvents", "amide solvents", "halogenated hydrocarbon solvents", "organic acid solvents" and the like. These solvents are preferably used in a mixture with water at an appropriate ratio. Of these, "alcohol solvents" are preferable.

The reaction temperature is generally −70 to 150° C., preferably −20 to 100° C.

The reaction time is generally 0.1 to 100 hr, preferably 0.1 to 40 hr.

The sulfone derivative or sulfoxide derivative, which is a compound (42) or compound (3-1) wherein $X^1$ is an oxidized sulfur atom, can be produced by subjecting compound (42) or compound (3-1) wherein $X^1$ is a sulfur atom to an oxidation reaction.

This reaction is carried out according to the method described in 4th Edition Jikken Kagaku Kouza 20 (The Chemical Society of Japan ed.), pages 276-278, 503, or a method analogous thereto.

Compound (41) can be produced according to a method known per se.

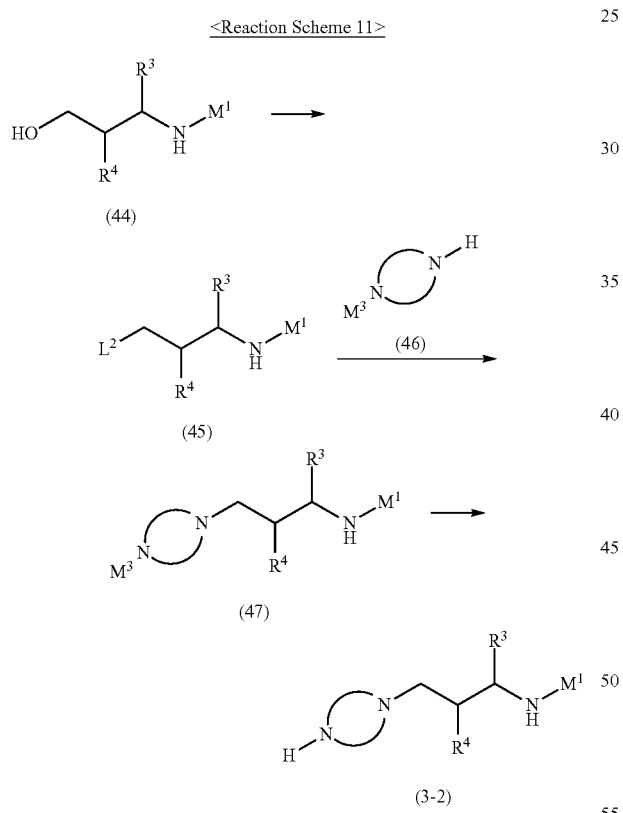

wherein each symbol is as defined above.

Compound (45) can be produced, for example, by subjecting compound (44) to a sulfonylation reaction.

This reaction is carried out in the same manner as in the production method of compound (18) in Reaction Scheme 4.

Compound (47) can be produced, for example, by reacting compound (45) with compound (46).

This reaction is carried out by reacting compound (45) with compound (46) in the presence of a base, in an inert solvent. The reaction may be carried out under microwave irradiation, as necessary.

The amount of compound (46) to be used is generally 1 to 10 equivalents, preferably 1 to 5 equivalents, relative to compound (45).

Examples of the above-mentioned "base" include "inorganic bases", "basic salts", "aromatic amines", "tertiary amines", "hydrides of alkali metal or alkaline earth metal" and the like. The amount of the "base" to be used is generally 1 to 10 equivalents, preferably 1 to 5 equivalents, relative to compound (45).

Examples of the above-mentioned "inert solvent" include "nitrile solvents", "amide solvents", "halogenated hydrocarbon solvents", "ether solvents" and the like. These solvents may be used in a mixture of two or more kinds thereof mixed at an appropriate ratio. Of these, THF, DMF and the like are preferable.

The reaction temperature is generally −100° C. to 200° C., preferably 0° C. to 150° C.

The reaction time is generally 5 min to 48 hr, preferably 30 min to 24 hr.

Compound (3-2) can be produced, for example, by subjecting compound (47) to a deprotection reaction. The deprotection reaction can be carried out according to a method known per se, for example, the method described in Protective Groups in Organic Synthesis, John Wiley and Sons (1980) or the like.

Compound (44) and compound (46) can be produced according to a method known per se.

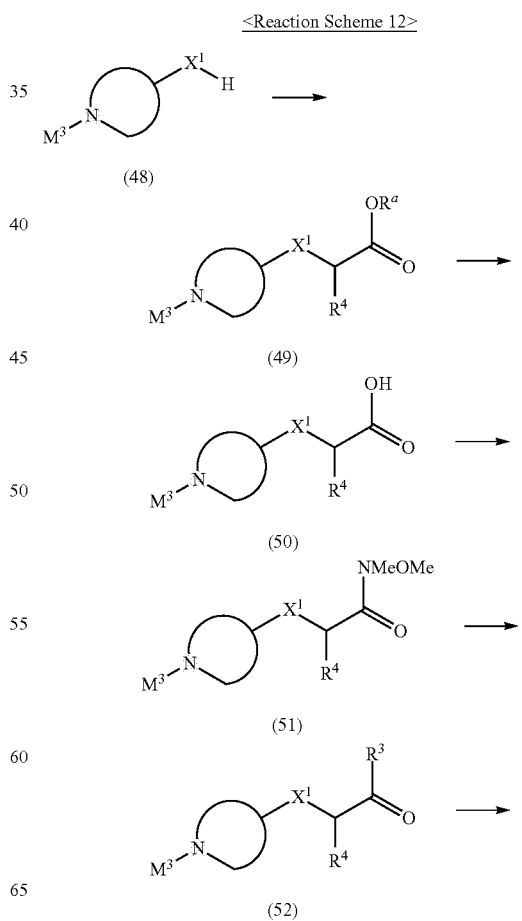

(20) structure: ring with M³-N, X¹ substituent to CH(R³)-CH(R⁴)-OH... shown as compound (20)

wherein R^a is an optionally substituted C_{1-6} alkyl group, and other symbols are as defined above.

Compound (49) can be produced, for example, by reacting compound (48) with an optionally substituted alkyl haloacetate or an optionally substituted alkyl diazoacetate.

The above-mentioned "reaction with an optionally substituted alkyl haloacetate" is carried out by reacting compound (48) with an optionally substituted alkyl haloacetate in the presence of a base, in an inert solvent. This reaction may be carried out in the presence of a phase-transfer catalyst, as necessary.

Examples of the above-mentioned "optionally substituted alkyl haloacetate" include ethyl bromoacetate, tert-butyl bromoacetate and the like. The amount of the "optionally substituted alkyl haloacetate" to be used is generally 1 to 10 equivalents, preferably 1 to 5 equivalents, relative to compound (48).

Examples of the above-mentioned "base" include "inorganic bases", "basic salts", "aromatic amines", "hydrides of alkali metal or alkaline earth metal", "metal alkoxides" and the like. The amount of the "base" to be used is generally 1 to 10 equivalents, preferably 1 to 5 equivalents, relative to compound (48).

Examples of the above-mentioned "inert solvent" include "aromatic solvents", "amide solvents", "halogenated hydrocarbon solvents", "ether solvents" and the like. These solvents are preferably used in a mixture with water or a mixture of two or more kinds thereof mixed at an appropriate ratio. Of these, THF, DMF and the like are preferable.

Examples of the above-mentioned "phase-transfer catalyst" include quaternary ammonium salts (e.g., tetrabutylammonium bromide, benzyltrioctylammonium chloride, tetrabutylammonium hydrogensulfate) and the like. The amount of the "phase-transfer catalyst" to be used is generally 0.001 to 10 equivalents, preferably 0.01 to 1 equivalent, relative to compound (48).

The reaction temperature is generally −100° C. to 150° C., preferably 0° C. to 100° C.

The reaction time is generally 5 min to 100 hr, preferably 30 min to 48 hr.

The above-mentioned "reaction with an optionally substituted alkyl diazoacetate" is carried out by reacting compound (48) with an optionally substituted alkyl diazoacetate in the presence of a metal catalyst, in an inert solvent.

Example of the above-mentioned "optionally substituted alkyl diazoacetate" include diazoethyl acetate and the like. The amount of the "optionally substituted alkyl diazoacetate" to be used is generally 1 to 10 equivalents, preferably 1 to 5 equivalents, relative to compound (48).

Examples of the above-mentioned "metal catalyst" include rhodium acetate dimer and the like. The amount of the "metal catalyst" to be used is generally 0.001 to 10 equivalents, preferably 0.01 to 1 equivalent, relative to compound (48).

Examples of the above-mentioned "inert solvent" include "aromatic solvents", "aliphatic hydrocarbon solvents", "nitrile solvents", "amide solvents", "halogenated hydrocarbon solvents", "ether solvents" and the like. These solvents may be used in a mixture of two or more kinds thereof mixed at an appropriate ratio. Of these, toluene, dichloromethane and the like are preferable.

The reaction temperature is generally −100° C. to 150° C., preferably 0° C. to 100° C.

The reaction time is generally 5 min to 48 hr, preferably 30 min to 24 hr.

Compound (50) can be produced, for example, by subjecting compound (49) to hydrolysis.

This reaction is carried out by reacting compound (49) with a base in an inert solvent.

Examples of the above-mentioned "base" include "inorganic bases" and the like. The amount of the "base" to be used is generally 1 to 10 equivalents, preferably 1 to 1.5 equivalents, relative to compound (49).

Examples of the above-mentioned "inert solvent" include "alcohol solvents", "ether solvents", "amide solvents", "halogenated hydrocarbon solvents" and the like. These solvents are preferably used in a mixture with water at an appropriate ratio. Of these, "alcohol solvents" containing water are preferable.

The reaction temperature is generally −78° C. to 150° C., preferably −20° C. to 100° C.

The reaction time is generally 5 min to 100 hr, preferably 30 min to 24 hr.

The production method of compound (50) by removing the carboxy-protecting group of compound (49) can also be carried out according to a method known per se, for example, the method described in Protective Groups in Organic Synthesis, John Wiley and Sons (1980) or the like.

Compound (51) can be produced, for example, by subjecting compound (50) to an amidation reaction with N,O-dimethylhydroxylamine.

The above-mentioned "amidation reaction" is carried out in the same manner as in the production method of the "amide derivative" described as one of the production methods of compound (I-1) in Reaction Scheme 2.

Compound (52) can be produced, for example, by reacting compound (51) with the corresponding organic metal reagent in an inert solvent.

This reaction is carried out in the same manner as in the production method of compound (29-1) in Reaction Scheme 8.

Compound (20) can be produced, for example, by subjecting compound (52) to a reduction reaction.

This reaction is carried out in the same manner as in the production method of compound (33) in Reaction Scheme 8.

Compound (48) can be produced according to a method known per se.

<Reaction Scheme 13>

(49): ring with M³-N, X substituent to CH(R⁴)-C(=O)-OR^a (53): ring with M³-N, X substituent to CH(R⁴)-CH₂-OH

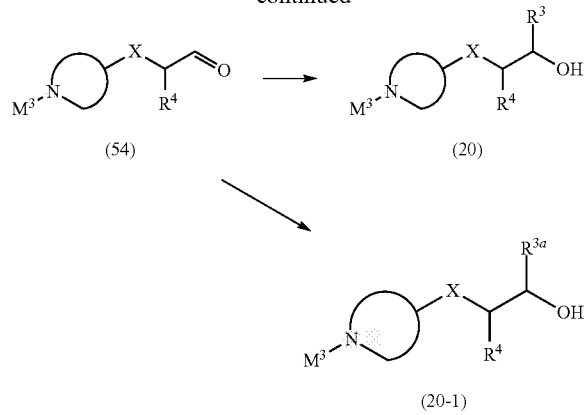

wherein $R^{3a}$ is a perfluoro $C_{1-6}$ alkyl group, and the other symbols are as defined above.

Compound (53) can be produced, for example, by subjecting compound (49) to a reduction reaction.

This reaction is carried out by reacting compound (49) with a reducing agent in an inert solvent.

Examples of the above-mentioned "reducing agent" include metal hydrides (e.g., diisobutylaluminum hydride), metal hydride complex compounds (e.g., sodium borohydride, lithium aluminum hydride, sodium aluminum hydride, calcium borohydride, sodium bis(2-methoxyethoxy)aluminum hydride) and the like. The amount of the "reducing agent" to be used is generally 0.1 to 20 equivalents, preferably 1 to 5 equivalents, relative to compound (49).

Examples of the above-mentioned "inert solvent" include "alcohol solvents", "aromatic solvents", "aliphatic hydrocarbon solvents", "ether solvents", "amide solvents" and the like. These solvents may be used in a mixture of two or more kinds thereof mixed at an appropriate ratio.

The reaction temperature is generally −70 to 150° C., preferably −20 to 100° C.

The reaction time is generally 0.1 to 100 hr, preferably 0.1 to 48 hr.

Compound (54) can be produced, for example, by subjecting compound (53) to an oxidation reaction.

This reaction is carried out by reacting compound (53) with an oxidant in an inert solvent. This reaction may be carried out in the presence of 1 to 10 equivalents of a base, as necessary.

Examples of the above-mentioned "oxidant" include tetrapropylammonium perruthenate, chromium trioxide, Dess-Martin reagent, sulfur trioxide pyridine complex and the like. The amount of the "oxidant" to be used is generally 1 to 10 equivalents, preferably 1 to 5 equivalents, relative to compound (53).

Examples of the above-mentioned "base" include "aromatic amines", "tertiary amines" and the like.

Examples of the above-mentioned "inert solvent" include "nitrile solvents", "amide solvents", "halogenated hydrocarbon solvents", "ether solvents", "aromatic solvents", "sulfoxide solvents" and the like. These solvents may be used in a mixture of two or more kinds thereof mixed at an appropriate ratio.

The reaction temperature is generally −100° C. to 50° C., preferably −78° C. to 0° C.

The reaction time is generally 5 min to 48 hr, preferably 30 min to 24 hr.

Compound (20) can be produced, for example, by reacting compound (54) with the corresponding organic metal reagent in an inert solvent.

Examples of the above-mentioned "organic metal reagent" include Grignard reagents (e.g., methylmagnesium bromide, methylmagnesium chloride), organic lithium reagents (e.g., methyllithium) and the like. The amount of the "organic metal reagent" to be used is generally 1 to 20 equivalents, preferably 1 to 5 equivalents, relative to compound (54).

Examples of the above-mentioned "inert solvent" include "aromatic solvents", "aliphatic hydrocarbon solvents", "ether solvents", "halogenated hydrocarbon solvents" and the like. These solvents may be used in a mixture of two or more kinds thereof mixed at an appropriate ratio. Of these, THF and the like are preferable.

The reaction temperature is generally −78° C. to 150° C., preferably −20° C. to 100° C.

The reaction time is generally 5 min to 48 hr, preferably 30 min to 24 hr.

Compound (20-1) can be produced, for example, by subjecting compound (54) to a perfluoroalkylation reaction.

This reaction solvent is carried out by reacting compound (54) with the corresponding perfluoroalkylating agent in the presence of a fluoride, in an inert. After completion of the above-mentioned reaction, desilylation reaction may be carried out, as necessary.

Examples of the above-mentioned "perfluoroalkylating agent" include trimethyl(perfluoroalkyl)silanes (e.g., trimethyl(trifluoromethyl)silane) and the like. The amount of the "perfluoroalkylating agent" to be used is generally 1 to 20 equivalents, preferably 1 to 5 equivalents, relative to compound (54).

Examples of the above-mentioned "fluoride" include tetraalkylammonium fluorides (e.g., tetrabutylammonium fluoride), metal fluorides (e.g., potassium fluoride) and the like. The amount of the "fluoride" to be used is generally a catalytic amount to 20 equivalents, preferably 0.1 to 5 equivalents, relative to compound (54).

Examples of the above-mentioned "inert solvent" include "aromatic solvents", "aliphatic hydrocarbon solvents", "ether solvents", "amide solvents", "halogenated hydrocarbon solvents" and the like. These solvents may be used in a mixture of two or more kinds thereof mixed at an appropriate ratio. Of these, THF and the like are preferable.

The reaction temperature is generally −78° C. to 150° C., preferably −20° C. to 100° C.

The reaction time is generally 5 min to 48 hr, preferably 30 min to 24 hr.

The above-mentioned "desilylation reaction" can be carried out according to a method known per se, for example, the method described in Protective Groups in Organic Synthesis, John Wiley and Sons (1980) or the like.

Compound (49) can be produced according to a method known per se.

<Reaction Scheme 14>

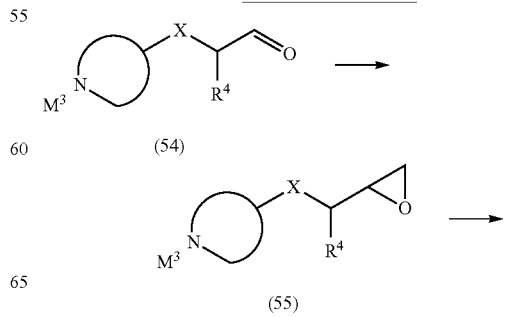

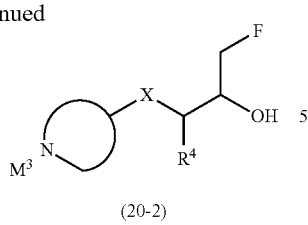

(20-2)

wherein each symbol is as defined above.

Compound (55) can be produced, for example, by subjecting compound (54) to an epoxidation reaction.

The epoxidation reaction can be carried out according to a method known per se, for example, the method described in Journal of American Chemical Society, pages 867-868, 1962 or the like, or a method analogous thereto.

This reaction is carried out by reacting compound (54) with a sulfur ylide in an inert solvent.

Examples of the above-mentioned "sulfur ylide" include dimethylsulfonium methylide, dimethyloxosulfonium methylide and the like. The amount of the "sulfur ylide" to be used is generally 1 to 10 equivalents, preferably 1 to 5 equivalents, relative to compound (54).

Examples of the above-mentioned "inert solvent" include "sulfoxide solvents", "ether solvents", "aromatic solvents" and the like. These solvents may be used in a mixture of two or more kinds thereof mixed at an appropriate ratio.

The reaction temperature is generally −100° C. to 150° C., preferably −78° C. to 100° C.

The reaction time is generally 5 min to 48 hr, preferably 30 min to 24 hr.

Compound (20-2) can be produced, for example, by subjecting compound (55) to a fluorination reaction.

The above-mentioned "fluorination reaction" is carried out by reacting compound (55) with a fluorinating agent in an inert solvent or without solvent.

Examples of the above-mentioned "fluorinating agent" include tetrabutylammonium dihydrogen trifluoride, potassium fluoride, tetrabutylammonium fluoride and the like. The amount of the "fluorinating agent" to be used is generally 1 to 10 equivalents, preferably 1 to 3 equivalents, relative to compound (55).

Examples of the above-mentioned "inert solvent" include "nitrile solvents", "amide solvents", "halogenated hydrocarbon solvents", "ether solvents", "aromatic solvents", "sulfoxide solvents" and the like. These solvents may be used in a mixture of two or more kinds thereof mixed at an appropriate ratio. Of these, chlorobenzene, DMF and the like are preferable.

The reaction temperature is generally −100° C. to 200° C., preferably 0° C. to 150° C.

The reaction time is generally 5 min to 48 hr, preferably 30 min to 24 hr.

Compound (54) can be produced according to a method known per se.

<Reaction Scheme 15>

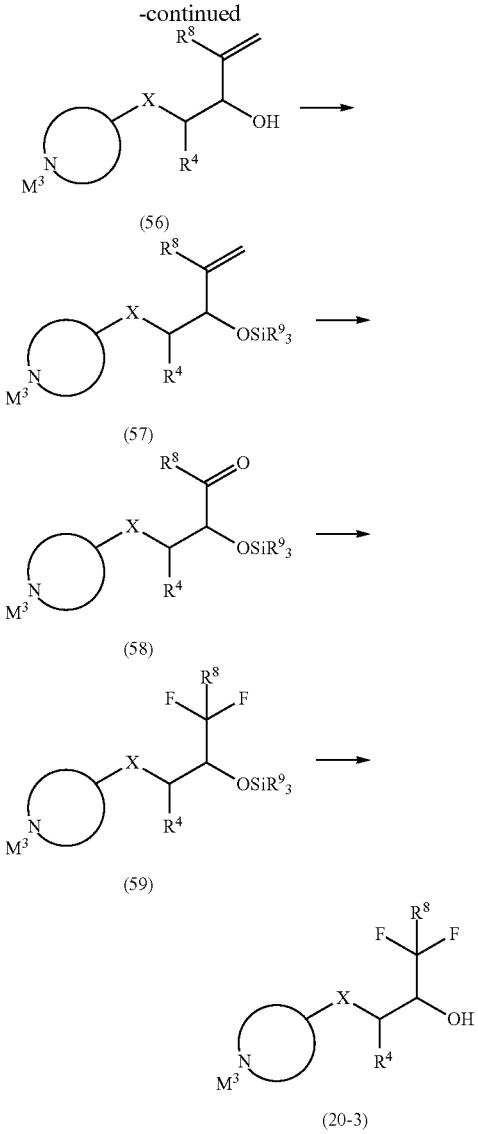

wherein $R^8$ is a hydrogen atom or a $C_{1-5}$ alkyl group optionally substituted by halogen atom(s), $R^9$ is a substituent, and the other symbols are as defined above.

Compound (56) can be produced, for example, by reacting compound (54) with the corresponding organic metal reagent in an inert solvent.

Examples of the above-mentioned "organic metal reagent" include Grignard reagents (e.g., vinylmagnesium bromide), organic lithium reagents (e.g., vinyllithium) and the like. The amount of the "organic metal reagent" to be used is generally 1 to 20 equivalents, preferably 1 to 5 equivalents, relative to compound (54).

Examples of the above-mentioned "inert solvent" include "aromatic solvents", "aliphatic hydrocarbon solvents", "ether solvents" and the like. These solvents may be used in a mixture of two or more kinds thereof mixed at an appropriate ratio. Of these, THF and the like are preferable.

The reaction temperature is generally −78° C. to 150° C., preferably −20° C. to 100° C.

The reaction time is generally 5 min to 48 hr, preferably 30 min to 24 hr.

Compound (57) can be produced, for example, by subjecting compound (56) to a silylation reaction.

The silylation reaction can be carried out according to a method known per se, for example, the method described in Protective Groups in Organic Synthesis, John Wiley and Sons (1980) or the like.

Compound (58) can be produced, for example, by subjecting compound (57) to an oxidative cleavage or an ozone oxidation.

This reaction is carried out by reacting compound (57) with an oxidant in an inert solvent. A reoxidant may be used again, as necessary.

Examples of the above-mentioned "oxidant" include osmium tetroxide, potassium permanganate, ozone and the like. The amount of the "oxidant" to be used is generally 0.001 to 10 equivalents, preferably 0.01 to 3 equivalents, relative to compound (57).

Examples of the above-mentioned "reoxidant" include sodium periodate and the like. The amount of the "reoxidant" to be used is generally 1 to 10 equivalents, preferably 1 to 3 equivalents, relative to the "oxidant".

Examples of the above-mentioned "inert solvent" include "ketone solvents", "nitrile solvents", "amide solvents", "halogenated hydrocarbon solvents", "ether solvents", "aromatic solvents" and the like. These solvents may be used in a mixture with water or a mixture of two or more kinds thereof mixed at an appropriate ratio.

The reaction temperature is generally −100° C. to 200° C., preferably 0° C. to 150° C.

The reaction time is generally 5 min to 48 hr, preferably 30 min to 24 hr.

Compound (59) can be produced, for example, by subjecting compound (58) to a fluorination reaction.

This reaction is carried out by reacting compound (58) with a fluorinating agent in an inert solvent.

Examples of the above-mentioned "fluorinating agent" include (diethylamino)sulfur trifluoride and the like. The amount of the "fluorinating agent" to be used is generally 1 to 10 equivalents, preferably 1 to 3 equivalents, relative to compound (58).

Examples of the above-mentioned "inert solvent" include "nitrile solvents", "amide solvents", "halogenated hydrocarbon solvents", "ether solvents", "aromatic solvents" and the like. These solvents may be used in a mixture of two or more kinds thereof mixed at an appropriate ratio. Of these, toluene, dichloromethane and the like are preferable.

The reaction temperature is generally −100° C. to 200° C., preferably 0° C. to 150° C.

The reaction time is generally 5 min to 48 hr, preferably 30 min to 24 hr.

Compound (20-3) can be produced, for example, by subjecting compound (59) to a desilylation reaction.

The desilylation reaction can be carried out according to a method known per se, for example, the method described in Protective Groups in Organic Synthesis, John Wiley and Sons (1980) or the like.

<Reaction Scheme 16>

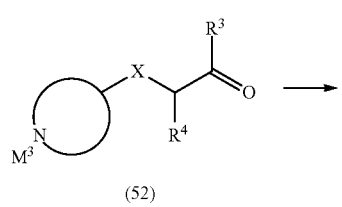

(52)

-continued

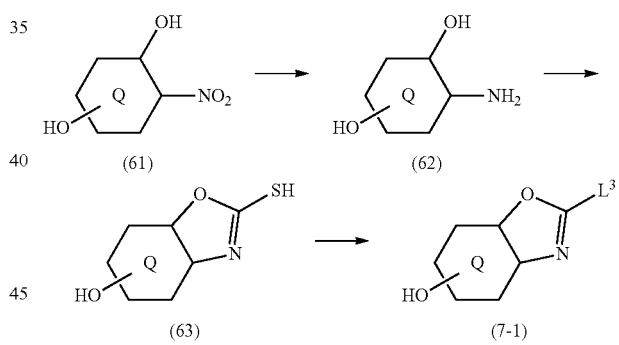

wherein each symbol is as defined above.

Compound (60) can be produced, for example, by subjecting compound (52) to a reductive amination reaction.

This reaction is carried out in the same manner as in the production method of compound (I-2) in Reaction Scheme 7.

Compound (A-2) can be produced, for example, by subjecting compound (60) to a deprotection reaction. The deprotection reaction can be carried out according to a method known per se, for example, the method described in Protective Groups in Organic Synthesis, John Wiley and Sons (1980) or the like.

Compound (52) can be produced according to a method known per se.

<Reaction Scheme 17> wherein each symbol is as defined above.

Compound (62) can be produced, for example, by subjecting compound (61) to a reduction reaction.

This reaction is carried out by reacting compound (61) in the presence of a metal catalyst and a hydrogen source, in an inert solvent.

Examples of the above-mentioned "metal catalyst" include palladium-carbon, palladium black, palladium chloride, platinum oxide, platinum black, Raney-nickel, Raney-cobalt and the like. The amount of the "metal catalyst" to be used is generally 0.001 to 100 equivalents, preferably 0.01 to 10 equivalents, relative to compound (61).

Examples of the above-mentioned "hydrogen source" include hydrogen gas, formic acid, formic acid amine salt, phosphinate, hydrazine and the like.

Examples of the above-mentioned "inert solvent" include "alcohol solvents", "nitrile solvents", "aromatic solvents", "aliphatic hydrocarbon solvents", "ether solvents", "ester solvents", "amide solvents", "halogenated hydrocarbon solvents" and the like. These solvents are preferably used in a mixture with water at an appropriate ratio. Of these, "alcohol solvents" are preferable.

The reaction temperature is generally −70 to 150° C., preferably −20 to 100° C.

The reaction time is generally 0.1 to 100 hr, preferably 0.1 to 40 hr.

This reaction can also be carried out by reacting compound (61) in the presence of reduced iron and a chloride, in an inert solvent mixed with water at an appropriate ratio.

The amount of the above-mentioned "reduced iron" to be used is generally 1 to 20 equivalents, preferably 2 to 10 equivalents, relative to compound (61).

Examples of the above-mentioned "chloride" include calcium chloride, ammonium chloride and the like. The amount of the "chloride" to be used is generally 0.1 to 10 equivalents, preferably 1 to 5 equivalents, relative to compound (61).

Examples of the above-mentioned "inert solvent" include "alcohol solvents", "aromatic solvents", "aliphatic hydrocarbon solvents", "ether solvents", "amide solvents", "halogenated hydrocarbon solvents" and the like.

The reaction temperature is generally −70 to 200° C., preferably 0 to 100° C.

The reaction time is generally 0.1 to 100 hr, preferably 0.1 to 40 hr.

Compound (63) can be produced, for example, by subjecting compound (62) to a cyclization reaction.

The above-mentioned "cyclization reaction" is carried out by reacting compound (62) with a thiocarbonylating agent in an inert solvent. The reaction may be carried out using 1 to 10 equivalents of a base, as necessary.

Examples of the above-mentioned "thiocarbonylating agent" include potassium ethylxanthate, 1,1'-thiocarbonyldiimidazole and the like. The amount of the "thiocarbonylating agent" to be used is generally 1 to 10 equivalents, relative to compound (62).

Examples of the above-mentioned "base" include "inorganic bases", "basic salts", "aromatic amines", "tertiary amines", "hydrides of alkali metal or alkaline earth metal", "metal alkoxides" and the like.

Examples of the above-mentioned "inert solvent" include "alcohol solvents", "amide solvents", "nitrile solvents", "aliphatic hydrocarbon solvents", "aromatic solvents", "halogenated hydrocarbon solvents", "ether solvents" and the like. These solvents may be used in a mixture of two or more kinds thereof mixed at an appropriate ratio.

The reaction temperature is generally −100° C. to 200° C., preferably 0° C. to 150° C.

The reaction time is generally 1 min to 48 hr, preferably 5 min to 24 hr.

Compound (7-1) can be produced, for example, by subjecting compound (63) to a halogenation or alkylation reaction.

This reaction is carried out in the same manner as in the production method of compound (26) in Reaction Scheme 6.

Compound (61) can be produced according to a method known per se.

<Reaction Scheme 18>

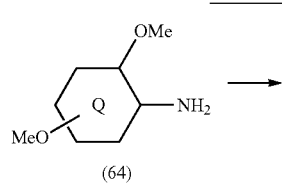

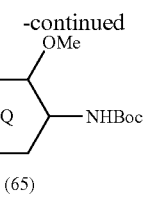

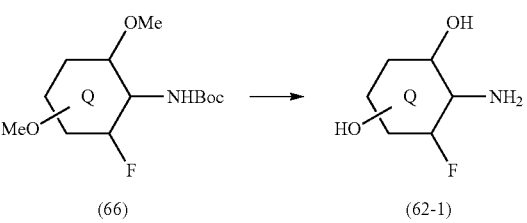

wherein each symbol is as defined above.

Compound (65) can be produced, for example, by subjecting compound (64) to a tert-butoxycarbonylation reaction.

This reaction can be carried out according to a method known per se, for example, the method described in Synthesis, pages 2784-2788, 2006 or the like.

This reaction can also be carried out according to a method known per se, for example, the method described in Protective Groups in Organic Synthesis, John Wiley and Sons (1980) or the like.

Compound (66) can be produced, for example, by subjecting compound (65) to a fluorination reaction.

The above-mentioned "fluorination reaction" is carried out by converting the hydrogen atom of compound (65) to a metal atom with an organic metal reagent in an inert solvent, and the reacting the resulting compound with a fluorinating agent.

Examples of the above-mentioned "organic metal reagent" include "alkyl metals", "metal amides" and the like. The amount of the "organic metal reagent" to be used is generally 2 to 10 equivalents, relative to compound (65).

Examples of the above-mentioned "fluorinating agent" include N-fluorobenzenesulfonimide and the like. The amount of the "fluorinating agent" to be used is generally 2 to 10 equivalents, relative to compound (65).

Examples of the above-mentioned "inert solvent" include "aliphatic hydrocarbon solvents", "aromatic solvents", "ether solvents" and the like. These solvents may be used in a mixture of two or more kinds thereof mixed at an appropriate ratio.

The reaction temperature is generally −100° C. to 200° C., preferably −100° C. to 100° C.

The reaction time is generally 1 min to 48 hr, preferably 5 min to 24 hr.

Compound (62-1) can be produced, for example, by subjecting compound (66) to a deprotection reaction. The deprotection reaction can be carried out according to a method known per se, for example, the method described in Protective Groups in Organic Synthesis, John Wiley and Sons (1980) or the like.

Compound (64) can be produced according to a method known per se.

<Reaction Scheme 19>

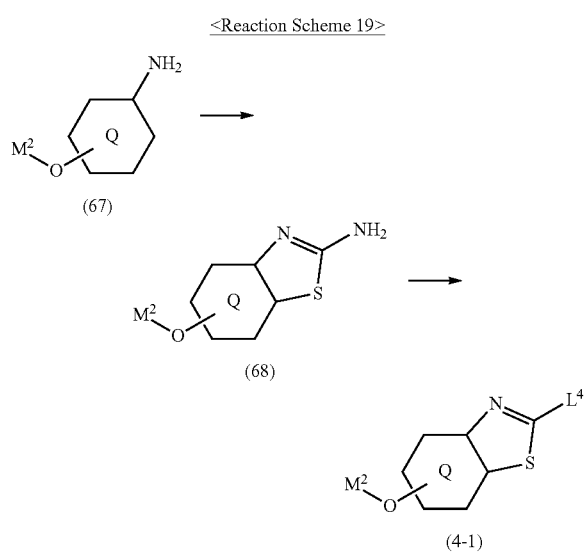

wherein $L^4$ is a halogen atom, and the other symbols are as defined above.

Compound (68) can be produced, for example, by subjecting compound (67) to a cyclization reaction.

This reaction is carried out by reacting compound (67) with a thiocyanate and a halogenating agent in an inert solvent or without solvent. One equivalent to an excess amount of an organic acid, relative to the thiocyanate, may be used, as necessary.

Examples of the above-mentioned "thiocyanate" include sodium thiocyanate, potassium thiocyanate, ammonium thiocyanate and the like. The amount of the "thiocyanate" to be used is generally 1 to 20 equivalents, preferably 1 to 10 equivalents, relative to compound (67).

Examples of the above-mentioned "organic acid" include acetic acid and the like.

Examples of the above-mentioned "halogenating agent" include bromine, N-bromosuccinimide, sulfuryl dichloride and the like. The amount of the "halogenating agent" to be used is generally 1 to 10 equivalents, preferably 1 to 5 equivalents, relative to compound (67).

Examples of the above-mentioned "inert solvent" include "nitrile solvents", "ether solvents", "amide solvents", a mixture of two or more kinds thereof, and the like.

The reaction temperature is generally −78° C. to 100° C., preferably −20° C. to 50° C.

The reaction time is generally 5 min to 100 hr, preferably 30 min to 10 hr.

Compound (4-1) can be produced, for example, by subjecting compound (68) to the Sandmeyer reaction.

This reaction is carried out by reacting compound (68) in the presence of a nitrite and a halogenated copper, in an inert solvent. The reaction may be carried out in the presence of 1 to 10 equivalents of hydrogen chloride, or 1 equivalent to an excess amount of an organic acid, as necessary.

Examples of the above-mentioned "nitrite" include sodium nitrite, potassium nitrite, tert-butyl nitrite, isoamyl nitrite and the like. The amount of the "nitrite" to be used is generally 1 to 3 equivalents, preferably 1 to 2 equivalents, relative to compound (68).

Examples of the above-mentioned "halogenated copper" include copper(I) bromide, copper(II) bromide, copper(I) chloride, copper(II) chloride and the like. The amount of the "halogenated copper" to be used is generally 0.5 to 3 equivalents, preferably 0.5 to 1.5 equivalents, relative to compound (68).

Examples of the above-mentioned "organic acid" include acetic acid and the like.

Examples of the above-mentioned "inert solvent" include "nitrile solvents", "ether solvents", "amide solvents", water, a mixture of two or more kinds thereof, and the like.

The reaction temperature is generally −78° C. to 50° C., preferably −20° C. to 10° C.

The reaction time is generally 5 min to 100 hr, preferably 30 min to 10 hr.

Compound (67) can be produced according to a method known per se.

<Reaction Scheme 20>

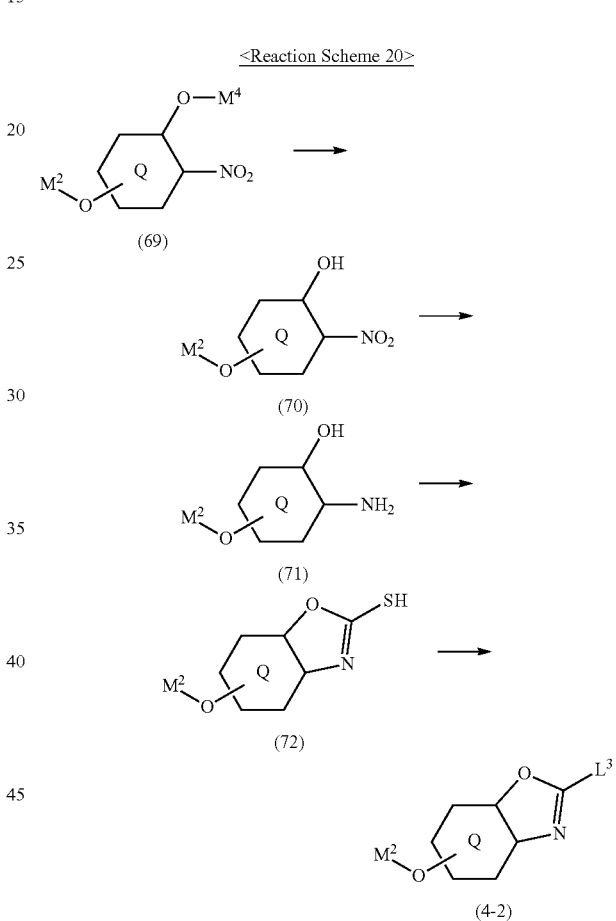

wherein $M^4$ is a hydroxy-protecting group, and the other symbols are as defined above.

Compound (70) can be produced, for example, by subjecting compound (69) to a deprotection reaction. The deprotection reaction can be carried out according to a method known per se, for example, the method described in Protective Groups in Organic Synthesis, John Wiley and Sons (1980) or the like.

Compound (71) can be produced, for example, by subjecting compound (70) to a reduction reaction.

This reaction is carried out in the same manner as in the production method of compound (62) in Reaction Scheme 17.

Compound (72) can be produced, for example, by subjecting compound (71) to a cyclization reaction.

This reaction is carried out in the same manner as in the production method of compound (63) in Reaction Scheme 17.

Compound (4-2) can be produced, for example, by subjecting compound (72) to a halogenation or alkylation reaction.

This reaction is carried out in the same manner as in the production method of compound (26) in Reaction Scheme 6.

Compound (69) can be produced according to a method known per se.

<Reaction Scheme 21>

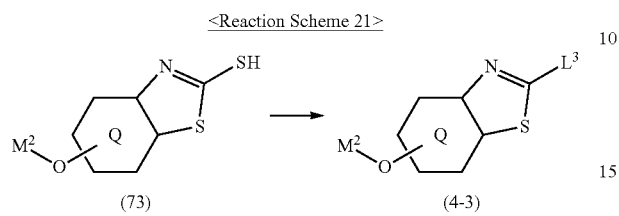

wherein each symbol is as defined above.

Compound (4-3) can be produced, for example, by subjecting compound (73) to a halogenation or alkylation reaction.

This reaction is carried out in the same manner as in the production method of compound (26) in Reaction Scheme 6.

Compound (73) can be produced according to a method known per se.

<Reaction Scheme 22>

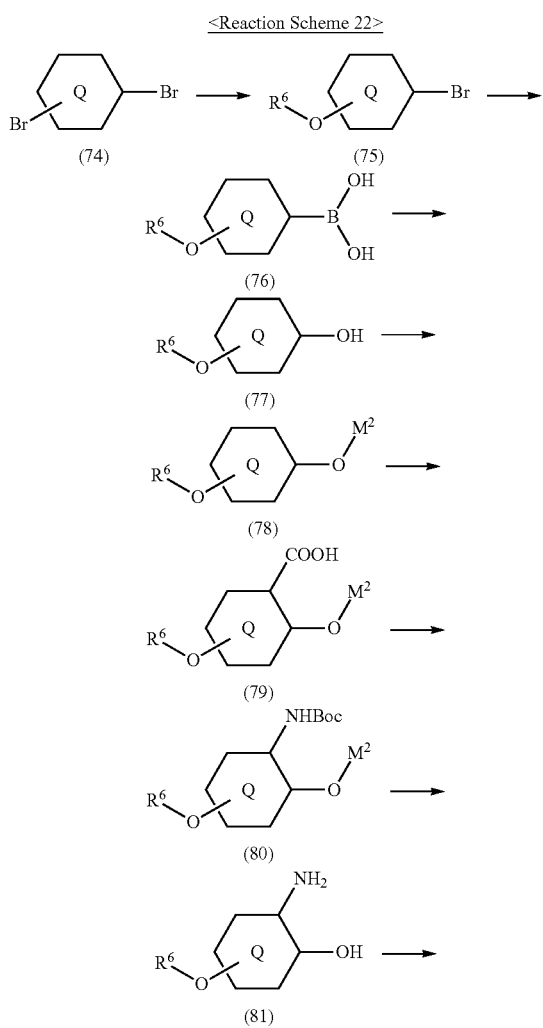

wherein each symbol is as defined above.

Compound (75) can be produced, for example, by reacting compound (74) with the compound $R^6OH$.

This reaction is carried out by reacting compound (74) with the compound $R^6OH$ in the presence of a base, in an inert solvent. The reaction may be carried out under microwave irradiation, as necessary. In addition, the reaction may be using, as a solvent, the "compound $R^6OH$" instead of the inert solvent, as necessary.

The amount of the above-mentioned "compound $R^6OH$" to be used is generally 1 to 10 equivalents, preferably 1 to 5 equivalents, relative to compound (74).

Examples of the above-mentioned "base" include "inorganic bases", "basic salts", "aromatic amines", "tertiary amines", "hydrides of alkali metal or alkaline earth metal", "alkyl metals", "metal alkoxides" and the like. The amount of the "base" to be used is generally 1 to 10 equivalents, preferably 1 to 5 equivalents, relative to the compound $R^6OH$.

Examples of the above-mentioned "inert solvent" include "nitrile solvents", "amide solvents", "halogenated hydrocarbon solvents", "ether solvents", "aromatic solvents" and the like. These solvents may be used in a mixture of two or more kinds thereof mixed at an appropriate ratio. Of these, THF, DMF and the like are preferable.

The reaction temperature is generally −100° C. to 200° C., preferably 0° C. to 150° C.

The reaction time is generally 5 min to 48 hr, preferably 30 min to 24 hr.

Compound (76) can be produced, for example, by subjecting compound (75) to a boronation reaction.

This reaction is carried out in the same manner as in the production method of compound (28) in Reaction Scheme 6.

Compound (77) can be produced, for example, by subjecting compound (76) to an oxidation reaction.

This reaction is carried out in the same manner as in the production method of compound (8) in Reaction Scheme 6.

Compound (78) can be produced, for example, by subjecting compound (77) to a hydroxyl-protection reaction. The hydroxy-protection reaction can be carried out according to a method known per se, for example, the method described in Protective Groups in Organic Synthesis, John Wiley and Sons (1980) or the like.

Compound (79) can be produced, for example, by subjecting compound (78) to a carboxylation reaction.

The above-mentioned "carboxylation reaction" is carried out, for example, by converting the hydrogen atom of compound (78) to a metal atom with an alkyl metal in an inert solvent, and then reacting the resulting compound with carbon dioxide.

Examples of the above-mentioned "alkyl metal" include alkyllithiums, alkylmagnesium halides and the like. The amount of the "alkyl metal" to be used is generally 1 equivalent to 10 equivalents, relative to compound (78).

The amount of the carbon dioxide to be used is generally 10 to 100 equivalents, relative to compound (78).

Examples of the above-mentioned "inert solvent" include "aliphatic hydrocarbon solvents", "aromatic solvents", "ether solvents" and the like. These solvents may be used in a mixture of two or more kinds thereof mixed at an appropriate ratio.

The reaction temperature is generally −100° C. to 200° C., preferably −100° C. to 100° C.

The reaction time is generally 1 min to 48 hr, preferably 5 min to 24 hr.

Compound (80) can be produced, for example, by subjecting compound (79) to a rearrangement reaction.

Compound (80) can be produced, for example, by subjecting compound (79) directly, or after conversion to a reactive derivative thereof (e.g., acid halides, acid amides, acid anhydrides, esters etc.) and the like, to a rearrangement reaction.

Examples of the above-mentioned "rearrangement reaction" include Curtius rearrangement, Hofmann rearrangement, Schmidt rearrangement and the like.

The rearrangement reaction using diphenylphosphoryl azide is exemplified in the followings.

The amount of the diphenylphosphoryl azide to be used is generally 1 to 3 equivalents, preferably 1 to 1.5 equivalents, relative to compound (79).

This reaction is carried out in the presence of a base, as necessary.

Examples of the above-mentioned "base" include "aromatic amines", "tertiary amines" and the like.

This reaction is advantageously carried out in an inert solvent. Examples of the solvent include "ether solvents", tert-butanol, "aromatic solvents" and the like. When a solvent other then tert-butanol is used, the corresponding tert-butoxycarbonyl compound can be produced by adding tert-butanol after the progress of the rearrangement.

The reaction time is generally about 10 min to about 48 hr, preferably about 15 min to about 24 hr.

The reaction temperature is generally −20° C. to 200° C., preferably 0° C. to 150° C.

The method described in "Jikken Kagaku Kouza (The Chemical Society of Japan ed.)", 4th Edition, vol. 20, pages 304 and 477-479, a method analogous thereto and the like are employed as other reaction conditions.

Compound (81) can be produced, for example, by subjecting compound (80) to a deprotection reaction. The deprotection reaction can be carried out according to a method known per se, for example, the method described in Protective Groups in Organic Synthesis, John Wiley and Sons (1980) or the like.

Compound (82) can be produced, for example, by subjecting compound (81) to a cyclization reaction.

This reaction is carried out in the same manner as in the production method of compound (63) in Reaction Scheme 17.

Compound (2-1) can be produced, for example, by subjecting compound (82) to a halogenation or alkylation reaction.

This reaction is carried out in the same manner as in the production method of compound (26) in Reaction Scheme 6.

Compound (74) can be produced according to a method known per se.

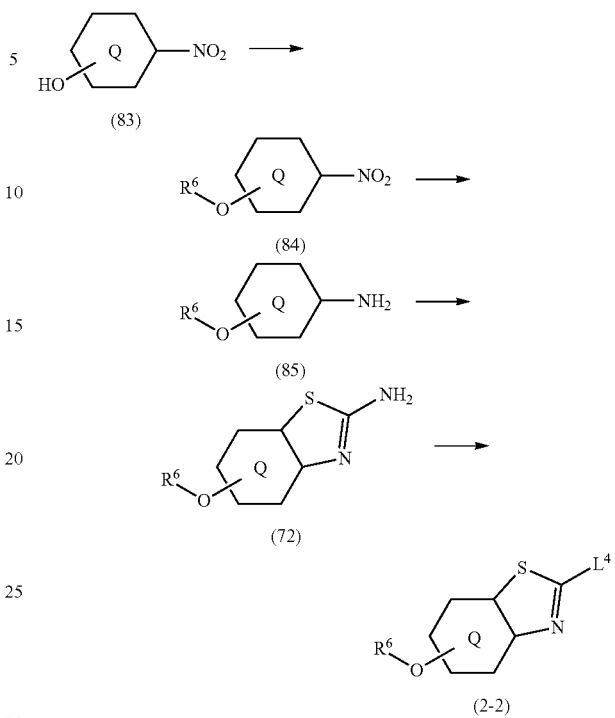

wherein each symbol is as defined above.

Compound (84) can be produced, for example, by subjecting compound (83) to an alkylation reaction.

This reaction is carried out in the same manner as in the method of producing compound (9) by an alkylation reaction of compound (8), as shown in Reaction Scheme 2.

Compound (85) can be produced, for example, by subjecting compound (84) to a reduction reaction.

This reaction is carried out in the same manner as in the production method of compound (62) in Reaction Scheme 17.

Compound (86) can be produced, for example, by subjecting compound (85) to a cyclization reaction.

This reaction is carried out in the same manner as in the production method of compound (68) in Reaction Scheme 19.

Compound (2-2) can be produced, for example, by subjecting compound (86) to the Sandmeyer reaction.

This reaction is carried out in the same manner as in the production method of compound (4-1) in Reaction Scheme 19.

Compound (83) can be produced according to a method known per se.

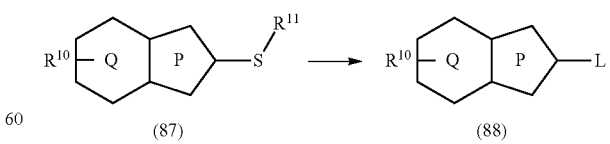

wherein $R^{10}$ is a substituent, $R^{11}$ is a $C_{1-6}$ alkyl group, $L^5$ is a $C_{1-6}$ alkylsulfonyl group or a $C_{1-6}$ alkylsulfinyl group, and the other symbols are as defined above.

Compound (88) can be produced, for example, by subjecting compound (87) to an oxidation reaction.

This reaction is carried out according to the method described in 4th Edition Jikken Kagaku Kouza 20 (The Chemical Society of Japan ed.), pages 276-278, 503, or a method analogous thereto.

Compound (87) can be produced according to a method known per se.

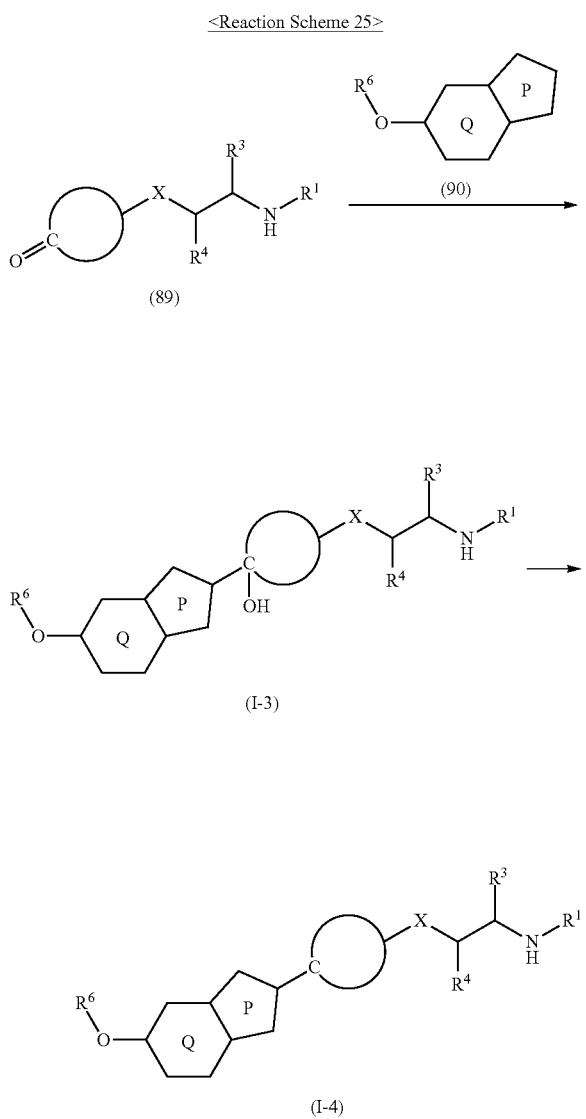

<Reaction Scheme 25>

(89)

(90)

(I-3)

(I-4)

wherein each symbol is as defined above.

Compound (I-3) can be produced, for example, by reacting compound (90) with compound (89).

This reaction is carried out by converting the hydrogen atom of compound (90) to a metal atom with an organic metal reagent in an inert solvent, and the reacting the resulting compound with compound (89).

Examples of the above-mentioned "organic metal reagent" include "alkyl metals", "aryl metals", "metal amides" and the like. The amount of the "organic metal reagent" to be used is generally 1 equivalent to 10 equivalents, relative to compound (90).

The amount of compound (90) to be used is generally 2 equivalents to 10 equivalents, relative to compound (89).

Examples of the above-mentioned "inert solvent" include "aliphatic hydrocarbon solvents", "aromatic solvents", "ether solvents" and the like. These solvents may be used in a mixture of two or more kinds thereof mixed at an appropriate ratio.

The reaction temperature is generally −100° C. to 100° C., preferably −78° C. to 50° C.

The reaction time is generally 1 min to 48 hr, preferably 5 min to 24 hr.

Compound (I-4) can be produced, for example, by subjecting compound (I-3) to a reduction reaction.

This reaction is carried out by reacting compound (I-3) with a reducing agent in an inert solvent. The reaction may be carried out in the presence of 1 equivalent to an excess amount of an organic acid, as necessary.

Examples of the above-mentioned "reducing agent" include trialkylsilane (e.g., triethylsilane) and the like. The amount of the "reducing agent" to be used is generally 1 to 20 equivalents, relative to compound (I-3).

Examples of the above-mentioned "organic acid" include acetic acid, trifluoroacetic acid and the like.

Examples of the above-mentioned "inert solvent" include "aromatic solvents", "aliphatic hydrocarbon solvents", "ether solvents", "halogenated hydrocarbon solvents" and the like. These solvents are preferably used in a mixture with water at an appropriate ratio.

The reaction temperature is generally −50 to 200° C., preferably −20 to 150° C.

The reaction time is generally 0.1 to 100 hr, preferably 0.1 to 40 hr.

This reaction can also be carried out, for example, by reacting compound (I-3) in the presence of a metal catalyst and a hydrogen source, in an inert solvent. The reaction may be carried out in the presence of 1 equivalent to an excess amount of an inorganic acid or an organic acid, as necessary.

Examples of the above-mentioned "metal catalyst" include palladium-carbon, palladium black, palladium chloride, platinum oxide, platinum black, Raney-nickel, Raney-cobalt and the like. The amount of the "metal catalyst" to be used is generally 0.001 to 100 equivalents, preferably 0.01 to 10 equivalents, relative to compound (I-3).

Examples of the above-mentioned "hydrogen source" include hydrogen gas, formic acid, formic acid amine salt, phosphinate, hydrazine and the like.

Examples of the above-mentioned "inorganic acid" include hydrogen chloride, sulfuric acid and the like.

Examples of the above-mentioned "organic acid" include acetic acid and the like.

Examples of the above-mentioned "inert solvent" include "alcohol solvents", "nitrile solvents", "aromatic solvents", "aliphatic hydrocarbon solvents", "ether solvents", "ester solvents", "amide solvents", "halogenated hydrocarbon solvents", "organic acid solvents" and the like. These solvents are preferably used in a mixture with water at an appropriate ratio. Of these, "alcohol solvents" are preferable.

The reaction temperature is generally −70 to 150° C., preferably −20 to 100° C.

The reaction time is generally 0.1 to 100 hr, preferably 0.1 to 40 hr.

Compounds (89) and (90) can be produced according to a method known per se.

<Reaction Scheme 26>

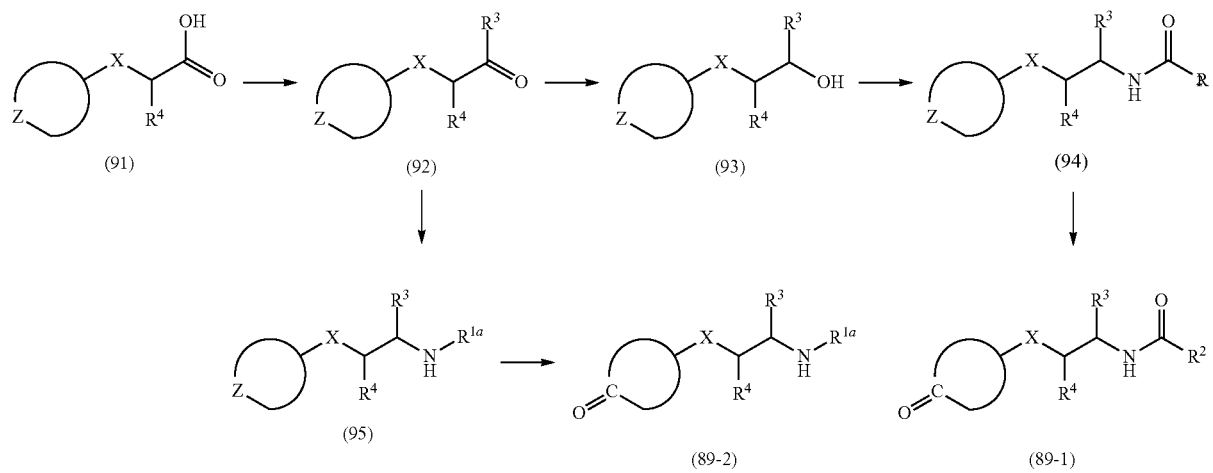

wherein Z is a protected carbonyl group, and the other symbols are as defined above.

Examples of the protected carbonyl group include cyclic acetals (e.g., 1,3-dioxane, 1,3-dioxolane), non-cyclic acetals (e.g., di-$C_{1-6}$ alkylacetal) and the like.

Compound (92) can be produced, for example, in the same manner as in the method of producing compound (52) from compound (50) in Reaction Scheme 12 and using compound (91).

Compound (93) can be produced, for example, by subjecting compound (92) to a reduction reaction.

This reaction is carried out in the same manner as in the production method of compound (20) in Reaction Scheme 12.

Compound (94) can be produced, for example, in the same manner as in the method of producing compound (24) from compound (20) in Reaction Scheme 5 and using compound (93).

Compound (89-1) can be produced, for example, by subjecting compound (94) to a deprotection reaction. The deprotection reaction can be carried out according to a method known per se, for example, the method described in Protective Groups in Organic Synthesis, John Wiley and Sons (1980) or the like.

Compound (95) can be produced, for example, in the same manner as in the method of producing compound (I-2) from compound (29) in Reaction Scheme 7 and using compound (92).

Compound (89-2) can be produced, for example, by subjecting compound (95) to a deprotection reaction. The deprotection reaction can be carried out according to a method known per se, for example, the method described in Protective Groups in Organic Synthesis, John Wiley and Sons (1980) or the like.

Compound (91) can be produced according to a method known per se.

<Reaction Scheme 27>

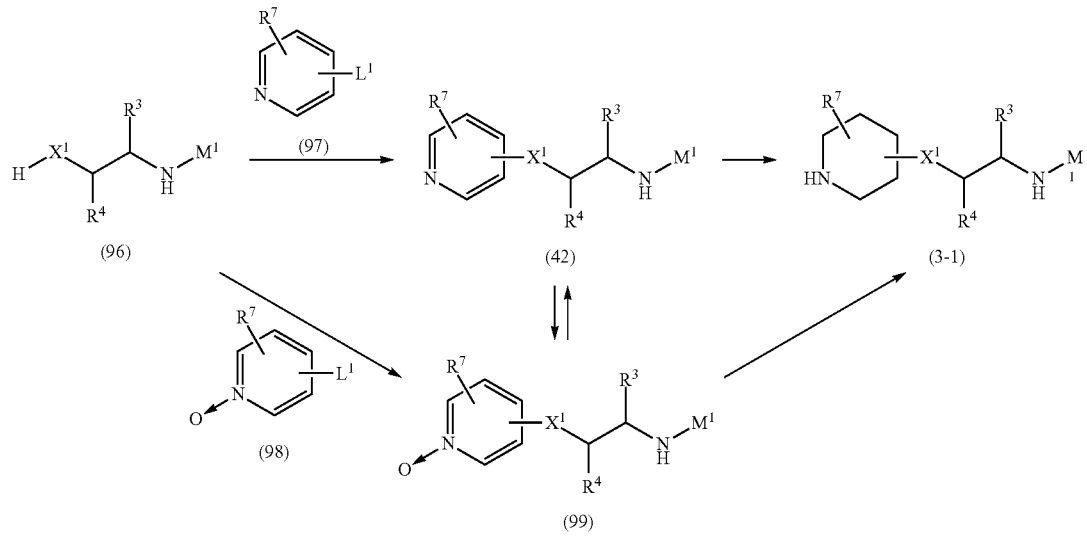

wherein each symbol is as defined above.

Compound (42) can be produced, for example, by subjecting compound (96) to a substitution reaction.

This reaction is carried out by reacting compound (96) with pyridine (97) substituted by a leaving group, which is optionally substituted, in the presence of a base, in an inert solvent.

The amount of the above-mentioned "pyridine substituted by a leaving group, which is optionally substituted" to be used is generally 0.1 to 10 equivalents, preferably 0.3 to 5 equivalents, relative to compound (96).

Examples of the above-mentioned "base" include "inorganic bases", "basic salts", "aromatic amines", "tertiary amines", "hydrides of alkali metal or alkaline earth metal", "metal alkoxides" and the like. The amount of the "base" to be used is generally 1 to 10 equivalents, preferably 1 to 5 equivalents, relative to compound (96).

Examples of the above-mentioned "inert solvent" include "aromatic solvents", "aliphatic hydrocarbon solvents", "ether solvents", "ester solvents", "amide solvents", "nitrile solvents" and the like. These solvents may be used in a mixture of two or more kinds thereof mixed at an appropriate ratio.

The reaction temperature is generally −70 to 200° C., preferably −20 to 150° C.

The reaction time is generally 0.1 to 100 hr, preferably 0.1 to 40 hr.

Compound (42) can also be produced, for example, by subjecting compound (99) to a reduction reaction.

This reaction is carried out by reacting compound (99) in the presence of a metal catalyst and a hydrogen source, in an inert solvent. This reaction may be carried out in the presence of a catalytic amount to an excess amount of an organic acid or 1 to 50 equivalents of hydrogen chloride, as necessary.

Examples of the above-mentioned "metal catalyst" include palladium-carbon, palladium black, palladium chloride, rhodium-carbon, platinum oxide, platinum black, platinum-palladium, Raney-nickel, Raney-cobalt and the like. The amount of the "metal catalyst" to be used is generally 0.001 to 1000 equivalents, preferably 0.01 to 100 equivalents, relative to compound (99).

Examples of the above-mentioned "hydrogen source" include hydrogen gas and the like. The pressure of the hydrogen gas used as a "hydrogen source" is generally 1 pressure to 100 pressures, preferably 1 pressure to 10 pressures.

Examples of the above-mentioned "organic acid" include acetic acid and the like.

Examples of the above-mentioned "inert solvent" include "alcohol solvents", "nitrile solvents", "aromatic solvents", "aliphatic hydrocarbon solvents", "ether solvents", "amide solvents", "halogenated hydrocarbon solvents", "organic acid solvents" and the like. These solvents are preferably used in a mixture with water at an appropriate ratio. Of these, "alcohol solvents" are preferable.

The reaction temperature is generally −70 to 150° C., preferably −20 to 100° C.

The reaction time is generally 0.1 to 100 hr, preferably 0.1 to 40 hr.

Compound (99) can be produced, for example, by subjecting compound (96) to a substitution reaction.

This reaction is carried out by reacting compound (96) with pyridine-N-oxide (98) substituted by a leaving group, which is optionally substituted, in the presence of a base, in an inert solvent.

The amount of the above-mentioned "pyridine-N-oxide substituted by a leaving group, which is optionally substituted" to be used is generally 0.1 to 10 equivalents, preferably 0.3 to 5 equivalents, relative to compound (96).

Examples of the above-mentioned "base" include "inorganic bases", "basic salts", "aromatic amines", "tertiary amines", "hydrides of alkali metal or alkaline earth metal", "metal alkoxides" and the like. The amount of the "base" to be used is generally 1 to 10 equivalents, preferably 1 to 5 equivalents, relative to compound (96).

Examples of the above-mentioned "inert solvent" include "aromatic solvents", "aliphatic hydrocarbon solvents", "ether solvents", "ester solvents", "amide solvents", "nitrile solvents" and the like. These solvents may be used in a mixture of two or more kinds thereof mixed at an appropriate ratio.

The reaction temperature is generally −70 to 200° C., preferably −20 to 150° C.

The reaction time is generally 0.1 to 100 hr, preferably 0.1 to 40 hr.

Compound (99) can also be produced, for example, by subjecting compound (42) to an oxidation reaction.

This reaction is carried out by reacting compound (42) in the presence of an oxidant, in an inert solvent.

Examples of the above-mentioned "oxidant" include peroxides such as hydrogen peroxide, persulfuric acid and the like; organic peroxides such as m-chloroperbenzoic acid and the like; persulfates such as OXONE® and the like, and the like. The amount of the "oxidant" to be used is generally 1 to 100 equivalents, preferably 1 to 10 equivalents, relative to compound (42).

Examples of the above-mentioned "inert solvent" include "alcohol solvents", "aromatic solvents", "aliphatic hydrocarbon solvents", "ether solvents", "amide solvents", "halogenated hydrocarbon solvents", acetic acid and the like. These solvents are preferably used in a mixture with water at an appropriate ratio. Of these, "halogenated hydrocarbon solvents" and "aromatic solvents" are preferable.

The reaction temperature is generally −70 to 150° C., preferably −20 to 100° C.

The reaction time is generally 0.1 to 100 hr, preferably 0.1 to 40 hr.

Compound (3-1) can be produced, for example, by subjecting compound (99) or compound (42) to a reduction reaction.

This reaction is carried out by reacting compound (99) or compound (42) in the presence of a metal catalyst and a hydrogen source, in an inert solvent. This reaction may be carried out in the presence of a catalytic amount to an excess amount of an organic acid or 1 to 50 equivalents of hydrogen chloride, as necessary.

Examples of the above-mentioned "metal catalyst" include palladium-carbon, palladium black, palladium chloride, rhodium-carbon, platinum oxide, platinum black, platinum-palladium, Raney-nickel, Raney-cobalt and the like. The amount of the "metal catalyst" to be used is generally 0.01 to 1000 equivalents, preferably 0.1 to 100 equivalents, relative to compound (42) or compound (99).

Examples of the above-mentioned "hydrogen source" include hydrogen gas and the like.

Examples of the above-mentioned "organic acid" include acetic acid and the like.

Examples of the above-mentioned "inert solvent" include "alcohol solvents", "nitrile solvents", "aromatic solvents", "aliphatic hydrocarbon solvents", "ether solvents", "amide solvents", "organic acid solvents" and the like. These solvents are preferably used in a mixture with water at an appropriate ratio. Of these, "alcohol solvents" are preferable.

The reaction temperature is generally −70 to 150° C., preferably −20 to 100° C.

The reaction time is generally 0.1 to 100 hr, preferably 0.1 to 40 hr.

<Reaction Scheme 28>

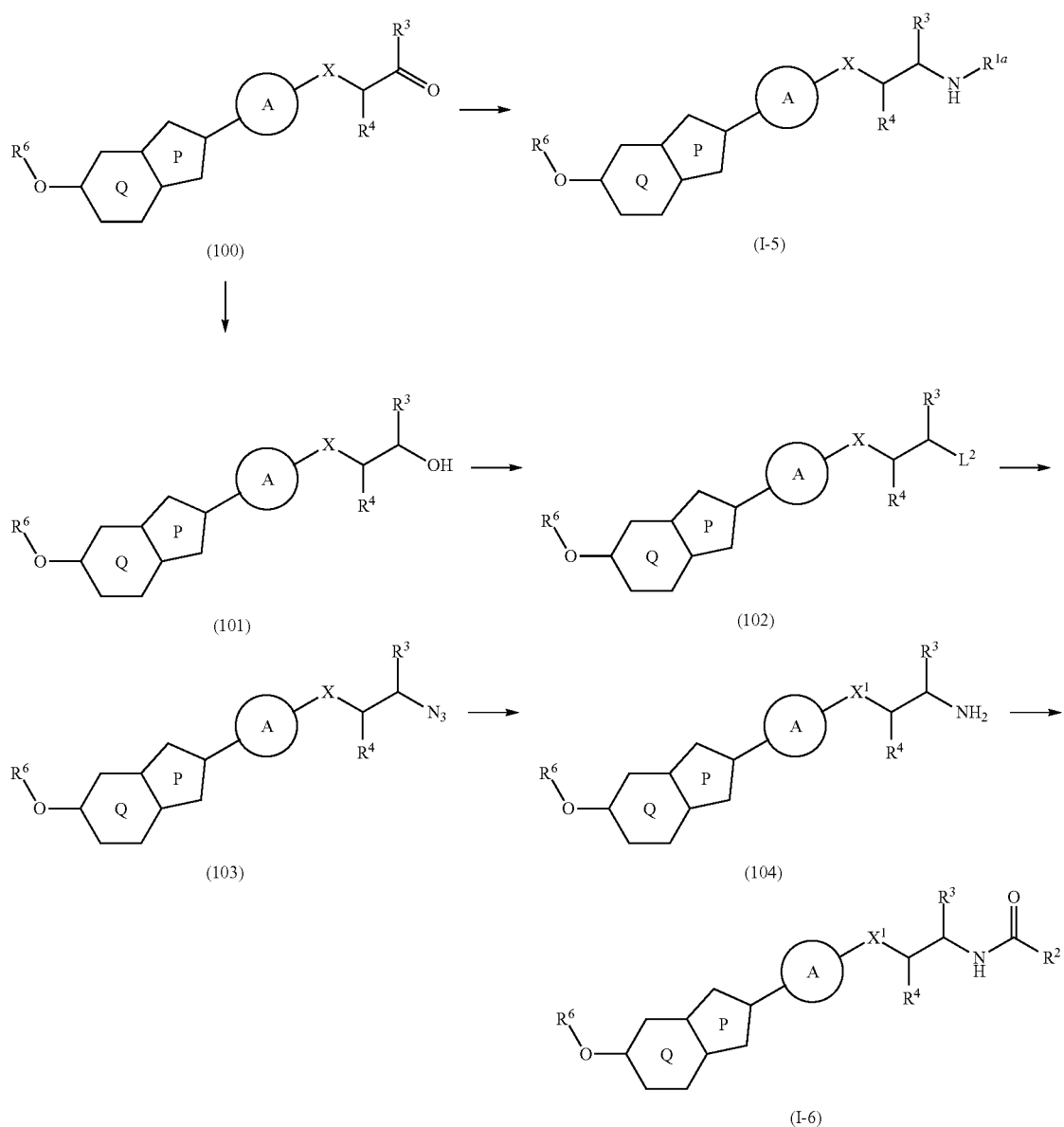

wherein each symbol is as defined above.

Compound (100) can be produced, for example, according to the production method of compound (100-1), compound (100-2) or compound (100-3) in Reaction Scheme 29, Reaction Scheme 30 or Reaction Scheme 32, or a method analogous thereto. Compound (100-1), compound (100-2) and compound (100-3) are encompassed in compound (100).

Compound (I-5) can be produced, for example, by subjecting compound (100) to a reductive amination reaction.

This reaction is carried out in the same manner as in the production method of compound (I-2) in Reaction Scheme 7.

Compound (104) can be produced, for example, in the same manner as in the method of producing compound (10) from compound (16) in Reaction Scheme 4 and using compound (100) as a starting material.

Compound (I-6) can be produced, for example, by subjecting compound (104) to an acylation reaction.

This reaction is carried out in the same manner as in the production method of compound (I-1) in Reaction Scheme 2.

<Reaction Scheme 29>

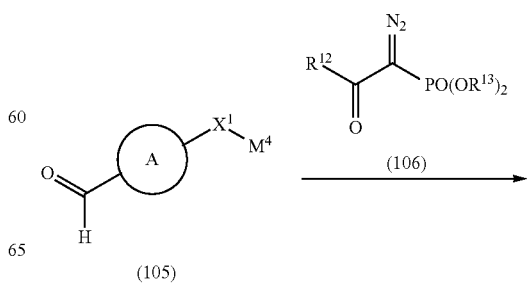

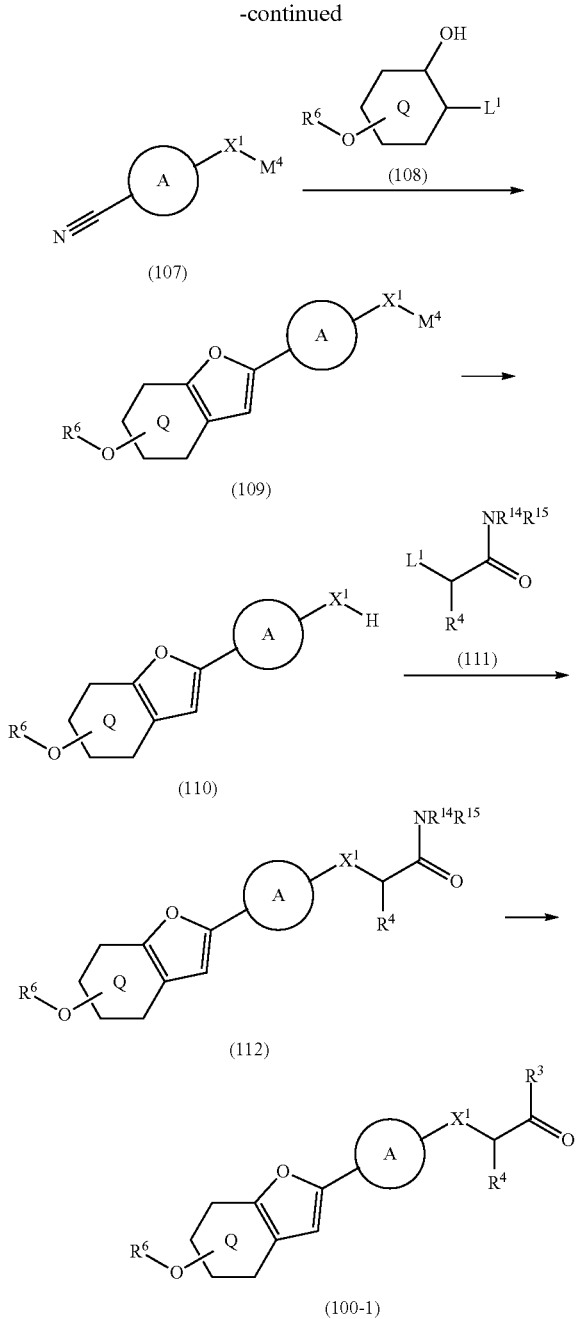

wherein $R^{12}$ and $R^{13}$ are each a substituent, $R^{14}$ and $R^{15}$ are each a substituent, or $R^{14}$ and $R^{15}$ in combination form a ring, and the other symbols are as defined above.

Compound (107) can be produced, for example, by reacting compound (105) with an α-diazophosphonate compound (106).

This reaction is carried out by reacting compound (105) with an α-diazophosphonate compound (106) in the presence of a base, in an inert solvent.

The amount of α-diazophosphonate compound (106) to be used is generally 1 to 20 equivalents, preferably 1 to 5 equivalents, relative to compound (105).

Examples of the above-mentioned "base" include "inorganic bases", "basic salts", "hydrides of alkali metal or alkaline earth metal", "metal alkoxides" and the like. The amount of the "base" to be used is generally 1 to 10 equivalents, preferably 1 to 5 equivalents, relative to compound (105).

Examples of the above-mentioned "inert solvent" include "alcohol solvents", "aromatic solvents", "aliphatic hydrocarbon solvents", "ether solvents", "ester solvents", "amide solvents" and the like. These solvents may be used in a mixture of two or more kinds thereof mixed at an appropriate ratio.

The reaction temperature is generally −78 to 150° C., preferably −78 to 100° C.

The reaction time is generally 0.1 to 100 hr, preferably 0.1 to 48 hr.

Compound (109) can be produced, for example, by subjecting compound (107) to a benzofuran ring-formation reaction with compound (108).

This reaction is carried out by reacting compound (107) with compound (108) in the presence of a transition metal catalyst and a base, in an inert solvent, under inert gas atmosphere. A ligand may be added, as necessary.

The amount of compound (107) to be used is generally 1 to 20 equivalents, preferably 1 to 5 equivalents, relative to compound (108).

Examples of the above-mentioned "transition metal catalyst" include palladium catalysts, nickel catalysts, iron catalysts, cobalt catalysts and the like. Examples of the palladium catalyst include bis(triphenylphosphine)palladium(II) dichloride and the like. The amount of the "transition metal catalyst" to be used is generally 0.001 to 1 equivalent, preferably 0.01 to 0.1 equivalents, relative to compound (108). In addition, copper catalyst and the like may be added as a co-catalyst. Examples of the copper catalyst include copper (I) iodide and the like. The amount of the "co-catalyst" to be used is generally 0.001 to 1 equivalent, preferably 0.01 to 0.5 equivalents, relative to compound (108).

Examples of the above-mentioned "ligand" include phosphine ligands. Examples of the phosphine ligand include triphenylphosphine and the like. The amount of the "ligand" to be used is generally 0.001 to 20 equivalents, preferably 0.01 to 1 equivalent, relative to compound (108).

Examples of the above-mentioned "base" include "aromatic amines", "tertiary amines" and the like. The amount of the "base" to be used is generally 0.1 to 20 equivalents, preferably 1 to 5 equivalents, relative to compound (108). The base may be used as a solvent.

Examples of the above-mentioned "inert solvent" include "amide solvents", "aromatic solvents", "aliphatic hydrocarbon solvents", "ether solvents", "ester solvents" and the like. These solvents may be used in a mixture of two or more kinds thereof mixed at an appropriate ratio.

Examples of the above-mentioned "inert gas" include nitrogen, argon and the like.

The reaction temperature is generally −70 to 150° C., preferably −20 to 150° C.

The reaction time is generally 0.1 to 100 hr, preferably 0.1 to 40 hr.

This reaction can also be carried out according to a method known per se, for example, the method described in Synthesis, pages 749-751, 1986 or the like, or a method analogous thereto.

Compound (110) can be produced, for example, by subjecting compound (109) to a deprotection reaction.

The deprotection reaction can be carried out according to a method known per se, for example, the method described in Protective Groups in Organic Synthesis, John Wiley and Sons (1980) or the like.

Compound (112) can be produced, for example, by reacting compound (110) with compound (111).

This reaction is carried out in the same manner as in the production method of compound (35) in Reaction Scheme 8.

Compound (100-1) can be produced, for example, by subjecting compound (112) to a substitution reaction with the corresponding organic metal reagent.

This reaction is carried out in the same manner as in the production method of compound (29-1) in Reaction Scheme 8.

<Reaction Scheme 30>

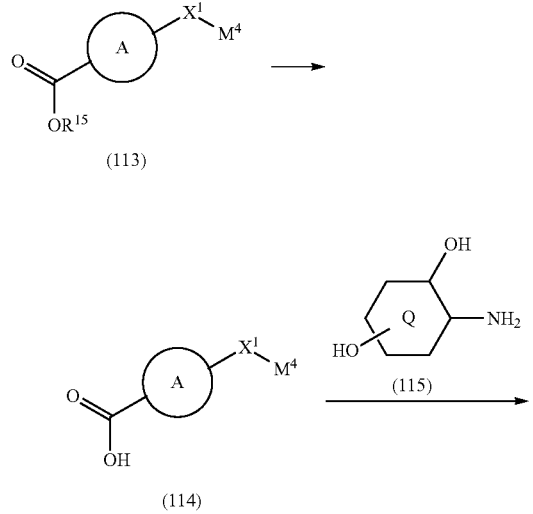

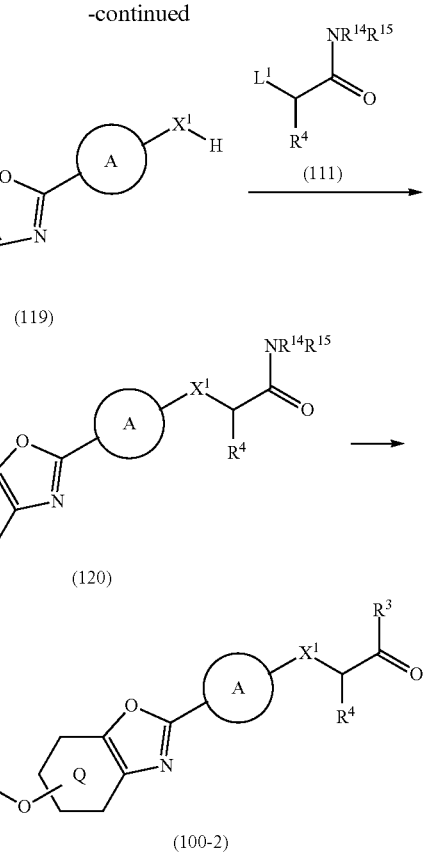

wherein $R^{16}$ is a carboxy-protecting group, and the other symbols are as defined above.

Compound (114) can be produced, for example, by subjecting compound (113) to a deprotection reaction.

The deprotection reaction can be carried out according to a method known per se, for example, the method described in Protective Groups in Organic Synthesis, John Wiley and Sons (1980) or the like.

Compound (116) can be produced, for example, by subjecting compound (114) to an amidation reaction with compound (115).

The above-mentioned "amidation reaction" is carried out in the same manner as in the production method of the "amide derivative" described as one of the production methods of compound (I-1) in Reaction Scheme 2.

Compound (117) can be produced, for example, by subjecting compound (116) to a cyclization reaction.

The above-mentioned "cyclization reaction" is carried out by reacting compound (116) in the presence of an activator, in an inert solvent.

Examples of the above-mentioned "activator" include p-toluenesulfonic acid, a combination of diethyl azodicarboxylate and triphenylphosphine, a combination of diisopropyl azodicarboxylate and triphenylphosphine, a combination of hexachloroethane, triphenylphosphine and a base, and the like. The amount of the "activator" to be used is generally 0.001 to 10 equivalents, preferably 0.01 to 8 equivalents, relative to compound (116).

Examples of the above-mentioned "inert solvent" include "aromatic solvents", "aliphatic hydrocarbon solvents", "ether solvents", "ester solvents", "amide solvents", "nitrile solvents", "halogenated hydrocarbon solvents" and the like.

These solvents may be used in a mixture of two or more kinds thereof mixed at an appropriate ratio.

Examples of the above-mentioned "base" include "aromatic amines", "tertiary amines" and the like.

The reaction temperature is generally −70° C. to 200° C., preferably −20° C. to 150° C.

The reaction time is generally 0.1 hr to 100 hr, preferably 0.1 hr to 40 hr.

Compound (118) can be produced, for example, by subjecting compound (117) to an alkylation reaction.

This reaction is carried out in the same manner as in the production method of compound (8) from compound (9) in Reaction Scheme 2.

Compound (119) can be produced, for example, by subjecting compound (118) to a deprotection reaction.

The deprotection reaction can be carried out according to a method known per se, for example, the method described in Protective Groups in Organic Synthesis, John Wiley and Sons (1980) or the like.

Compound (120) can be produced, for example, by reacting compound (119) with compound (111).

This reaction is carried out in the same manner as in the production method of compound (35) in Reaction Scheme 8.

Compound (100-2) can be produced, for example, by subjecting compound (120) to a substitution reaction with the corresponding organic metal reagent.

This reaction is carried out in the same manner as in the production method of compound (29-1) in Reaction Scheme 8.

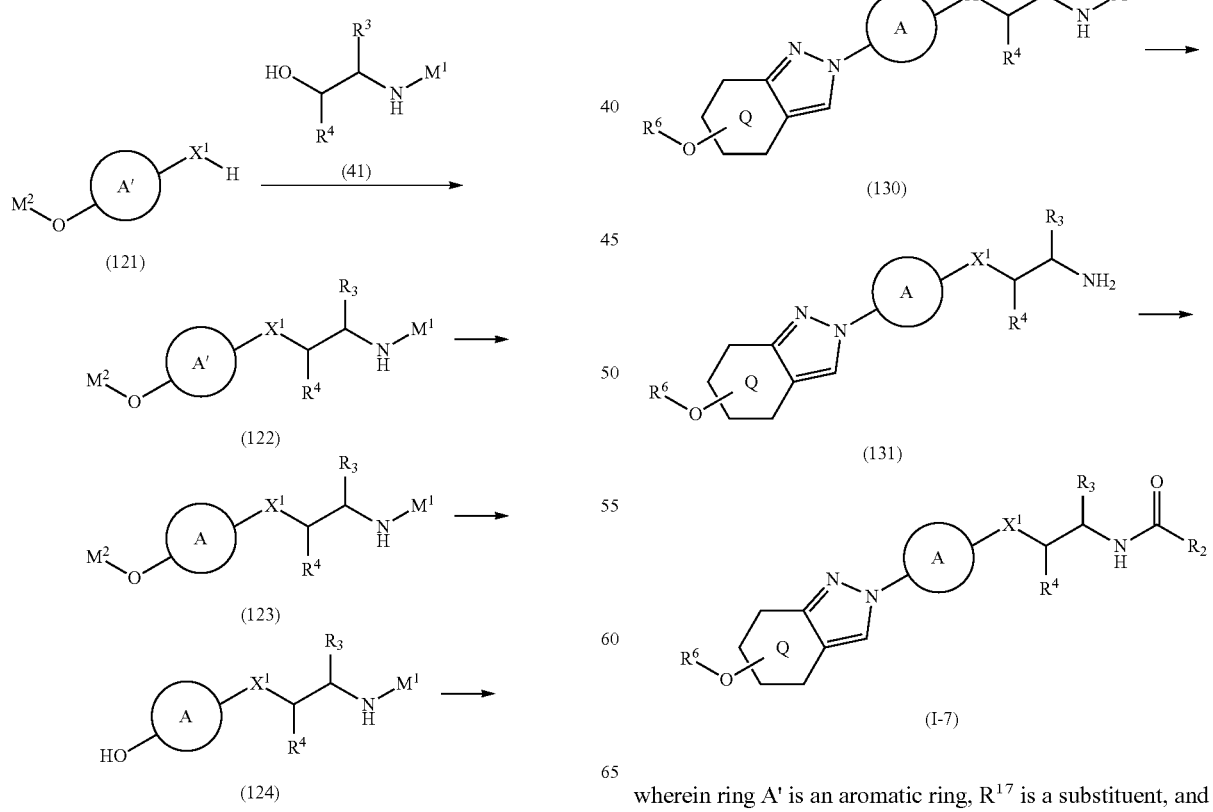

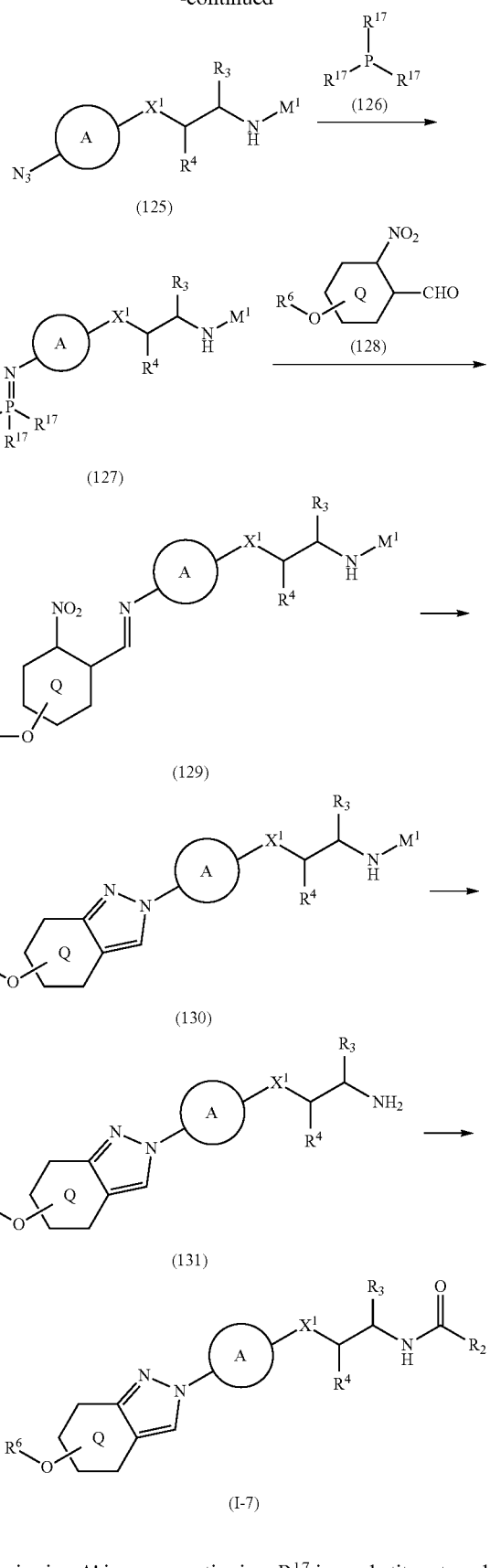

wherein ring A' is an aromatic ring, $R^{17}$ is a substituent, and the other symbols are as defined above.

Compound (122) can be produced, for example, by subjecting compound (121) to the Mitsunobu reaction with compound (41).

This reaction is carried out in the same manner as in the production method of compound (42) in Reaction Scheme 10.

Compound (123) can be produced, for example, by subjecting compound (122) to a reduction reaction.

This reaction is carried out in the same manner as in the production method of compound (42) in Reaction Scheme 27.

Compound (124) can be produced, for example, by subjecting compound (123) to a deprotection reaction.

The deprotection reaction can be carried out according to a method known per se, for example, the method described in Protective Groups in Organic Synthesis, John Wiley and Sons (1980) or the like.

Compound (125) can be produced, for example, by subjecting compound (124) to an azidation reaction.

The above-mentioned "azidation reaction" is carried out by reacting compound (124) with an azidating agent in the presence of an activator, in an inert solvent.

Examples of the above-mentioned "azidating agent" include diphenylphosphinoazide (DPPA) and the like. The amount of the "azidating agent" to be used is generally 1 to 10 equivalents, preferably 1 to 5 equivalents, relative to compound (124).

Examples of the above-mentioned "activator" include a combination of diethyl azodicarboxylate and triphenylphosphine, a combination of diisopropyl azodicarboxylate and triphenylphosphine, a combination of hexachloroethane, triphenylphosphine and a base, and the like. The amount of the "activator" to be used is generally 0.001 to 10 equivalents, preferably 0.01 to 8 equivalents, relative to compound (124).

Examples of the above-mentioned "inert solvent" include "aromatic solvents", "aliphatic hydrocarbon solvents", "ether solvents", "ester solvents", "amide solvents", "nitrile solvents", "halogenated hydrocarbon solvents" and the like. These solvents may be used in a mixture of two or more kinds thereof mixed at an appropriate ratio.

The reaction temperature is generally −70° C. to 200° C., preferably −20° C. to 150° C.

The reaction time is generally 0.1 hr to 100 hr, preferably 0.1 hr to 40 hr.

The above-mentioned "azidation reaction" can also be carried out by compound (124) with an azidating agent in the presence of a base, in an inert solvent.

Examples of the above-mentioned "azidating agent" include diphenylphosphinoazide (DPPA) and the like. The amount of the "azidating agent" to be used is generally 1 to 10 equivalents, preferably 1 to 5 equivalents, relative to compound (124).

Examples of the above-mentioned "base" include "aromatic amines", "tertiary amines" and the like. The amount of the "base" to be used is generally 1 to 10 equivalents, preferably 1 to 5 equivalents, relative to compound (124).

Examples of the above-mentioned "inert solvent" include "aromatic solvents", "aliphatic hydrocarbon solvents", "ether solvents", "ester solvents", "amide solvents", "nitrile solvents", "halogenated hydrocarbon solvents" and the like. These solvents may be used in a mixture of two or more kinds thereof mixed at an appropriate ratio.

The reaction temperature is generally −70° C. to 200° C., preferably −20° C. to 150° C.

The reaction time is generally 0.1 hr to 100 hr, preferably 0.1 hr to 40 hr.

Compound (127) can be produced, for example, by reacting compound (125) with organic phosphorus compound (126).

This reaction is carried out by reacting compound (125) with organic phosphorus compound (126) in an inert solvent.

Examples of the above-mentioned "organic phosphorus compound" include triphenylphosphine, tributylphosphine and the like. The amount of the "organic phosphorus compound" to be used is generally 1 to 20 equivalents, preferably 1 to 5 equivalents, relative to compound (125).

Examples of the above-mentioned "inert solvent" include "aromatic solvents", "aliphatic hydrocarbon solvents", "ether solvents", "ester solvents", "amide solvents", "nitrile solvents", "halogenated hydrocarbon solvents" and the like. These solvents may be used in a mixture of two or more kinds thereof mixed at an appropriate ratio. In addition, the reaction may be carried out without solvent.

The reaction temperature is generally 0° C. to 200° C., preferably 0° C. to 150° C.

The reaction time is generally 0.1 hr to 100 hr, preferably 0.1 hr to 40 hr.

This reaction can also be carried out according to a method known per se, for example, the method described in Tetrahedron, pages 437-472, 1981 or the like, or a method analogous thereto.

Compound (129) can be produced, for example, by subjecting compound (127) to a condensation reaction with compound (128).

This reaction is carried out by reacting compound (127) with compound (128) in an inert solvent. The amount of compound (128) to be used is generally 1 to 10 equivalents, preferably 1 to 5 equivalents, relative to compound (127).

Examples of the above-mentioned "inert solvent" include "aromatic solvents", "aliphatic hydrocarbon solvents", "ether solvents", "ester solvents", "amide solvents", "alcohol solvents", "nitrile solvents", "halogenated hydrocarbon solvents" and the like. These solvents may be used in a mixture of two or more kinds thereof mixed at an appropriate ratio. In addition, the reaction may be carried out without solvent.

The reaction temperature is generally −78° C. to 200° C., preferably 0° C. to 150° C.

The reaction time is generally 0.1 hr to 100 hr, preferably 0.1 hr to 40 hr.

Compound (130) can be produced, for example, by subjecting compound (129) to a cyclization reaction.

The above-mentioned "cyclization reaction" is carried out by reacting compound (129) with an organic phosphorus compound in an inert solvent.

Examples of the above-mentioned "organic phosphorus compound" include triethyl phosphite, trimethyl phosphite and the like. The amount of the "organic phosphorus compound" to be used is generally 1 to 100 equivalents, preferably 1 to 10 equivalents, relative to compound (129).

Examples of the above-mentioned "inert solvent" include "aromatic solvents", "aliphatic hydrocarbon solvents", "ether solvents", "ester solvents", "amide solvents", "nitrile solvents", "halogenated hydrocarbon solvents" and the like. These solvents may be used in a mixture of two or more kinds thereof mixed at an appropriate ratio. In addition, the reaction may be carried out without solvent.

The reaction temperature is generally 0° C. to 200° C., preferably 50° C. to 200° C.

The reaction time is generally 0.1 hr to 100 hr, preferably 0.1 hr to 40 hr.

Compound (131) can be produced, for example, by subjecting compound (130) to a deprotection reaction.

The deprotection reaction can be carried out according to a method known per se, for example, the method described in Protective Groups in Organic Synthesis, John Wiley and Sons (1980) or the like.

Compound (I-7) can be produced, for example, by subjecting compound (131) to an acylation reaction.

This reaction is carried out in the same manner as in the production method of compound (I-1) in Reaction Scheme 2.

<Reaction Scheme 32>

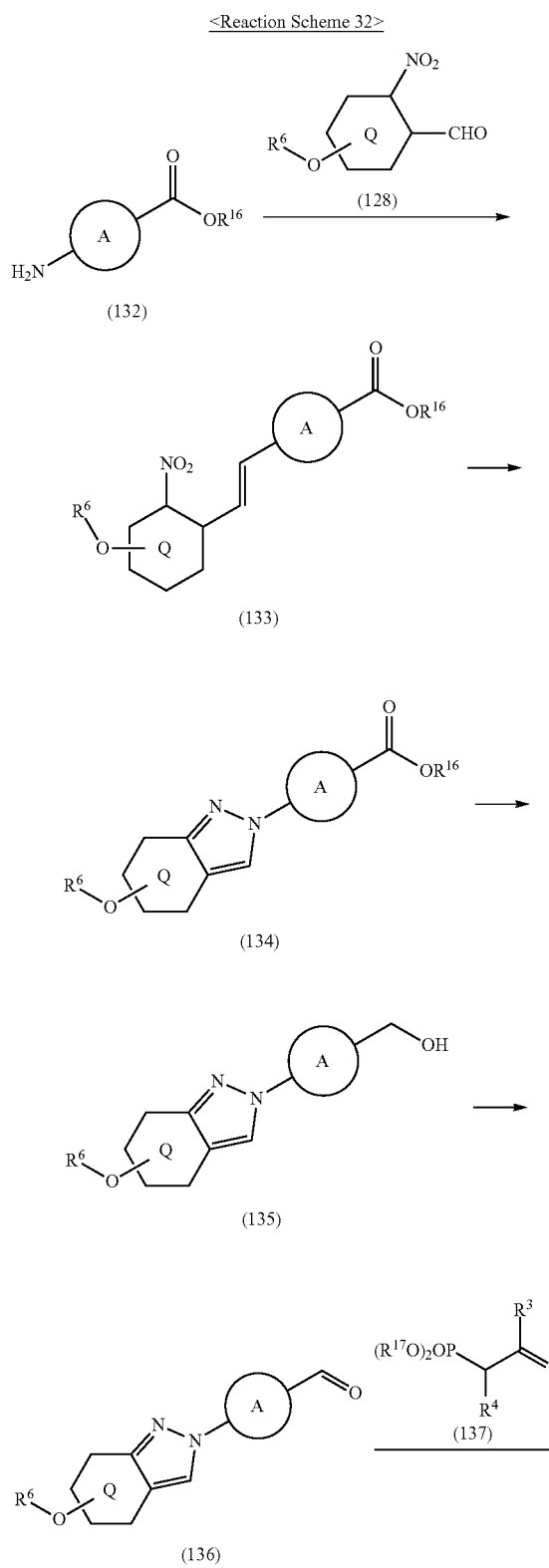

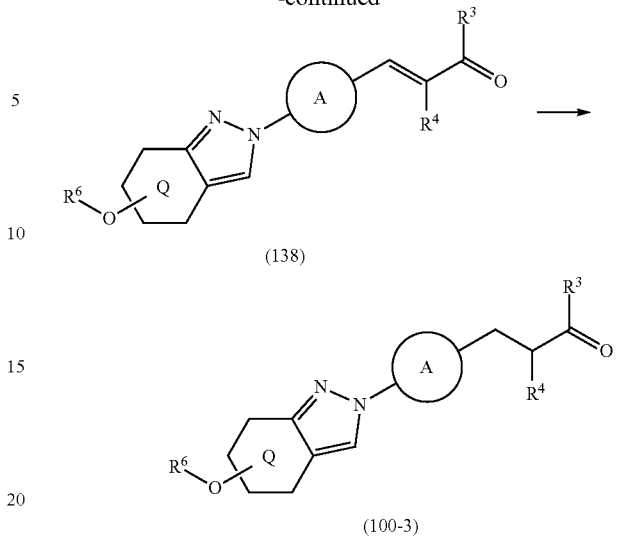

wherein each symbol is as defined above.

Compound (133) can be produced, for example, by subjecting compound (132) to a condensation reaction with compound (128).

This reaction is carried out by reacting compound (132) with compound (128) in an inert solvent. An acid and the like can be used, as necessary.

The amount of compound (128) to be used is generally 1 to 20 equivalents, preferably 1 to 5 equivalents, relative to compound (132).

Examples of the above-mentioned "acid" include hydrochloric acid, p-toluenesulfonic acid and the like. The amount of the "acid" to be used is generally 0.001 to 20 equivalents, preferably 0.01 to 5 equivalents, relative to compound (132).

Examples of the above-mentioned "inert solvent" include "aromatic solvents", "aliphatic hydrocarbon solvents", "ether solvents", "ester solvents", "amide solvents", "nitrile solvents", "halogenated hydrocarbon solvents" and the like. These solvents may be used in a mixture of two or more kinds thereof mixed at an appropriate ratio. In addition, the reaction may be carried out without solvent.

The reaction temperature is generally 0° C. to 200° C., preferably 50° C. to 150° C.

The reaction time is generally 0.1 hr to 100 hr, preferably 0.1 hr to 40 hr.

Compound (134) can be produced, for example, compound (133) to a cyclization reaction.

This reaction is carried out in the same manner as in the production method of compound (130) in Reaction Scheme 31.

Compound (135) can be produced, for example, by subjecting compound (134) to a reduction reaction.

The above-mentioned "reduction reaction" is carried out by reacting compound (134) in the presence of a reducing agent, in an inert solvent.

Examples of the above-mentioned "reducing agent" include metal hydrides (e.g., sodium bis(2-methoxyethoxy) aluminum hydride, diisobutylaluminum hydride), metal hydride complex compounds (e.g., sodium borohydride, lithium borohydride, lithium aluminum hydride, sodium aluminum hydride) and the like. The amount of the "reducing agent" to be used is generally 0.1 to 20 equivalents, preferably 1 to 5 equivalents, relative to compound (134).

Examples of the above-mentioned "inert solvent" include "alcohol solvents", "aromatic solvents", "aliphatic hydrocarbon solvents", "ether solvents", "amide solvents" and the like. These solvents may be used in a mixture of two or more kinds thereof mixed at an appropriate ratio.

The reaction temperature is generally −70° C. to 150° C., preferably −20° C. to 100° C.

The reaction time is generally 0.1 hr to 100 hr, preferably 0.1 hr to 40 hr.

Compound (136) can be produced, for example, by subjecting compound (135) to an oxidation reaction.

The above-mentioned "oxidation reaction" can be carried out according to a method known per se, for example, the method described in Journal of Medicinal Chemistry, pages 5282-5290, 2006 or the like, or a method analogous thereto.

This reaction is carried out by reacting compound (135) with an oxidant in an inert solvent.

Examples of the above-mentioned "oxidant" include manganese dioxide, tetrapropylammonium perruthenate, chromium trioxide, Dess-Martin reagent and the like. The amount of the "oxidant" to be used is generally 1 to 5 equivalents, preferably 1 to 1.5 equivalents, relative to compound (135).

Examples of the above-mentioned "inert solvent" include "nitrile solvents", "amide solvents", "halogenated hydrocarbon solvents", "ether solvents", "aromatic solvents" and the like. These solvents may be used in a mixture of two or more kinds thereof mixed at an appropriate ratio. Of these, "nitrile solvents", "ether solvents", "halogenated hydrocarbon solvents" and the like are preferable.

The reaction temperature is generally −100 to 50° C., preferably −78 to 0° C.

The reaction time is generally 5 min to 48 hr, preferably 30 min to 24 hr.

Compound (138) can be produced, for example, by reacting compound (136) with compound (137).

This reaction is carried out by reacting compound (136) with compound (137) in the presence of a base, in an inert solvent.

The amount of compound (137) to be used is generally 1 to 5 equivalents, preferably 1 to 2 equivalents, relative to compound (136).

Examples of the above-mentioned "base" include "inorganic bases", "basic salts", "aromatic amines", "tertiary amines", "hydrides of alkali metal or alkaline earth metal", "metal alkoxides" and the like. The amount of the "base" to be used is generally 1 to 5 equivalents, preferably 1 to 2 equivalents, relative to compound (136).

Examples of the above-mentioned "inert solvent" include "aromatic solvents", "aliphatic hydrocarbon solvents", "ether solvents", "ester solvents", "amide solvents", "nitrile solvents" and the like. These solvents may be used in a mixture of two or more kinds thereof mixed at an appropriate ratio.

The reaction temperature is generally −78 to 200° C., preferably −20 to 100° C.

The reaction time is generally 0.1 hr to 100 hr, preferably 0.1 to 40 hr.

Compound (100-3) can be produced, for example, by subjecting compound (138) to a reduction reaction.

This reaction is carried out in the same manner as in the production method of compound (42) from compound (99) in Reaction. Scheme 27. The reaction used for formula (II) and (I') is carried out in the same manner as in the production method of compound (I-1) in Reaction Scheme 2.

In compound (I) thus obtained, a functional group within a molecule can also be converted to a desired functional group by a combination of chemical reactions known per se. Examples of the chemical reaction here include oxidation reaction, reduction reaction, alkylation reaction, acylation reaction, ureation reaction, hydrolysis reaction, amination reaction, esterification reaction, aryl coupling reaction, deprotection reaction and the like.

Compound (I) obtained by the above-mentioned production methods can be isolated and purified by a known means, for example, solvent extraction, liquid conversion, phase transfer, crystallization, recrystallization, chromatography and the like.

When compound (I) contains an optical isomer, a stereoisomer, a regioisomer or a rotamer, these are also encompassed in compound (I), and can be obtained as a single product according to synthesis and separation methods known per se. For example, when compound (I) contains an optical isomer, an optical isomer resolved from this compound is also encompassed in compound (I).

The optical isomer can be produced by a method known per se.

Compound (I) may be a crystal.

Crystals of compound (I) (hereinafter sometimes to be abbreviated as the crystals of the present invention) can be produced by crystallization according to crystallization methods known per se.

In the present specification, the melting point means that measured using, for example, a micromelting point apparatus (Yanako, MP-500D or Buchi, B-545), a DSC (differential scanning calorimetry) device (SEIKO, EXSTAR6000) or the like.

In general, the melting points vary depending on the measurement apparatuses, the measurement conditions and the like. The crystal in the present specification may show different values from the melting point described in the present specification, as long as they are within each of a general error range.

The crystal of the present invention is superior in physicochemical properties (e.g., melting point, solubility, stability) and biological properties (e.g., pharmacokinetics (absorption, distribution, metabolism, excretion), efficacy expression), and thus it is extremely useful as a medicament.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bound silica gel. In HPLC (high performance liquid chromatography), C18 means use of octadecyl-bound silica gel. The ratios of elution solvents are volume mixing ratios, unless otherwise specified.

In the following Examples, the following abbreviations are used.
mp: melting point
THF: tetrahydrofuran
DMF: N,N-dimethylformamide
DMA: N,N-dimethylacetamide
DME: 1,2-dimethoxyethane
WSC: 1-ethyl-3-(3-dimethylaminopropyl)carbodiimide hydrochloride
HOBt: 1-hydroxybenzotriazole 1 hydrate ¹H NMR (protone nuclear magnetic resonance spectrum) was measured by Fourier-transform type NMR. For the analysis, ACD/SpecManager (trade name) and the like were used. Peaks with very mild protons such as hydroxyl group, amino group and the like are note described.

Other abbreviations used in the specification mean the following.
s: singlet
d: doublet
t: triplet
q: quartet
m: multiplet
br: broad
J: coupling constant
Hz: hertz
$CDCl_3$: deuterated chloroform
DMSO-$d_6$: $d_6$-dimethyl sulfoxide
¹H-NMR: protone nuclear magnetic resonance
TFA: trifluoroacetic acid MS (mass spectrum) was measured by LC/MS (liquid chromatography mass spectrometer). As the ionization method, ESI (ElectroSpray Ionization) method, or APCI (Atmospheric Pressure Chemical Ionization) method was used. The data indicates those found. Generally, a molecular ion peak is observed. In the case of a compound having a tert-butoxycarbonyl group (-Boc), a peak after elimination of a tert-butoxycarbonyl group or tert-butyl group may be observed as a fragment ion. In the case of a compound having a hydroxyl group (—OH), a peak after elimination of $H_2O$ may be observed as a fragment ion. In the case of a salt, a molecular ion peak or fragment ion peak of free form is generally observed.

The elemental analysis value (Anal.) shows Calculated (Calcd) and Found.

Reference Example 1 tert-butyl [(1S)-1-methyl-2-(piperidin-4-yloxy)ethyl] carbamate

A mixture of tert-butyl [(1S)-2-hydroxy-1-methylethyl] carbamate (30 g), 4-nitropyridine-N-oxide (25.2 g), tripotassium phosphate (109.0 g) and propionitrile (150 mL) was stirred at 90 to 100° C. for 6 hr. After allowing to cool to room temperature, water (100 mL) was added, and the mixture was extracted with ethyl acetate (300 mL). The ethyl acetate layer was concentrated to give tert-butyl {(1S)-1-methyl-2-[(1-oxidepyridin-4-yl)oxy]ethyl}carbamate (50 g) as a brown oil.

tert-Butyl {(1S)-1-methyl-2-[(1-oxidepyridin-4-yl)oxy] ethyl}carbamate (50 g), acetic acid (500 mL) and 10% palladium-carbon (12 g) were charged into pressure-resistant reactor vessel, and the mixture was stirred at 50° C. for 6 hr at 0.5 MPa hydrogen pressure. The mixture was allowed to cool to room temperature, and the pressure was reduced to normal level. The insoluble material was removed by filtration, and the filtrate was concentrated. Ethyl acetate (450 mL) was added thereto, and the mixture was extracted with 10% aqueous citric acid solution (450 mL). The ethyl acetate layer was extracted again with 10% aqueous citric acid solution (225 mL). The aqueous layers were combined, adjusted to pH 12 with 8M aqueous sodium hydroxide solution, and extracted twice with toluene (450 mL). The toluene layers were combined and concentrated to give tert-butyl [(1S)-1-methyl-2-(pyridin-4-yloxy)ethyl]carbamate (30 g) as a pale-yellow oil.

tert-Butyl [(1S)-1-methyl-2-(pyridin-4-yloxy)ethyl]carbamate (30 g), acetic acid (300 mL) and 10% palladium-carbon (7.5 g) were charged into pressure-resistant reactor vessel, and the mixture was stirred at 80° C. for 6 hr at 0.8 MPa hydrogen pressure. The mixture was allowed to cool to room temperature, and the pressure was reduced to normal level. The insoluble material was removed by filtration, and the filtrate was concentrated. Ethyl acetate (300 mL) was added to the residue, and the mixture was extracted with 10% aqueous citric acid solution (300 mL). The ethyl acetate layer was extracted again with 10% aqueous citric acid solution (150 mL). The aqueous layers were combined, adjusted to pH 12 with 8M aqueous sodium hydroxide solution, and extracted twice with toluene (300 mL). The toluene layers were combined and concentrated. Methanol (30 mL), ethyl acetate (120 mL) and succinic acid (12.1 g) were added to the residue and the mixture was stirred to give crystals. After stirring for 1 hr, diisopropyl ether (150 mL) was added, and the mixture was stirred for 1 hr. The resulting crystals were collected by filtration, washed with diisopropyl ether (150 mL) and dried to give the title compound (32.9 g) as white crystals.

¹H NMR (500 MHz, DMSO-$d_6$) δ 1.00 (3H, d), 1.37 (9H, s), 1.5-1.7 (2H, m), 1.8-2.0 (2H, m), 2.29 (4H, s), 2.6-3.0 (2H, m), 3.0-3.2 (2H, m), 3.2-3.4 (2H, m), 3.45-3.7 (2H, m), 6.6-6.7 (1H, m)

Example 1

N-[(1S)-2-({1-[6-(cyclopropylmethoxy)-1,3-benzoxazol-2-yl]piperidin-4-yl}oxy)-1-methylethyl]acetamide A) (2S)-2-[(tert-butoxycarbonyl)amino]propyl 4-methylbenzenesulfonate A mixture of tert-butyl [(1S)-2-hydroxy-1-methylethyl] carbamate (10.0 g), tosyl chloride (12.0 g) and pyridine (100 mL) was stirred for 30 min under ice-cooling, and at room temperature for 2 hr. Tosyl chloride (6.0 g) was further added to the reaction mixture, and the mixture was stirred at room temperature overnight. 0.5M Hydrochloric acid was added to the reaction mixture, and the mixture was extracted with ethyl acetate. The obtained organic layer was washed with saturated brine and dried over anhydrous magnesium sulfate. The solvent was evaporated under reduced pressure and the residue was purified by silica gel column chromatography (hexane/ethyl acetate) to give the title compound as a white solid (13.5 g).

¹H NMR (300 MHz, DMSO-$d_6$) δ 0.97 (3H, d, J=6.8 Hz) 1.34 (9H, s) 2.42 (3H, s) 3.49-3.96 (3H, m) 6.86 (1H, d, J=7.6 Hz) 7.48 (2H, d, J=8.1 Hz) 7.78 (2H, d, J=8.1 Hz).

B) tert-butyl [(1S)-1-methyl-2-(pyridin-4-yloxy) ethyl]carbamate

To a suspension of sodium hydride (oil, 60%, 1.61 g) in DMF (50 mL) was added 4-hydroxypyridine (3.83 g) under ice-cooling. The reaction mixture was stirred for 30 min under ice-cooling, and (2S)-2-[(tert-butoxycarbonyl)amino] propyl 4-methylbenzenesulfonate (13.3 g) was added thereto in small portions under ice-cooling. The reaction mixture was stirred for 2 hr under ice-cooling, and at 60° C. for 3 hr. Water was added to the reaction mixture, and the mixture was extracted with ethyl acetate. The obtained organic layer was washed with saturated brine and dried over anhydrous magnesium sulfate. The solvent was evaporated under reduced pressure and the residue was purified by silica gel column chromatography (hexane/ethyl acetate) to give the title compound (2.10 g).

¹H NMR (300 MHz, DMSO-d₆) δ 1.06-1.14 (3H, m) 1.38 (9H, s) 3.76-3.98 (3H, m) 6.76-7.07 (3H, m) 8.27-8.47 (2H, m).

C) tert-butyl [(1S)-1-methyl-2-(piperidin-4-yloxy)ethyl]carbamate

To a solution of tert-butyl [(1S)-1-methyl-2-(pyridin-4-yloxy)ethyl]carbamate (1.03 g) in acetic acid (10 mL)/ethanol (10 mL) was added platinum oxide (500 mg), and the reaction mixture was stirred at room temperature for 5 hr under a hydrogen atmosphere. The catalyst was filtered off, and the filtrate was concentrated. The obtained residue was dissolved in 0.5 M hydrochloric acid, and the solution was washed with ethyl acetate, basified with potassium carbonate, and extracted with ethyl acetate. The extract was washed with saturated brine, and dried over anhydrous sodium sulfate. The solvent was evaporated to give the title compound (805 mg).

¹H NMR (300 MHz, CDCl₃) δ 1.17 (3H, d, J=6.9 Hz), 1.36-1.47 (11H, m), 1.86-1.91 (2H, m), 2.55-2.64 (2H, m), 3.03-3.10 (2H, m), 3.30-3.44 (3H, m), 3.78 (1H, m), 4.71 (1H, m).

D) 2-sulfanyl-1,3-benzoxazol-6-ol

A suspension of 4-aminobenzene-1,3-diol hydrochloride (25.6 g), potassium ethylxanthate (76.1 g) and potassium hydroxide (13.3 g) in ethanol (450 mL) was stirred for 16 hr with heating under reflux. After allowing to cool to room temperature, the mixture was concentrated under reduced pressure, water (400 mL) was added thereto and the insoluble material was filtered through celite. To the filtrate were added 6 M hydrochloric acid (40 mL), and then 1 M hydrochloric acid (300 mL). The precipitate was collected, and washed successively with water, acetonitrile and diisopropyl ether to give the title compound (16.8 g).

¹H NMR (300 MHz, DMSO-d₆) δ 6.72 (1H, dd, J=8.7, 2.3 Hz), 6.89 (1H, d, J=1.9 Hz), 7.04 (1H, d, J=8.3 Hz), 9.75 (1H, s), 13.62 (1H, brs).

E) 2-chloro-1,3-benzoxazol-6-ol

To a suspension of 2-sulfanyl-1,3-benzoxazol-6-ol (1.00 g) in thionyl chloride (4.36 mL) was added DMF (0.278 mL), and the mixture was stirred with heating at 80° C. for 5 min. After allowing to cool to room temperature, the mixture was concentrated under reduced pressure. The residue was dissolved in ethyl acetate/THF (1:1), and the solution was washed with saturated aqueous sodium hydrogen carbonate solution, and dried over anhydrous sodium sulfate. The solvent was evaporated under reduced pressure, and the obtained residue was triturated with acetonitrile. The obtained powder was washed with diisopropyl ether to give the title compound (483 mg).

¹H NMR (300 MHz, CDCl₃) δ 5.13 (1H, s), 6.85 (1H, dd, J=2.1, 8.7 Hz), 6.99 (1H, d, J=2.1 Hz), 7.50 (1H, d, J=8.7 Hz).

F) tert-butyl [(1S)-2-{[1-(6-hydroxy-1,3-benzoxazol-2-yl)piperidin-4-yl]oxy}-1-methylethyl]carbamate To a solution of tert-butyl [(1S)-1-methyl-2-(piperidin-4-yloxy)ethyl]carbamate (308 mg) and N,N-diisopropylethylamine (0.311 mL) in DMF (2 mL) was added 2-chloro-1,3-benzoxazol-6-ol (202 mg), and the mixture was stirred at room temperature for 5 hr. Ethyl acetate was added to the reaction mixture, and the mixture was washed with saturated brine and dried over anhydrous sodium sulfate. The extract was applied to silica gel chromatography (NH, ethyl acetate), and concentrated under reduced pressure. The obtained residue was purified by silica gel chromatography (hexane/ethyl acetate) to give the title compound (446 mg).

¹H NMR (300 MHz, CDCl₃) δ 1.17 (3H, d, J=6.6 Hz), 1.45 (9H, s), 1.65-1.71 (2H, m), 1.90-1.98 (2H, m), 3.43-3.54 (5H, m), 3.83 (3H, m), 4.66 (1H, brs), 6.64-6.67 (1H, m), 6.83 (1H, d, J=2.4 Hz), 7.13 (1H, d, J=8.7 Hz).

G) tert-butyl [(1S)-2-({1-[6-(cyclopropylmethoxy)-1,3-benzoxazol-2-yl]piperidin-4-yl}oxy)-1-methylethyl]carbamate To a solution of tert-butyl [(1S)-2-{[1-(6-hydroxy-1,3-benzoxazol-2-yl)piperidin-4-yl]oxy}-1-methylethyl]carbamate (445 mg) in DMF (3 mL) were added potassium carbonate (471 mg) and (bromomethyl)cyclopropane (0.331 mL), and the mixture was stirred with heating at 60° C. for 7 hr under a nitrogen atmosphere. The reaction mixture was allowed to cool to room temperature, diluted with ethyl acetate, washed with saturated brine, and dried over anhydrous sodium sulfate. The extract was applied to silica gel chromatography (NH, ethyl acetate), and concentrated under reduced pressure, and the obtained residue was purified by silica gel chromatography (hexane/ethyl acetate) to give the title compound (439 mg).

¹H NMR (300 MHz, CDCl₃) δ 0.32-0.37 (2H, m), 0.61-0.67 (2H, m), 1.18 (3H, d, J=6.6 Hz), 1.24-1.30 (1H, m), 1.45 (9H, s), 1.66-1.77 (2H, m), 1.90-1.96 (2H, m), 3.43-3.59 (5H, m), 3.78 (2H, d, J=6.9 Hz), 3.83-3.91 (3H, m), 4.65 (1H, br), 6.75 (1H, dd, J=2.4, 8.7 Hz), 6.87 (1H, d, J=2.1 Hz), 7.20 (1H, d, J=8.7 Hz).

H) N-[(1S)-2-({1-[6-(cyclopropylmethoxy)-1,3-benzoxazol-2-yl]piperidin-4-yl}oxy)-1-methylethyl]acetamide To tert-butyl [(1S)-2-({1-[6-(cyclopropylmethoxy)-1,3-benzoxazol-2-yl]piperidin-4-yl}oxy)-1-methylethyl]carbamate (438 mg) was added 4M hydrogen chloride/ethyl acetate (5 mL), and the mixture was stirred at room temperature for 30 min and concentrated. Pyridine (2.5 mL) and acetic anhydride (0.186 mL) were added to the residue, and the mixture was stirred at room temperature for 2 hr. After concentration, the residue was dissolved in ethyl acetate, and the solution was washed successively with 10% aqueous potassium carbonate solution and saturated brine, and dried over anhydrous sodium sulfate. The extract was applied to silica gel chromatography (NH, ethyl acetate) and concentrated under reduced pressure, and the obtained solid was washed with diisopropyl ether to give the title compound (295 mg).

¹H NMR (300 MHz, CDCl₃) δ 0.32-0.37 (2H, m), 0.61-0.67 (2H, m), 1.20 (3H, d, J=6.9 Hz), 1.23-1.32 (1H, m), 1.68-1.76 (2H, m), 1.92-1.98 (5H, m), 3.41-3.60 (5H, m), 3.78 (2H, d, J=6.9 Hz), 3.86-3.94 (2H, m), 4.11-4.21 (1H, m), 5.64 (1H, d, J=7.8 Hz), 6.75 (1H, dd, J=2.7, 8.4 Hz), 6.87 (1H, d, J=2.7 Hz), 7.21 (1H, d, J=8.4 Hz).

mp 120° C.

Anal. Calcd for C₂₁H₂₉N₃O₄: C, 65.09; H, 7.54; N, 10.84. Found: C, 65.02; H, 7.53; N, 10.84.

I) N-[(1S)-2-({1-[6-(cyclopropylmethoxy)-1,3-benzoxazol-2-yl]piperidin-4-yl}oxy)-1-methylethyl]acetamide

I-A) (2S)-1-({1-[6-(cyclopropylmethoxy)-1,3-benzoxazol-2-yl]piperidin-4-yl}oxy)propan-2-amine monohydrochloride To a solution of tert-butyl [(1S)-2-({1-[6-(cyclopropylmethoxy)-1,3-benzoxazol-2-yl]piperidin-4-yl}oxy)-1-methylethyl]carbamate (41.4 g) in ethyl acetate (200 mL) was added 4M hydrogen chloride/ethyl acetate (200 mL) at room temperature, and the mixture was stirred at room temperature for 4 hr and concentrated. The obtained residue was recrystallized from hexane/ethanol to give the title compound (17.5 g) as white crystals.

$^1$H NMR (300 MHz, DMSO-d$_6$) δ 0.26-0.36 (2H, m), 0.56 (2H, dd, J=7.9, 1.9 Hz), 1.13-1.28 (4H, m), 1.57-1.74 (2H, m), 1.85-2.01 (2H, m), 3.28-3.40 (1H, m), 3.43-3.53 (3H, m), 3.53-3.70 (2H, m), 3.74-3.89 (4H, m), 6.79 (1H, d, J=2.3 Hz), 7.11 (1H, d, J=2.3 Hz), 7.18 (1H, d, J=8.7 Hz), 7.99 (3H, brs).

MS (ESI+): [M+H]$^+$ 346.3.

I-B) N-[(1S)-2-({1-[6-(cyclopropylmethoxy)-1,3-benzoxazol-2-yl]piperidin-4-yl}oxy)-1-methylethyl]acetamide To a solution of (2S)-1-({1-[6-(cyclopropylmethoxy)-1,3-benzoxazol-2-yl]piperidin-4-yl}oxy)propan-2-amine monohydrochloride (17.6 g) in pyridine (85 mL) was added acetic anhydride (12.6 mL) at room temperature, and the mixture was stirred at room temperature for 2 hr. The reaction mixture was diluted with water, and extracted with ethyl acetate. The organic layer was washed with water, 1M hydrochloric acid and saturated brine, and dried over anhydrous magnesium sulfate. The solvent was evaporated under reduced pressure. The obtained residue was recrystallized from hexane/ethyl acetate to give the title compound (12.0 g) as white crystals.

$^1$H NMR (300 MHz, DMSO-d$_6$) δ 0.22-0.36 (2H, m), 0.45-0.63 (2H, m), 1.04 (3H, d, J=6.8 Hz), 1.13-1.28 (1H, m), 1.43-1.63 (2H, m), 1.79 (3H, s), 1.83-1.99 (2H, m), 3.21-3.30 (1H, m), 3.35-3.45 (3H, m), 3.48-3.63 (1H, m), 3.70-3.83 (4H, m), 3.83-3.96 (1H, m), 6.66-6.78 (1H, m), 7.01-7.10 (1H, m), 7.10-7.19 (1H, m), 7.62-7.74 (1H, m).

mp 122-123° C.

Anal. Calcd for C$_{21}$H$_{29}$N$_3$O$_4$: C, 65.09; H, 7.54; N, 10.84. Found: C, 65.19; H, 7.56; N, 10.85.

optical purity 99.9% ee

Example 2

N-[(1S)-2-({1-[5-(cyclopropylmethoxy)-1,3-benzoxazol-2-yl]piperidin-4-yl}oxy)-1-methylethyl]acetamide A) 2-aminobenzene-1,4-diol hydrochloride A suspension of 2-nitrobenzene-1,4-diol (1.00 g) and 10% palladium carbon (containing water (50%), 1.00 g) in 1 M hydrochloric acid (13 mL) was stirred at room temperature for 5 hr under a hydrogen atmosphere. The reaction mixture was filtered, the filtrate was concentrated under reduced pressure, and the obtained solid was washed with ethyl acetate to give the title compound (949 mg).

$^1$H NMR (300 MHz, DMSO-d$_6$) δ 6.60 (1H, dd, J=8.7, 2.6 Hz), 6.73 (1H, d, J=2.6 Hz), 6.80 (1H, d, J=8.7 Hz), 9.20 (1H, brs), 9.54 (2H, brs), 9.78 (1H, brs).

B) 2-sulfanyl-1,3-benzoxazol-5-ol

To a solution of 2-aminobenzene-1,4-diol hydrochloride (3.58 g) in pyridine (40 mL) was added potassium ethylxanthate (3.91 g), and the mixture was stirred with heating under reflux for 3 hr. After allowing to cool to room temperature, the reaction solution was concentrated under reduced pressure, and the obtained residue was dissolved in water, and the solution was acidified with 1M hydrochloric acid. The precipitated solid was collected, and washed with water to give the title compound (2.08 g).

$^1$H NMR (300 MHz, DMSO-d$_6$) δ 6.58 (1H, d, J=2.3 Hz), 6.60-6.66 (1H, m), 7.29 (1H, d, J=8.7 Hz), 9.68 (1H, s), 13.58 (1H, brs).

C) tert-butyl [(1S)-2-{[1-(5-hydroxy-1,3-benzoxazol-2-yl)piperidin-4-yl]oxy}-1-methylethyl]carbamate To a suspension of 2-sulfanyl-1,3-benzoxazol-5-ol (190 mg) in thionyl chloride (0.830 mL) was added DMF (2 drops), and the mixture was stirred with heating at 60° C. for 5 min. After allowing to cool to room temperature, the mixture was concentrated under reduced pressure. The residue was dissolved in ethyl acetate, and the solution was washed with saturated aqueous sodium hydrogen carbonate solution and saturated brine, and dried over anhydrous magnesium sulfate. The solvent was concentrated, and the obtained residue was dissolved in DMF (5 mL). tert-Butyl [(1S)-1-methyl-2-(piperidin-4-yloxy)ethyl]carbamate (590 mg) and N,N-diisopropylethylamine (0.209 mL) were added thereto, and the mixture was stirred at room temperature for 1.5 hr. Ethyl acetate was added to the reaction mixture, and the mixture was washed with saturated brine and dried over anhydrous magnesium. The solvent was evaporated under reduced pressure, and the obtained residue was purified by silica gel chromatography (hexane/ethyl acetate) to give the title compound (345 mg).

$^1$H NMR (300 MHz, CDCl$_3$) δ 1.18 (3H, d, J=6.8 Hz), 1.45 (9H, s), 1.66-1.77 (2H, m), 1.88-1.96 (2H, m), 3.44 (2H, d, J=4.5 Hz), 3.47-3.61 (3H, m), 3.63-3.91 (2H, m), 4.66 (1H, brs), 5.37 (1H, brs), 6.49 (1H, dd, J=8.5, 2.5 Hz), 6.83 (1H, d, J=2.7 Hz), 7.06 (1H, d, J=8.3 Hz).

D) tert-butyl [(1S)-2-({1-[5-(cyclopropylmethoxy)-1,3-benzoxazol-2-yl]piperidin-4-yl}oxy)-1-methylethyl]carbamate To a solution of tert-butyl [(1S)-2-{[1-(5-hydroxy-1,3-benzoxazol-2-yl)piperidin-4-yl]oxy}-1-methylethyl]carbamate (345 mg) in DMF (5 mL) were added potassium carbonate (366 mg) and (bromomethyl)cyclopropane (0.171 mL), and the mixture was stirred with heating at 60° C. for 1.5 hr under a nitrogen atmosphere. The reaction mixture was allowed to cool to room temperature, diluted with ethyl acetate, washed with saturated brine, and dried over anhydrous magnesium sulfate. The solvent was evaporated under reduced pressure, and the obtained residue was purified by silica gel chromatography (hexane/ethyl acetate) to give the title compound (375 mg).

$^1$H NMR (300 MHz, CDCl$_3$) δ 0.32-0.37 (2H, m), 0.60-0.66 (2H, m), 1.18 (3H, d, J=6.8 Hz), 1.27-1.31 (1H, m), 1.45 (9H, s), 1.70-1.77 (2H, m), 1.89-1.98 (2H, m), 3.44 (2H, d, J=4.5 Hz), 3.47-3.61 (3H, m), 3.79 (2H, d, J=6.8 Hz), 3.85-3.93 (3H, m), 4.86 (1H, brs), 6.58 (1H, dd, J=8.7, 2.7 Hz), 6.91 (1H, d, J=2.3 Hz), 7.10 (1H, d, J=8.7 Hz).

E) N-[(1S)-2-({1-[5-(cyclopropylmethoxy)-1,3-benzoxazol-2-yl]piperidin-4-yl}oxy)-1-methylethyl]acetamide To tert-butyl [(1S)-2-({1-[5-(cyclopropylmethoxy)-1,3-benzoxazol-2-yl]piperidin-4-yl}oxy)-1-methylethyl]carbamate (375 mg) was added 4M hydrogen chloride/ethyl acetate (5 mL), and the mixture was stirred at room temperature for 15 min and concentrated. Pyridine (5 mL) and acetic anhydride (5 mL) were added to the residue, and the mixture was stirred at room temperature for 10 min. The reaction mixture was concentrated, the residue was purified by silica gel chromatography (NH, hexane/ethyl acetate), and the obtained solid was washed with diethyl ether-hexane to give the title compound (183 mg).

$^1$H NMR (300 MHz, CDCl$_3$) δ 0.32-0.37 (2H, m), 0.60-0.66 (2H, m), 1.20 (3H, d, J=6.8 Hz), 1.22-1.34 (1H, m), 1.64-1.77 (2H, m), 1.90-1.98 (5H, m), 3.42-3.61 (5H, m), 3.79 (2H, d, J=6.8 Hz), 3.88-3.96 (2H, m), 4.11-4.23 (1H, m), 5.63 (1H, d, J=7.9 Hz), 6.59 (1H, dd, J=8.7, 2.6 Hz), 6.91 (1H, d, J=2.6 Hz), 7.10 (1H, d, J=8.7 Hz).

mp 104-106° C.

Anal. Calcd for C$_{21}$H$_{29}$N$_3$O$_4$: C, 65.09; H, 7.54; N, 10.84. Found: C, 65.06; H, 7.49; N, 10.94.

F) N-[(1S)-2-({1-[5-(cyclopropylmethoxy)-1,3-benzoxazol-2-yl]piperidin-4-yl}oxy)-1-methylethyl] acetamide To tert-butyl [(1S)-2-({1-[5-(cyclopropylmethoxy)-1,3-benzoxazol-2-yl]piperidin-4-yl}oxy)-1-methylethyl]carbamate (30.1 g) was added 4M hydrogen chloride/ethyl acetate (200 mL), and the mixture was stirred at room temperature for 30 min. After stirring, the mixture was concentrated. Pyridine (100 mL) and acetic anhydride (100 mL) were added to the residue, and the mixture was stirred at room temperature for 15 min. After concentration, the residue was purified by silica gel chromatography (NH, hexane/ethyl acetate), and the obtained crystals were recrystallized from hexane/ethyl acetate to give the title compound (17.4 g) as white crystals.

$^1$H NMR (300 MHz, CDCl$_3$) δ 0.26-0.40 (2H, m), 0.55-0.73 (2H, m), 1.20 (3H, d, J=6.8 Hz), 1.22-1.35 (1H, m), 1.60-1.77 (2H, m), 1.77-1.95 (2H, m), 1.95-2.00 (3H, m), 3.34-3.65 (5H, m), 3.79 (2H, d, J=6.8 Hz), 3.84-3.99 (2H, m), 4.08-4.27 (1H, m), 5.70 (1H, brs), 6.59 (1H, dd, J=8.5, 2.1 Hz), 6.91 (1H, d, J=2.6 Hz), 7.10 (1H, d, J=8.7 Hz).

mp 99-100° C.

Anal. Calcd for C$_{21}$H$_{29}$N$_3$O$_4$: C, 65.09; H, 7.54; N, 10.84. Found: C, 64.98; H, 7.84; N, 10.74.

optical purity >99.9% ee

Example 3

N-[(1S)-2-({1-[5-(cyclopropylmethoxy)-1,3-benzothiazol-2-yl]piperidin-4-yl}oxy)-1-methylethyl] acetamide

A) 2-chloro-5-methoxy-1,3-benzothiazole

A mixture of 5-methoxy-1,3-benzothiazole-2-thiol (500 mg), thionyl chloride (2 mL) and DMF (1 drop) was stirred at 50° C. for 3 days. Saturated aqueous sodium hydrogen carbonate solution was added to the reaction mixture, and the obtained mixture was extracted with ethyl acetate. The extract was washed with saturated brine, and dried over anhydrous sodium sulfate. The solvent was evaporated under reduced pressure and the residue was purified by silica gel column chromatography (ethyl acetate/hexane) to give the title compound (211 mg).

$^1$H NMR (300 MHz, DMSO-d$_6$) δ 3.84 (3H, s), 7.15 (1H, dd, J=9.0, 2.5 Hz), 7.53 (1H, d, J=2.5 Hz), 7.97 (1H, d, J=9.0 Hz).

B) tert-butyl [(1S)-2-{[1-(5-methoxy-1,3-benzothiazol-2-yl)piperidin-4-yl]oxy}-1-methylethyl]carbamate A mixture of 2-chloro-5-methoxy-1,3-benzothiazole (143 mg), tert-butyl [(1S)-1-methyl-2-(piperidin-4-yloxy)ethyl]carbamate (186 mg), N,N-diisopropylethylamine (93 mg) and DMF (3 mL) was stirred at 150° C. for 1.5 hr under microwave irradiation. Water was added to the reaction mixture, and the obtained mixture was extracted with ethyl acetate. The extract was washed with saturated brine, and dried over anhydrous sodium sulfate. The solvent was evaporated under reduced pressure and the residue was purified by silica gel column chromatography (ethyl acetate/hexane) to give the title compound (194 mg).

$^1$H NMR (300 MHz, DMSO-d$_6$) δ 1.02 (3H, d, J=6.8 Hz), 1.37 (9H, s), 1.44-1.70 (2H, m), 1.81-1.97 (2H, m), 3.18-3.30 (1H, m), 3.33-3.84 (10H, m), 6.67 (2H, dd, J=8.7, 2.5 Hz), 7.03 (1H, d, J=2.5 Hz), 7.59 (1H, d, J=8.7 Hz).

C) N-[(1S)-2-({1-[5-(cyclopropylmethoxy)-1,3-benzothiazol-2-yl]piperidin-4-yl}oxy)-1-methylethyl] acetamide A mixture of tert-butyl [(1S)-2-{[1-(5-methoxy-1,3-benzothiazol-2-yl)piperidin-4-yl]oxy}-1-methylethyl]carbamate (194 mg) and hydrogen bromide (25% acetic acid solution, 5 mL) was stirred at 120° C. for 5 hr. The reaction mixture was concentrated under reduced pressure, to the obtained residue were added acetic anhydride (3 mL) and pyridine (3 mL), and the obtained mixture was stirred at room temperature overnight. The reaction mixture was concentrated under reduced pressure, to the obtained residue were added THF (5 mL), methanol (5 mL) and 1M sodium hydroxide (5 and the obtained mixture was stirred at room temperature for 3 hr. The reaction mixture was neutralized with 1M hydrochloric acid and extracted with ethyl acetate. The extract was washed with saturated brine, and dried over anhydrous sodium sulfate. The solvent was evaporated under reduced pressure. To the obtained residue were added (bromomethyl)cyclopropane (93 mg), potassium carbonate (95 mg) and DMF (2 mL), and the mixture was stirred at 60° C. for 3 days. Water was added to the reaction mixture, and the obtained mixture was extracted with ethyl acetate. The extract was washed with saturated brine, and dried over anhydrous sodium sulfate. The solvent was evaporated under reduced pressure and the residue was purified by silica gel column chromatography (ethyl acetate/hexane/methanol) and recrystallized from THF/ethyl acetate/hexane to give the title compound (82 mg).

$^1$H NMR (300 MHz, DMSO-d$_6$) δ 0.22-0.41 (2H, m), 0.47-0.64 (2H, m), 1.04 (3H, d, J=6.8 Hz), 1.10-1.31 (1H, m), 1.43-1.66 (2H, m), 1.79 (3H, s), 1.83-2.03 (2H, m), 3.16-4.04 (10H, m), 6.67 (1H, dd, J=8.7, 2.5 Hz), 6.99 (1H, d, J=2.5 Hz), 7.57 (1H, d, J=8.7 Hz), 7.70 (1H, d, J=7.9 Hz).

mp 115-116° C.

Example 4

N-[2-({1-[6-(cyclopropylmethoxy)-1,3-benzoxazol-2-yl]piperidin-4-yl}oxy)-1-methylethyl]isoxazol-3-amine

A) tert-butyl 4-[2-(morpholin-4-yl)-2-oxoethoxy]piperidine-1-carboxylate

To a suspension of tert-butyl 4-hydroxypiperidine-1-carboxylate (5.00 g) and tert-butoxy potassium (5.57 g) in THF (124 mL) was added 4-(chloroacetyl)morpholine (4.84 mL), and the mixture was stirred at room temperature overnight. Distilled water was added to the reaction mixture, the mixture was extracted with ethyl acetate, and the solution was washed with saturated brine, and dried over anhydrous sodium sulfate. The solvent was concentrated under reduced pressure, and the obtained solid was washed with hexane-ethyl acetate to give the title compound (4.74 g).

MS (ESI+): [M+H]$^+$ 329.2.

B) 2-{4-[2-(morpholin-4-yl)-2-oxoethoxy]piperidin-1-yl}-1,3-benzoxazol-6-ol

To tert-butyl 4-[2-(morpholin-4-yl)-2-oxoethoxy]piperidine-1-carboxylate (4.30 g) was added 4M hydrogen chloride/ethyl acetate (20 mL), and the mixture was stirred at room temperature for 15 min and concentrated. The residue was dissolved in DMF (30 mL), 2-chloro-1,3-benzoxazol-6-ol (1.48 g) and N,N-diisopropylethylamine (4.00 mL) were added thereto, and the mixture was stirred at 80° C. overnight. The reaction mixture was allowed to cool to room temperature, and diluted with ethyl acetate. The diluted solution was washed with saturated aqueous potassium carbonate solution and saturated brine, and dried over anhydrous sodium sulfate. The solvent was evaporated under reduced pressure and the residue was purified by silica gel chromatography (NH, hexane/ethyl acetate/methanol) to give the title compound (2.81 g).

MS (ESI+): [M+H]$^+$ 362.3.

C) 6-(cyclopropylmethoxy)-2-{4-[2-(morpholin-4-yl)-2-oxoethoxy]piperidin-1-yl}-1,3-benzoxazole To a solution of 2-{4-[2-(morpholin-4-yl)-2-oxoethoxy]piperidin-1-yl}-1,3-benzoxazol-6-ol (2.81 g) in DMF (26 mL) were added potassium carbonate (3.22 g) and (bromomethyl)cyclopropane (1.51 mL), and the mixture was stirred at 80° C. overnight. The reaction mixture was allowed to cool to room temperature, and diluted with ethyl acetate. The diluted solution was washed with distilled water and saturated brine, and dried over anhydrous sodium sulfate. The solvent was evaporated under reduced pressure and the residue was purified by silica gel chromatography (NH, hexane/ethyl acetate) to give the title compound (2.10 g).

MS (ESI+): [M+H]$^+$ 416.5.

D) 1-({1-[6-(cyclopropylmethoxy)-1,3-benzoxazol-2-yl]piperidin-4-yl}oxy)propan-2-one To a solution of 6-(cyclopropylmethoxy)-2-{4-[2-(morpholin-4-yl)-2-oxoethoxy]piperidin-1-yl}-1,3-benzoxazole (2.10 g) in THF (17 mL) was added methylmagnesium chloride (3.0 M THF solution, 5.06 mL), and the mixture was stirred at room temperature for 3 hr. Saturated aqueous ammonium chloride solution was added to the reaction mixture, and the mixture was extracted with ethyl acetate. The extract was washed with saturated brine, and dried over anhydrous sodium sulfate. The solvent was evaporated under reduced pressure and the residue was purified by silica gel chromatography (hexane/ethyl acetate) to give the title compound (1.31 g).

MS (ESI+): [M+H]$^+$ 345.1

E) N-[2-({1-[6-(cyclopropylmethoxy)-1,3-benzoxazol-2-yl]piperidin-4-yl}oxy)-1-methylethyl]isoxazol-3-amine To a solution of 1-({1-[6-(cyclopropylmethoxy)-1,3-benzoxazol-2-yl]piperidin-4-yl}oxy)propan-2-one (400 mg) and isoxazol-3-amine (0.129 mL) in methanol (6 mL) and acetic acid (0.300 mL) was added decaborane (213 mg), and the mixture was stirred at room temperature for 3 hr. 1M Hydrochloric acid was added to the reaction mixture, and the mixture was stirred at room temperature for 30 min, and extracted with ethyl acetate. The extract was washed with saturated brine and dried over anhydrous sodium sulfate. The solvent was evaporated under reduced pressure and the residue was purified by silica gel chromatography (hexane/ethyl acetate). The obtained residue was applied to preparative HPLC (C18, mobile phase: water/acetonitrile (containing 0.1% TFA)). Saturated aqueous sodium hydrogen carbonate solution was added to the obtained fraction, and the mixture was extracted with ethyl acetate and the extract was dried over anhydrous sodium sulfate. The residue was concentrated under reduced pressure to give the title compound (126 mg).

$^1$H NMR (300 MHz, CDCl$_3$) δ 0.31-0.40 (2H, m), 0.60-0.69 (2H, m), 1.21-1.35 (4H, m), 1.50-1.82 (2H, m), 1.88-2.01 (2H, m), 3.41-3.68 (5H, m), 3.72-3.95 (5H, m), 4.09-4.18 (1H, m), 5.84 (1H, d, J=1.9 Hz), 6.76 (1H, dd, J=8.7, 2.3 Hz), 6.88 (1H, d, J=2.7 Hz), 7.21 (1H, d, J=8.7 Hz), 8.04 (1H, d, J=1.5 Hz).

Example 5

N-(3-{1-[6-(cyclopropylmethoxy)-1,3-benzoxazol-2-yl]piperidin-4-yl}-1-methylpropyl)acetamide

A) (2E)-N-methoxy-N-methyl-3-(pyridin-4-yl)prop-2-enamide

Oxalyl chloride (8.5 mL) was added dropwise to a suspension of (2E)-3-(pyridin-4-yl)prop-2-enoic acid (10 g) and DMF (2 drops) in THF (150 mL) at room temperature, and the mixture was stirred at room temperature for 3 hr. The solvent was evaporated under reduced pressure and the residue was diluted with THF (50 mL). The resulting solution was added to a solution of N,O-dimethylhydroxylamine hydrochloride (6.54 g) and triethylamine (18.7 mL) in DMF (150 mL) under ice-cooling. The reaction mixture was stirred at room temperature for 15 hr and the solvent was evaporated under reduced pressure. Ethyl acetate and saturated aqueous sodium hydrogen carbonate solution were added to the residue, and the organic layer was separated. The organic layer was washed with saturated aqueous sodium hydrogen carbonate solution and saturated brine, dried over anhydrous magnesium sulfate, and passed through a silica gel pad (NH). The filtrate was concentrated under reduced pressure to give the title compound (9.1 g).

$^1$H NMR (300 MHz, DMSO-d$_6$) δ 3.23 (3H, s), 3.76 (3H, s), 7.33 (1H, d, J=15.9 Hz), 7.54 (1H, d, J=15.9 Hz), 7.64-7.74 (2H, m), 8.55-8.70 (2H, m).

B) tert-butyl 4-{3-[methoxy(methyl)amino]-3-oxopropyl}piperidine-1-carboxylate A solution of (2E)-N-methoxy-N-methyl-3-(pyridin-4-yl)prop-2-enamide (2.00 g), 5% rhodium/carbon (containing water (50%), 0.4 g) and acetic acid (1.25 g) in methanol (40 mL) was stirred for 4 hr under ice-cooling under a hydrogen atmosphere (5 atm). The reaction mixture was allowed to cool to room temperature and filtered, and the filtrate was concentrated under reduced pressure. The residue was dissolved in a mixed solvent of THF (25 mL) and water (10 mL), di-tert-butyl dicarbonate (4.36 g) and 2M aqueous sodium hydroxide solution (25 mL) were added, and the mixture was stirred at room temperature for 15 hr. The reaction mixture was diluted with ethyl acetate and water, and extracted with ethyl acetate. The organic layer was washed with saturated brine, dried over anhydrous magnesium sulfate and concentrated under reduced pressure. The residue was purified by silica gel column chromatography (hexane/ethyl acetate) to give the title compound (2.59 g).

$^1$H NMR (300 MHz, DMSO-$d_6$) δ 0.82-1.05 (2H, m), 1.31-1.49 (12H, m), 1.55-1.73 (2H, m), 2.38 (2H, t, J=7.5 Hz), 2.55-2.76 (2H, m), 3.07 (3H, s), 3.65 (3H, s), 3.84-3.97 (2H, m).

C) tert-butyl 4-(3-oxobutyl)piperidine-1-carboxylate

Methylmagnesium bromide (1 M THF solution, 30 mL) was added dropwise to a solution of tert-butyl 4-{3-[methoxy(methyl)amino]-3-oxopropyl}piperidine-1-carboxylate (4.5 g) in THF (50 mL) under ice-cooling, and the reaction mixture was stirred at room temperature for 3 hr. The reaction mixture was poured into saturated aqueous ammonium chloride solution, and the mixture was extracted with ethyl acetate. The extract was washed with water and saturated brine, dried over anhydrous magnesium sulfate, and concentrated under reduced pressure to give the title compound (3.70 g).

$^1$H NMR (300 MHz, DMSO-$d_6$) δ 0.80-1.03 (2H, m), 1.24-1.47 (12H, m), 1.59 (2H, d, J=12.9 Hz), 2.07 (3H, s), 2.44 (2H, t, J=7.4 Hz), 2.53-2.76 (2H, m), 3.90 (2H, d, J=12.5 Hz).

D) tert-butyl 4-(3-hydroxybutyl)piperidine-1-carboxylate

To a solution of tert-butyl 4-(3-oxobutyl)piperidine-1-carboxylate (3.7 g) in ethanol (40 mL) was added sodium borohydride (550 mg) at room temperature, and the mixture was stirred at room temperature for 30 min. The solvent was evaporated under reduced pressure and the residue was dissolved in ethyl acetate and water. The organic layer was separated, washed with water and saturated brine, dried over anhydrous magnesium sulfate, and concentrated under reduced pressure to give the title compound (3.71 g).

$^1$H NMR (300 MHz, DMSO-$d_6$) δ 0.74-0.98 (2H, m), 1.02 (3H, d, J=6.0 Hz), 1.07-1.35 (5H, m), 1.38 (9H, s), 1.61 (2H, d, J=11.3 Hz), 2.54-2.76 (2H, m), 3.45-3.60 (1H, m), 3.90 (2H, d, J=12.8 Hz), 4.32 (1H, d, J=4.5 Hz).

E) tert-butyl 4-(3-azidobutyl)piperidine-1-carboxylate

Methanesulfonyl chloride (3.21 g) was added to a solution of tert-butyl 4-(3-hydroxybutyl)piperidine-1-carboxylate (3.6 g) and triethylamine (2.83 g) in ethyl acetate (50 mL) under ice-cooling, and the mixture was stirred at room temperature for 15 min. The resulting precipitate was filtered off. The filtrate was washed with water and saturated brine, dried over anhydrous magnesium sulfate, and concentrated under reduced pressure. The residue was dissolved in DMF (50 mL), sodium azide (1.82 g) was added thereto, and the mixture was stirred with heating at 80° C. for 3 hr. The reaction mixture was allowed to cool to room temperature, and the solvent was evaporated under reduced pressure. The residue was diluted with diethyl ether and water, and the organic layer was separated. The organic layer was washed with saturated brine, dried over anhydrous magnesium sulfate and concentrated under reduced pressure to give the title compound (3.81 g).

$^1$H NMR (300 MHz, DMSO-$d_6$) δ 0.82-1.05 (2H, m), 1.19 (3H, d, J=6.4 Hz), 1.21-1.36 (3H, m), 1.38 (9H, s), 1.40-1.51 (2H, m), 1.61 (2H, d, J=13.6 Hz), 2.55-2.74 (2H, m), 3.45-3.60 (1H, m), 3.91 (2H, d, J=12.8 Hz).

F) tert-butyl 4-(3-aminobutyl)piperidine-1-carboxylate

A suspension of tert-butyl 4-(3-azidobutyl)piperidine-1-carboxylate (3.81 g) and 5% palladium/carbon (containing water (50%), 800 mg) in methanol (100 mL) was stirred at room temperature for 15 hr under a hydrogen atmosphere. The reaction mixture was filtered, and the filtrate was concentrated under reduced pressure to give the title compound (3.59 g).

$^1$H NMR (300 MHz, DMSO-$d_6$) δ 0.81-1.01 (5H, m), 1.11-1.36 (7H, m), 1.38 (9H, s), 1.61 (2H, d, J=11.7 Hz), 2.55-2.77 (2H, m), 3.21-3.44 (1H, m), 3.90 (2H, d, J=12.8 Hz).

G) tert-butyl 4-[3-(acetylamino)butyl]piperidine-1-carboxylate

A solution of tert-butyl 4-(3-aminobutyl)piperidine-1-carboxylate (3.58 g) and acetic anhydride (4.13 g) in ethyl acetate (100 mL) was heated under reflux for 3 hr. The reaction mixture was allowed to cool to room temperature, washed with aqueous citric acid solution and saturated brine, and dried over anhydrous magnesium sulfate. The solvent was evaporated under reduced pressure and the residue was purified by silica gel column chromatography (hexane/ethyl acetate) to give the title compound (2.65 g).

$^1$H NMR (300 MHz, DMSO-$d_6$) δ 0.78-1.04 (5H, m), 1.07-1.22 (2H, m), 1.25-1.46 (12H, m), 1.60 (2H, d, J=12.1 Hz), 1.76 (3H, s), 2.55-2.79 (2H, m), 3.54-3.78 (1H, m), 3.90 (2H, d, J=12.4 Hz), 7.61 (1H, d, J=7.9 Hz).

H) N-[1-methyl-3-(piperidin-4-yl)propyl]acetamide hydrochloride

To a solution of tert-butyl 4-[3-(acetylamino)butyl]piperidine-1-carboxylate (2.65 g) in ethyl acetate (30 mL) was added 4 M hydrogen chloride/ethyl acetate (10 mL), and the mixture was stirred at room temperature for 3 hr. The resulting precipitate was collected by filtration to give the title compound (2.06 g).

$^1$H NMR (300 MHz, DMSO-$d_6$) δ 1.00 (3H, d, J=6.4 Hz), 1.09-1.59 (7H, m), 1.63-1.85 (5H, m), 2.77 (2H, q, J=11.5 Hz), 3.09-3.31 (2H, m), 3.55-3.81 (1H, m), 7.81 (1H, d, J=7.9 Hz), 8.97 (1H, brs), 9.15 (1H, brs).

I) N-{3-[1-(6-hydroxy-1,3-benzoxazol-2-yl)piperidin-4-yl]-1-methylpropyl}acetamide A solution of N-[1-methyl-3-(piperidin-4-yl)propyl]acetamide hydrochloride (500 mg), 2-chloro-1,3-benzoxazol-6-ol (361 mg) and N,N-diisopropylethylamine (826 mg) in DMF (15 mL) was stirred at 100° C. for 10 hr. The reaction mixture was allowed to cool, and the solvent was evaporated under reduced pressure. The residue was diluted with ethyl acetate/THF mixed solvent (10/1), and the solution was washed with saturated brine, and dried over anhydrous magnesium sulfate. The solvent was evaporated under reduced pressure and the residue was purified by silica gel column chromatography (hexane/ethyl acetate) to give the title compound (543 mg).

$^1$H NMR (300 MHz, DMSO-$d_6$) δ 1.00 (3H, d, J=6.8 Hz), 1.07-1.27 (4H, m), 1.32-1.48 (3H, m), 1.62-1.82 (5H, m), 2.92-3.05 (2H, m), 3.57-3.81 (1H, m), 3.94-4.13 (2H, m), 6.57 (1H, dd, J=8.4, 2.0 Hz), 6.79 (1H, d, J=2.0 Hz), 7.04 (1H, d, J=8.4 Hz), 7.63 (1H, d, J=8.3 Hz), 9.19 (1H, s).

J) N-(3-{1-[6-(cyclopropylmethoxy)-1,3-benzoxazol-2-yl]piperidin-4-yl}-1-methylpropyl)acetamide To a solution of N-{3-[1-(6-hydroxy-1,3-benzoxazol-2-yl)piperidin-4-yl]-1-methylpropyl}acetamide (0.49 g) in DMF (15 mL) were added potassium carbonate (0.41 g) and (bromomethyl)cyclopropane (0.41 g), and the mixture was stirred at 100° C. for 6 hr. The reaction mixture was allowed to cool to room temperature, and diluted with ethyl acetate. The extract was washed with saturated brine and dried over anhydrous sodium sulfate. The solvent was evaporated under reduced pressure and the residue was purified by silica gel chromatography (ethyl acetate/methanol) and recrystallized from ethyl acetate/methanol to give the title compound (313 mg).
$^1$H NMR (300 MHz, DMSO-$d_6$) δ 0.25-0.36 (2H, m), 0.49-0.61 (2H, m), 1.00 (3H, d, J=6.8 Hz), 1.04-1.29 (5H, m), 1.29-1.52 (3H, m), 1.64-1.82 (5H, m), 2.93-3.10 (2H, m), 3.61-3.75 (1H, m), 3.78 (2H, d, J=6.8 Hz), 4.06 (2H, d, J=12.9 Hz), 6.72 (1H, dd, J=8.6, 2.3 Hz), 7.05 (1H, d, J=2.3 Hz), 7.13 (1H, d, J=8.6 Hz), 7.62 (1H, d, J=8.3 Hz).
mp 131-132° C.
Anal. Calcd for $C_{22}H_{31}N_3O_3$: C, 68.54; H, 8.11; N, 10.90. Found: C, 68.50; H, 8.19; N, 10.74.

Example 5a

N-[(1S)-(3-{1-[6-(cyclopropylmethoxy)-1,3-benzoxazol-2-yl]piperidin-4-yl}-1-methylpropyl)]acetamide A racemate (1.20 g) of N-(3-{1-[6-(cyclopropylmethoxy)-1,3-benzoxazol-2-yl]piperidin-4-yl}-1-methylpropyl)acetamide was separated by HPLC (column: CHIRALPAK AD (trade name), 50 mmID×500 mmL, Daicel Chemical Industries Ltd., mobile phase: hexane/2-propanol=500/500) to give the title compound (532 mg) having a longer retention time. This was recrystallized from hexane/ethyl acetate to give the title compound (496 mg) as white crystals.
$^1$H NMR (300 MHz, DMSO-$d_6$) δ 0.22-0.36 (2H, m), 0.47-0.63 (2H, m), 1.00 (3H, d, J=6.4 Hz), 1.05-1.30 (5H, m), 1.30-1.53 (3H, m), 1.62-1.79 (5H, m), 2.93-3.15 (2H, m), 3.59-3.76 (1H, m), 3.78 (2H, d, J=6.8 Hz), 4.06 (2H, d, J=12.8 Hz), 6.72 (1H, dd, J=8.4, 2.3 Hz), 7.05 (1H, d, J=2.3 Hz), 7.13 (1H, d, J=8.4 Hz), 7.62 (1H, d, J=7.9 Hz).
Anal. Calcd for $C_{22}H_{31}N_3O_3$: C, 68.54; H, 8.11; N, 10.90. Found: C, 68.45; H, 8.41; N, 10.83.
mp 138.2-138.4° C.
retention time 11.7 min
optical purity 99.8% ee Example 6

N-[(1S)-2-({1-[5-(cyclobutylmethoxy)-1,3-benzoxazol-2-yl]piperidin-4-yl}oxy)-1-methylethyl]acetamide A) tert-butyl [(1S)-2-({1-[5-(cyclobutylmethoxy)-1,3-benzoxazol-2-yl]piperidin-4-yl}oxy)-1-methylethyl]carbamate To a solution of tert-butyl [(1S)-2-{[1-(5-hydroxy-1,3-benzoxazol-2-yl)piperidin-4-yl]oxy}-1-methylethyl]carbamate (389 mg) in DMF (5 mL) were added potassium carbonate (413 mg) and (bromomethyl)cyclobutane (297 mg), and the mixture was stirred with heating at 60° C. for 6 hr under a nitrogen atmosphere. The reaction mixture was allowed to cool to room temperature, diluted with ethyl acetate, washed with saturated brine, and dried over anhydrous magnesium sulfate. The solvent was evaporated under reduced pressure, and the obtained residue was purified by silica gel chromatography (hexane/ethyl acetate) to give the title compound (380 mg).
$^1$H NMR (300 MHz, CDCl$_3$) δ1.18 (3H, d, J=6.4 Hz), 1.45 (9H, s), 1.66-1.77 (2H, m), 1.83-2.00 (6H, m), 2.09-2.17 (2H, m), 2.71-2.81 (1H, m), 3.44-3.61 (5H, m), 3.76-3.93 (5H, m), 4.65 (1H, brs), 6.57 (1H, dd, J=8.7, 2.7 Hz), 6.91 (1H, d, J=2.3 Hz), 7.09 (1H, d, J=8.7 Hz).

B) N-[(1S)-2-({1-[5-(cyclobutylmethoxy)-1,3-benzoxazol-2-yl]piperidin-4-yl}oxy)-1-methylethyl]acetamide To tert-butyl [(1S)-2-({1-[5-(cyclobutylmethoxy)-1,3-benzoxazol-2-yl]piperidin-4-yl}oxy)-1-methylethyl]carbamate (380 mg) was added 4M hydrogen chloride/ethyl acetate (5 mL), and the mixture was stirred at room temperature for 15 min and concentrated. Pyridine (5 mL) and acetic anhydride (5 mL) were added to the residue, and the mixture was stirred at room temperature for 10 min. After concentration, the residue was purified by silica gel chromatography (NH, hexane/ethyl acetate), and the obtained solid was washed with diethyl ether to give the title compound (158 mg).
$^1$H NMR (300 MHz, CDCl$_3$) δ 1.20 (3H, d, J=6.4 Hz), 1.65-1.77 (2H, m), 1.84-1.98 (9H, m), 2.06-2.18 (2H, m), 2.72-2.85 (1H, m), 3.43-3.62 (5H, m), 3.88-3.96 (4H, m), 4.11-4.24 (1H, m), 5.62 (1H, d, J=9.8 Hz), 6.58 (1H, dd, J=8.7, 2.6 Hz), 6.91 (1H, d, J=2.3 Hz), 7.10 (1H, d, J=8.7 Hz).
mp 109-110° C.
Anal. Calcd for $C_{22}H_{31}N_3O_4$: C, 65.81; H, 7.78; N, 10.47. Found: C, 65.68; H, 7.83; N, 10.41.

Example 7

N-[2-({1-[6-(cyclopropylmethoxy)-1,3-benzoxazol-2-yl]piperidin-4-yl}oxy)-1-methylethyl]-4-methylisoxazol-3-amine To a solution of 1-({1-[6-(cyclopropylmethoxy)-1,3-benzoxazol-2-yl]piperidin-4-yl}oxy)propan-2-one (50 mg) and 4-methylisoxazol-3-amine (21.4 mg) in methanol (1 mL) and acetic acid (50 μL) was added decaborane (26.6 mg), and the mixture was stirred at room temperature overnight. The reaction mixture was diluted with ethyl acetate, washed with distilled water and saturated brine, and dried over anhydrous sodium sulfate. The solvent was evaporated under reduced pressure and the residue was purified by silica gel chromatography (NH, hexane/ethyl acetate). 1M Hydrochloric acid was added thereto, and the mixture was extracted with ethyl acetate. The extract was washed with saturated brine and dried over anhydrous sodium sulfate. The solvent was evaporated under reduced pressure to give the title compound (42.1 mg).
$^1$H NMR (300 MHz, CDCl$_3$) δ 0.31-0.38 (2H, m), 0.60-0.69 (2H, m), 1.23-1.34 (4H, m), 1.77-2.01 (7H, m), 3.46-3.67 (5H, m), 3.71-3.96 (6H, m), 6.77 (1H, dd, J=8.7, 2.3 Hz), 6.88 (1H, d, J=2.3 Hz), 7.21-7.25 (1H, m), 7.81 (1H, s).

Example 8

N-[2-({1-[6-(cyclopropylmethoxy)-1,3-benzoxazol-2-yl]azetidin-3-yl}oxy)-1-methylethyl]acetamide

A) ethyl {[1-(diphenylmethyl)azetidin-3-yl]oxy}acetate

To a suspension of 1-(diphenylmethyl)azetidin-3-ol (12 g) and rhodium(II) acetate dimer (1.1 g) in toluene (150 mL) was added dropwise ethyl diazoacetate (6.28 g) at 80° C. The mixture was stirred at 80° C. for 3 hr. Furthermore, ethyl diazoacetate (6.28 g) was added dropwise at 80° C., and the mixture was stirred at 80° C. for 3 hr. The mixture was allowed to cool, and filtered through a silica gel short column. The filtrate was concentrated under reduced pressure and the residue was purified by silica gel chromatography (hexane/ethyl acetate) to give the title compound (9.0 g).

$^1$H NMR (300 MHz, DMSO-$d_6$) δ 1.16 (3H, t, J=7.2 Hz), 2.75-2.92 (2H, m), 3.27-3.45 (2H, m), 3.98-4.22 (5H, m), 4.41 (1H, s), 7.12-7.21 (2H, m), 7.22-7.31 (4H, m), 7.41 (4H, d, J=7.2 Hz).

B) 2-{[1-(diphenylmethyl)azetidin-3-yl]oxy}-N-methoxy-N-methylacetamide

2M Aqueous sodium hydroxide solution (25 mL) was added to a solution of ethyl {[1-(diphenylmethyl)azetidin-3-yl]oxy}acetate (8.0 g) in ethanol (100 mL), and the mixture was stirred at 50° C. for 3 hr. The reaction mixture was allowed to cool, and the solvent was concentrated under reduced pressure. The residue was adjusted to pH=3 with 1 M hydrochloric acid, and the mixture was extracted with ethyl acetate/THF (4/1) mixed solvent. The obtained organic layer was washed with saturated brine and dried over anhydrous magnesium sulfate. The solvent was evaporated under reduced pressure. 1.4 g from the obtained residue (6.5 g) was dissolved in DMF (50 mL), WSC (0.91 g), HOBt (0.72 g), N,O-dimethylhydroxyamine hydrochloride (0.46 g) and triethylamine (1.31 mL) were added thereto, and the mixture was stirred at 80° C. for 6 hr. The mixture was allowed to cool, and the solvent was evaporated under reduced pressure. The residue was diluted with ethyl acetate, and the mixture was washed with water, saturated aqueous sodium carbonate solution and saturated brine, dried over anhydrous magnesium sulfate and concentrated under reduced pressure. The residue was purified by silica gel chromatography (hexane/ethyl acetate) to give the title compound (0.79 g).

$^1$H NMR (300 MHz, DMSO-$d_6$) δ 2.79-2.89 (2H, m), 3.04 (3H, s), 3.33-3.39 (2H, m), 3.62 (3H, s), 4.11-4.21 (3H, m), 4.40 (1H, s), 7.11-7.22 (2H, m), 7.23-7.31 (2H, m), 7.31-7.45 (6H, m).

C) 3-(2-azidopropoxy)-1-(diphenylmethyl)azetidine

By a method similar to Example 5, steps C to E, and using 2-{[1-(diphenylmethyl)azetidin-3-yl]oxy}-N-methoxy-N-methylacetamide (0.7 g), the title compound (350 mg) was obtained.

$^1$H NMR (300 MHz, DMSO-$d_6$) δ 1.08 (3H, d, J=6.8 Hz), 2.70-2.84 (2H, m), 3.21-3.31 (1H, m), 3.35-3.46 (3H, m), 3.61-3.79 (1H, m), 4.08-4.20 (1H, m), 4.41 (1H, s), 7.11-7.22 (2H, m), 7.22-7.31 (4H, m), 7.37-7.47 (4H, m).

D) N-(2-{[1-(diphenylmethyl)azetidin-3-yl]oxy}-1-methylethyl)acetamide

A solution of 3-(2-azidopropoxy)-1-(diphenylmethyl)azetidine (350 mg) and triphenylphosphine (340 mg) in THF/water (15 mL/5 mL) was heated under reflux for 2 hr. The mixture was allowed to cool, 1M hydrochloric acid was added thereto, and the mixture was washed with diethyl ether. The obtained aqueous solution was neutralized with saturated aqueous sodium hydrogen carbonate solution, and the mixture was extracted with ethyl acetate. The obtained organic layer was dried over anhydrous magnesium sulfate and concentrated under reduced pressure. The residue was dissolved in ethyl acetate (15 mL), acetic anhydride (1 mL) was added thereto, and the mixture was stirred at 60° C. for 5 hr. The mixture was allowed to cool, washed with water and saturated brine, dried over anhydrous magnesium sulfate and concentrated under reduced pressure to give the title compound (0.31 g).

MS (ESI+): [M+H]$^+$ 339.1.

E) N-(2-{[1-(6-hydroxy-1,3-benzoxazol-2-yl)azetidin-3-yl]oxy}-1-methylethyl)acetamide A suspension of N-(2-{[1-(diphenylmethyl)azetidin-3-yl]oxy}-1-methylethyl)acetamide (300 mg) and 5% palladium hydroxide (60 mg) in methanol (15 mL) was stirred at 60° C. for 6 hr under a hydrogen atmosphere (1 atm). The mixture was allowed to cool and filtered. The filtrate was concentrated under reduced pressure. The residue was dissolved in DMF (10 mL), and 2-chloro-1,3-benzoxazol-6-ol (151 mg) and N,N-diisopropylethylamine (233 mg) were added thereto. The mixture was stirred at 80° C. for 3 hr and allowed to cool. 1M Hydrochloric acid was added thereto, and the mixture was washed with diethyl ether. The obtained aqueous solution was neutralized with saturated aqueous sodium hydrogen carbonate solution, and extracted with a mixed solvent of ethyl acetate/THF (5/1). The obtained organic layer was washed with saturated brine, dried over anhydrous magnesium sulfate and concentrated under reduced pressure to give the title compound (270 mg).

MS (ESI+): [M+H]$^+$ 306.1.

F) N-[2-({1-[6-(cyclopropylmethoxy)-1,3-benzoxazol-2-yl]azetidin-3-yl}oxy)-1-methylethyl]acetamide By a method similar to Example 1, step G, and using N-(2-{[1-(6-hydroxy-1,3-benzoxazol-2-yl)azetidin-3-yl]oxy}-1-methylethyl)acetamide (250 mg), the title compound (60 mg) was obtained.

Example 9

N-[(1S)-1-methyl-2-({1-[6-(2,2,2-trifluoroethoxy)-1,3-benzoxazol-2-yl]piperidin-4-yl}oxy)ethyl]acetamide By a method similar to Example 1, steps G and H, and using tert-butyl [(1S)-2-{[1-(6-hydroxy-1,3-benzoxazol-2-yl)piperidin-4-yl]oxy}-1-methylethyl]carbamate and 2,2,2-trifluoroethyl trifluoromethanesulfonate, the title compound was obtained.

Example 10

N-[(1S)-2-{[1-(6-ethoxy-1,3-benzothiazol-2-yl)piperidin-4-yl]oxy}-1-methylethyl]acetamide

A) tert-butyl [(1S)-2-{[1-(6-hydroxy-1,3-benzothiazol-2-yl)piperidin-4-yl]oxy}-1-methylethyl]carbamate By a method similar to Example 3, step B, and using 2-chloro-1,3-benzothiazol-6-ol, the title compound was obtained.

¹H NMR (300 MHz, DMSO-d₆) δ 1.01 (3H, d, J=6.8 Hz), 1.37 (9H, s), 1.45-1.64 (2H, m), 1.79-1.96 (2H, m), 3.16-3.41 (4H, m), 3.47-3.80 (4H, m), 6.57-6.82 (2H, m), 7.11 (1H, d, J=2.3 Hz), 7.25 (1H, d, J=8.7 Hz), 9.21 (1H, s).

B) N-[(1S)-2-{[1-(6-ethoxy-1,3-benzothiazol-2-yl)piperidin-4-yl]oxy}-1-methylethyl]acetamide By a method similar to Example 1, steps G and H, and using tert-butyl [(1S)-2-{[1-(6-hydroxy-1,3-benzothiazol-2-yl)piperidin-4-yl]oxy}-1-methylethyl]carbamate and iodoethane, the title compound was obtained.

¹H NMR (300 MHz, DMSO-d₆) δ 1.04 (3H, d, J=6.4 Hz), 1.32 (3H, t, J=7.1 Hz), 1.46-1.67 (2H, m), 1.78 (3H, s), 1.82-2.01 (2H, m), 3.16-3.46 (4H, m), 3.48-3.63 (1H, m), 3.65-3.81 (2H, m), 3.82-3.94 (1H, m), 4.00 (2H, q, J=7.1 Hz), 6.85 (1H, dd, J=8.7, 2.7 Hz), 7.33 (1H, d, J=8.7 Hz), 7.37 (1H, d, J=2.7 Hz), 7.71 (1H, d, J=8.0 Hz).

mp 129-131° C.

Example 11

N-[(1S)-2-({1-[6-(cyclopropylmethoxy)-1,3-benzothiazol-2-yl]piperidin-4-yl}oxy)-1-methylethyl]acetamide By a method similar to Example 1, steps G and H, and using tert-butyl [(1S)-2-{[1-(6-hydroxy-1,3-benzothiazol-2-yl)piperidin-4-yl]oxy}-1-methylethyl]carbamate, the title compound was obtained.

¹H NMR (300 MHz, DMSO-d₆) δ 0.25-0.36 (2H, m), 0.47-0.62 (2H, m), 1.04 (3H, d, J=6.8 Hz), 1.11-1.31 (1H, m), 1.46-1.66 (2H, m), 1.78 (3H, s), 1.83-2.00 (2H, m), 3.20-3.43 (4H, m), 3.49-3.63 (1H, m), 3.64-3.98 (5H, m), 6.86 (1H, dd, J=8.7, 2.7 Hz), 7.33 (1H, d, J=8.7 Hz), 7.36 (1H, d, J=2.7 Hz), 7.71 (1H, d, J=8.0 Hz).

mp 121-122° C.

Example 12

N-[(1S)-1-methyl-2-({1-[6-(2,2,2-trifluoroethoxy)-1,3-benzothiazol-2-yl]piperidin-4-yl}oxy)ethyl]acetamide By a method similar to Example 1, steps G and H, and using tert-butyl [(1S)-2-{[1-(6-hydroxy-1,3-benzothiazol-2-yl)piperidin-4-yl]oxy}-1-methylethyl]carbamate and 2,2,2-trifluoroethyl trifluoromethanesulfonate, the title compound was obtained.

¹H NMR (300 MHz, DMSO-d₆) δ 1.04 (3H, d, J=6.8 Hz), 1.46-1.65 (2H, m), 1.78 (3H, s), 1.82-2.00 (2H, m), 3.04-3.44 (4H, m), 3.50-3.96 (4H, m), 4.73 (2H, q, J=9.1 Hz), 6.99 (1H, dd, J=8.9, 2.7 Hz), 7.38 (1H, d, J=8.9 Hz), 7.54 (1H, d, J=2.7 Hz), 7.71 (1H, d, J=8.0 Hz).

mp 129-131° C.

Example 13

N-[(1S)-2-({1-[6-(2,2-difluoroethoxy)-1,3-benzoxazol-2-yl]piperidin-4-yl}oxy)-1-methylethyl]acetamide By a method similar to Example 1, steps G and H, and using tert-butyl [(1S)-2-{[1-(6-hydroxy-1,3-benzoxazol-2-yl)piperidin-4-yl]oxy}-1-methylethyl]carbamate and 2,2-difluoroethyl trifluoromethanesulfonate, the title compound was obtained.

Example 14

N-[(1S)-2-({1-[6-(cyclopropylmethoxy)-7-fluoro-1,3-benzoxazol-2-yl]piperidin-4-yl}oxy)-1-methylethyl]acetamide A) 2-fluoro-3-methoxy-6-nitrophenol To a solution of 2-fluoro-1,3-dimethoxy-4-nitrobenzene (1.5 g) in toluene (100 mL) was added 1 M tribromoborane hexane solution (16 mL) at 0° C., and the mixture was stirred at room temperature for 15 hr. Water was added to the reaction mixture at 0° C., and the mixture was stirred at room temperature for 10 min. The reaction solution was extracted with ethyl acetate, and the obtained organic layer was washed with saturated brine, dried over anhydrous magnesium sulfate and concentrated under reduced pressure to give the title compound (860 mg).

¹H NMR (300 MHz, DMSO-d₆) δ 4.01 (3H, s), 6.63 (1H, dd, J=9.8, 7.2 Hz), 7.95 (1H, dd, J=9.7, 2.1 Hz), 10.61 (1H, s).

B) 6-amino-2-fluoro-3-methoxyphenol

A suspension of 2-fluoro-3-methoxy-6-nitrophenol (300 mg) and 5% palladium hydroxide (40 mg) in ethanol (10 mL) and THF (5 mL) was stirred at room temperature for 15 hr under a hydrogen atmosphere (1 atm). The mixture was filtered, and the filtrate was concentrated under reduced pressure to give the title compound (220 mg).

¹H NMR (300 MHz, DMSO-d₆) δ 3.67 (3H, s), 6.12-6.42 (2H, m).

C) 7-fluoro-6-methoxy-1,3-benzoxazole-2-thiol

To a solution of 6-amino-2-fluoro-3-methoxyphenol (220 mg) in ethanol (10 mL) was added potassium ethylxanthate (450 mg), and the mixture was stirred at 80° C. for 64 hr. After allowing to cool to room temperature, the mixture was concentrated under reduced pressure. The obtained residue was dissolved in water, and the solution was acidified with 1 M hydrochloric acid. After stirring for 10 min, the mixture was extracted with ethyl acetate, and the obtained organic layer was washed with saturated brine, dried over anhydrous magnesium sulfate, and concentrated under reduced pressure to give the title compound (147 mg).

MS (ESI+): [M+H]⁺ 199.97.

D) tert-butyl [(1S)-2-{[1-(7-fluoro-6-methoxy-1,3-benzoxazol-2-yl)piperidin-4-yl]oxy}-1-methylethyl]carbamate By a method similar to Example 1, steps E and F, and using 7-fluoro-6-methoxy-1,3-benzoxazole-2-thiol, the title compound was obtained.

MS (ESI+): [M+H]⁺ 424.45.

E) N-[(1S)-2-({1-[6-(cyclopropylmethoxy)-7-fluoro-1,3-benzoxazol-2-yl]piperidin-4-yl}oxy)-1-methylethyl]acetamide By a method similar to Example 3, step C, and using tert-butyl [(1S)-2-{[1-(7-fluoro-6-methoxy-1,3-benzoxazol-2-yl)piperidin-4-yl]oxy}-1-methylethyl]carbamate, the title compound was obtained.

Example 15

N-[(1S)-2-({1-[6-(cyclopropylmethoxy)-4-fluoro-1,3-benzoxazol-2-yl]piperidin-4-yl}oxy)-1-methylethyl]acetamide A) tert-butyl(2,4-dimethoxyphenyl)carbamate To a solution of tribromoindium (120 mg) and di-tert-butyl dicarbonate (7.1 g) in THF (50 mL) was added 2,4-dimethoxyaniline (5.0 g). The reaction mixture was stirred at room temperature for 30 min and extracted with ethyl acetate. The obtained organic layer was washed with saturated brine, dried over anhydrous magnesium sulfate, and concentrated under reduced pressure. The residue was purified by silica gel chromatography (hexane/ethyl acetate) to give the title compound (8.0 g).

$^1$H NMR (300 MHz, CDCl$_3$) δ 1.51 (9H, s), 3.78 (3H, s), 3.83 (3H, s), 6.40-6.51 (2H, m), 6.82 (1H, brs), 7.90 (1H, brs)

B) tert-butyl (2-fluoro-4,6-dimethoxyphenyl)carbamate

To a solution of tert-butyl (2,4-dimethoxyphenyl)carbamate (1.0 g) and tetramethylenediamine (1.4 mL) in THF (10 mL) was added 1.6 M n-butyllithium-hexane solution (7.5 mL) at −78° C., and the mixture was stirred at the same temperature for 20 min and then at 0° C. for 1 hr. To the reaction mixture was added a solution of N-fluoro-N-(phenylsulfonyl)benzenesulfonamide (1.8 g) in THF (10 mL) at −78° C., and the mixture was allowed to warm to room temperature and stirred for 15 hr. Saturated aqueous ammonium chloride solution was added to the reaction mixture, and the mixture was extracted with ethyl acetate, washed with saturated brine, dried over anhydrous magnesium sulfate and concentrated under reduced pressure. The residue was purified by silica gel chromatography (hexane/ethyl acetate) to give the title compound (530 mg).

$^1$H NMR (300 MHz, CDCl$_3$) δ 1.45 (9H, s), 3.80 (3H, s), 3.81 (3H, d, J=1.51 Hz), 6.82 (1H, m), 7.25 (1H, m), 8.31 (1H, s).

C) 4-fluoro-2-sulfanyl-1,3-benzoxazol-6-ol

To a solution of tert-butyl (2-fluoro-4,6-dimethoxyphenyl) carbamate (530 mg) in toluene (20 mL) was added 1M tribromoborane hexane solution (6.1 mL) at 0° C., and the mixture was stirred at room temperature for 15 hr. Water was added to the mixture at 0° C., and the mixture was stirred at room temperature for 10 min. The mixture was washed with ethyl acetate, and the aqueous layer was concentrated under reduced pressure to give a solid. The obtained solid was washed with ethanol and dried under reduced pressure. To a solution of the obtained solid in ethanol (10 mL) was added potassium ethylxanthate (610 mg), and the mixture was stirred at 90° C. for 15 hr. After allowing to cool to room temperature, the mixture was concentrated under reduced pressure. The obtained residue was dissolved in water, and the solution was acidified with 1 M hydrochloric acid. After stirring for 10 min, the mixture was extracted with ethyl acetate, and the obtained organic layer was washed with saturated brine, dried over anhydrous magnesium sulfate and concentrated under reduced pressure. The residue was purified by silica gel chromatography (hexane/ethyl acetate) to give the title compound (190 mg).

MS (ESI+): [M+H]$^+$ 186.07.

D) N-[(1S)-2-({1-[6-(cyclopropylmethoxy)-4-fluoro-1,3-benzoxazol-2-yl]piperidin-4-yl}oxy)-1-methylethyl]acetamide By a method similar to Example 1, steps E to H, and using 4-fluoro-2-sulfanyl-1,3-benzoxazol-6-ol, the title compound was obtained.

Example 16

N-[(1S)-2-({1-[5-(cyclopropylmethoxy)-6-fluoro-1,3-benzothiazol-2-yl]piperidin-4-yl}oxy)-1-methylethyl]acetamide A) 6-fluoro-5-methoxy-1,3-benzothiazol-2-amine A suspension of 4-fluoro-3-methoxyaniline (1.00 g) and potassium thiocyanate (2.07 g) in acetic acid (20 mL) was stirred at room temperature for 20 min, and a solution of bromine (0.380 mL) in acetic acid (1 mL) was added thereto over 5 min. The reaction mixture was stirred at room temperature for 30 min, neutralized with saturated aqueous sodium hydrogen carbonate solution, and extracted with ethyl acetate. The obtained organic layer was dried over anhydrous magnesium sulfate, and the solvent was evaporated under reduced pressure. The residue was purified by silica gel column chromatography (hexane/ethyl acetate) to give the title compound (670 mg).

$^1$H NMR (300 MHz, CDCl$_3$) δ 3.91 (3H, s), 5.19 (2H, brs), 7.16 (1H, d, J=7.6 Hz), 7.29 (1H, d, J=10.2 Hz).

B) 2-chloro-6-fluoro-5-methoxy-1,3-benzothiazole

A suspension of copper(II) chloride (546 mg) and tert-butyl nitrite (0.600 mL) in acetonitrile (10 mL) was stirred at 50° C. for 20 min. To the reaction mixture was added a solution of 6-fluoro-5-methoxy-1,3-benzothiazol-2-amine (670 mg) in acetonitrile (10 mL), and the mixture was further stirred at 50° C. for 30 min. 1M Hydrochloric acid and saturated brine were added to the reaction mixture, and the insoluble material was filtered. The filtrate was extracted with ethyl acetate, the filtered insoluble material was dissolved in THF, and the solution was combined with the organic layer. The mixture was applied to silica gel column chromatography (ethyl acetate). The solvent was evaporated under reduced pressure and the obtained solid was washed with ethyl acetate/hexane to give the title compound (350 mg).

$^1$H NMR (300 MHz, DMSO-d$_6$) δ 3.93 (3H, s), 7.76 (1H, d, J=7.9 Hz), 8.03 (1H, d, J=10.9 Hz).

C) N-[(1S)-2-({1-[5-(cyclopropylmethoxy)-6-fluoro-1,3-benzothiazol-2-yl]piperidin-4-yl}oxy)-1-methylethyl]acetamide By a method similar to Example 3, steps B and C, and using 2-chloro-6-fluoro-5-methoxy-1,3-benzothiazole, the title compound was obtained.

Example 17

1-[(1S)-2-({1-[6-(cyclopropylmethoxy)-1,3-benzoxazol-2-yl]piperidin-4-yl}oxy)-1-methylethyl]-3-methylurea To tert-butyl [(1S)-2-({1-[6-(cyclopropylmethoxy)-1,3-benzoxazol-2-yl]piperidin-4-yl}oxy)-1-methylethyl]carbamate (300 mg) was added 4M hydrogen chloride/ethyl acetate (4 mL), and the mixture was stirred at room temperature for 20 min and concentrated. The residue was dissolved in acetonitrile (3.4 mL), methyl isocyanate (59.6 μL) and triethylamine (470 μL) were added thereto, and the mixture was stirred at room temperature for 1 hr. The reaction mixture was diluted with ethyl acetate, washed with saturated brine, and dried over anhydrous sodium sulfate. The solvent was evaporated under reduced pressure and the residue was purified by silica gel chromatography (NH, hexane/ethyl acetate). The obtained solid was washed with hexane and ethyl acetate to give the title compound (149 mg).

Example 18

1-[(1S)-2-({1-[6-(cyclopropylmethoxy)-1,3-benzoxazol-2-yl]piperidin-4-yl}oxy)-1-methylethyl]-3-ethylurea By a method similar to Example 17, and using tert-butyl [(1S)-2-({1-[6-(cyclopropylmethoxy)-1,3-benzoxazol-2-yl]piperidin-4-yl}oxy)-1-methylethyl]carbamate and ethyl isocyanate, the title compound was obtained.

Example 19 methyl [(1S)-2-({1-[6-(cyclopropylmethoxy)-1,3-benzoxazol-2-yl]piperidin-4-yl}oxy)-1-methylethyl]carbamate By a method similar to Example 17, and using tert-butyl [(1S)-2-({1-[6-(cyclopropylmethoxy)-1,3-benzoxazol-2-yl]piperidin-4-yl}oxy)-1-methylethyl]carbamate and methyl chlorocarbonate, the title compound was obtained.

Example 20

N-[(1S)-1-methyl-2-{[1-(5-propoxy-1,3-benzoxazol-2-yl)piperidin-4-yl]oxy}ethyl]acetamide A) tert-butyl [(1S)-1-methyl-2-{[1-(5-propoxy-1,3-benzoxazol-2-yl)piperidin-4-yl]oxy}ethyl]carbamate By a method similar to Example 6, step A, and using tert-butyl [(1S)-2-{[1-(5-hydroxy-1,3-benzoxazol-2-yl)piperidin-4-yl]oxy}-1-methylethyl]carbamate (412 mg) and 1-bromopropane (0.282 mL), the title compound (367 mg) was obtained.
MS (ESI+): [M+H]+ 434.5.

B) N-[(1S)-1-methyl-2-{[1-(5-propoxy-1,3-benzoxazol-2-yl)piperidin-4-yl]oxy}ethyl]acetamide By a method similar to Example 6, step B, and using tert-butyl [(1S)-1-methyl-2-{[1-(5-propoxy-1,3-benzoxazol-2-yl)piperidin-4-yl]oxy}ethyl]carbamate (367 mg), the title compound (215 mg) was obtained.

Example 21

N-[(1S)-2-{[1-(6-ethoxy-1,3-benzoxazol-2-yl)piperidin-4-yl]oxy}-1-methylethyl]acetamide By a method similar to Example 1, steps G to H, and using tert-butyl [(1S)-2-{[1-(6-hydroxy-1,3-benzoxazol-2-yl)piperidin-4-yl]oxy}-1-methylethyl]carbamate and iodoethane, the title compound was obtained.

Example 22

N-[(1S)-1-methyl-2-{[1-(6-propoxy-1,3-benzoxazol-2-yl)piperidin-4-yl]oxy}ethyl]acetamide By a method similar to Example 1, steps G to H, and using tert-butyl [(1S)-2-{[1-(6-hydroxy-1,3-benzoxazol-2-yl)piperidin-4-yl]oxy}-1-methylethyl]carbamate and 1-iodopropane, the title compound was obtained.

Example 23

N-[(1S)-1-methyl-2-({1-[6-(1-methylethoxy)-1,3-benzoxazol-2-yl]piperidin-4-yl}oxy)ethyl]acetamide By a method similar to Example 1, steps G to H, and using tert-butyl [(1S)-2-{[1-(6-hydroxy-1,3-benzoxazol-2-yl)piperidin-4-yl]oxy}-1-methylethyl]carbamate and 2-iodopropane, the title compound was obtained.

Example 24

N-{1-[({1-[6-(cyclopropylmethoxy)-1,3-benzoxazol-2-yl]piperidin-4-yl}oxy)methyl]-2,2,2-trifluoroethyl}acetamide A) benzyl 4-(2-hydroxyethoxy)piperidine-1-carboxylate A mixture of sodium borohydride (10.1 g), calcium chloride (13.3 g), ethanol (100 mL) and THF (50 mL) was stirred at 0° C. for 30 min. After stirring, a mixture of benzyl 4-(2-ethoxy-2-oxoethoxy)piperidine-1-carboxylate (9.68 g) and THF (50 mL) was added dropwise at 0° C., and the obtained mixture was stirred at room temperature for 2 days. Saturated aqueous ammonium chloride solution was added thereto, and the insoluble material was filtered off. The filtrate was concentrated under reduced pressure. The residue was extracted with ethyl acetate, and the extract was washed with saturated brine, and dried over anhydrous sodium sulfate. The solvent was evaporated under reduced pressure and the residue was purified by silica gel column chromatography (ethyl acetate/hexane) to give the title compound (6.33 g).
$^1$H NMR (300 MHz, DMSO-$d_6$) δ 1.25-1.49 (2H, m), 1.70-1.89 (2H, m), 2.98-3.26 (2H, m), 3.38-3.55 (5H, m), 3.58-3.80 (2H, m), 4.47-4.62 (1H, m), 5.06 (2H, s), 7.16-7.46 (5H, m).

B) benzyl 4-(2-oxoethoxy)piperidine-1-carboxylate

To a mixture of benzyl 4-(2-hydroxyethoxy)piperidine-1-carboxylate (6.33 g), triethylamine (15.9 mL) and dimethyl sulfoxide (30 mL) were added dropwise a mixture of sulfur trioxide pyridine complex (10.8 g) and dimethyl sulfoxide (30 mL) at room temperature, and the obtained mixture was stirred at room temperature for 1 hr. Water was added thereto, and the obtained mixture was extracted with ethyl acetate. The extract was washed with 1M hydrochloric acid and saturated brine, and dried over anhydrous sodium sulfate. The solvent was evaporated under reduced pressure and the residue was purified by silica gel column chromatography (ethyl acetate/hexane) to give the title compound (4.28 g).

¹H NMR (300 MHz, DMSO-d₆) δ 1.27-1.55 (2H, m), 1.70-1.95 (2H, m), 3.12 (2H, brs), 3.44-3.88 (3H, m), 4.22 (2H, s), 5.07 (2H, s), 7.12-7.51 (5H, m), 9.58 (1H, s).

C) benzyl 4-(3,3,3-trifluoro-2-hydroxypropoxy)piperidine-1-carboxylate

A mixture of benzyl 4-(2-oxoethoxy)piperidine-1-carboxylate (2.00 g), trimethyl(trifluoromethyl)silane (1.23 g), tetrabutylammonium fluoride (1 M THF solution, 1 drop) and THF (20 mL) was stirred at 0° C. for 1 hr, and then at room temperature for 3 days. Water was added thereto, and the obtained mixture was extracted with ethyl acetate. The extract was washed with saturated brine, and dried over anhydrous sodium sulfate. The solvent was evaporated under reduced pressure and the residue was dissolved in THF (20 mL). Tetrabutylammonium fluoride (1 M THF solution, 8.65 mL) was added thereto at 0° C., and the obtained mixture was stirred at 0° C. for 2 hr. 1M Hydrochloric acid was added, and the obtained mixture was extracted with ethyl acetate. The extract was washed with saturated brine, and dried over anhydrous sodium sulfate. The solvent was evaporated under reduced pressure and the residue was purified by silica gel column chromatography (ethyl acetate/hexane) to give the title compound (1.60 g).

¹H NMR (300 MHz, DMSO-d₆) δ 1.26-1.53 (2H, m), 1.66-1.89 (2H, m), 3.01-3.27 (2H, m), 3.41-3.76 (5H, m), 4.04-4.23 (1H, m), 5.06 (2H, s), 6.34 (1H, d, J=5.7 Hz), 7.19-7.51 (5H, m).

D) benzyl 4-{3,3,3-trifluoro-2-[(methylsulfonyl)oxy]propoxy}piperidine-1-carboxylate A mixture of benzyl 4-(3,3,3-trifluoro-2-hydroxypropoxy)piperidine-1-carboxylate (983 mg), mesyl chloride (0.438 mL), triethylamine (0.789 mL) and THF (10 mL) was stirred at 0° C. for 1 hr, and then at room temperature overnight. Water was added thereto, and the obtained mixture was extracted with ethyl acetate. The extract was washed with saturated brine, and dried over anhydrous sodium sulfate. The solvent was evaporated under reduced pressure and the residue was purified by silica gel column chromatography (ethyl acetate/hexane) to give the title compound (1.12 g).

¹H NMR (300 MHz, DMSO-d₆) δ 1.24-1.53 (2H, m), 1.68-1.91 (2H, m), 2.97-3.25 (2H, m), 3.35 (3H, s), 3.55-3.93 (5H, m), 5.06 (2H, s), 5.29-5.54 (1H, m), 7.14-7.44 (5H, m).

E) benzyl 4-(2-azido-3,3,3-trifluoropropoxy)piperidine-1-carboxylate

A mixture of benzyl 4-{3,3,3-trifluoro-2-[(methylsulfonyl)oxy]propoxy}piperidine-1-carboxylate (1.31 g), sodium azide (1.00 g), 15-crown-5-ether (3.39 g) and dimethyl sulfoxide (5 mL) was stirred at 100° C. for 3 days. Water was added thereto, and the obtained mixture was extracted with ethyl acetate. The extract was washed with saturated brine, and dried over anhydrous sodium sulfate. The solvent was evaporated under reduced pressure and the residue was purified by silica gel column chromatography (ethyl acetate/hexane) to give the title compound (294 mg).

¹H NMR (300 MHz, DMSO-d₆) δ 1.29-1.55 (2H, m), 1.71-1.90 (2H, m), 3.03-3.27 (2H, m), 3.49-3.96 (5H, m), 4.63-4.91 (1H, m), 5.07 (2H, s), 7.13-7.51 (5H, m).

F) N-{1-[({1-[6-(cyclopropylmethoxy)-1,3-benzoxazol-2-yl]piperidin-4-yl}oxy)methyl]-2,2,2-trifluoroethyl}acetamide By a method similar to Example 8, D and E (except that palladium carbon was used instead of palladium hydroxide) and Example 1, step G, and using benzyl 4-(2-azido-3,3,3-trifluoropropoxy)piperidine-1-carboxylate (451 mg), the title compound (120 mg) was obtained.

¹H NMR (300 MHz, DMSO-d₆) δ 0.23-0.39 (2H, m), 0.48-0.63 (2H, m), 1.06-1.29 (1H, m), 1.42-1.65 (2H, m), 1.92 (5H, s), 3.26-3.49 (2H, m), 3.54-3.88 (7H, m), 4.48-4.94 (1H, m), 6.73 (1H, dd, J=8.7, 2.3 Hz), 7.06 (1H, d, J=2.3 Hz), 7.14 (1H, d, J=8.7 Hz), 8.46 (1H, d, J=9.4 Hz).

mp 126-127° C.

Example 25

N-[2-({1-[6-(cyclopropylmethoxy)-1,3-benzoxazol-2-yl]piperidin-4-yl}oxy)-1-(fluoromethyl)ethyl]acetamide A) benzyl 4-(oxiran-2-ylmethoxy)piperidine-1-carboxylate A mixture of trimethylsulfoxonium iodide (2.17 g), sodium hydride (oil, 60%, 395 mg) and dimethyl sulfoxide (20 mL) was stirred at room temperature for 1 hr, and benzyl 4-(2-oxoethoxy)piperidine-1-carboxylate (2.28 g) was added thereto. The obtained mixture was stirred at room temperature for 3 days. Water was added thereto, and the obtained mixture was extracted with ethyl acetate. The extract was washed with saturated brine, and dried over anhydrous sodium sulfate. The solvent was evaporated under reduced pressure and the residue was purified by silica gel column chromatography (ethyl acetate/hexane) to give the title compound (208 mg).

¹H NMR (300 MHz, DMSO-d₆) δ 1.26-1.50 (2H, m), 1.65-1.92 (2H, m), 2.54 (1H, dd, J=5.3, 2.6 Hz), 2.67-2.76 (1H, m), 2.99-3.22 (3H, m), 3.23-3.32 (1H, m), 3.45-3.60 (1H, m), 3.62-3.84 (3H, m), 5.06 (2H, s), 7.14-7.50 (5H, m).

B) benzyl 4-(3-fluoro-2-hydroxypropoxy)piperidine-1-carboxylate

A mixture of benzyl 4-(oxiran-2-ylmethoxy)piperidine-1-carboxylate (1.81 g) and tetrabutylammonium dihydrogen trifluoride (3.74 g) was stirred at 120° C. overnight. The reaction mixture was purified by silica gel column chromatography (ethyl acetate/hexane) to give the title compound (960 mg).

¹H NMR (300 MHz, DMSO-d₆) δ 1.26-1.49 (2H, m), 1.68-1.89 (2H, m), 2.97-3.26 (2H, m), 3.35-3.89 (6H, m), 4.18-4.58 (2H, m), 5.06 (2H, s), 5.12 (1H, d, J=5.3 Hz), 7.10-7.50 (5H, m).

C) benzyl 4-(2-azido-3-fluoropropoxy)piperidine-1-carboxylate

By a method similar to Example 5, step E (except that dimethyl sulfoxide was used as a solvent instead of DMF), and using benzyl 4-(3-fluoro-2-hydroxypropoxy)piperidine-1-carboxylate (960 mg), the title compound (557 mg) was obtained.

¹H NMR (300 MHz, DMSO-d₆) δ 1.31-1.54 (2H, m), 1.63-1.89 (2H, m), 2.98-3.29 (2H, m), 3.46-3.78 (5H, m), 3.81-4.11 (1H, m), 4.27-4.75 (2H, m), 5.06 (2H, s), 7.13-7.49 (5H, m).

D) N-[2-({1-[6-(cyclopropylmethoxy)-1,3-benzoxazol-2-yl]piperidin-4-yl}oxy)-1-(fluoromethyl)ethyl]acetamide By a method similar to Example 24, F, and using benzyl 4-(2-azido-3-fluoropropoxy)piperidine-1-carboxylate (250 mg), the title compound (127 mg) was obtained.

¹H NMR (300 MHz, DMSO-$d_6$) δ 0.22-0.36 (2H, m), 0.48-0.64 (2H, m), 1.10-1.31 (1H, m), 1.40-1.71 (2H, m), 1.79-1.98 (5H, m), 3.27-3.65 (5H, m), 3.69-3.86 (4H, m), 3.93-4.23 (1H, m), 4.26-4.59 (2H, m), 6.73 (1H, dd, J=8.4, 2.3 Hz), 7.06 (1H, d, J=2.3 Hz), 7.14 (1H, d, J=8.4 Hz), 7.99 (1H, d, J=8.3 Hz).

mp 120-121° C.

Example 26

N-[2-({8-[6-(cyclopropylmethoxy)-1,3-benzoxazol-2-yl]-8-azabicyclo[3.2.1]oct-3-yl}oxy)-1-methylethyl]isoxazol-3-amine

A) 8-(6-hydroxy-1,3-benzoxazol-2-yl)-8-azabicyclo[3.2.1]octan-3-one

By a method similar to Example 1, step F, and using 8-azabicyclo[3.2.1]octan-3-one and 2-chloro-1,3-benzoxazol-6-ol, the title compound was obtained.

MS (ESI+): [M+H]⁺ 259.1.

B) 8-[6-(cyclopropylmethoxy)-1,3-benzoxazol-2-yl]-8-azabicyclo[3.2.1]octan-3-one By a method similar to Example 4, step C, and using 8-(6-hydroxy-1,3-benzoxazol-2-yl)-8-azabicyclo[3.2.1]octan-3-one, the title compound was obtained.

MS (ESI+): [M+H]⁺ 313.1.

C) 8-[(6-(cyclopropylmethoxy)-1,3-benzoxazol-2-yl]-8-azabicyclo[3.2.1]octan-3-ol By a method similar to Example 5, step D, and using 8-[6-(cyclopropylmethoxy)-1,3-benzoxazol-2-yl]-8-azabicyclo[3.2.1]octan-3-one, the title compound was separately obtained as two kinds of isomers.

MS (ESI+): [M+H]⁺ 315.1 (retention time short by NH silica gel column chromatography).

MS (ESI+): [M+H]⁺ 315.2 (retention time long by NH silica gel column chromatography).

D) 6-(cyclopropylmethoxy)-2-{3-[2-(morpholin-4-yl)-2-oxoethoxy]-8-azabicyclo[3.2.1]oct-8-yl}-1,3-benzoxazole By a method similar to Example 4, step A, and using 8-[6-(cyclopropylmethoxy)-1,3-benzoxazol-2-yl]-8-azabicyclo[3.2.1]octan-3-ol, the title compound was obtained (short retention time).

MS (ESI+): [M+H]⁺ 442.3.

E) 1-({8-[6-(cyclopropylmethoxy)-1,3-benzoxazol-2-yl]-8-azabicyclo[3.2.1]oct-3-yl}oxy)propan-2-one By a method similar to Example 4, step D, and using 6-(cyclopropylmethoxy)-2-{3-[2-(morpholin-4-yl)-2-oxoethoxy]-8-azabicyclo[3.2.1]oct-8-yl}-1,3-benzoxazole, the title compound was obtained.

MS (ESI+): [M+H]⁺ 371.0.

F) N-[2-({8-[6-(cyclopropylmethoxy)-1,3-benzoxazol-2-yl]-8-azabicyclo[3.2.1]oct-3-yl}oxy)-1-methylethyl]isoxazol-3-amine By a method similar to Example 4, step E, and using 1-({8-[6-(cyclopropylmethoxy)-1,3-benzoxazol-2-yl]-8-azabicyclo[3.2.1]oct-3-yl}oxy)propan-2-one, the title compound was obtained.

Example 27

N-[2-({8-[6-(cyclopropylmethoxy)-1,3-benzoxazol-2-yl]-8-azabicyclo[3.2.1]oct-3-yl}oxy)-1-methylethyl]isoxazol-3-amine

A) 6-(cyclopropylmethoxy)-2-{3-[2-(morpholin-4-yl)-2-oxoethoxy]-8-azabicyclo[3.2.1]oct-8-yl}-1,3-benzoxazole By a method similar to Example 4, step A, and using 8-[(6-(cyclopropylmethoxy)-1,3-benzoxazol-2-yl]-8-azabicyclo[3.2.1]octan-3-ol, the title compound was obtained (long retention time).

MS (ESI+): [M+H]⁺ 442.1.

B) 1-({8-[6-(cyclopropylmethoxy)-1,3-benzoxazol-2-yl]-8-azabicyclo[3.2.1]oct-3-yl}oxy)propan-2-one By a method similar to Example 4, step D, and using 6-(cyclopropylmethoxy)-2-{3-[2-(morpholin-4-yl)-2-oxoethoxy]-8-azabicyclo[3.2.1]oct-8-yl}-1,3-benzoxazole, the title compound was obtained.

MS (ESI+): [M+H]⁺ 371.2.

C) N-[2-({8-[6-(cyclopropylmethoxy)-1,3-benzoxazol-2-yl]-8-azabicyclo[3.2.1]oct-3-yl}oxy)-1-methylethyl]isoxazol-3-amine By a method similar to Example 4, step E, and using 1-({8-[6-(cyclopropylmethoxy)-1,3-benzoxazol-2-yl]-8-azabicyclo[3.2.1]oct-3-yl}oxy)propan-2-one, the title compound was obtained.

Example 28

N-[(1S)-2-({1-[5-(cyclopropylmethoxy)[1,3]oxazolo[5,4-b]pyridin-2-yl]piperidin-4-yl}oxy)-1-methylethyl]acetamide

A) tert-butyl [(1S)-2-{[1-(5-bromo[1,3]oxazolo[5,4-b]pyridin-2-yl)piperidin-4-yl]oxy}-1-methylethyl]carbamate By a method similar to Example 2, step C, and using 5-bromo[1,3]oxazolo[5,4-b]pyridine-2-thiol (241 mg), the title compound (382 mg) was obtained.

MS (ESI+): [M+H]⁺ 457.2.

B) tert-butyl [(1S)-2-{[1-(5-hydroxy[1,3]oxazolo[5,4-b]pyridin-2-yl)piperidin-4-yl]oxy}-1-methylethyl]carbamate To a solution of tert-butyl [(1S)-2-{[1-(5-bromo[1,3]oxazolo[5,4-b]pyridin-2-yl)piperidin-4-yl]oxy}-1-methylethyl]carbamate (484 mg) in THF (3 mL) was added 1.6M n-butyllithium-hexane solution (1.70 mL) at −78° C., and the mixture was stirred at the same temperature for 20 min. Trimethyl borate (0.355 mL) was added to the reaction mixture, and the mixture was allowed to warm to room temperature and stirred for 30 min. 30% Hydrogen peroxide water (3 mL) and 8M aqueous sodium hydroxide solution (1 mL) were added to the reaction mixture, and the mixture was stirred at room temperature for 30 min. The reaction mixture was neutralized with 1M hydrochloric acid, and extracted with ethyl acetate, and the extract was dried over magnesium sulfate. The solvent was evaporated under reduced pressure, and the obtained residue was purified by silica gel column chromatography (hexane/ethyl acetate) to give the title compound (68.1 mg).

MS (ESI+): [M+H]+ 393.4.

C) N-[(1S)-2-({1-[5-(cyclopropylmethoxy)[1,3]oxazolo[5,4-b]pyridin-2-yl]piperidin-4-yl}oxy)-1-methylethyl]acetamide By a method similar to Example 1, steps G and H, and using tert-butyl [(1S)-2-{[1-(5-hydroxy[1,3]oxazolo[5,4-b]pyridin-2-yl)piperidin-4-yl]oxy}-1-methylethyl]carbamate, the title compound was obtained.

Example 29

N-[(1S)-3-{4-[6-(cyclopropylmethoxy)-1,3-benzoxazol-2-yl]piperazin-1-yl}-1-methylpropyl]acetamide

A) benzyl 4-{(3S)-3-[(tert-butoxycarbonyl)amino]butyl}piperazine-1-carboxylate To a solution of tert-butyl [(1S)-3-hydroxy-1-methylpropyl]carbamate (1.00 g) and triethylamine (1.47 mL) in THF (15 mL) was added methanesulfonyl chloride (0.614 mL), and the mixture was stirred at room temperature for 15 min. Saturated aqueous sodium hydrogen carbonate solution was added to the reaction mixture, and the mixture was extracted with ethyl acetate. The obtained organic layer was dried over anhydrous magnesium sulfate, and the solvent was evaporated under reduced pressure. A solution of the residue, benzyl 1-piperazinecarboxylate (1.75 g) and triethylamine (1.48 mL) in DMF (15 mL) was stirred at 60° C. for 3 hr. The reaction mixture was diluted with ethyl acetate, washed with saturated brine, and dried over anhydrous magnesium sulfate. The solvent was evaporated under reduced pressure, and the obtained residue was purified by silica gel column chromatography (hexane/ethyl acetate) to give the title compound (1.10 g).

MS (ESI+): [M+H]+ 392.4.

B) N-[(1S)-3-{4-[6-(cyclopropylmethoxy)-1,3-benzoxazol-2-yl]piperazin-1-yl}-1-methylpropyl]acetamide To a solution of benzyl 4-{(3S)-3-[(tert-butoxycarbonyl)amino]butyl}piperazine-1-carboxylate (1.10 g) in ethanol (10 mL) was added 10% palladium carbon (1.50 g), and the mixture was stirred at room temperature for 30 min under a hydrogen atmosphere. The reaction mixture was filtered, and the filtrate was evaporated under reduced pressure to give tert-butyl [(1S)-1-methyl-3-(piperazin-1-yl)propyl]carbamate. By a method similar to Example 1, steps F to H, and using the obtained compound, the title compound was obtained.

Example 30

N-[2-({1-[6-(cyclopropylmethoxy)-1,3-benzoxazol-2-yl]pyrrolidin-3-yl}oxy)-1-methylethyl]acetamide By a method similar to Example 4, step A, and then Example 5, steps C to J, and using tert-butyl 3-hydroxypyrrolidine-1-carboxylate, the title compound was obtained.

Example 31

N-[(1S)-2-({1-[6-(cyclopropylmethoxy)-1,3-benzoxazol-2-yl]piperidin-3-yl}oxy)-1-methylethyl]acetamide By a method similar to Example 1, steps B, C, F, G and H, and using 3-hydroxypyridine, the title compound was obtained.

Example 32

N-[(1S)-2-({1-[5-(cyclopropylmethoxy)[1,3]oxazolo[5,4-c]pyridin-2-yl]piperidin-4-yl}oxy)-1-methylethyl]acetamide

A) 5-bromo-2-(cyclopropylmethoxy)pyridine

To a solution of cyclopropylmethanol (0.890 mL) in DMF (30 mL) was added sodium hydride (oil, 60%, 440 mg), and the mixture was stirred at room temperature for 10 min. To this mixture was added 2,5-dibromopyridine (2.00 g), and the mixture was stirred at 70° C. for 1 hr. Water was added to the reaction mixture, and the mixture was extracted with ethyl acetate. The organic layer was washed twice with saturated brine, and dried over anhydrous magnesium sulfate. The solvent was evaporated under reduced pressure, and the obtained residue was purified by silica gel column chromatography (hexane/ethyl acetate) to give the title compound (1.88 g).

$^1$H NMR (CDCl$_3$) δ 0.31-0.36 (2H, m), 0.58-0.64 (2H, m), 1.20-1.33 (1H, m), 4.09 (2H, d, J=7.2 Hz), 6.68 (1H, d, J=9.5 Hz), 7.63 (1H, dd, J=8.9, 2.5 Hz), 8.16 (1H, d, J=2.3 Hz).

B) 6-(cyclopropylmethoxy)pyridin-3-ol

To a solution of 5-bromo-2-(cyclopropylmethoxy)pyridine (1.88 g) in THF (15 mL) was added 1.6M n-butyllithium-hexane solution (7.25 mL) at −78° C., and the mixture was stirred at the same temperature for 20 min. Trimethylborane (1.29 mL) was added to this solution, and the mixture was stirred at −78° C. for 30 min. The reaction mixture was heated to 0° C., aqueous hydrogen peroxide (30%, 5 mL) and 8M aqueous sodium hydroxide solution (1.55 mL) were added thereto, and the mixture was stirred for 15 min. Water was added to the reaction mixture, the mixture was extracted twice with ethyl acetate, and the combined organic layer was dried over anhydrous magnesium sulfate. The solvent was evaporated under reduced pressure, and the obtained residue was purified by silica gel column chromatography (hexane/ethyl acetate) to give the title compound (855 mg).

$^1$H NMR (CDCl$_3$) δ 0.30-0.35 (2H, m), 0.57-0.63 (2H, m), 1.19-1.32 (1H, m), 4.04 (2H, d, J=6.8 Hz), 5.59 (1H, brs), 6.69 (1H, d, J=9.5 Hz), 7.19 (1H, dd, J=8.9, 3.2 Hz), 7.74 (1H, d, J=2.7 Hz).

C) 2-(cyclopropylmethoxy)-5-(methoxymethoxy)pyridine

To a suspension of 6-(cyclopropylmethoxy)pyridin-3-ol (855 mg) and potassium carbonate (1.44 g) in DMF (15 mL)

was added chloromethyl methyl ether (0.635 mL), and the mixture was stirred at room temperature for 1 hr. Water was added to the reaction mixture, and the mixture was extracted with ethyl acetate. The organic layer was washed twice with saturated brine, and dried over anhydrous magnesium sulfate. The solvent was evaporated under reduced pressure, and the obtained residue was purified by silica gel column chromatography (hexane/ethyl acetate) to give the title compound (789 mg) as an oil.

$^1$H NMR (CDCl$_3$) δ 0.31-0.36 (2H, m), 0.57-0.63 (2H, m), 1.22-1.32 (1H, m), 3.49 (3H, s), 4.07 (2H, d, J=7.2 Hz), 5.09 (2H, s), 6.71 (1H, d, J=9.1 Hz), 7.33 (1H, dd, J=9.1, 3.0 Hz), 7.92 (1H, d, J=3.0 Hz).

D) 2-(cyclopropylmethoxy)-5-(methoxymethoxy) pyridine-4-carboxylic acid

To a solution of 2-(cyclopropylmethoxy)-5-(methoxymethoxy)pyridine (1.41 g) in THF (15 mL) was added 1.6M n-butyllithium-hexane solution (6.3 mL) at −78° C., and the mixture was stirred at the same temperature for 30 min. The reaction mixture was allowed to warm to room temperature while bubbling a carbon dioxide gas therein. 1M Hydrochloric acid (10 mL) was added, and the mixture was extracted with ethyl acetate. The organic layer was washed with saturated brine, and dried over anhydrous magnesium sulfate. The solvent was evaporated under reduced pressure, and the obtained solid was washed with diisopropyl ether and hexane to give the title compound (810 mg).

MS (ESI+): [M+H]$^+$ 254.3.

E) tert-butyl [2-(cyclopropylmethoxy)-5-(methoxymethoxy)pyridin-4-yl]carbamate To a solution of 2-(cyclopropylmethoxy)-5-(methoxymethoxy)pyridine-4-carboxylic acid (810 mg) in tert-butyl alcohol (16 mL) were added diphenylphosphorylazide (0.831 mL) and N,N-diisopropylethylamine (0.669 mL), and the mixture was refluxed for 11 hr. The solvent was evaporated under reduced pressure, brine was added thereto, and the mixture was extracted with ethyl acetate. The obtained organic layer was washed with saturated brine, and dried over anhydrous magnesium sulfate. The solvent was evaporated under reduced pressure, and the obtained residue was purified by silica gel column chromatography (hexane/ethyl acetate) to give the title compound (737 mg).

$^1$H NMR (CDCl$_3$) δ 0.26-0.41 (2H, m), 0.49-0.65 (2H, m), 1.13-1.36 (1H, m), 1.53 (9H, s), 3.51 (3H, s), 4.03 (2H, d, J=7.2 Hz), 5.13 (2H, s), 7.20 (1H, s), 7.52 (1H, s), 7.85 (1H, s).

F) 5-(cyclopropylmethoxy)[1,3]oxazolo[5,4-c]pyridine-2-thiol

A mixture of tert-butyl [2-(cyclopropylmethoxy)-5-(methoxymethoxy)pyridin-4-yl]carbamate (737 mg), 6 M hydrochloric acid (0.75 mL), and THF (4 mL) was stirred at 45° C. for 1 hr. The reaction mixture was basified with aqueous sodium hydrogen carbonate solution, and extracted with ethyl acetate. The obtained organic layer was washed with saturated brine, and dried over anhydrous magnesium sulfate. The solvent was evaporated under reduced pressure and the obtained residue was used for the next reaction without further purification.

To the above-mentioned residue were added ethyl acetate (2 mL), methanol (8 mL) and 4M hydrogen chloride/ethyl acetate (5 mL), and the mixture was stirred at room temperature overnight and at 40° C. for 1 hr. The solvent was evaporated under reduced pressure and the obtained residue was used for the next reaction without further purification.

To the above-mentioned residue were added ethanol (7 mL) and potassium ethylxanthate (1.45 g), and the mixture was refluxed for 2 hr. 1M hydrochloric acid (9 mL) was added to the reaction mixture, and the resulting solid was collected by filtration to give the title compound (238 mg).

$^1$H NMR (DMSO-d$_6$) δ 0.09-0.41 (2H, m), 0.41-0.64 (2H, m), 1.10-1.36 (1H, m), 4.08 (2H, d, J=6.8 Hz), 6.59 (1H, s), 8.22 (1H, s), 14.07 (1H, brs)

G) tert-butyl [(1S)-2-({1-[5-(cyclopropylmethoxy)[1,3]oxazolo[5,4-c]pyridin-2-yl]piperidin-4-yl}oxy)-1-methylethyl]carbamate A mixture of 5-(cyclopropylmethoxy)[1,3]oxazolo[5,4-c]pyridine-2-thiol (238 mg), methyl iodide (0.101 mL), potassium carbonate (442 mg) and DMF (3 mL) was stirred at room temperature for 10 min. The solvent was evaporated under reduced pressure and the obtained residue was used for the next reaction without further purification.

To the above-mentioned residue were added tert-butyl [(1S)-1-methyl-2-(piperidin-4-yloxy)ethyl]carbamate (303 mg) and DMF (3 mL), and the mixture was stirred at 90° C. for 2 hr. Saturated brine was added to the reaction mixture, and the mixture was extracted twice with ethyl acetate. The obtained organic layers were combined, washed with saturated brine, and dried over anhydrous magnesium sulfate. The solvent was evaporated under reduced pressure, and the obtained residue was purified by silica gel column chromatography (hexane/ethyl acetate) to give the title compound (328 mg).

MS (ESI+): [M+H]$^+$ 447.4.

H) N-[(1S)-2-({1-[5-(cyclopropylmethoxy)[1,3]oxazolo[5,4-c]pyridin-2-yl]piperidin-4-yl}oxy)-1-methylethyl]acetamide To tert-butyl [(1S)-2-({1-[5-(cyclopropylmethoxy)[1,3]oxazolo[5,4-c]pyridin-2-yl]piperidin-4-yl}oxy)-1-methylethyl]carbamate (328 mg) was added 2M hydrogen chloride/methanol (4 mL), and the mixture was stirred at room temperature for 10 min and concentrated. Pyridine (4 mL) and acetic anhydride (0.5 mL) were added to the residue, and the mixture was stirred at room temperature for 5 min. The reaction mixture was concentrated, saturated brine was added to the residue, and the mixture was extracted with ethyl acetate. The obtained organic layer was washed with saturated brine, and dried over anhydrous magnesium sulfate. The solvent was evaporated under reduced pressure, and the obtained residue was purified by silica gel column chromatography (methanol/ethyl acetate). The obtained solid was washed with diisopropyl ether to give the title compound (197 mg).

Example 33

N-[(1S)-1-methyl-2-({1-[6-(2-methylpropoxy)-1,3-benzoxazol-2-yl]piperidin-4-yl}oxy)ethyl]acetamide

A) tert-butyl [(1S)-1-methyl-2-({1-[6-(2-methylpropoxy)-1,3-benzoxazol-2-yl]piperidin-4-yl}oxy)ethyl]carbamate To a solution of tert-butyl [(1S)-2-{[1-(6-hydroxy-1,3-benzoxazol-2-yl)piperidin-4-yl]oxy}-1-methylethyl]carbamate (150 mg) in DMF (5 mL) were added potassium carbonate (210 mg) and 1-iodo-2-methylpropane (190 mg), and the mixture was stirred at room temperature for 15 hr. The reaction mixture was diluted with ethyl acetate, washed with saturated brine, and dried over anhydrous magnesium sulfate. The solvent was evaporated under reduced pressure, and the obtained residue was purified by silica gel chromatography (hexane/ethyl acetate) to give the title compound (97 mg).

$^1$H NMR (300 MHz, CDCl$_3$) δ 1.02 (6H, d, J=6.8 Hz), 1.18 (3H, d, J=6.8 Hz), 1.45 (9H, s), 1.65-1.81 (2H, m), 1.84-2.01 (2H, m), 2.01-2.17 (1H, m), 3.34-3.62 (5H, m), 3.71 (2H, d, J=6.8 Hz), 3.75-3.96 (3H, m), 4.57-4.77 (1H, m), 6.75 (1H, dd, J=8.7, 2.3 Hz), 6.87 (1H, d, J=2.3 Hz), 7.21 (1H, d, J=8.3 Hz).

MS (ESI+): [M+H]$^+$ 448.5.

B) N-[(1S)-1-methyl-2-({1-[6-(2-methylpropoxy)-1,3-benzoxazol-2-yl]piperidin-4-yl}oxy)ethyl]acetamide To tert-butyl [(1S)-1-methyl-2-({1-[6-(2-methylpropoxy)-1,3-benzoxazol-2-yl]piperidin-4-yl}oxy)ethyl]carbamate (97 mg) was added 4 M hydrogen chloride/ethyl acetate (5 mL), and the mixture was stirred at room temperature for 15 min and concentrated. To the residue were added pyridine (5 mL) and acetic anhydride (5 mL), and the mixture was stirred at room temperature for 15 min. The reaction solution was concentrated under reduced pressure, and the residue was purified by silica gel chromatography (ethyl acetate/methanol), and recrystallized from ethyl acetate/hexane to give the title compound (52 mg).

$^1$H NMR (300 MHz, CDCl$_3$) δ 1.02 (6H, d, J=6.8 Hz), 1.20 (3H, d, J=6.8 Hz), 1.61-1.80 (2H, m), 1.98 (3H, s), 1.89-1.97 (2H, m), 2.02-2.13 (1H, m), 3.39-3.53 (4H, m), 3.53-3.63 (1H, m), 3.71 (2H, d, J=6.4 Hz), 3.83-3.99 (2H, m), 4.11-4.24 (1H, m), 5.55-5.69 (1H, m), 6.75 (1H, dd, J=8.5, 2.5 Hz), 6.87 (1H, d, J=2.3 Hz), 7.22 (1H, d, J=8.3 Hz).

mp 103-105° C.

Anal. Calcd for C$_{21}$H$_{31}$N$_3$O$_4$: C, 64.76; H, 8.02; N, 10.79. Found: C, 64.70; H, 8.12; N, 10.62.

Example 34

N-[(1S)-2-({1-[6-(cyclobutylmethoxy)-1,3-benzoxazol-2-yl]piperidin-4-yl}oxy)-1-methylethyl]acetamide

A) tert-butyl [(1S)-2-({1-[6-(cyclobutylmethoxy)-1,3-benzoxazol-2-yl]piperidin-4-yl}oxy)-1-methylethyl]carbamate To a solution of tert-butyl [(1S)-2-{[1-(6-hydroxy-1,3-benzoxazol-2-yl)piperidin-4-yl]oxy}-1-methylethyl]carbamate (200 mg) in DMF (5 mL) were added potassium carbonate (210 mg) and (iodomethyl)cyclobutane (150 mg), and the mixture was stirred at room temperature for 15 hr. Potassium carbonate (210 mg) and (iodomethyl)cyclobutane (150 mg) were added to the reaction mixture, and the mixture was stirred at room temperature for 15 hr. The reaction mixture was diluted with ethyl acetate, washed with saturated brine, and dried over anhydrous magnesium sulfate. The solvent was evaporated under reduced pressure, and the obtained residue was purified by silica gel chromatography (hexane/ethyl acetate) to give the title compound (130 mg).

$^1$H NMR (300 MHz, CDCl$_3$) δ 1.18 (3H, d, J=6.8 Hz), 1.45 (9H, s), 1.61-1.80 (2H, m), 1.80-2.03 (6H, m), 2.08-2.27 (2H, m), 2.59-2.91 (1H, m) 3.31-3.69 (5H, m) 3.76-3.92 (3H, m), 3.92 (2H, d, J=6.8 Hz), 4.52-4.76 (1H, m), 6.75 (1H, dd, J=8.7, 2.3 Hz) 6.87 (1H, d, J=2.3 Hz), 7.21 (1H, d, J=8.3 Hz).

MS (ESI+): [M+H]$^+$ 460.5.

B) N-[(1S)-2-({1-[6-(cyclobutylmethoxy)-1,3-benzoxazol-2-yl]piperidin-4-yl}oxy)-1-methylethyl]acetamide To tert-butyl [(1S)-2-({1-[6-(cyclobutylmethoxy)-1,3-benzoxazol-2-yl]piperidin-4-yl}oxy)-1-methylethyl]carbamate (130 mg) was added 4M hydrogen chloride/ethyl acetate (5 mL), and the mixture was stirred at room temperature for 15 min and concentrated. Pyridine (5 mL) and acetic anhydride (5 mL) were added to the residue, and the mixture was stirred at room temperature for 15 min. The reaction mixture was concentrated under reduced pressure, and the residue was purified by silica gel chromatography (ethyl acetate/methanol) and recrystallized from ethyl acetate/hexane to give the title compound (73 mg).

$^1$H NMR (300 MHz, CDCl$_3$) δ 1.20 (3H, d, J=6.8 Hz), 1.63-1.79 (2H, m), 1.81-1.97 (6H, m), 1.98 (3H, s), 2.07-2.22 (2H, m), 2.66-2.87 (1H, m), 3.35-3.64 (5H, m), 3.76-3.97 (2H, m), 3.92 (2H, d, J=6.8 Hz), 4.07-4.28 (1H, m), 5.53-5.72 (1H, m), 6.76 (1H, dd, J=8.7, 2.2 Hz), 6.87 (1H, d, J=2.3 Hz) 7.21 (1H, d, J=8.7 Hz).

Anal. Calcd for C$_{22}$H$_{31}$N$_3$O$_4$: C, 65.81; H, 7.78; N, 10.47. Found: C, 65.69; H, 7.71; N, 10.47.

Example 35

N-[(1S)-2-({1-[6-(2-cyclopropylethoxy)-1,3-benzoxazol-2-yl]piperidin-4-yl}oxy)-1-methylethyl]acetamide

A) tert-butyl [(1S)-2-({1-[6-(2-cyclopropylethoxy)-1,3-benzoxazol-2-yl]piperidin-4-yl}oxy)-1-methylethyl]carbamate To a solution of 2-cyclopropylethanol (550 mg) in THF (10 mL) were added triethylamine (0.80 mL) and methanesulfonyl chloride (0.50 mL), and the mixture was stirred at room temperature for 30 min. The reaction mixture was added to a suspension of tert-butyl [(1S)-2-{[1-(6-hydroxy-1,3-benzoxazol-2-yl)piperidin-4-yl]oxy}-1-methylethyl]carbamate (250 mg) and potassium carbonate (1.8 g) in DMF (10 mL), and the mixture was stirred at room temperature for 15 hr. The reaction mixture was diluted with ethyl acetate, washed with saturated brine, and dried over anhydrous magnesium sulfate. The solvent was evaporated under reduced pressure, and the obtained residue was purified by silica gel chromatography (hexane/ethyl acetate) to give the title compound (190 mg).

$^1$H NMR (300 MHz, CDCl$_3$) δ 0.05-0.15 (2H, m), 0.44-0.56 (2H, m), 0.70-0.93 (1H, m), 1.18 (3H, d, J=6.8 Hz), 1.45 (9H, s), 1.58-1.82 (4H, m), 1.84-2.02 (2H, m), 3.32-3.52 (4H, m), 3.52-3.66 (1H, m), 3.74-3.95 (3H, m), 3.96-4.08 (2H, m), 4.66 (1H, brs), 6.76 (1H, dd, J=8.5, 2.5 Hz), 6.88 (1H, d, J=2.3 Hz), 7.22 (1H, d, J=8.7 Hz).

MS (ESI+): [M+H]$^+$ 460.5.

B) N-[(1S)-2-({1-[6-(2-cyclopropylethoxy)-1,3-benzoxazol-2-yl]piperidin-4-yl}oxy)-1-methylethyl]acetamide To tert-butyl [(1S)-2-({1-[6-(2-cyclopropylethoxy)-1,3-benzoxazol-2-yl]piperidin-4-yl}oxy)-1-methylethyl]carbamate (190 mg) was added 4M hydrogen chloride/ethyl acetate (5 mL), and the mixture was stirred at room temperature for 15 min, and concentrated. Pyridine (10 mL) and acetic anhydride (5 mL) were added to the residue, and the mixture was stirred at room temperature for 15 min. The reaction mixture was concentrated under reduced pressure and the residue was purified by silica gel chromatography (ethyl acetate/methanol), and recrystallized from ethyl acetate/hexane to give the title compound (43 mg).

$^1$H NMR (300 MHz, CDCl$_3$) δ 0.04-0.17 (2H, m), 0.37-0.54 (2H, m), 0.71-0.95 (1H, m), 1.20 (3H, d, J=6.8 Hz), 1.62-1.81 (4H, m), 1.83-1.96 (2H, m), 1.98 (3H, s), 3.40-3.52 (4H, m), 3.52-3.62 (1H, m), 3.84-3.97 (2H, m), 4.02 (2H, t, J=6.8 Hz), 4.08-4.25 (1H, m), 5.52-5.70 (1H, m), 6.77 (1H, dd, J=8.7, 2.3 Hz), 6.89 (1H, d, J=2.7 Hz), 7.22 (1H, d, J=8.3 Hz).

Anal. Calcd for C$_{22}$H$_{31}$N$_3$O$_4$: C, 65.81; H, 7.78; N, 10.47. Found: C, 65.71; H, 7.91; N, 10.49.

Example 35a

N-[(1S)-2-({1-[6-(2-cyclopropylethoxy)-1,3-benzoxazol-2-yl]piperidin-4-yl}oxy)-1-methylethyl]acetamide To tert-butyl [(1S)-2-({1-[6-(2-cyclopropylethoxy)-1,3-benzoxazol-2-yl]piperidin-4-yl}oxy)-1-methylethyl]carbamate (5.84 g) was added 4M hydrogen chloride/ethyl acetate (50 mL), and the mixture was stirred at room temperature for 15 min, and concentrated. Pyridine (50 mL) and acetic anhydride (50 mL) were added to the residue, and the mixture was stirred at room temperature for 20 min. The reaction mixture was concentrated under reduced pressure, and the residue was purified by silica gel chromatography (NH, ethyl acetate/hexane) and recrystallized from ethyl acetate/hexane to give the title compound (3.83 g) as white crystals.

$^1$H NMR (300 MHz, CDCl$_3$) δ 0.08-0.16 (2H, m), 0.40-0.56 (2H, m), 0.77-0.95 (1H, m), 1.20 (3H, d, J=6.8 Hz), 1.60-1.78 (4H, m), 1.86-2.03 (5H, m), 3.32-3.66 (5H, m), 3.82-3.97 (2H, m), 4.02 (2H, t, J=6.6 Hz), 4.10-4.26 (1H, m), 5.67 (1H, brs), 6.77 (1H, dd, J=8.5, 2.4 Hz), 6.89 (1H, d, J=2.3 Hz), 7.22 (1H, d).

Anal. Calcd for C$_{22}$H$_{31}$N$_3$O$_4$: C, 65.81; H, 7.78; N, 10.47. Found: C, 65.79; H, 7.81; N, 10.47.

mp 99.3-99.6° C.

Example 36

N-[(1S)-2-({1-[6-(cyclobutyloxy)-1,3-benzoxazol-2-yl]piperidin-4-yl}oxy)-1-methylethyl]acetamide A) tert-butyl [(1S)-2-({1-[6-(cyclobutyloxy)-1,3-benzoxazol-2-yl]piperidin-4-yl}oxy)-1-methylethyl]carbamate To a solution of tert-butyl [(1S)-2-{[1-(6-hydroxy-1,3-benzoxazol-2-yl)piperidin-4-yl]oxy}-1-methylethyl]carbamate (500 mg) in DMF (5 mL) were added cesium carbonate (1.7 g) and bromocyclobutane (265 mg), and the mixture was stirred at room temperature for 15 hr and at 60° C. for 3 hr. The reaction mixture was diluted with ethyl acetate, washed with saturated brine, and dried over anhydrous magnesium sulfate. The solvent was evaporated under reduced pressure, and the obtained residue was purified by silica gel chromatography (hexane/ethyl acetate) to give the title compound (378 mg).

MS (ESI+): [M+H]$^+$ 446.6.

B) N-[(1S)-2-({1-[6-(cyclobutyloxy)-1,3-benzoxazol-2-yl]piperidin-4-yl}oxy)-1-methylethyl]acetamide By a method similar to Example 1, step H, and using tert-butyl [(1S)-2-({1-[6-(cyclobutyloxy)-1,3-benzoxazol-2-yl]piperidin-4-yl}oxy)-1-methylethyl]carbamate, the title compound was obtained.

Example 37

N-[(1S)-2-({1-[6-(cyclopropylmethoxy)-5-fluoro-1,3-benzothiazol-2-yl]piperidin-4-yl}oxy)-1-methylethyl]acetamide A) 1-(cyclopropylmethoxy)-2-fluoro-4-nitrobenzene By a method similar to Example 1, step G, and using 2-fluoro-4-nitrophenol, the title compound was obtained.

$^1$H NMR (300 MHz, CDCl$_3$) δ 0.36-0.47 (2H, m), 0.66-0.76 (2H, m), 1.29-1.39 (1H, m), 3.99 (2H, d, J=7.2 Hz), 7.00 (1H, t, J=8.4 Hz), 7.98-8.06 (2H, m).

B) 4-(cyclopropylmethoxy)-3-fluoroaniline

A suspension of 1-(cyclopropylmethoxy)-2-fluoro-4-nitrobenzene (18.3 g) and 5% palladium carbon (containing water (50%), 1.84 g) in methanol (289 mL) was stirred for 3 hr under a hydrogen atmosphere. The reaction mixture was filtered, and the filtrate was concentrated under reduced pressure to give the title compound (15.2 g).

$^1$H NMR (300 MHz, CDCl$_3$) δ 0.26-0.36 (2H, m), 0.54-0.66 (2H, m), 1.20-1.30 (1H, m), 3.50 (2H, brs), 3.78 (2H, d, J=7.2 Hz), 6.34-6.37 (1H, m), 6.46 (1H, dd, J=12.4, 2.4 Hz), 6.80 (1H, t, J=8.8 Hz).

C) 2-chloro-6-(cyclopropylmethoxy)-5-fluoro-1,3-benzothiazole

By a method similar to Example 16, steps A and B, and using 4-(cyclopropylmethoxy)-3-fluoroaniline, the title compound was obtained.

$^1$H NMR (300 MHz, CDCl$_3$) δ 0.33-0.45 (2H, m), 0.63-0.75 (2H, m), 1.29-1.43 (1H, m), 3.92 (2H, d, J=6.8 Hz), 7.27 (1H, d, J=7.2 Hz), 7.65 (1H, d, J=10.8 Hz).

MS (ESI+): [M+H]$^+$ 258.1.

D) tert-butyl [(1S)-2-({1-[6-(cyclopropylmethoxy)-5-fluoro-1,3-benzothiazol-2-yl]piperidin-4-yl}oxy)-1-methylethyl]carbamate By a method similar to Example 1, step F, and using 2-chloro-6-(cyclopropylmethoxy)-5-fluoro-1,3-benzothiazole, the title compound was obtained.

MS (ESI+): [M+H]$^+$ 480.4.

E) N-[(1S)-2-({1-[6-(cyclopropylmethoxy)-5-fluoro-1,3-benzothiazol-2-yl]piperidin-4-yl}oxy)-1-methylethyl]acetamide By a method similar to Example 1, step H, and using tert-butyl [(1S)-2-({1-[6-(cyclopropylmethoxy)-5-fluoro-1,3-benzothiazol-2-yl]piperidin-4-yl}oxy)-1-methylethyl]carbamate, the title compound was obtained.

Example 38

N-[2-({trans-4-[6-(cyclopropylmethoxy)-1-benzofuran-2-yl]cyclohexyl}oxy)-1-methylethyl]acetamide

A) ethyl 4-{[tert-butyl(diphenyl)silyl]oxy}cyclohexanecarboxylate

A solution of ethyl 4-hydroxycyclohexanecarboxylate (5 g), tert-butyl(chloro)diphenylsilane (8.30 mL) and imidazole (2.17 g) in DMF (50 mL) was stirred at room temperature overnight. The reaction mixture was extracted with ethyl acetate and water. The obtained organic layer was washed with saturated brine, dried over anhydrous magnesium sulfate and concentrated under reduced pressure. The obtained residue was purified by silica gel chromatography (hexane/ethyl acetate) to give the title compound (12.2 g).

$^1$H NMR (300 MHz, DMSO-d$_6$) δ 0.98-1.06 (9H, m), 1.17-1.23 (5H, m), 1.23-1.63 (4H, m), 1.68-1.94 (2H, m), 2.15-2.38 (1H, m), 3.51-3.95 (1H, m), 4.03-4.09 (2H, m), 7.37-7.46 (6H, m), 7.55-7.65 (4H, m).

MS (ESI+): [M+H]$^+$ 411.1

B) (4-{[tert-butyl(diphenyl)silyl]oxy}cyclohexyl)methanol

To a suspension of lithium aluminum hydride (1.13 g) in THF (100 mL) was slowly added a solution of ethyl 4-{[tert-butyl(diphenyl)silyl]oxy}cyclohexanecarboxylate (12.2 g) in THF (100 mL) under ice-cooling. The reaction mixture was stirred at 0° C. for 1 hr, and water (1.2 mL) and 1M aqueous sodium hydroxide solution (1.2 mL) were successively added thereto. The mixture was stirred at room temperature for 30 min, and water (3.6 mL) was further added thereto. The mixture was stirred at room temperature for 1 hr, and the insoluble material was filtered off through celite under reduced pressure. The obtained residue was purified by silica gel chromatography (hexane/ethyl acetate) to give the title compound (9.38 g).

$^1$H NMR (300 MHz, DMSO-d$_6$) δ 0.60-0.83 (1H, m), 0.92-1.09 (9H, m), 1.23-1.84 (8H, m), 3.05-3.29 (2H, m), 3.44-4.00 (1H, m), 4.26-4.41 (1H, m), 7.32-7.48 (6H, m), 7.54-7.67 (4H, m).

C) 4-{[tert-butyl(diphenyl)silyl]oxy}cyclohexanecarbaldehyde

To a solution of (4-{[tert-butyl(diphenyl)silyl]oxy}cyclohexyl)methanol (7.38 g) and triethylamine (8.37 mL) in DMSO (50 mL) was added sulfur trioxide pyridine complex (9.56 g). The reaction mixture was stirred at room temperature for 3 hr and extracted with diethyl ether and water. The obtained organic layer was washed with saturated brine, dried over anhydrous magnesium sulfate, and concentrated under reduced pressure. The obtained residue was purified by silica gel chromatography (hexane/ethyl acetate) to give the title compound (5.83 g).

$^1$H NMR (300 MHz, DMSO-d$_6$) δ 1.01 (9H, s), 1.21-1.64 (5H, m), 1.65-1.91 (3H, m), 2.14-2.38 (1H, m), 3.47-3.97 (1H, m), 7.33-7.53 (6H, m), 7.53-7.67 (4H, m), 9.40-9.66 (1H, m).

D) tert-butyl[(4-ethynylcyclohexyl)oxy]diphenylsilane

A suspension of 4-{[tert-butyl(diphenyl)silyl]oxy}cyclohexanecarbaldehyde (4.74 g), dimethyl (1-diazo-2-oxopropyl)phosphonate (2.98 g) and potassium carbonate (3.57 g) in methanol (40 mL) was stirred at room temperature for 2 hr. The reaction mixture was extracted with ethyl acetate and water. The obtained organic layer was washed with saturated brine, dried over anhydrous magnesium sulfate, and concentrated under reduced pressure. The obtained residue was purified by silica gel chromatography (hexane/ethyl acetate) to give the title compound (4.15 g).

$^1$H NMR (300 MHz, DMSO-d$_6$) δ 0.94-1.07 (9H, m), 1.26-1.92 (8H, m), 2.21-2.46 (1H, m), 2.72-2.94 (1H, m), 3.58-3.85 (1H, m), 7.36-7.53 (6H, m), 7.53-7.66 (4H, m).

MS (ESI+): [M+H]$^+$ 363.2

E) tert-butyl({4-[6-(cyclopropylmethoxy)-1-benzofuran-2-yl]cyclohexyl}oxy)diphenylsilane A solution of tert-butyl [(4-ethynylcyclohexyl)oxy]diphenylsilane (3.52 g), 5-(cyclopropylmethoxy)-2-iodophenol (2.82 g), bis(triphenylphosphine)palladium(II) dichloride (0.34 g), copper iodide (0.09 g) and 1,1,3,3-tetramethylguanidine (3.65 mL) in DMF (30 mL) was stirred at room temperature overnight under an argon atmosphere. The reaction mixture was extracted with ethyl acetate and water. The obtained organic layer was washed with saturated brine, dried over anhydrous magnesium sulfate, and concentrated under reduced pressure. The obtained residue was purified by silica gel chromatography (hexane/ethyl acetate) to give the title compound (3.36 g).

$^1$H NMR (300 MHz, DMSO-d$_6$) δ 0.24-0.38 (2H, m), 0.49-0.61 (2H, m), 0.96-1.08 (9H, m), 1.19-1.58 (5H, m), 1.60-1.97 (4H, m), 2.59-2.85 (1H, m), 3.60-3.73 (1H, m), 3.74-3.88 (2H, m), 6.28-6.55 (1H, m), 6.72-6.86 (1H, m), 6.98-7.13 (1H, m), 7.27-7.37 (1H, m), 7.37-7.52 (6H, m), 7.53-7.69 (4H, m).

F) trans-4-[6-(cyclopropylmethoxy)-1-benzofuran-2-yl]cyclohexanol

A solution of a solution of tert-butyl({4-[6-(cyclopropylmethoxy)-1-benzofuran-2-yl]cyclohexyl}oxy)diphenylsilane (3.36 g) and tetrabutylammonium fluoride in THF (1.0 M, 12.8 mL) in THF (30 mL) was stirred at room temperature overnight and extracted with ethyl acetate and water. The obtained organic layer was washed with saturated brine, dried over anhydrous magnesium sulfate, and concentrated under reduced pressure. The obtained residue was purified by silica gel chromatography (hexane/ethyl acetate) to give the title compound (0.66 g).

$^1$H NMR (300 MHz, DMSO-d$_6$) δ 0.23-0.38 (2H, m), 0.47-0.64 (2H, m), 1.08-1.56 (5H, m), 1.85-1.97 (2H, m), 1.97-2.09 (2H, m), 2.57-2.73 (1H, m), 3.36-3.54 (1H, m), 3.81 (2H, d, J=6.8 Hz), 4.60 (1H, d, J=4.5 Hz), 6.41 (1H, s), 6.80 (1H, dd, J=8.3, 2.3 Hz), 7.06 (1H, d, J=2.3 Hz), 7.36 (1H, d, J=8.3 Hz).

MS (ESI+): [M+H]$^+$ 287.2

G) 4-[({trans-4-[6-(cyclopropylmethoxy)-1-benzofuran-2-yl]cyclohexyl}oxy)acetyl]morpholine A suspension of trans-4-[6-(cyclopropylmethoxy)-1-benzofuran-2-yl]cyclohexanol (611 mg), 4-(chloroacetyl)morpholine (1.05 g) and tert-butoxy potassium (718 mg) in THF (10 mL) was stirred at room temperature overnight and extracted with ethyl acetate and water. The obtained organic layer was washed with saturated brine, dried over anhydrous magnesium sulfate, and concentrated under reduced pressure.

The obtained residue was purified by silica gel chromatography (hexane/ethyl acetate) to give the title compound (882 mg).

¹H NMR (300 MHz, DMSO-d₆) δ 0.27-0.36 (2H, m), 0.51-0.61 (2H, m), 1.21-1.28 (1H, m), 1.27-1.54 (4H, m), 2.03-2.15 (4H, m), 2.63-2.78 (1H, m), 3.33-3.39 (1H, m), 3.39-3.49 (4H, m), 3.56 (4H, brs), 3.82 (2H, d, J=6.8 Hz), 4.17 (2H, s), 6.43 (1H, s), 6.75-6.88 (1H, m), 7.07 (1H, d, J=1.9 Hz), 7.37 (1H, d, J=8.3 Hz).

MS (ESI+): [M+H]⁺ 414.0

H) 1-({trans-4-[6-(cyclopropylmethoxy)-1-benzofuran-2-yl]cyclohexyl}oxy)propan-2-one To a solution of 4-[({trans-4-[6-(cyclopropylmethoxy)-1-benzofuran-2-yl]cyclohexyl}oxy)acetyl]morpholine (881 mg) in THF (10 mL) was added a solution (1.5 M, 2.84 mL) of methylmagnesium bromide in toluene/THF under ice-cooling. The mixture was stirred at 0° C. for 1 hr and extracted with ethyl acetate and 1M hydrochloric acid. The obtained organic layer was washed with saturated brine, dried over anhydrous magnesium sulfate, and concentrated under reduced pressure. The obtained residue was purified by silica gel chromatography (hexane/ethyl acetate) to give the title compound (556 mg).

¹H NMR (300 MHz, DMSO-d₆) δ 0.23-0.37 (2H, m), 0.48-0.62 (2H, m), 1.21-1.53 (5H, m), 2.01-2.16 (7H, m), 2.62-2.79 (1H, m), 3.26-3.31 (1H, m), 3.82 (2H, d, J=7.2 Hz), 4.14 (2H, s), 6.43 (1H, s), 6.80 (1H, dd, J=8.5, 2.1 Hz), 7.06 (1H, d, J=2.3 Hz), 7.36 (1H, d, J=8.3 Hz).

I) 1-({trans-4-[6-(cyclopropylmethoxy)-1-benzofuran-2-yl]cyclohexyl}oxy)propan-2-ol To a solution of 1-({trans-4-[6-(cyclopropylmethoxy)-1-benzofuran-2-yl]cyclohexyl}oxy)propan-2-one (556 mg) in ethanol (10 mL) was added sodium borohydride (123 mg) under ice-cooling. The mixture was stirred at 0° C. for 1 hr and extracted with ethyl acetate and 1M hydrochloric acid. The obtained organic layer was washed with saturated brine, dried over anhydrous magnesium sulfate, and concentrated under reduced pressure. The obtained residue was purified by silica gel chromatography (hexane/ethyl acetate) to give the title compound (555 mg).

¹H NMR (300 MHz, DMSO-d₆) δ 0.22-0.38 (2H, m), 0.50-0.64 (2H, m), 1.03 (3H, d, J=6.0 Hz), 1.19-1.58 (5H, m), 2.01-2.13 (4H, m), 2.60-2.77 (1H, m), 3.15-3.31 (3H, m), 3.57-3.75 (1H, m), 3.82 (2H, d, J=6.8 Hz), 4.42-4.57 (1H, m), 6.43 (1H, s), 6.75-6.87 (1H, m), 7.02-7.10 (1H, m), 7.36 (1H, d, J=8.3 Hz).

MS (ESI+): [M+H]⁺ 345.1

J) 2-({trans-4-[6-(cyclopropylmethoxy)-1-benzofuran-2-yl]cyclohexyl}oxy)-1-methylethyl methanesulfonate A suspension of 1-({trans-4-[6-(cyclopropylmethoxy)-1-benzofuran-2-yl]cyclohexyl}oxy)propan-2-ol (555 mg), triethylamine (0.34 mL) and methanesulfonyl chloride (0.19 mL) in THF (5 mL) was stirred at room temperature for 1 hr and extracted with ethyl acetate and water. The obtained organic layer was washed with saturated brine, dried over anhydrous magnesium sulfate, and concentrated under reduced pressure. The obtained residue was purified by silica gel chromatography (hexane/ethyl acetate) to give the title compound (624 mg).

¹H NMR (300 MHz, DMSO-d₆) δ 0.26-0.37 (2H, m), 0.50-0.64 (2H, m), 1.22-1.57 (8H, m), 2.01-2.13 (4H, m), 2.63-2.81 (1H, m), 3.16 (3H, s), 3.35-3.42 (1H, m), 3.47-3.65 (2H, m), 3.82 (2H, d, J=6.8 Hz), 4.69-4.83 (1H, m), 6.44 (1H, s), 6.76-6.86 (1H, m), 7.07 (1H, d, J=1.9 Hz), 7.37 (1H, d, J=8.7 Hz).

MS (ESI+): [M+H]⁺ 423.0

K) 2-[trans-4-(2-azidopropoxy)cyclohexyl]-6-(cyclopropylmethoxy)-1-benzofuran A suspension of 2-({trans-4-[6-(cyclopropylmethoxy)-1-benzofuran-2-yl]cyclohexyl}oxy)-1-methylethyl methanesulfonate 624 mg) and sodium azide (480 mg) in DMF (5 mL) was stirred at 60° C. overnight. The reaction mixture was allowed to cool to room temperature, and extracted with ethyl acetate and water. The obtained organic layer was washed with saturated brine, dried over anhydrous magnesium sulfate, and concentrated under reduced pressure. The obtained residue was purified by silica gel chromatography (hexane/ethyl acetate) to give the title compound (397 mg).

¹H NMR (300 MHz, DMSO-d₆) δ 0.25-0.36 (2H, m), 0.50-0.62 (2H, m), 1.10 (3H, d, J=6.8 Hz), 1.21-1.57 (5H, m), 2.02-2.14 (4H, m), 2.64-2.79 (1H, m), 3.33-3.38 (1H, m), 3.38-3.47 (1H, m), 3.54-3.63 (1H, m), 3.65-3.78 (1H, m), 3.82 (2H, d, J=6.8 Hz), 6.44 (1H, s), 6.74-6.84 (1H, m), 7.05-7.09 (1H, m), 7.37 (1H, d, J=8.7 Hz).

L) 1-({trans-4-[6-(cyclopropylmethoxy)-1-benzofuran-2-yl]cyclohexyl}oxy)propan-2-amine A solution of 2-[trans-4-(2-azidopropoxy)cyclohexyl]-6-(cyclopropylmethoxy)-1-benzofuran (397 mg) and triphenylphosphine (564 mg) in THF (4 mL)/water (2 mL) was stirred at 60° C. overnight. The reaction mixture was allowed to cool to room temperature, and extracted with ethyl acetate and water. The obtained organic layer was washed with saturated brine, dried over anhydrous magnesium sulfate, and concentrated under reduced pressure. The obtained residue was purified by silica gel chromatography (ethyl acetate/methanol) to give the title compound (373 mg).

¹H NMR (300 MHz, DMSO-d₆) δ 0.26-0.36 (2H, m), 0.51-0.61 (2H, m), 0.93 (3H, d, J=6.4 Hz), 1.21-1.37 (3H, m), 1.37-1.55 (2H, m), 1.55-1.79 (2H, m), 2.05 (4H, brs), 2.63-2.77 (1H, m), 2.82-2.95 (1H, m), 3.11-3.19 (1H, m), 3.19-3.24 (1H, m), 3.82 (2H, d, J=7.2 Hz), 6.43 (1H, s), 6.82 (2H, dd, J=8.3, 2.3 Hz), 7.06 (1H, d, J=1.9 Hz), 7.36 (1H, d, J=8.7 Hz).

MS (ESI+): [M+H]⁺ 344.2

M) N-[2-({trans-4-[6-(cyclopropylmethoxy)-1-benzofuran-2-yl]cyclohexyl}oxy)-1-methylethyl]acetamide A solution of 1-({trans-4-[6-(cyclopropylmethoxy)-1-benzofuran-2-yl]cyclohexyl}oxy)propan-2-amine (373 mg) and acetic anhydride (0.51 mL) in pyridine (4 mL) was stirred at room temperature for 2 hr. The reaction mixture was concentrated under reduced pressure, and the obtained residue was purified by silica gel chromatography (NH, hexane/ethyl acetate). The obtained residue was recrystallized from ethyl acetate and hexane to give the title compound (265 mg) as white crystals.

¹H NMR (300 MHz, DMSO-d₆) δ 0.24-0.36 (2H, m), 0.47-0.61 (2H, m), 0.98-1.08 (3H, m), 1.12-1.56 (5H, m), 1.78 (3H, s), 1.93-2.13 (4H, m), 2.68-2.77 (1H, m), 3.16-3.29

(2H, m), 3.34-3.39 (1H, m), 3.75-3.90 (3H, m), 6.38-6.47 (1H, m), 6.73-6.87 (1H, m), 7.02-7.09 (1H, m), 7.32-7.41 (1H, m), 7.60-7.73 (1H, m).
MS (ESI+): [M+Na]$^+$ 407.9
mp 104-105° C.
Anal. Calcd for $C_{23}H_{31}NO_4$: C, 71.66; H, 8.11; N, 3.63. Found: C, 71.67; H, 8.23; N, 3.64.

Example 39

N-[2-({trans-4-[6-(cyclopropylmethoxy)-1,3-benzoxazol-2-yl]cyclohexyl}oxy)-1-methylethyl]acetamide

A) ethyl trans-4-{[tert-butyl(diphenyl)silyl]oxy}cyclohexanecarboxylate

A solution of ethyl trans-4-hydroxycyclohexanecarboxylate (5 g), tert-butyl(chloro)diphenylsilane (7.93 mL) and imidazole (2.17 g) in DMF (50 mL) was stirred at room temperature overnight and extracted with ethyl acetate and water. The obtained organic layer was washed with saturated brine, dried over anhydrous magnesium sulfate, and concentrated under reduced pressure. The obtained residue was purified by silica gel chromatography (hexane/ethyl acetate) to give the title compound (10.1 g).
$^1$H NMR (300 MHz, DMSO-$d_6$) δ 1.00 (9H, s), 1.13-1.27 (5H, m), 1.28-1.48 (2H, m), 1.66-1.88 (4H, m), 2.16-2.31 (1H, m), 3.51-3.68 (1H, m), 3.93-4.03 (2H, m), 7.39-7.50 (6H, m), 7.54-7.66 (4H, m).

B) trans-4-{[tert-butyl(diphenyl)silyl]oxy}-N-(2,4-dihydroxyphenyl)cyclohexanecarboxamide A solution of ethyl trans-4-{[tert-butyl(diphenyl)silyl]oxy}cyclohexanecarboxylate (2 g) and 1M aqueous sodium hydroxide solution (9.74 mL) in THF (10 mL)/methanol (10 mL) was stirred at 60° C. for 2 hr. The reaction mixture was allowed to cool to room temperature, acidified with 1M hydrochloric acid, and extracted with ethyl acetate. The obtained organic layer was washed with saturated brine, dried over anhydrous magnesium sulfate, and concentrated under reduced pressure. To the obtained residue were added 4-aminobenzene-1,3-diol hydrochloride (0.79 g), HATU (2.22 g), N,N-diisopropylethylamine (1.02 mL) and DMF (10 mL), and the mixture was stirred at 60° C. overnight. The reaction mixture was allowed to cool to room temperature, and extracted with ethyl acetate and water. The obtained organic layer was washed with saturated brine, dried over anhydrous magnesium sulfate, and concentrated under reduced pressure. The obtained residue was purified by silica gel chromatography (hexane/ethyl acetate) to give the title compound (0.88 g).
$^1$H NMR (300 MHz, DMSO-$d_6$) δ 1.01 (9H, s), 1.21-1.48 (4H, m), 1.64-1.92 (4H, m), 2.20-2.39 (1H, m), 3.51-3.71 (1H, m), 6.06-6.20 (1H, m), 6.26 (1H, s), 7.14-7.27 (1H, m), 7.36-7.53 (6H, m), 7.56-7.69 (4H, m), 9.03 (1H, s), 9.06-9.13 (1H, m), 9.41-9.60 (1H, m).
MS (ESI+): [M+H]$^+$ 490.2

C) 2-(trans-4-{[tert-butyl(diphenyl)silyl]oxy}cyclohexyl)-6-(cyclopropylmethoxy)-1,3-benzoxazole A solution of trans-4-{[tert-butyl(diphenyl)silyl]oxy}-N-(2,4-dihydroxyphenyl)cyclohexanecarboxamide (0.88 g), a solution (1.9 M, 1.31 mL) of diisopropyl azodicarboxylate in toluene and triphenylphosphine (0.71 g) in THF (10 mL) was stirred at room temperature overnight. The reaction mixture was concentrated under reduced pressure. The obtained residue was purified by silica gel chromatography (hexane/ethyl acetate). To the obtained residue were added (bromomethyl)cyclopropane (0.35 mL), potassium carbonate (498 mg) and DMF (5 mL), and the mixture was stirred at 60° C. for 2 hr. The reaction mixture was allowed to cool to room temperature, and extracted with ethyl acetate and water. The obtained organic layer was washed with saturated brine, dried over anhydrous magnesium sulfate, and concentrated under reduced pressure. The obtained residue was purified by silica gel chromatography (hexane/ethyl acetate) to give the title compound (714 mg).
$^1$H NMR (300 MHz, DMSO-$d_6$) δ 0.24-0.37 (2H, m), 0.47-0.63 (2H, m), 1.02 (9H, s), 1.21-1.24 (1H, m), 1.37-1.61 (4H, m), 1.77-1.96 (2H, m), 2.03-2.12 (2H, m), 2.82-3.00 (1H, m), 3.65-3.78 (1H, m), 3.82 (2H, d, J=6.8 Hz), 6.90 (1H, dd, J=8.7, 2.3 Hz), 7.21 (1H, d, J=2.3 Hz), 7.37-7.53 (7H, m), 7.57-7.72 (4H, m).
MS (ESI+): [M+H]$^+$ 526.1

D) trans-4-[6-(cyclopropylmethoxy)-1,3-benzoxazol-2-yl]cyclohexanol

A solution of a solution (1.0 M, 2.72 mL) of 2-(trans-4-{[tert-butyl(diphenyl)silyl]oxy}cyclohexyl)-6-(cyclopropylmethoxy)-1,3-benzoxazole (714 mg) and tetrabutylammonium fluoride in THF in THF (5 mL) was stirred at room temperature overnight and extracted with ethyl acetate and water. The obtained organic layer was washed with saturated brine, dried over anhydrous magnesium sulfate, and concentrated under reduced pressure. The obtained residue was purified by silica gel chromatography (hexane/ethyl acetate) to give the title compound (311 mg).
$^1$H NMR (300 MHz, DMSO-$d_6$) δ 0.27-0.37 (2H, m), 0.52-0.62 (2H, m), 1.19-1.40 (3H, m), 1.49-1.68 (2H, m), 1.85-1.97 (2H, m), 2.04-2.16 (2H, m), 2.79-2.93 (1H, m), 3.39-3.51 (1H, m), 3.84 (2H, d, J=6.8 Hz), 4.63 (1H, d, J=4.1 Hz), 6.91 (1H, dd, J=8.7, 2.3 Hz), 7.23-7.27 (1H, m, J=2.3 Hz), 7.51 (1H, d, J=8.7 Hz).
MS (ESI+): [M+H]$^+$ 288.1

E) 6-(cyclopropylmethoxy)-2-[trans-4-(2-(morpholin-4-yl)-2-oxoethoxy)cyclohexyl]-1,3-benzoxazole A suspension of trans-4-[6-(cyclopropylmethoxy)-1,3-benzoxazol-2-yl]cyclohexanol (311 mg), 4-(chloroacetyl)morpholine (532 mg) and tert-butoxy potassium (365 mg) in THF (5 mL) was stirred at room temperature overnight and extracted with ethyl acetate and water. The obtained organic layer was washed with saturated brine, dried over anhydrous magnesium sulfate, and concentrated under reduced pressure. The obtained residue was purified by silica gel chromatography (hexane/ethyl acetate) to give the title compound (427 mg).
$^1$H NMR (300 MHz, DMSO-$d_6$) δ 0.25-0.38 (2H, m), 0.51-0.62 (2H, m), 1.21-1.28 (1H, m), 1.28-1.50 (2H, m), 1.50-1.69 (2H, m), 2.03-2.22 (4H, m), 2.85-3.02 (1H, m), 3.34-3.40 (1H, m), 3.39-3.49 (4H, m), 3.56 (4H, brs), 3.85 (2H, d, J=6.8 Hz), 4.17 (2H, s), 6.91 (1H, dd, J=8.7, 2.3 Hz), 7.26 (1H, d, J=2.3 Hz), 7.51 (1H, d, J=8.7 Hz).
MS (ESI+): [M+H]$^+$ 415.0

F) 1-({trans-4-[6-(cyclopropylmethoxy)-1,3-benzoxazol-2-yl]cyclohexyl}oxy)propan-2-one To a solution of 6-(cyclopropylmethoxy)-2-[trans-4-(2-(morpholin-4-yl)-2-oxoethoxy)cyclohexyl]-1,3-benzoxazole (427 mg) in THF (5 mL) was added a solution (1.5 M, 1.37 mL) of methylmagnesium bromide in toluene/THF under ice-cooling. The reaction mixture was stirred at 0° C. for 1 hr, and extracted with ethyl acetate and 1M hydrochloric acid. The obtained organic layer was washed with saturated brine, dried over anhydrous magnesium sulfate, and concentrated under reduced pressure. The obtained residue was purified by silica gel chromatography (hexane/ethyl acetate) to give the title compound (260 mg).

$^1$H NMR (300 MHz, DMSO-d$_6$) δ 0.23-0.40 (2H, m), 0.49-0.66 (2H, m), 1.09-1.44 (4H, m), 1.50-1.69 (2H, m), 2.06 (3H, s), 2.07-2.20 (3H, m), 2.84-3.01 (1H, m), 3.33-3.40 (1H, m), 3.85 (2H, d, J=7.2 Hz), 4.14 (2H, s), 6.91 (1H, dd, J=8.9, 2.4 Hz), 7.25 (1H, d, J=2.3 Hz), 7.52 (1H, d, J=8.7 Hz).

MS (ESI+): [M+H]$^+$ 344.1

G) 1-({trans-4-[6-(cyclopropylmethoxy)-1,3-benzoxazol-2-yl]cyclohexyl}oxy)propan-2-ol To a solution of 1-({trans-4-[6-(cyclopropylmethoxy)-1,3-benzoxazol-2-yl]cyclohexyl}oxy)propan-2-one (259 mg) in ethanol (5 mL) was added sodium borohydride (57 mg) under ice-cooling. The reaction mixture was stirred at 0° C. for 1 hr, and extracted with ethyl acetate and 1M hydrochloric acid. The obtained organic layer was washed with saturated brine, dried over anhydrous magnesium sulfate, and concentrated under reduced pressure. The obtained residue was purified by silica gel chromatography (hexane/ethyl acetate) to give the title compound (271 mg).

$^1$H NMR (300 MHz, DMSO-d$_6$) δ 0.27-0.37 (2H, m), 0.53-0.62 (2H, m), 1.04 (3H, d, J=6.4 Hz), 1.20-1.41 (3H, m), 1.52-1.69 (2H, m), 2.01-2.20 (4H, m), 2.85-2.98 (1H, m), 3.16-3.29 (2H, m), 3.32-3.37 (1H, m), 3.63-3.76 (1H, m), 3.85 (2H, d, J=6.8 Hz), 4.49 (1H, d, J=4.5 Hz), 6.91 (1H, dd, J=8.7, 2.6 Hz), 7.25 (1H, d, J=2.3 Hz), 7.52 (1H, d, J=8.7 Hz).

MS (ESI+): [M+H]$^+$ 346.1

H) 2-({trans-4-[6-(cyclopropylmethoxy)-1,3-benzoxazol-2-yl]cyclohexyl}oxy)-1-methylethyl methanesulfonate To a solution of 1-({trans-4-[6-(cyclopropylmethoxy)-1,3-benzoxazol-2-yl]cyclohexyl}oxy)propan-2-ol (271 mg) and triethylamine (0.22 mL) in THF (5 mL) was added methanesulfonyl chloride (0.1 mL) under ice-cooling. The reaction mixture was stirred at room temperature for 1 hr, and extracted with ethyl acetate and water. The obtained organic layer was washed with saturated brine, dried over anhydrous magnesium sulfate, and concentrated under reduced pressure. The obtained residue was purified by silica gel chromatography (hexane/ethyl acetate) to give the title compound (283 mg).

$^1$H NMR (300 MHz, DMSO-d$_6$) δ 0.25-0.39 (2H, m), 0.49-0.64 (2H, m), 1.21-1.46 (6H, m), 1.52-1.72 (2H, m), 2.01-2.20 (4H, m), 2.83-3.04 (1H, m), 3.16 (3H, s), 3.34-3.46 (1H, m), 3.46-3.66 (2H, m), 3.85 (2H, d, J=7.2 Hz), 4.67-4.87 (1H, m), 6.85-6.96 (1H, m), 7.20-7.29 (1H, m), 7.46-7.58 (1H, m).

MS (ESI+): [M+H]$^+$ 424.0

I) 2-[trans-4-(2-azidopropoxy)cyclohexyl]-6-(cyclopropylmethoxy)-1,3-benzoxazole A suspension of 2-({trans-4-[6-(cyclopropylmethoxy)-1,3-benzoxazol-2-yl]cyclohexyl}oxy)-1-methylethyl methanesulfonate 283 mg) and sodium azide (271 mg) in DMF (3 mL) was stirred at 60° C. overnight. The reaction mixture was allowed to cool to room temperature, and extracted with ethyl acetate and water. The obtained organic layer was washed with saturated brine, dried over anhydrous magnesium sulfate, and concentrated under reduced pressure. The obtained residue was purified by silica gel chromatography (hexane/ethyl acetate) to give the title compound (249 mg).

$^1$H NMR (300 MHz, DMSO-d$_6$) δ 0.27-0.36 (2H, m), 0.50-0.63 (2H, m), 1.10 (3H, d, J=6.4 Hz), 1.21-1.31 (1H, m), 1.29-1.45 (2H, m), 1.51-1.73 (2H, m), 2.01-2.21 (4H, m), 2.86-3.03 (1H, m), 3.33-3.48 (2H, m), 3.55-3.64 (1H, m), 3.65-3.78 (1H, m), 3.85 (2H, d, J=7.2 Hz), 6.91 (1H, dd, J=8.7, 2.6 Hz), 7.25 (1H, d, J=2.3 Hz), 7.52 (1H, d, J=8.7 Hz).

MS (ESI+): [M+H]$^+$ 371.0

J) 1-({trans-4-[6-(cyclopropylmethoxy)-1,3-benzoxazol-2-yl]cyclohexyl}oxy)propan-2-amine A solution of 2-[trans-4-(2-azidopropoxy)cyclohexyl]-6-(cyclopropylmethoxy)-1,3-benzoxazole (249 mg) and triphenylphosphine (353 mg) in THF (4 mL)/water (2 mL) was stirred at 60° C. overnight. The reaction mixture was allowed to cool to room temperature, and extracted with ethyl acetate and water. The obtained organic layer was washed with saturated brine, dried over anhydrous magnesium sulfate, and concentrated under reduced pressure. The obtained residue was purified by silica gel chromatography (ethyl acetate/methanol) to give the title compound (172 mg).

$^1$H NMR (300 MHz, DMSO-d$_6$) δ 0.25-0.37 (2H, m), 0.51-0.63 (2H, m), 0.93 (3H, d, J=6.4 Hz), 1.18-1.44 (3H, m), 1.51-1.71 (3H, m), 2.01-2.23 (4H, m), 2.80-2.98 (2H, m), 3.05-3.26 (4H, m), 3.85 (2H, d, J=7.2 Hz), 6.91 (1H, dd, J=8.7, 2.6 Hz), 7.25 (1H, d, J=2.3 Hz), 7.52 (1H, d, J=8.7 Hz).

MS (ESI+): [M+H]$^+$ 345.0

K) N-[2-({trans-4-[6-(cyclopropylmethoxy)-1,3-benzoxazol-2-yl]cyclohexyl}oxy)-1-methylethyl]acetamide A solution of 1-({trans-4-[6-(cyclopropylmethoxy)-1,3-benzoxazol-2-yl]cyclohexyl}oxy)propan-2-amine (172 mg) and acetic anhydride (0.24 mL) in pyridine (4 mL) was stirred at room temperature for 2 hr. The reaction mixture was concentrated under reduced pressure, and the obtained residue was purified by silica gel chromatography (NH, hexane/ethyl acetate). The obtained residue was recrystallized from ethyl acetate and hexane to give the title compound (95 mg) as white crystals.

$^1$H NMR (300 MHz, DMSO-d$_6$) δ 0.26-0.37 (2H, m), 0.50-0.62 (2H, m), 1.03 (3H, d, J=6.8 Hz), 1.15-1.42 (3H, m), 1.50-1.70 (2H, m), 1.79 (3H, s), 1.95-2.19 (4H, m), 2.84-2.99 (1H, m), 3.21-3.29 (2H, m), 3.36-3.41 (1H, m), 3.79-3.93 (3H, m), 6.91 (1H, dd, J=8.7, 2.6 Hz), 7.24 (1H, d, J=2.3 Hz), 7.53 (1H, d, J=8.7 Hz), 7.68 (1H, d, J=7.5 Hz).

MS (ESI+): [M+H]$^+$ 387.0 mp 131-132° C.

Anal. Calcd for $C_{22}H_{30}N_2O_4$: C, 68.37; H, 7.82; N, 7.25. Found: C, 68.10; H, 7.92; N, 7.18.

Example 40

N-[(1S)-2-({trans-4-[6-(2-cyclopropylethoxy)-2H-indazol-2-yl]cyclohexyl}oxy)-1-methylethyl]acetamide

A) 4-(2-cyclopropylethoxy)-1-methyl-2-nitrobenzene

A suspension of 4-methyl-3-nitrophenol (3 g), 2-cyclopropylethyl methanesulfonate (3.22 g) and potassium carbonate (2.71 g) in DMF (100 mL) was stirred at 80° C. for 6 hr. The reaction mixture was allowed to cool to room temperature, and the solvent was evaporated under reduced pressure. The obtained residue was extracted with ethyl acetate and water, and the organic layer was washed with saturated brine, dried over anhydrous magnesium sulfate, and concentrated under reduced pressure. The obtained residue was purified by silica gel chromatography (NH, hexane/ethyl acetate) to give the title compound (3.65 g).

$^1$H NMR (300 MHz, DMSO-d$_6$) δ 0.04-0.24 (2H, m), 0.38-0.56 (2H, m), 0.73-0.92 (1H, m), 1.50-1.72 (2H, m), 2.42 (3H, s), 4.09 (2H, t, J=6.6 Hz), 7.20-7.27 (1H, m), 7.40 (1H, d, J=8.3 Hz), 7.50 (1H, d, J=2.6 Hz).

B) 4-(2-cyclopropylethoxy)-2-nitrobenzaldehyde

A solution of 2,2'-azobis(isobutyronitrile) (0.122 g), N-bromosuccinimide (3.19 g) and 4-(2-cyclopropylethoxy)-1-methyl-2-nitrobenzene (3.30 g) in ethyl acetate (100 mL) was refluxed for 8 hr. The reaction mixture was allowed to cool to room temperature, washed with saturated aqueous sodium hydrogen carbonate solution and saturated brine, and dried over anhydrous magnesium sulfate. The obtained solution was filtered with a short silica gel pad, and the filtrate was concentrated under reduced pressure. The obtained residue was dissolved in acetonitrile (150 mL), and molecular sieves 4A (10 g) and 4-methylmorpholine N-oxide (2.02 g) were added thereto at 0° C. The reaction mixture was stirred under a nitrogen atmosphere at room temperature for 3 hr, and concentrated under reduced pressure. The obtained residue was purified by silica gel chromatography (hexane/ethyl acetate) to give the title compound (1.90 g).

$^1$H NMR (300 MHz, DMSO-d$_6$) δ 0.07-0.24 (2H, m), 0.31-0.57 (2H, m), 0.72-0.97 (1H, m), 1.53-1.74 (2H, m), 4.24 (2H, t, J=6.6 Hz), 7.44 (1H, dd, J=8.7, 2.3 Hz), 7.62 (1H, d, J=2.3 Hz), 7.95 (1H, d, J=8.3 Hz), 10.04 (1H, s).

C) 4-({(2S)-2-[(tert-butoxycarbonyl)amino]propyl}oxy)phenyl acetate

To a solution of 4-hydroxyphenyl acetate (60.8 g), tert-butyl [(1S)-2-hydroxy-1-methylethyl]carbamate (70 g) and triphenylphosphine (105 g) in THF (300 mL) was added dropwise a solution (1.9 M, 210 mL) of diisopropyl azodicarboxylate in toluene at 0° C., and the mixture was stirred at room temperature for 16 hr. The reaction mixture was concentrated under reduced pressure, the residue was suspended in diethyl ether, and the precipitate was removed by filtration. The filtrate was concentrated, and the residue was purified by silica gel chromatography (hexane/ethyl acetate), and then by silica gel chromatography (NH, hexane/ethyl acetate) to give the title compound (70.9 g).

$^1$H NMR (300 MHz, DMSO-d$_6$) δ 1.11 (3H, d, J=6.0 Hz), 1.38 (9H, s), 2.23 (3H, s), 3.54-3.96 (3H, m), 6.87 (1H, d), 6.90-6.96 (2H, m), 6.98-7.09 (2H, m).

D) tert-butyl [(1S)-2-(4-hydroxyphenoxy)-1-methylethyl]carbamate

A mixture of 4-({(2S)-2-[(tert-butoxycarbonyl)amino]propyl}oxy)phenyl acetate (70 g), potassium carbonate (156 g) and methanol (800 mL) was stirred at room temperature for 3 days. The reaction mixture was concentrated under reduced pressure, and the obtained residue was neutralized with aqueous citric acid solution, and diluted with ethyl acetate. The organic layer was washed with saturated brine and dried over anhydrous magnesium sulfate. The solvent was evaporated under reduced pressure to give the title compound (40.5 g).

MS (ESI+): [M+H]$^+$ 168.1

E) tert-butyl {(1S)-2-[(cis-4-hydroxycyclohexyl)oxy]-1-methylethyl}carbamate

A suspension of tert-butyl [(1S)-2-(4-hydroxyphenoxy)-1-methylethyl]carbamate (40 g) and 5% rhodium-carbon (containing water (50%), 8.0 g) in methanol (600 mL) was stirred at 60° C. for 3 hr under a hydrogen atmosphere (5 atm). The catalyst was removed by filtration, and the filtrate was concentrated. The residue was purified by silica gel chromatography (hexane/ethyl acetate) to give the title compound (8.3 g).

$^1$H NMR (300 MHz, DMSO-d$_6$) δ 1.01 (3H, d, J=6.8 Hz), 1.35-1.40 (10H, m), 1.40-1.54 (5H, m), 1.55-1.75 (2H, m), 2.94-3.23 (1H, m), 3.20-3.30 (2H, m), 3.39-3.71 (2H, m), 4.37 (1H, d, J=3.8 Hz), 6.59 (1H, d, J=7.6 Hz).

F) tert-butyl {(1S)-2-[(trans-4-azidocyclohexyl)oxy]-1-methylethyl}carbamate

To a solution of tert-butyl {(1S)-2-[(cis-4-hydroxycyclohexyl)oxy]-1-methylethyl}carbamate (5.00 g), triphenylphosphine (7.20 g) and diphenylphosphorylazide (5.03 g) in toluene (200 mL) was added dropwise a solution (1.9 M, 14.4 mL) of diisopropyl azodicarboxylate in toluene, and the mixture was stirred at room temperature for 16 hr. The reaction mixture was concentrated under reduced pressure, the residue was suspended in diethyl ether, and the precipitate was removed by filtration. The filtrate was concentrated, and the residue was purified by silica gel chromatography(hexane/ethyl acetate) to give the title compound (1.05 g).

$^1$H NMR (300 MHz, DMSO-d$_6$) δ 0.99 (3H, d, J=6.8 Hz), 1.19-1.35 (4H, m), 1.37 (9H, s), 1.88 (4H, d, J=9.1 Hz), 3.15 (1H, dd, J=9.4, 6.8 Hz), 3.22-3.39 (2H, m), 3.43-3.67 (2H, m), 6.61 (1H, d, J=7.6 Hz).

G) tert-butyl [(1S)-2-({trans-4-[6-(2-cyclopropylethoxy)-2H-indazol-2-yl]cyclohexyl}oxy)-1-methylethyl]carbamate A solution of 4-(2-cyclopropylethoxy)-2-nitrobenzaldehyde (0.79 g), tert-butyl {(1S)-2-[(trans-4-azidocyclohexyl)oxy]-1-methylethyl}carbamate (1.0 g), triphenylphosphine (3.08 g) and triethyl phosphite (3.08 g) in toluene (10 mL) was refluxed for 3 hr. The reaction mixture was allowed to cool, and concentrated under reduced pressure. To the obtained residue was added triethyl phosphite (4.0 g), and the mixture was stirred at 160° C. for 4 hr. The reaction mixture was allowed to cool, and purified by silica gel chromatography (hexane/ethyl acetate) to give the title compound (1.2 g).

MS (ESI+): [M+H]$^+$ 458.2

H) N-[(1S)-2-({trans-4-[6-(2-cyclopropylethoxy)-2H-indazol-2-yl]cyclohexyl}oxy)-1-methylethyl]acetamide To a solution of tert-butyl [(1S)-2-({trans-4-[6-(2-cyclopropylethoxy)-2H-indazol-2-yl]cyclohexyl}oxy)-1-methylethyl]carbamate (1.2 g) in ethyl acetate (30 mL) was added 4M hydrogen chloride/ethyl acetate (10 mL), and the mixture was stirred at room temperature for 5 hr. The reaction mixture was concentrated under reduced pressure, the obtained residue was dissolved in pyridine (10 mL), and acetic anhydride (1 mL) was added thereto at room temperature. The reaction mixture was stirred at room temperature for 3 hr, and concentrated under reduced pressure. The obtained residue was dissolved in ethyl acetate and water, and the solution was extracted with ethyl acetate. The organic layer was washed successively with water, saturated aqueous sodium hydrogen carbonate solution and saturated brine, dried over anhydrous magnesium sulfate and concentrated under reduced pressure. The obtained residue was separated by HPLC (C18, mobile phase: ammonium hydrogen carbonate aqueous solution/acetonitrile), and water was added to the obtained fraction. The mixture was extracted with ethyl acetate, dried over anhydrous magnesium sulfate, and concentrated under reduced pressure to give the title compound (153 mg).

$^1$H NMR (300 MHz, DMSO-d$_6$) δ 0.05-0.22 (2H, m), 0.36-0.52 (2H, m), 0.73-0.96 (1H, m), 1.04 (3H, d, J=6.8 Hz), 1.19-1.48 (2H, m), 1.56-1.73 (2H, m), 1.79 (3H, s), 1.84-2.02 (2H, m), 2.10 (4H, d, J=10.5 Hz), 3.16-3.29 (1H, m), 3.33-3.46 (2H, m), 3.86 (1H, dt, J=13.4, 6.5 Hz), 4.03 (2H, t, J=6.4 Hz), 4.26-4.51 (1H, m), 6.67 (1H, dd, J=8.9, 2.1 Hz), 6.90 (1H, d, J=1.5 Hz), 7.53 (1H, d, J=9.0 Hz), 7.69 (1H, d, J=7.9 Hz), 8.23 (1H, s).

MS (ESI+): [M+H]$^+$ 400.3 mp 98-99° C.

Anal. Calcd for C$_{23}$H$_{33}$N$_3$O$_3$: C, 69.14; H, 8.33; N, 10.52. Found: C, 69.00; H, 8.35; N, 10.43.

Example 41

N-(3-{trans-4-[6-(cyclopropylmethoxy)-2H-indazol-2-yl]cyclohexyl}-1-methylpropyl)acetamide A) 4-(cyclopropylmethoxy)-1-methyl-2-nitrobenzene Potassium carbonate (48.7 g) and (bromomethyl)cyclopropane (34.2 mL) were added to a solution of 4-methyl-3-nitrophenol (49.1 g) in DMF (320 mL) at room temperature, and the reaction mixture was stirred at 60° C. overnight. The solvent was evaporated under reduced pressure, and the residue was dissolved in diethyl ether, and the solution was washed 3 times with water. The aqueous layer was extracted again with diethyl ether, and the combined organic layer was washed with saturated brine, dried over anhydrous magnesium sulfate, and concentrated under reduced pressure to give the title compound (66.4 g).

$^1$H NMR (300 MHz, CDCl$_3$) δ 0.31-0.42 (2H, m), 0.62-0.72 (2H, m), 1.16-1.36 (1H, m), 2.52 (3H, s), 3.83 (2H, d, J=7.2 Hz), 7.07 (1H, dd, J=8.7, 2.6 Hz), 7.21 (1H, d, J=8.7 Hz), 7.49 (1H, d, J=2.6 Hz).

B) 1-(bromomethyl)-4-(cyclopropylmethoxy)-2-nitrobenzene

To a mixture of 4-(cyclopropylmethoxy)-1-methyl-2-nitrobenzene (66.4 g) and a solution of N-bromosuccinimide (68.4 g) in ethyl acetate (1.0 L) was added 2,2'-azobis(2-methylpropionitrile) (2.63 g) in 5 portions at 90° C. The reaction mixture was stirred at 90° C. overnight. To the reaction mixture were added N-bromosuccinimide (34.2 g) and 2,2'-azobis(2-methylpropionitrile) (1.32 g) at 90° C. The mixture was allowed to cool to room temperature, concentrated under reduced pressure and left standing overnight. The resulting crystals were collected by filtration, washed with methanol, and dried under reduced pressure to give the title compound (49.9 g).

$^1$H NMR (300 MHz, CDCl$_3$) δ 0.33-0.42 (2H, m), 0.64-0.73 (2H, m), 1.20-1.38 (1H, m), 3.87 (2H, d, J=7.2 Hz), 4.79 (2H, s), 7.12 (1H, dd, J=8.7, 2.6 Hz), 7.44 (1H, d, J=8.7 Hz), 7.54 (1H, d, J=2.6 Hz).

C) 4-(cyclopropylmethoxy)-2-nitrobenzaldehyde

To a solution of 1-(bromomethyl)-4-(cyclopropylmethoxy)-2-nitrobenzene (11.4 g) in acetonitrile (200 mL) were added molecular sieves 4 Å (55 g) and N-methylmorpholine (9.37 g) at room temperature. Under an argon atmosphere, the reaction mixture was stirred at room temperature for 1 hr, and filtered through celite. The obtained filtrate was concentrated under reduced pressure, and the residue was dissolved in diethyl ether and the solution was washed twice with 6N hydrochloric acid and once with water. The organic layer was washed with saturated brine, dried over anhydrous magnesium sulfate, and concentrated under reduced pressure. The residue was purified by silica gel chromatography (hexane/ethyl acetate) to give the title compound (6.39 g).

$^1$H NMR (300 MHz, CDCl$_3$) δ 0.36-0.45 (2H, m), 0.66-0.78 (2H, m), 1.23-1.40 (1H, m), 3.96 (2H, d, J=6.8 Hz), 7.22 (1H, dd, J=8.7, 2.6 Hz), 7.50 (1H, d, J=2.6 Hz), 7.97 (1H, d, J=8.7 Hz), 10.29 (1H, s).

D) methyl trans-4-[6-(cyclopropylmethoxy)-2H-indazol-2-yl]cyclohexanecarboxylate Methyl trans-4-aminocyclohexanecarboxylate monohydrochloride (10.0 g) was dissolved in ethyl acetate (50 mL), THF (10 mL) and saturated aqueous potassium carbonate solution (20 mL) under ice-cooling, and the mixture was extracted with a mixed solvent of ethyl acetate/THF (5/1). The combined organic layer was dried over anhydrous magnesium sulfate, and concentrated under reduced pressure to give a colorless powder (5.98 g). A mixture of the obtained powder (5.98 g), 4-(cyclopropylmethoxy)-2-nitrobenzaldehyde (8.41 g) and toluene (200 mL) was refluxed for 15 hr. The reaction mixture was allowed to cool to room temperature, and the solvent was evaporated under reduced pressure. The residue was dissolved in triethyl phosphite (25.3 g), and the mixture was stirred at 190° C. for 5 hr. The reaction mixture was allowed to cool to room temperature and purified by silica gel chromatography (hexane/ethyl acetate) to give the title compound (6.98 g).

MS (ESI+): [M+H]$^+$ 329.2

E) {trans-4-[6-(cyclopropylmethoxy)-2H-indazol-2-yl]cyclohexyl}methanol

To a suspension of lithium aluminum hydride (0.462 g) in THF (100 mL) was added dropwise a solution of methyl trans-4-[6-(cyclopropylmethoxy)-2H-indazol-2-yl]cyclohexanecarboxylate (4.00 g) in THF (100 mL) under ice-cooling. The reaction mixture was stirred under ice-cooling for 2 hr, and water (0.462 mL), 5N aqueous sodium hydroxide solution (0.462 mL) and water (0.462 mL) were carefully added successively thereto. The reaction mixture was stirred under ice-cooling for 30 min, and the resulting precipitate was filtered off. The obtained filtrate was concentrated under reduced pressure to give the title compound (3.51 g).

35 $^1$H NMR (300 MHz, DMSO-d$_6$) δ 0.25-0.40 (2H, m), 0.49-0.66 (2H, m), 0.97-1.34 (3H, m), 1.45 (1H, ddd, J=8.7, 6.0, 3.0 Hz), 1.80-1.96 (4H, m), 2.05-2.20 (2H, m), 3.23-3.34 (2H, m), 3.82 (2H, d, J=7.2 Hz), 4.22-4.40 (1H, m), 4.46 (1H, t, J=5.3 Hz), 6.68 (1H, dd, J=8.9, 2.1 Hz), 6.86 (1H, d, J=2.3 Hz), 7.52 (1H, d, J=8.7 Hz), 8.23 (1H, s).

F) trans-4-[6-(cyclopropylmethoxy)-2H-indazol-2-yl]cyclohexanecarbaldehyde

To a solution of {trans-4-[6-(cyclopropylmethoxy)-2H-indazol-2-yl]cyclohexyl}methanol (3.50 g) in acetonitrile (100 mL) was added Dess-Martin reagent (5.93 g), and the mixture was stirred at room temperature for 5 hr. The reaction mixture was poured into ice water, and the mixture was extracted with ethyl acetate. The organic layer was washed with saturated brine, dried over anhydrous magnesium sulfate, and concentrated under reduced pressure. The residue was purified by silica gel chromatography (hexane/ethyl acetate) to give the title compound (3.30 g).

$^1$H NMR (300 MHz, DMSO-$d_6$) δ 0.24-0.42 (2H, m), 0.49-0.69 (2H, m) 1.20-1.32 (1H, m), 1.33-1.54 (2H, m), 1.79-2.04 (2H, m), 2.04-2.27 (4H, m), 2.30-2.47 (1H, m), 3.82 (2H, d, J=7.2 Hz), 4.22-4.50 (1H, m), 6.69 (1H, dd, J=8.9, 2.1 Hz), 6.86 (1H, d, J=1.9 Hz), 7.53 (1H, d, J=9.0 Hz), 8.23 (1H, s), 9.63 (1H, s).

G) (3E)-4-{trans-4-[6-(cyclopropylmethoxy)-2H-indazol-2-yl]cyclohexyl}but-3-en-2-one Sodium hydride (0.292 g) was added to a solution of dimethyl 2-oxopropylphosphonate (2.021 g) in 1,2-dimethoxyethane (50 mL) under ice-cooling in small portions. The reaction mixture was stirred for 1 hr under ice-cooling, and a solution of trans-4-[6-(cyclopropylmethoxy)-2H-indazol-2-yl]cyclohexanecarbaldehyde (3.30 g) in 1,2-dimethoxyethane (50 mL) was added under ice-cooling. The reaction mixture was stirred at room temperature for 3 hr, poured into 1N hydrochloric acid under ice-cooling and the mixture was extracted with ethyl acetate. The organic layer was washed with saturated brine, dried over anhydrous magnesium sulfate, and concentrated under reduced pressure. The residue was purified by silica gel chromatography (hexane/ethyl acetate) to give the title compound (2.85 g).

MS (ESI+): [M+H]$^+$ 339.2

H) 4-{trans-4-[6-(cyclopropylmethoxy)-2H-indazol-2-yl]cyclohexyl}butan-2-one A mixture of (3E)-4-{trans-4-[6-(cyclopropylmethoxy)-2H-indazol-2-yl]cyclohexyl}but-3-en-2-one (2.85 g), palladium-activated carbon ethylenediamine complex (0.538 g) and ethyl acetate (100 mL) was stirred at room temperature for 15 hr under a hydrogen atmosphere. The catalyst was removed by filtration, and the filtrate was concentrated under reduced pressure to give the title compound (2.75 g).

MS (ESI+): [M+H]$^+$ 341.3

I) 4-{trans-4-[6-(cyclopropylmethoxy)-2H-indazol-2-yl]cyclohexyl}butan-2-ol

Sodium borohydride (0.306 g) was added to a solution of 4-{trans-4-[6-(cyclopropylmethoxy)-2H-indazol-2-yl]cyclohexyl}butan-2-one (2.75 g) in ethanol (100 mL) under ice-cooling in small portions. The reaction mixture was stirred at room temperature for 1 hr, and the mixture was concentrated under reduced pressure. The residue was diluted with water, and the mixture was extracted with ethyl acetate. The organic layer was washed with saturated brine, dried over anhydrous magnesium sulfate, and concentrated under reduced pressure. The residue was purified by silica gel chromatography (hexane/ethyl acetate) to give the title compound (2.46 g).

MS (ESI+): [M+H]$^+$ 343.3

J) 3-{trans-4-[6-(cyclopropylmethoxy)-2H-indazol-2-yl]cyclohexyl}-1-methylpropyl methanesulfonate To a solution of 4-{trans-4-[6-(cyclopropylmethoxy)-2H-indazol-2-yl]cyclohexyl}butan-2-ol (2.45 g) and triethylamine (1.50 mL) in THF (50 mL) was added dropwise a solution of sulfonyl chloride (0.83 mL) in THF (50 mL) under ice-cooling, and the mixture was stirred for 1 hr under ice-cooling. The reaction mixture was poured into 1N hydrochloric acid under ice-cooling, and the mixture was extracted with ethyl acetate. The organic layer was washed with water, aqueous sodium hydrogen carbonate solution and saturated brine, dried over anhydrous magnesium sulfate, and concentrated under reduced pressure to give the title compound (2.98 g).

MS (ESI+): [M+H]$^+$ 421.3

K) 2-[trans-4-(3-azidobutyl)cyclohexyl]-6-(cyclopropylmethoxy)-2H-indazole

A mixture of 3-{trans-4-[6-(cyclopropylmethoxy)-2H-indazol-2-yl]cyclohexyl}-1-methylpropyl methanesulfonate (2.95 g), sodium azide (1.37 g) and DMF (100 mL) was stirred at 80° C. for 2 hr. The reaction mixture was allowed to cool to room temperature, and concentrated under reduced pressure. The residue was diluted with ethyl acetate and water, and the organic layer was separated. The organic layer was washed with saturated brine, dried over anhydrous magnesium sulfate, and concentrated under reduced pressure. The residue was purified by silica gel chromatography (hexane/ethyl acetate) to give the title compound (2.50 g).

$^1$H NMR (300 MHz, DMSO-$d_6$) δ 0.25-0.41 (2H, m), 0.48-0.63 (2H, m), 1.00-1.39 (9H, m), 1.43-1.60 (2H, m), 1.73-1.96 (4H, m), 2.10 (2H, d, J=9.1 Hz), 3.48-3.64 (1H, m), 3.82 (2H, d, J=6.8 Hz), 4.19-4.48 (1H, m), 6.68 (1H, dd, J=8.9, 2.1 Hz), 6.86 (1H, s), 7.52 (1H, d, J=9.1 Hz), 8.22 (1H, s).

L) N-(3-{trans-4-[6-(cyclopropylmethoxy)-2H-indazol-2-yl]cyclohexyl}-1-methylpropyl)acetamide A mixture of 2-[trans-4-(3-azidobutyl)cyclohexyl]-6-(cyclopropylmethoxy)-2H-indazole (2.45 g), triphenylphosphine (1.75 g), water (30 mL) and THF (30 mL) was stirred at room temperature for 3 days. The organic solvent was evaporated under reduced pressure, and the obtained aqueous solution was acidified with 6N hydrochloric acid (pH=1), and washed twice with diethyl ether. The aqueous solution was basified with potassium carbonate and extracted with a mixed solvent of ethyl acetate/THF (10/1). The combined organic layer was washed with saturated brine, dried over anhydrous magnesium sulfate, and concentrated under reduced pressure. The residue was dissolved in pyridine (30 mL), and acetic anhydride (3.15 mL) was added at room temperature. The reaction mixture was stirred at room temperature for 3 hr, and the solvent was evaporated under reduced pressure. The residue was diluted with 1N hydrochloric acid, and the mixture was extracted with ethyl acetate. The organic layer was washed with saturated brine, dried over anhydrous magnesium sulfate, and concentrated under reduced pressure. The residue was purified by silica gel chromatography (hexane/ethyl acetate, ethyl acetate/methanol), and the obtained solid was recrystallized from hexane/ethyl acetate to give the title compound (1.29 g) as colorless crystals.

$^1$H NMR (300 MHz, DMSO-$d_6$) δ 0.17-0.41 (2H, m), 0.49-0.69 (2H, m), 1.02 (3H, d, J=6.4 Hz), 1.06-1.31 (6H, m), 1.32-1.47 (2H, m), 1.67-1.93 (7H, m), 2.09 (2H, d, J=9.5 Hz), 3.52-3.76 (1H, m), 3.82 (2H, d, J=7.2 Hz), 4.19-4.48 (1H, m), 6.68 (1H, dd, J=9.1, 1.9 Hz), 6.85 (1H, s), 7.52 (1H, d, J=9.1 Hz), 7.61 (1H, d, J=8.3 Hz), 8.21 (1H, s).

MS (ESI+): [M+H]$^+$ 384.2 mp 139-140° C.

Anal. Calcd for $C_{23}H_{33}N_3O_2$: C, 72.03; H, 8.67; N, 10.96. Found: C, 71.90; H, 8.75; N, 10.91.

Example compounds produced by the above-mentioned method, or a method analogous thereto are shown in the following Tables 1 to 5. The MS values in the Tables are those found.

TABLE 1

| Example | IUPAC Name | Structure | MS |
| --- | --- | --- | --- |
| 1 | N-[(1S)-2-({1-[6-(cyclopropylmethoxy)-1,3-benzoxazol-2-yl]piperidin-4-yl}oxy)-1-methylethyl]acetamide | 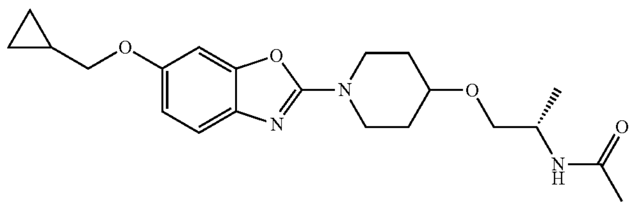 [SMILES: CC(=O)N[C@@H](C)COC1CCN(c2nc3ccc(OCC4CC4)cc3o2)CC1] | 388.2 |
| 2 | N-[(1S)-2-({1-[5-(cyclopropylmethoxy)-1,3-benzoxazol-2-yl]piperidin-4-yl}oxy)-1-methylethyl]acetamide | 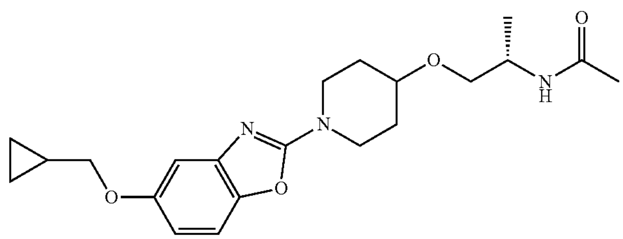 [SMILES: CC(=O)N[C@@H](C)COC1CCN(c2nc3cc(OCC4CC4)ccc3o2)CC1] | 388.1 |
| 3 | N-[(1S)-2-({1-[5-(cyclopropylmethoxy)-1,3-benzothiazol-2-yl]piperidin-4-yl}oxy)-1-methylethyl]acetamide | 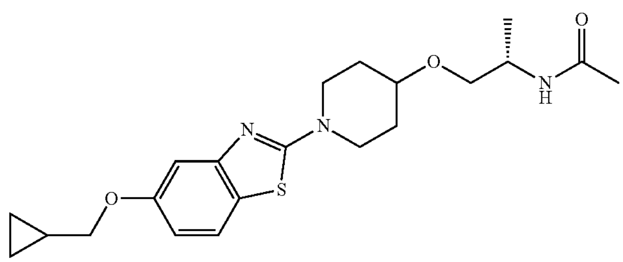 [SMILES: CC(=O)N[C@@H](C)COC1CCN(c2nc3cc(OCC4CC4)ccc3s2)CC1] | 404.4 |
| 4 | N-[2-({1-[6-(cyclopropylmethoxy)-1,3-benzoxazol-2-yl]piperidin-4-yl}oxy)-1-methylethyl]isoxazol-3-amine | 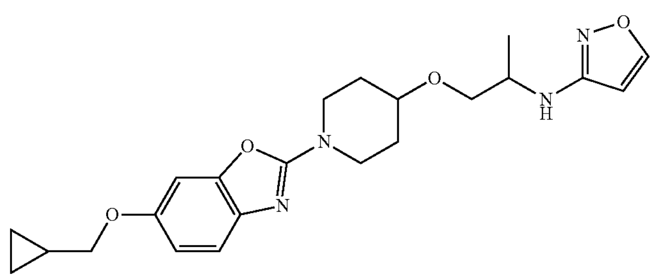 [SMILES: CC(COC1CCN(c2nc3ccc(OCC4CC4)cc3o2)CC1)Nc1ccon1] | 413.2 |
| 5 | N-(3-{1-[6-(cyclopropylmethoxy)-1,3-benzoxazol-2-yl]piperidin-4-yl}-1-methylpropyl)acetamide | 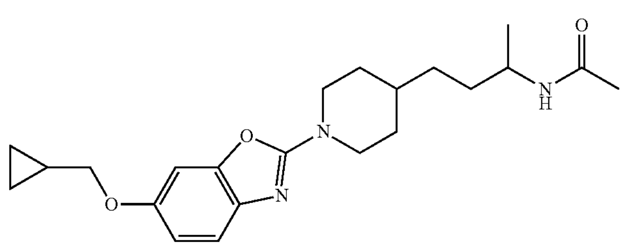 [SMILES: CC(=O)NC(C)CCC1CCN(c2nc3ccc(OCC4CC4)cc3o2)CC1] | 386.5 |

TABLE 1-continued

| Example | IUPAC Name | Structure | MS |
|---|---|---|---|
| 5a | N-[(1S)-3-{1-[6-(cyclopropylmethoxy)-1,3-benzoxazol-2-yl]piperidin-4-yl}-1-methylpropyl]acetamide | 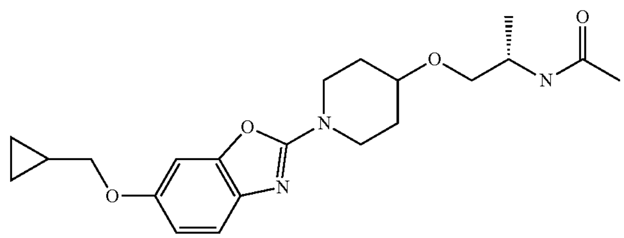 [SMILES: CC(=O)N[C@@H](C)COC1CCN(c2nc3ccc(OCC4CC4)cc3o2)CC1] | 386.5 |
| 6 | N-[(1S)-2-({1-[5-(cyclobutylmethoxy)-1,3-benzoxazol-2-yl]piperidin-4-yl}oxy)-1-methylethyl]acetamide | 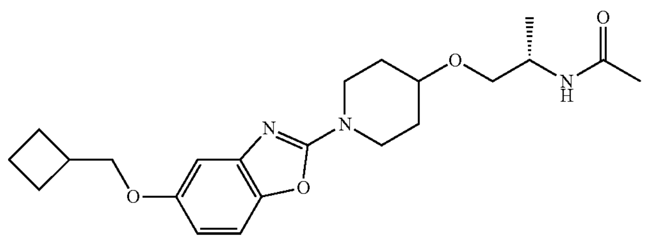 [SMILES: CC(=O)N[C@@H](C)COC1CCN(c2nc3cc(OCC4CCC4)ccc3o2)CC1] | 402.3 |
| 7 | N-[2-({1-[6-(cyclopropylmethoxy)-1,3-benzoxazol-2-yl]piperidin-4-yl}oxy)-1-methylethyl]-4-methylisoxazol-3-amine | 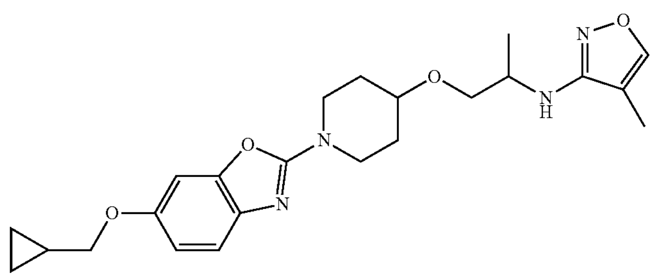 [SMILES: Cc1conc1NC(C)COC1CCN(c2nc3ccc(OCC4CC4)cc3o2)CC1] | 427.4 |
| 8 | N-[2-({1-[6-(cyclopropylmethoxy)-1,3-benzoxazol-2-yl]azetidin-3-yl}oxy)-1-methylethyl]acetamide | 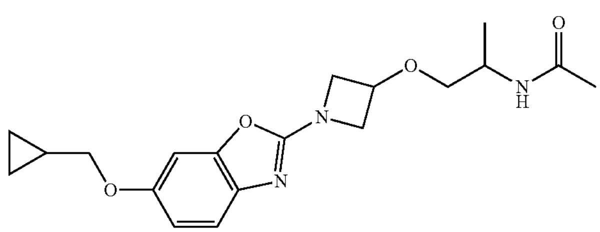 [SMILES: CC(=O)NC(C)COC1CN(c2nc3ccc(OCC4CC4)cc3o2)C1] | 360.1 |

TABLE 2

| Example | IUPAC Name | Structure | MS |
|---|---|---|---|
| 9 | N-[(1S)-1-methyl-2-({1-[6-(2,2,2-trifluoroethoxy)-1,3-benzoxazol-2-yl]piperidin-4-yl}oxy)ethyl]acetamide | 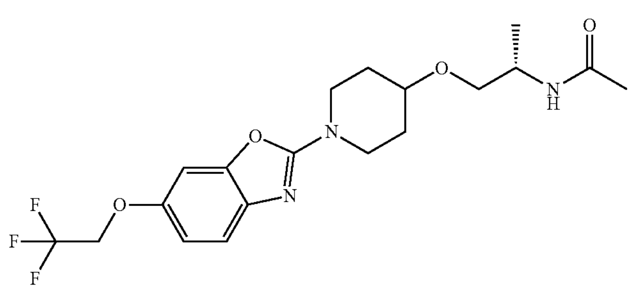 [SMILES: CC(=O)N[C@@H](C)COC1CCN(c2nc3ccc(OCC(F)(F)F)cc3o2)CC1] | 416.4 |

TABLE 2-continued

| Example | IUPAC Name | Structure | MS |
|---|---|---|---|
| 10 | N-[(1S)-2-{[1-(6-ethoxy-1,3-benzothiazol-2-yl)piperidin-4-yl]oxy}-1-methylethyl]acetamide | 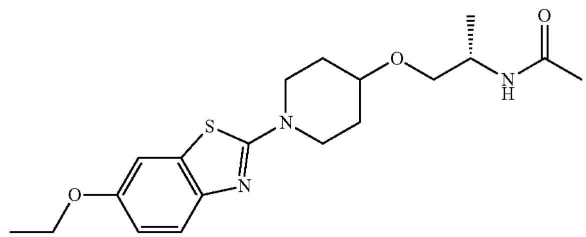 [SMILES: CCOc1ccc2nc(N3CCC(OC[C@H](C)NC(C)=O)CC3)sc2c1] | 378.1 |
| 11 | N-[(1S)-2-({1-[6-(cyclopropylmethoxy)-1,3-benzothiazol-2-yl]piperidin-4-yl}oxy)-1-methylethyl]acetamide | 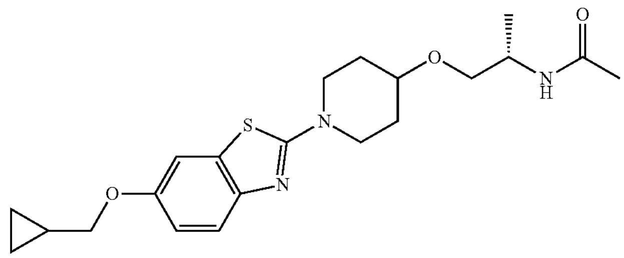 [SMILES: CC(=O)N[C@@H](C)COC1CCN(c2nc3ccc(OCC4CC4)cc3s2)CC1] | 404.2 |
| 12 | N-[(1S)-1-methyl-2-({1-[6-(2,2,2-trifluoroethoxy)-1,3-benzothiazol-2-yl]piperidin-4-yl}oxy)ethyl]acetamide | 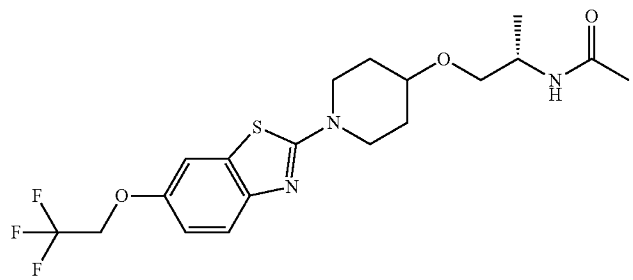 [SMILES: CC(=O)N[C@@H](C)COC1CCN(c2nc3ccc(OCC(F)(F)F)cc3s2)CC1] | 432.2 |
| 13 | N-[(1S)-2-({1-[6-(2,2-difluoroethoxy)-1,3-benzoxazol-2-yl]piperidin-4-yl}oxy)-1-methylethyl]acetamide | 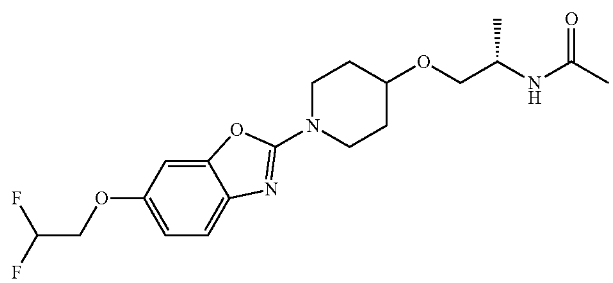 [SMILES: CC(=O)N[C@@H](C)COC1CCN(c2nc3ccc(OCC(F)F)cc3o2)CC1] | 398.3 |
| 14 | N-[(1S)-2-({1-[6-(cyclopropylmethoxy)-7-fluoro-1,3-benzoxazol-2-yl]piperidin-4-yl}oxy)-1-methylethyl]acetamide | 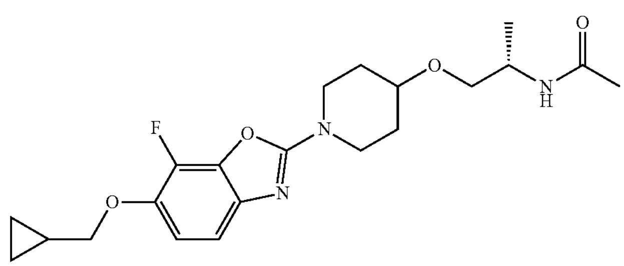 [SMILES: CC(=O)N[C@@H](C)COC1CCN(c2nc3ccc(OCC4CC4)c(F)c3o2)CC1] | 406 |
| 15 | N-[(1S)-2-({1-[6-(cyclopropylmethoxy)-4-fluoro-1,3-benzoxazol-2-yl]piperidin-4-yl}oxy)-1-methylethyl]acetamide | 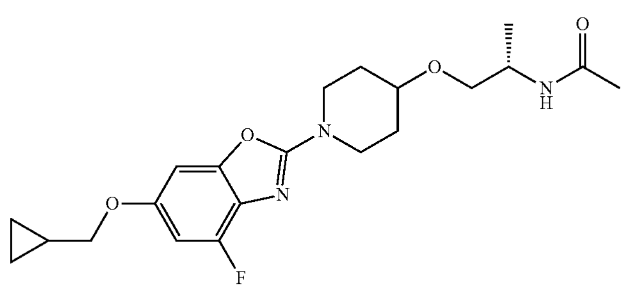 [SMILES: CC(=O)N[C@@H](C)COC1CCN(c2nc3c(F)cc(OCC4CC4)cc3o2)CC1] | 406 |

TABLE 2-continued

| Example | IUPAC Name | Structure | MS |
|---|---|---|---|
| 16 | N-[(1S)-2-({1-[5-(cyclopropylmethoxy)-6-fluor-1,3-benzothiazol-2-yl]piperidin-4-yl}oxy)-1-methylethyl]acetamide | 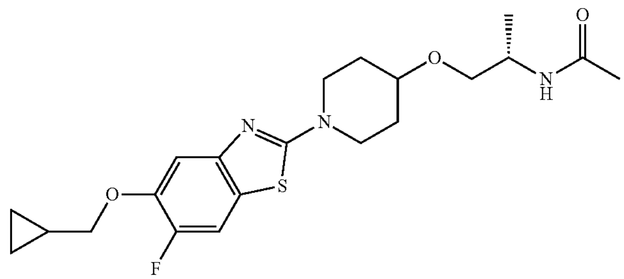 [SMILES: CC(=O)N[C@@H](C)COC1CCN(c2nc3cc(OCC4CC4)c(F)cc3s2)CC1] | 422.2 |
| 17 | 1-[(1S)-2-({1-[6-(cyclopropylmethoxy)-1,3-benzoxazol-2-yl]piperidin-4-yl}oxy)-1-methylethyl]-3-methylurea | 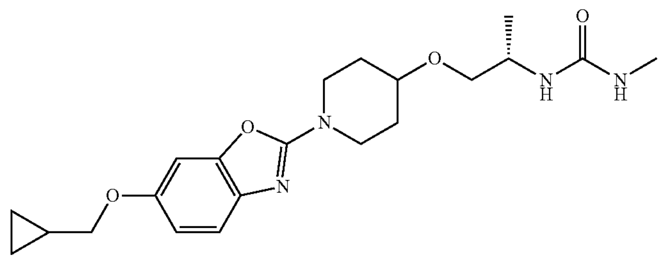 [SMILES: CNC(=O)N[C@@H](C)COC1CCN(c2nc3ccc(OCC4CC4)cc3o2)CC1] | 403.4 |

TABLE 3

| Example | IUPAC Name | Structure | MS |
|---|---|---|---|
| 18 | 1-[(1S)-2-({1-[6-(cyclopropylmethoxy)-1,3-benzoxazol-2-yl]piperidin-4-yl}oxy)-1-methylethyl]-3-ethylurea | 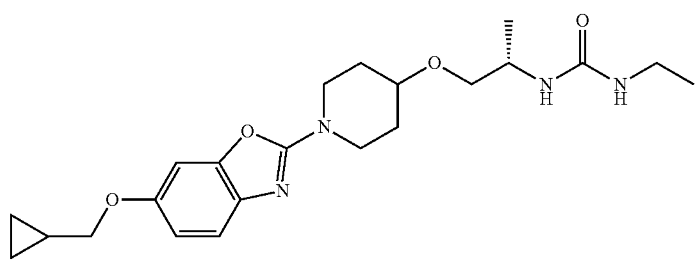 [SMILES: CCNC(=O)N[C@@H](C)COC1CCN(c2nc3ccc(OCC4CC4)cc3o2)CC1] | 417.4 |
| 19 | methyl [(1S)-2-({1-[6-(cyclopropylmethoxy)-1,3-benzoxazol-2-yl]piperidin-4-yl}oxy)-1-methylethyl]carbamate | 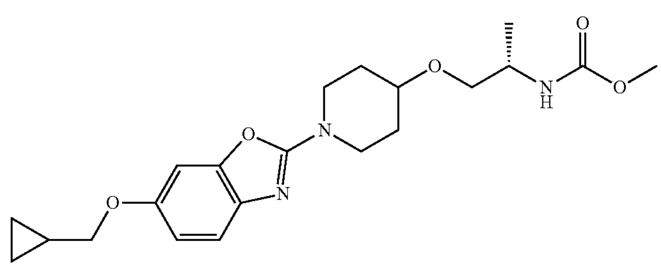 [SMILES: COC(=O)N[C@@H](C)COC1CCN(c2nc3ccc(OCC4CC4)cc3o2)CC1] | 404 |
| 20 | N-[(1S)-1-methyl-2-{[1-(5-propoxy-1,3-benzoxazol-2-yl)piperidin-4-yl]oxy}ethyl]acetamide | 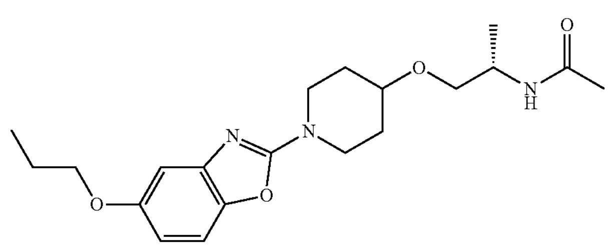 [SMILES: CCCOc1ccc2oc(N3CCC(OC[C@H](C)NC(C)=O)CC3)nc2c1] | 376.1 |

TABLE 3-continued

| Example | IUPAC Name | Structure | MS |
|---|---|---|---|
| 21 | N-[(1S)-2-{[1-(6-ethoxy-1,3-benzoxazol-2-yl)piperidin-4-yl]oxy}-1-methylethyl]acetamide | 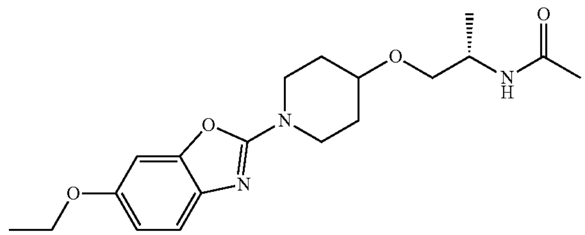 [SMILES: CCOc1ccc2nc(N3CCC(OC[C@H](C)NC(C)=O)CC3)oc2c1] | 362.3 |
| 22 | N-[(1S)-1-methyl-2-{[1-(6-propoxy-1,3-benzoxazol-2-yl)piperidin-4-yl]oxy}ethyl]acetamide | 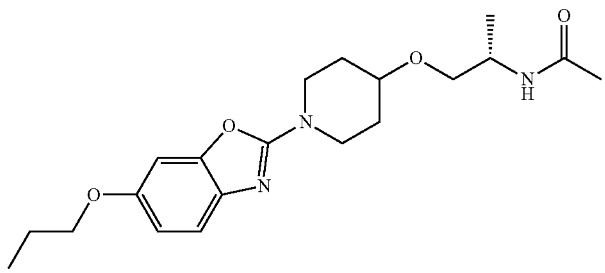 [SMILES: CCCOc1ccc2nc(N3CCC(OC[C@H](C)NC(C)=O)CC3)oc2c1] | 376.4 |
| 23 | N-[(1S)-1-methyl-2-({1-[6-(1-methylethoxy)-1,3-benzoxazol-2-yl]piperidin-4-yl}oxy)ethyl]acetamide | 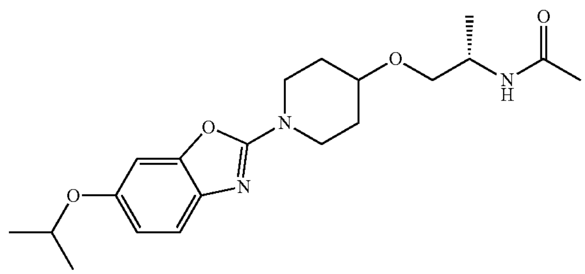 [SMILES: CC(=O)N[C@@H](C)COC1CCN(c2nc3ccc(OC(C)C)cc3o2)CC1] | 376.4 |
| 24 | N-{1-[({1-[6-(cyclopropylmethoxy)-1,3-benzoxazol-2-yl]piperidin-4-yl}oxy)methyl]-2,2,2-trifluoroethyl}acetamide | 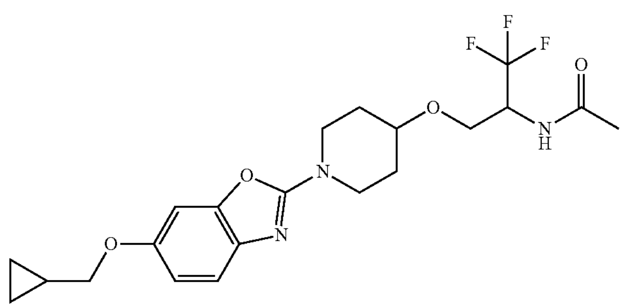 [SMILES: CC(=O)NC(COC1CCN(c2nc3ccc(OCC4CC4)cc3o2)CC1)C(F)(F)F] | 442.4 |
| 25 | N-[2-({1-[6-(cyclopropylmethoxy)-1,3-benzoxazol-2-yl]piperidin-4-yl}oxy)-1-(fluoromethyl)ethyl]acetamide | 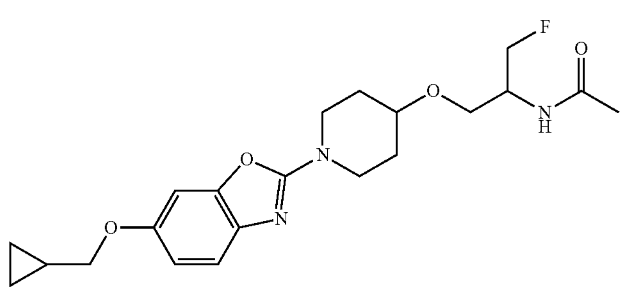 [SMILES: CC(=O)NC(CF)COC1CCN(c2nc3ccc(OCC4CC4)cc3o2)CC1] | 406.4 |

TABLE 3-continued

| Example | IUPAC Name | Structure | MS |
|---|---|---|---|
| 26 | N-[2-({8-[6-(cyclopropylmethoxy)-1,3-benzexazol-2-yl]-8-azabicyclo[3.2.1]oct-3-yl}oxy)-1-methylethyl]isoxazol-3-amine | 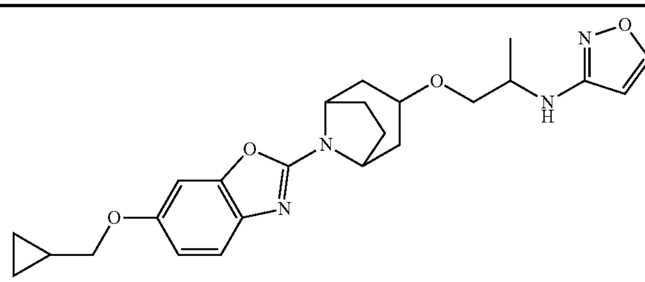 | 439.4 |

TABLE 4

| Example | IUPAC Name | Structure | MS |
|---|---|---|---|
| 27 | N-[2-({8-[6-(cyclopropylmethoxy)-1,3-benzoxazol-2-yl]-8-azabicyclo[3.2.1]oct-3-yl}oxy)-1-methylethyl]isoxazol-3-amine | 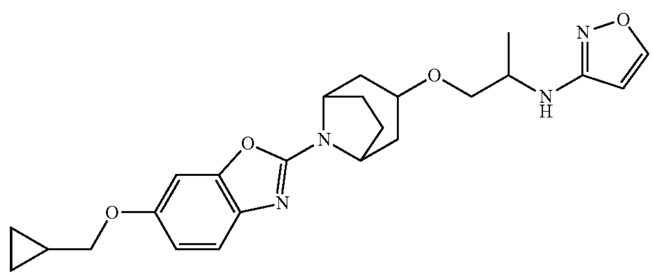 [SMILES: CC(COC1CC2CCC(C1)N2c1nc2ccc(OCC3CC3)cc2o1)Nc1ccon1] | 439.4 |
| 28 | N-[(1S)-2-({1-[5-(cyclopropylmethoxy)[1,3]oxazolo[5,4-b]pyridin-2-yl]piperidin-4-yl}oxy)-1-methylethyl]acetamide | 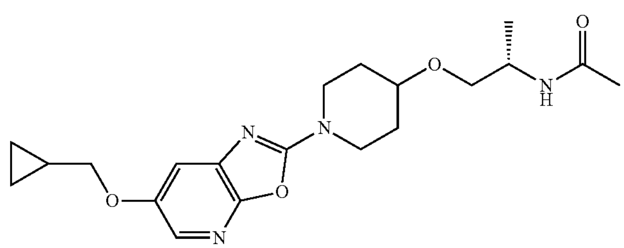 [SMILES: CC(=O)N[C@@H](C)COC1CCN(c2nc3cc(OCC4CC4)cnc3o2)CC1] | 389.5 |
| 29 | N-[(1S)-3-{4-[6-(cyclopropylmethoxy)-1,3-benzoxazol-2-yl]piperazin-1-yl}-1-methylpropyl]acetamide | 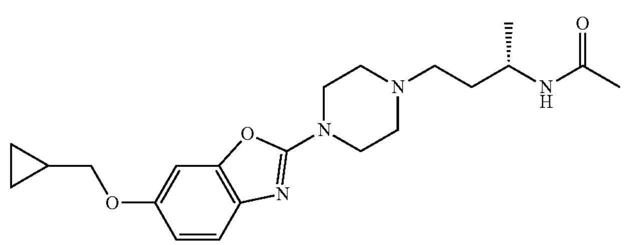 [SMILES: CC(=O)N[C@@H](C)CCN1CCN(c2nc3ccc(OCC4CC4)cc3o2)CC1] | 387.4 |
| 30 | N-[2-({1-[6-(cyclopropylmethoxy)-1,3-benzoxazol-2-yl]pyrrolidin-3-yl}oxy)-1-methylethyl]acetamide | 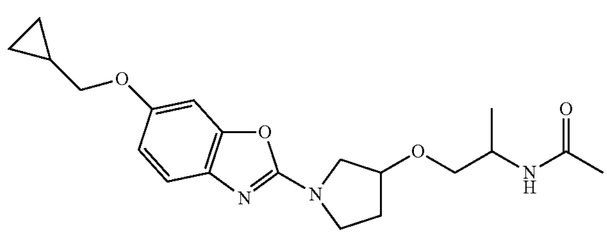 [SMILES: CC(=O)NC(C)COC1CCN(c2nc3ccc(OCC4CC4)cc3o2)C1] | 374 |

TABLE 4-continued

| Example | IUPAC Name | Structure | MS |
|---|---|---|---|
| 31 | N-[(1S)-2-({1-[6-(cyclopropylmethoxy)-1,3-benzoxazol-2-yl]piperidin-3-yl}oxy)-1-methylethyl]acetamide | 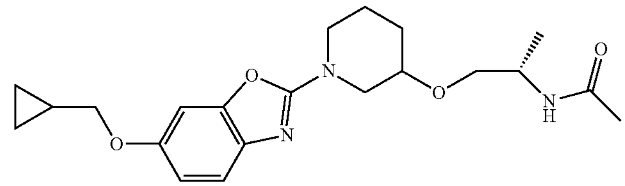 [SMILES: CC(=O)N[C@@H](C)COC1CCCN(c2nc3ccc(OCC4CC4)cc3o2)C1] | 388.2 |
| 32 | N-[(1S)-2-({1-[5-(cyclopropylmethoxy)[1,3]oxazolo[5,4-c]pyridin-2-yl]piperidin-4-yl)oxy)-1-methylethyl]acetamide | 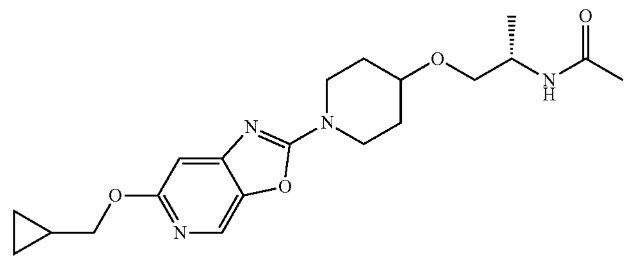 [SMILES: CC(=O)N[C@@H](C)COC1CCN(c2nc3cc(OCC4CC4)ncc3o2)CC1] | 389.5 |
| 33 | N-[(1S)-1-methyl-2-({1-[6-(2-methylpropoxy)-1,3-benzoxazol-2-yl]piperidin-4-yl}oxy)ethyl]acetamide | 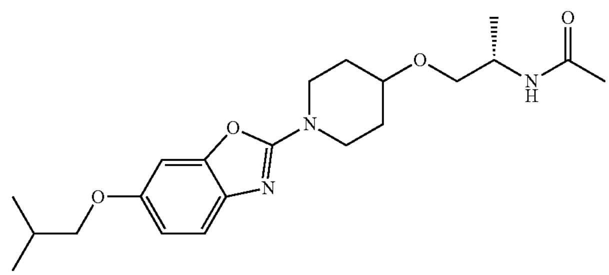 [SMILES: CC(=O)N[C@@H](C)COC1CCN(c2nc3ccc(OCC(C)C)cc3o2)CC1] | 390.4 |
| 34 | N-[(1S)-2-({1-[6-(cyclobutylmethoxy)-1,3-benzoxazol-2-yl]piperidin-4-yl}oxy)-1-methylethyl]acetamide | 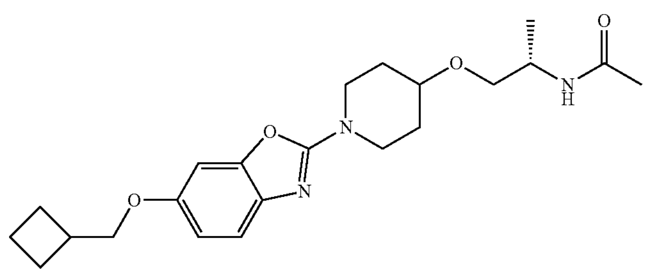 [SMILES: CC(=O)N[C@@H](C)COC1CCN(c2nc3ccc(OCC4CCC4)cc3o2)CC1] | 402.4 |
| 35 | N-[(1S)-2-({1-[6-(2-cyclopropylethoxy)-1,3-benzoxazol-2-yl]piperidin-4-yl}oxy)-1-methylethyl]acetamide | 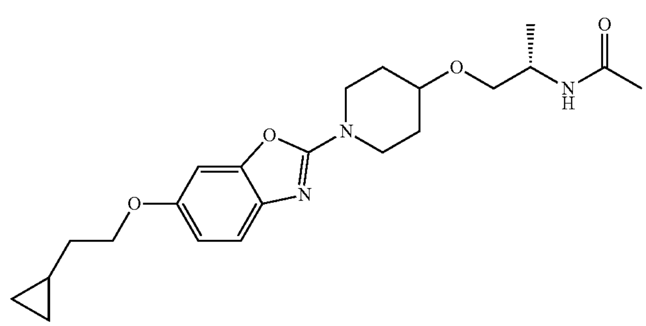 [SMILES: CC(=O)N[C@@H](C)COC1CCN(c2nc3ccc(OCCC4CC4)cc3o2)CC1] | 402.3 |

TABLE 5

| Example | IUPAC Name | Structure | MS |
|---|---|---|---|
| 36 | N-[(1S)-2-({1-[6-(cyclobutyloxy)-1,3-benzoxazol-2-yl]piperidin-4-yl}oxy)-1-methylethyl]acetamide | 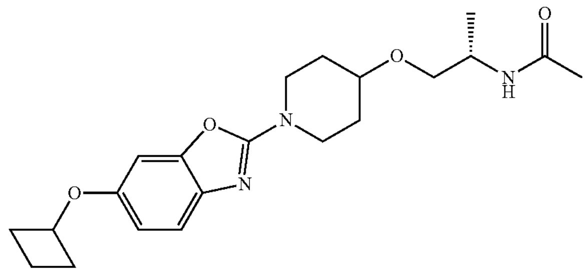 [SMILES: CC(=O)N[C@@H](C)COC1CCN(c2nc3ccc(OC4CCC4)cc3o2)CC1] | 388.2 |
| 37 | N-[(1S)-2-({1-[6-(cyclopropylmethoxy)-5-fluoro-1,3-benzothiazol-2-yl]piperidin-4-yl}oxy)-1-methylethyl]acetamide | 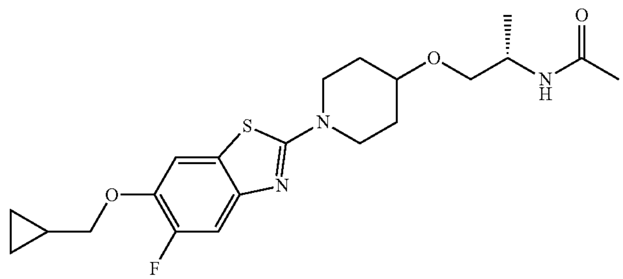 [SMILES: CC(=O)N[C@@H](C)COC1CCN(c2nc3cc(F)c(OCC4CC4)cc3s2)CC1] | 422.3 |
| 38 | N-[2-({trans-4-[6-(cyclopropylmethoxy)-1-benzofuran-2-yl]cyclohexyl}oxy)-1-methylethyl]acetamide | 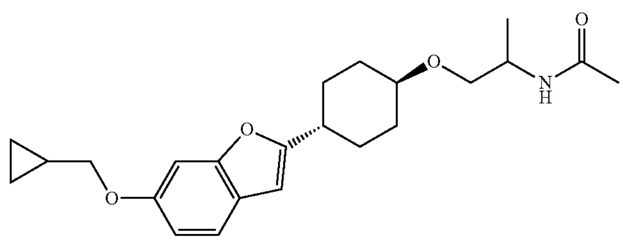 [SMILES: CC(=O)NC(C)CO[C@H]1CC[C@H](c2cc3ccc(OCC4CC4)cc3o2)CC1] | 407.9 ([M + Na]$^+$) |
| 39 | N-[2-({trans-4-[6-(cyclopropylmethoxy)-1,3-benzoxazol-2-yl]cyclohexyl}oxy)-1-methylethyl]acetamide | 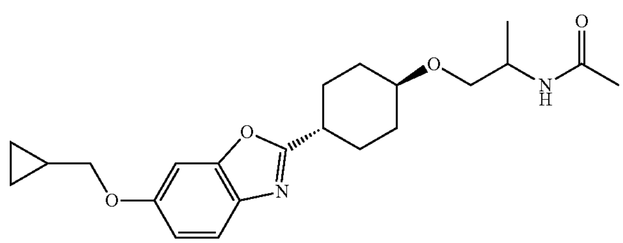 [SMILES: CC(=O)NC(C)CO[C@H]1CC[C@H](c2nc3ccc(OCC4CC4)cc3o2)CC1] | 387 |
| 40 | N-[(1S)-2-({trans-4-[6-(2-cyclopropylethoxy)-2H-indazol-2-yl]cyclohexyl}oxy)-1-methylethyl]acetamide | 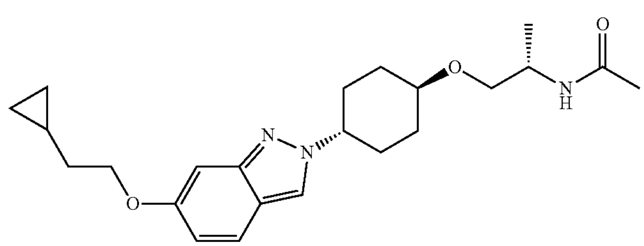 [SMILES: CC(=O)N[C@@H](C)CO[C@H]1CC[C@H](n2cc3ccc(OCCC4CC4)cc3n2)CC1] | 400.3 |
| 41 | N-(3-{trans-4-[6-(cyclopropylmethoxy)-2H-indazol-2-yl]cyclohexyl}-1-methylpropyl)acetamide | 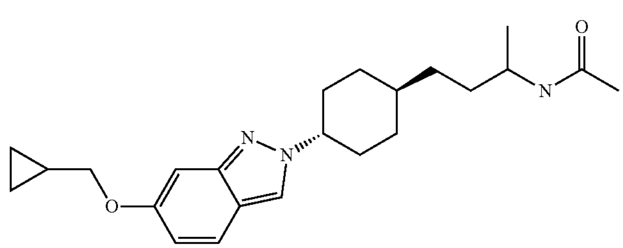 [SMILES: CC(=O)NC(C)CC[C@H]1CC[C@H](n2cc3ccc(OCC4CC4)cc3n2)CC1] | 384.2 |

Experimental Example 1

The ACC2 inhibitory action of the compound of the present invention was evaluated by the following method.

(1) Cloning of Human ACC2 Gene and Preparation of Recombinant Baculovirus

Human ACC2 gene was cloned by PCR using a human skeletal muscle cDNA library (Clontech) as a template and Primer 1 and Primer 2 shown below. Primer 1 and Primer 2 were prepared by adding SalI, XbaI restriction enzyme recognition sequences based on the information of the base sequence of human ACC2 gene (Genbank Accession U89344).

```
Primer 1:
                                       (SEQ ID NO: 1)
5'-AAAAGTCGACCCACCATGGTCTTGCTTCTTTGTCTATCTTG-3'

Primer 2:
                                       (SEQ ID NO: 2)
5'-TTTTTCTAGATCAGGTAGAGGCCGGGCTGTCCATG-3'
```

PCR was performed using Pyrobest DNA polymerase (TAKARA BIO INC.). The obtained PCR product was cloned to pT7 Blue vector (Novagen) and after confirmation of the base sequence, digested with restriction enzymes SalI and XbaI. The obtained DNA fragment was inserted into pFAST-BacHTa (Invitrogen) digested with restriction enzymes SalI and XbaI to give expression plasmid ACC2/pFAST-BacHTa.

A plasmid for expression of ACC2 without a mitochondrial targeting sequence was prepared by PCR using the expression plasmid as a template, and Primer 3 (SalI restriction enzyme recognition sequence was added) and Primer 4 prepared by reference to the information of human ACC2 gene base sequence (Genbank Accession U89344).

```
Primer 3:
                                       (SEQ ID NO: 3)
5'-CCAGGTCGACCCGCCAACGGGACTGGGACACAAGG-3'

Primer 4:
                                       (SEQ ID NO: 4)
5'-CGCACTCTCAGTTTCCCGGATTCCC-3'
```

PCR was performed using Pyrobest-DNA polymerase (TAKARA BIO INC.). The obtained PCR product was cloned to pT7 Blue vector (Novagen) and after confirmation of the base sequence, digested with restriction enzymes SalI and AflII. The obtained DNA fragment was inserted into ACC2/pFAST-BacHTa digested with restriction enzymes SalI and AflII to give expression plasmid ACC2mito7/pFAST-BacHTa.

Using the expression plasmid ACC2mito7/pFAST-BacHTa and BAC-TO-BAC Baculovirus Expression System (Invitrogen), virus stock BAC-ACC2 of recombinant Baculovirus (N terminal deleted (hereinafter Nd)) was prepared.

(2) Preparation of ACC2 (Nd) Protein

SF-9 cells (Invitrogen) were inoculated to a medium (2 L) for insect cells (Sf-900IISFM medium (Invitrogen) containing 10% fetal bovine serum (Trace), 50 mg/L Gentamicin (Invitrogen), 0.1% Pluronic F-68 (Invitrogen)) at $0.5 \times 10^6$ cells/mL, and cultured with shaking in Wave Bioreactor (Wave) at 27° C., 20 rpm, rocking angle 6°, oxygen concentration 30%.

On day 4 of the culture, 3 L of the medium for insect cells was added, the rocking angle was set to 8°, and the cells were further cultured. On day 5 of the culture, 100 mL of recombinant Baculovirus BAC-ACC2 (Nd) was added, 5 L of the medium for insect cells was further added, the rocking angle was set to 11°, and the cells were cultured for 3 days. The culture medium was centrifuged at 1000×g for 10 min to give virus-infected cells. The cells were washed with phosphate buffered saline (Invitrogen) and centrifuged under the same conditions. The obtained cells were cryopreserved at −80° C.

The cryopreserved cells were thawed in ice and suspended in 900 mL of 25 mM HEPES buffer (pH 7.5) containing 10% Glycerol, 0.13 M NaCl, 1 mM EDTA, 25 mM Sodium β-Glycerophosphate and 1 mM Sodium Orthovanadate, and supplemented with Complete Protease Inhibitor (Nippon Boehringer Ingelheim Co., Ltd.). The obtained suspension was homogenized three times in a polytron homogenizer (Kinematica) at 20,000 rpm for 30 sec. The obtained cell disruption solution was clarified by centrifugation at 31000×g for 60 min, and filtered through a 0.45 μm filter. The filtrate was passed through a column packed with 60 mL of Ni-NTA Super Flow Gel (QUIAGEN) at a flow rate of about 5 mL/min. The column was washed with buffer A (50 mM HEPES (pH 7.5) containing 0.3 M NaCl), further washed with buffer A containing 20 mM Imidazole, and eluted with buffer A containing 100 mM Imidazole. The eluate was concentrated with Vivaspin 20 (Vivascience) with a molecular weight cut off of 30K. The obtained concentrate was dialyzed against 50 mM HEPES (pH 7.5) containing 10 mM $MgCl_2$, 2 mM Dithiothreitol, 10 mM Tripotassium Citrate and 0.3 M NaCl. The inner dialysate was filtered through a 0.22 μm filter to give ACC2 (Nd). The obtained ACC2 (Nd) was cryopreserved at −80° C.

(3) Measurement of ACC2 Inhibitory Activity

ACC2 (Nd) (1.1 mg/ml) obtained in the above-mentioned (2) was diluted with an enzyme reaction buffer (50 mM HEPES (pH 7.5), 10 mM $MgCl_2$, 10 mM Tripotassium Citrate, 2 mM Dithiothreitol, 0.75 mg/ml Fatty acid free BSA) to a concentration of 6.4 μg/ml, and the mixture was added to each well of a 384 well assay plate (Nunc 265196) by 10 μl. A test compound dissolved in dimethyl sulfoxide (DMSO) was diluted with an enzyme reaction buffer and the resulting solution (5 μl) was added to each well. The mixture was incubated at 30° C. for 20 min. Then, a substrate solution (50 mM $KHCO_3$, 200 μM ATP, 200 μM Acetyl-CoA, 5 μl) was added to each well, and the mixture was reacted at 30° C. for 20 min (test compound addition group).

In addition, a reaction was performed in the same manner as above and without adding the test compound (test compound non-addition group).

Furthermore, a reaction was performed in the same manner as above and without adding the test compound and Acetyl-CoA (control group).

The reaction was quenched by adding a malachite green solution to each of the obtained reaction mixtures by 5 μl and stirring the mixtures. The obtained reaction mixture was left standing at room temperature for 20 min, and absorbance (620 nm) was measured using wallac1420 (PerkinElmer Japan Co., Ltd.). The above-mentioned malachite green solution was prepared by mixing Solution A (0.12% malachite green solution, prepared with $5NH_2SO_4$, preserved at 4° C. in shading), Solution B (7.5% aqueous ammonium molybdate solution, prepared when in use) and Solution C (11% aqueous Tween 20 solution, preserved at room temperature) at a ratio of Solution A:Solution B:Solution C=100:25:2 (volume ratio).

ACC2 inhibitory rate (%) was determined according to the following calculation formula.

(1−(absorbance of test compound addition group−absorbance of control group)÷(absorbance of test compound non-addition group−absorbance of control group))×100

The inhibitory rates against ACC2 at 10 μM are shown in Table 6.

TABLE 6

| test compound (Example No.) | ACC2 inhibitory rate (%) |
|---|---|
| 1 | 97 |
| 2 | 100 |
| 3 | 104 |
| 4 | 100 |
| 5 | 104 |
| 5a | 106 |
| 6 | 98 |
| 7 | 100 |
| 33 | 99 |
| 34 | 102 |
| 35 | 102 |

As is clear from Table 6, the test compounds showed a superior ACC2 inhibitory action.

Experimental Example 2

5-week-old male F344/Jcl rats (CLEA Japan, Inc., Tokyo) were acclimated to the rearing environment for 1 week after purchase and the diet was changed to Western diet (D12079B, Research diet). They were used for the experiment of Respiratory quotient (RQ) measurement at 8-week-old. For the RQ measurement experiment, the body weight was measured in the late afternoon (15:30-16:30) of the previous day and the morning (8:00-9:00) of the day, and the rats with high or low body weight increase were excluded. To the animals were administered by gavage 15 mL/kg of a liquid diet (F2LCW, Oriental Yeast Co., Ltd) prepared to a concentration of 4.95 g/15 mL (1.436 kcal/mL), and they were placed in an indirect calorimeter (Oxymax) chamber manufactured by Columbus Instruments, and RQ was recorded every 10 min. RQ values were confirmed about 1 hr after the start of the measurement and the animals were grouped (5 per group) such that a difference between groups would be small. For medication, a solvent (0.5% Methyl Cellulose, Wako Pure Chemical Industries, Ltd.) or a test compound (0.5% Methyl Cellulose suspension) was administered by gavage at 5 mL/kg. RQ was measured at 10 minute intervals from 0 to 3 hours after administration, and the average thereof was calculated. All values are shown in mean±standard deviation and statistical analysis was performed by the Dunnett-test.

TABLE 7

| compound | dose | average RQ of 0 to 3 hours after administration |
|---|---|---|
| control group | 0 | 0.834 ± 0.031 |
| Example 1 | 20 mg/kg | 0.795 ± 0.013 * |
| Example 2 | 20 mg/kg | 0.787 ± 0.019 ** |

Mean ± S.D., N = 5,
* $P \leq 0.05$,
** $P \leq 0.01$ (Dunnett test)

As is clear from Table 7, the test compounds showed superior respiratory quotient (RQ) lowering effect.

Experimental Example 3

6-week-old male F344/Jcl rats (CLEA Japan, Inc., Tokyo) were individually reared immediately after purchase and Western diet (D12079B, Research diet) was given. From the next day, an acclimation dosing (0.5% Methyl Cellulose, 5 mL/kg, oral administration) was started (once between 8:00 AM and 11:00 AM) and body weight and food consumption amount were appropriately measured. The rats with body weight and consumption amount extremely out of the average values in the acclimation dosing period were excluded. At the stage of 7-week-old, the body weight, food consumption amount, and body fat by Echo-MRI were measured, and the rats were grouped (6 per group) based on these measurement results. During 4 weeks of the test period, body weight was measured between 8:00 AM and 11:00 AM, and a solvent (0.5% Methyl Cellulose) or a test compound (0.5% Methyl Cellulose suspension) was consecutively administered by gavage at 5 mL/kg.

4 Weeks later, the body weight was measured in the morning. All values show mean±standard deviation and Williams' test and t-test were used for statistical analysis.

TABLE 8

| compound | dose (mg/kg/day) | body weight after administration for 4 weeks | comparison with control group |
|---|---|---|---|
| control group | 0 | 282.3 ± 13.0 | — |
| Example 1 | 20 | 265.1 ± 7.2 * | −6.1% |
| Example 2 | 10 | 267.2 ± 4.1 # | −5.4% |
| Example 2 | 20 | 265.4 ± 10.8 # | −6.0% |

Mean ± S.D., N = 6,
* $P \leq 0.05$ (t-test),
$P \leq 0.025$ (Williams test)

As is clear from Table 8, the test compounds showed a superior anti-obesity action.

Formulation Example 1

Production of Capsule

| 1) | compound of Example 1 | 30 mg |
|---|---|---|
| 2) | finely divided powder cellulose | 10 mg |
| 3) | lactose | 19 mg |
| 4) | magnesium stearate | 1 mg |
| | total | 60 mg |

1), 2), 3) and 4) are mixed and filled in a gelatin capsule.

Formulation Example 2

Production of Tablets

| 1) | compound of Example 1 | 30 g |
|---|---|---|
| 2) | lactose | 50 g |
| 3) | cornstarch | 15 g |
| 4) | calcium carboxymethylcellulose | 44 g |
| 5) | magnesium stearate | 1 g |
| | 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture was punched by a tableting machine, whereby 1000 tablets containing 30 mg of the compound of Example 1 per tablet are obtained.

INDUSTRIAL APPLICABILITY

The compound of the present invention has ACC (acetyl-CoA carboxylase) inhibitory action, and is useful for the prophylaxis or treatment of obesity, diabetes, hypertension, hyperlipidemia, cardiac failure, diabetic complications, metabolic syndrome, sarcopenia, cancer and the like.

This application is based on patent application No. 102718/2010 filed in Japan, the contents of which are hereby incorporated by reference.

The invention claimed is:

1. A compound represented by formula (I)

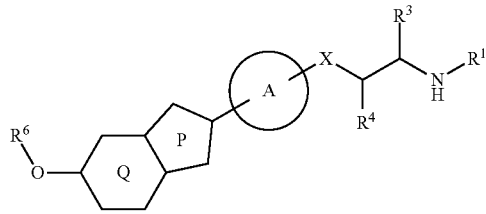

wherein:

R¹ is (1) a group represented by the formula: —COR², wherein R² is
  (a) a $C_{1-6}$ alkyl group;
  (b) a $C_{1-6}$ alkoxy group; or
  (c) an amino group optionally mono- or di-substituted by $C_{1-6}$ alkyl group(s); or
(2) a 5-membered aromatic heterocyclic group optionally substituted by 1 to 3 substituents selected from a $C_{1-6}$ alkyl group;

R³ is a $C_{1-6}$ alkyl group optionally substituted by 1 to 3 halogen atoms;

R⁴ is a hydrogen atom;

X is O or $CH_2$;

ring A is a 4- to 6-membered nitrogen-containing non-aromatic heterocycle (the heterocycle is optionally crosslinked) or cyclohexane;

ring P and ring Q are condensed to form

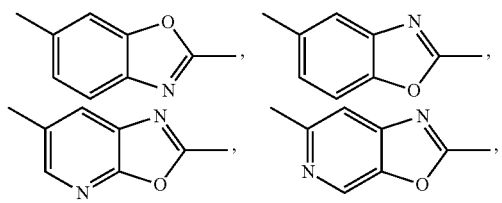

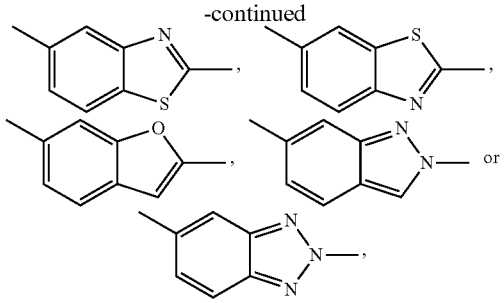

in each of which ring Q is optionally substituted by 1 to 3 halogen atoms; and

R⁶ is a $C_{1-6}$ alkyl group optionally substituted by 1 to 3 substituents selected from the group consisting of a halogen atom and a $C_{3-6}$ cycloalkyl group, or a salt thereof.

2. The compound or salt of claim 1, wherein ring A is azetidine, pyrrolidine, piperidine, piperazine, 8-azabicyclo[3.2.1]octane or cyclohexane.

3. N-[(1S)-2-({1-[6-(Cyclopropylmethoxy)-1,3-benzoxazol-2-yl]piperidin-4-yl}oxy)-1-methylethyl]acetamide or a salt thereof.

4. N-[(1S)-2-({1-[5-(Cyclopropylmethoxy)-1,3-benzoxazol-2-yl]piperidin-4-yl}oxy)-1-methylethyl]acetamide or a salt thereof.

5. N-[(1S)-3-{1-[6-(Cyclopropylmethoxy)-1,3-benzoxazol-2-yl]piperidin-4-yl}-1-methylpropyl]acetamide or a salt thereof.

6. N-[(1S)-2-({1-[6-(2-Cyclopropylethoxy)-1,3-benzoxazol-2-yl]piperidin-4-yl}oxy)-1-methylethyl]acetamide or a salt thereof.

7. A pharmaceutical composition comprising the compound or salt of claim 1 and a pharmacologically acceptable carrier.

8. The pharmaceutical composition of claim 7, which is an acetyl-CoA carboxylase inhibitor.

9. The pharmaceutical composition of claim 7, which is a composition for the treatment of obesity, diabetes, hypertension, hyperlipidemia, cardiac failure, diabetic complications, metabolic syndrome, sarcopenia or cancer.

* * * * *